US009469681B2

(12) United States Patent
Hill et al.

(10) Patent No.: US 9,469,681 B2
(45) Date of Patent: Oct. 18, 2016

(54) FUSION PROTEINS FORMING TRIMERS

(71) Applicant: APOGENIX GMBH, Heidelberg (DE)

(72) Inventors: Oliver Hill, Neckarsteinach (DE);
Marcus Branschaedel, Laupheim (DE);
Christian Gieffers, Dossenheim (DE);
Meinolf Thiemann, Schriesheim (DE)

(73) Assignee: APOGENIX AG, Heidelberg (DE)

( * ) Notice: Subject to any disclaimer, the term of this patent is extended or adjusted under 35 U.S.C. 154(b) by 300 days.

(21) Appl. No.: 14/160,240

(22) Filed: Jan. 21, 2014

(65) Prior Publication Data

US 2014/0171622 A1 Jun. 19, 2014

Related U.S. Application Data

(63) Continuation of application No. 13/143,531, filed as application No. PCT/EP2009/050233 on Jan. 9, 2009, now Pat. No. 8,664,366.

(51) Int. Cl.
| C07K 14/00 | (2006.01) |
|---|---|
| C07K 7/06 | (2006.01) |
| C07K 16/00 | (2006.01) |
| C07K 14/525 | (2006.01) |
| C07K 14/47 | (2006.01) |
| C07K 14/705 | (2006.01) |
| C12N 15/62 | (2006.01) |

(52) U.S. Cl.
CPC ............... *C07K 14/525* (2013.01); *C07K 7/06* (2013.01); *C07K 14/00* (2013.01); *C07K 14/4726* (2013.01); *C07K 14/70575* (2013.01); *C07K 16/00* (2013.01); *C12N 15/62* (2013.01); *C07K 2319/00* (2013.01); *C07K 2319/21* (2013.01); *C07K 2319/22* (2013.01); *C07K 2319/70* (2013.01)

(58) Field of Classification Search
CPC ........ C07K 14/25; C07K 7/06; C07K 14/00; C07K 16/00
See application file for complete search history.

(56) References Cited

U.S. PATENT DOCUMENTS

| 7,300,774 | B1 * | 11/2007 | Kornbluth | ........ | C07K 14/70575 435/69.5 |
| 7,332,298 | B2 * | 2/2008 | Kornbluth | ........ | C07K 14/70575 435/320.1 |
| 8,383,774 | B2 * | 2/2013 | Hill | ........ | C07K 14/525 435/252.3 |
| 8,664,366 | B2 * | 3/2014 | Hill | ........ | C07K 14/4726 530/387.3 |
| 8,907,063 | B2 * | 12/2014 | Hill | ........ | C07K 14/525 435/320.1 |
| 9,212,211 | B2 * | 12/2015 | Hill | ........ | C07K 14/525 |
| 2004/0047873 | A1 | 3/2004 | Al-Shamkhani et al. | | |
| 2004/0197076 | A1 * | 10/2004 | Tseng | ........ | H04N 21/4383 386/213 |
| 2004/0197876 | A1 | 10/2004 | Tschopp et al. | | |
| 2004/0247563 | A1 | 12/2004 | Lynch et al. | | |
| 2009/0325867 | A1 | 12/2009 | Cohen et al. | | |
| 2010/0199364 | A1 | 8/2010 | Hill et al. | | |
| 2010/0322922 | A1 | 12/2010 | Martin-Villalba et al. | | |
| 2011/0111494 | A1 | 5/2011 | Hill et al. | | |

FOREIGN PATENT DOCUMENTS

| WO | WO 95/31540 | 11/1995 |
| WO | WO 97/01633 | 1/1997 |
| WO | WO 01/42298 | 6/2001 |
| WO | WO 02/090553 | 11/2002 |
| WO | WO 03/086301 | 10/2003 |
| WO | WO 2004/024925 | 3/2004 |
| WO | WO 2007/102690 | 9/2007 |
| WO | WO 2009/007120 | 1/2009 |

OTHER PUBLICATIONS

Crouch et al., (JBC 2006, 281:18008-18014).*
Crouch, et al.; "Protein Structure and Folding: Contributions of Phenylalanine 335 to Ligand Recognition by Human Surfactant Protein D: Ring Interactions with SP-D Ligands"; The Journal of Biological Chemistry; vol. 281, pp. 18008-18014 (2006).
Hakansson et al.; "Collectin Structure: a review [In Process Citation]"; Protein Science; vol. 9, pp. 1607-1617 (2000).
Haswell, et al.; "Analysis of the Oligomeric Requirement for Signaling by CD40 using Soluble Multimeric Forms of its Ligand, CD 154"; Eur. J. Immunol.; vol. 31, pp. 3094-3100 (2001).
Holler, N. et al.: "Two Adjacent Trimeric Fas Ligands Are Required for Fas Signaling and Formation of a Death-Inducing Signaling Complex", Molecular and Cellular Biology, American Society for Microbiology; vol. 23, No. 4, pp. 1428-1440 (Feb. 2003).
Hoppe, et al.: "A parallel three stranded a-helical bundle at the nucleation site of collagen triple-helix formation", FEBS Letters; vol. 344, pp. 191-195 (1994).
Kishore, et al.; "Surfactant Proteins SP-A and SP-D: Structure, Function and Receptors"; Molecular Immunology; vol. 43, pp. 1293-1315 (2006).
Kornbluth, et al.: "CD40L (CD154) fusion protein with pulmonary surfactant protein D as a prototype for soluble multimeric TNF superfamily ligand molecules", FASEB Journal, Fed. of American Soc. for Experimental Biology; vol. 14, No. 6 (Apr. 20, 2000).
Sano, et al.; "The Lung Colectins, SP-A and SP-D, Modulate Pulmonary Innate Immunity"; vol. 42, pp. 279-287 (2005).
Wu et al.; "Trimeric Coiled-Coil Domain of Human Pulmonary Surfactant Protein D Enhances Zinc-Binding Ability and Biologic Activity of Soluble TRAIL"; Molecular Immunology; vol. 46, pp. 2381-2388 (2009).

* cited by examiner

*Primary Examiner* — Cherie M Stanfield
(74) *Attorney, Agent, or Firm* — Perkins Coie LLP; Viola T. Kung

(57) ABSTRACT

The present invention refers to fusion proteins comprising a neck region and carbohydrate recognition domain of a collectin trimerization domain, a linker element and an effector polypeptide. Further the invention refers to a nucleic acid encoding the said fusion protein. The fusion proteins, the nucleic acid, and the cell are suitable as pharmaceutical composition or for therapeutic, diagnostic and/or research applications as described herein.

13 Claims, 38 Drawing Sheets

SEC of affinity purified CD95L-ASPD

Silver gel of SEC fractions A1-A11 from affinity purified CD95L-ASPD

Caspase activity on Jurkat cells induced by SEC fractions A1-A15 from affinity purified CD95L-ASPD

Cytotoxicity of CD95L-ASPD on WM35, HT1080 and HeLa cells

SEC of affinity purified LIGHT-ASPD

Binding of HVEM-Fc to immobilized LIGHT-ASPD

Western blot from HEK cells transiently transfected with TRAIL-constructs

Caspase activity in Jurkat T-cells

Size exclusion chromatography of TRAIL-ASPD

Cytotoxic activity of TRAIL-ASPD against human cancer cells

TRAIL-ASPD induced caspase activity in Jurkat

Cytotoxicity assay with TRAIL-ASPD or TRAIL-DSPD on HT1080 cells

Western blot from transiently transfected HEK cells transiently transfected with TRAIL-SPD-constructs or TRAIL-receptor selective SPD constructs.

TRAIL-Receptor selective ligands (TRAILR1mut and TRAILR2mut) immobilized on Streptactin plates, are differentially detected by TRAIL-Receptor 1-Fc or TRAIL-Receptor 2-Fc

A

B

C

D

Binding of TRAIL-Receptors to Receptor-selective "mutein" ligands

Size exclusion chromatography of affinity purified TRAILR1mut-ASPD

Silver stained SDS-PAGE of SEC fractions A1-A14 from affinity purified TRAILR1mut-ASPD

Figure 18

Caspase activity of SEC fractions A1-A14 from affinity purified TRAILR1mut-ASPD on Jurkat cells Size exclusion chromatography of affinity purified TRAILR2mut-ASPD Silver stained SDS-PAGE of SEC fractions A1-A14 from affinity purified TRAILR2mut-ASPD Jurkat Kill Assay Jurkat of SEC fractions A1-A14 from affinity purified TRAILR2mut-ASPD Cytotoxic activity of TRAIL-ASPD, TRAILR1mut-ASPD and TRAILR2mut-ASPD on human cancer cells.

Receptor selective TRAIL-SPD proteins are highly souble

SEC of affinity purified TRAIL-ASPD_F335A

Silver stained SDS-PAGE of SEC fractions A1-A13

Cytotoxic effect of TRAIL-ASPD_F335A on human cancer cells

SEC of affinity purified TRAIL-ASPD_F335D

Silver stained SDS-PAGE of SEC from affinity purified TRAIL-ASPD_F335D

Cytotoxic effect TRAIL-SPD_F335D on human cancer cells

Binding of TRAIL-ASPD fusion protein to carbohydrates

Pharmacokinetics of TRAIL-ASPD (A) or TRAIL-ASPD_F335 D (B) Fusion Proteins

Caspase activity in primary human hepatocytes

Western Blot of supernatants from HEK293 cells transiently transfected with trimerized APRIL constructs TACI-Fc binds to APRIL-ASPD Schematic drawing of the domain organization of the collectin SP-D. The collagen and neck regions trimerize collectins and the N-terminus further oligomerizes trimers into tetramers or hexamers of trimers. The CRD mediates binding to carbohydrates and is also involved in trimerization.

Schematic picture representing the general structure of TNF-SF
proteins. "■ ■ ■" designates cell membrane, N-terminus located within the cell, 1. anti-parallel β-fold of receptor-binding domain (RBD), 2. interface of RBD and cell membrane, 3. protease cleavage site.

Schematic picture representing the structure of the native TNF-SF trimer. Cylindric structures (1) represent RBDs, N-termini (2) forming the stalk and connecting the RBD with the cell membrane.

Figure 38

Schematic picture representing the modification introduced to minimize the TNF-SF-RBD. The N-terminal stalk is deleted.

1. anti-parallel β-fold of receptor-binding domain (RBD), 2. interface of RBD and cell membrane Silver gel of affinity purified Sp-sc006-ASPD-St.

Size exclusion chromatography of affinity purified Sp-sc006-ASPD-St.

SEQUENCE LISTING

<160> NUMBER OF SEQ ID NOS: 63

<210> SEQ ID NO 1
<211> LENGTH: 205
<212> TYPE: PRT
<213> ORGANISM: Homo sapiens
<220> FEATURE:
<221> NAME/KEY: DOMAIN
<222> LOCATION: (59)..(205)
<223> OTHER INFORMATION: Preferred receptor binding domain -continued
<220> FEATURE:
<221> NAME/KEY: DOMAIN
<222> LOCATION: (60)..(205)
<223> OTHER INFORMATION: Preferred receptor binding domain
<300> PUBLICATION INFORMATION:
<308> DATABASE ACCESSION NUMBER: NP_000586
<309> DATABASE ENTRY DATE: 2009-01-04
<313> RELEVANT RESIDUES IN SEQ ID NO: (1)..(205)

<400> SEQUENCE: 1

Met Thr Pro Pro Glu Arg Leu Phe Leu Pro Arg Val Cys Gly Thr Thr
1 5 10 15

Leu His Leu Leu Leu Leu Gly Leu Leu Leu Val Leu Leu Pro Gly Ala
20 25 30

Gln Gly Leu Pro Gly Val Gly Leu Thr Pro Ser Ala Ala Gln Thr Ala
35 40 45

Arg Gln His Pro Lys Met His Leu Ala His Ser Thr Leu Lys Pro Ala
50 55 60

Ala His Leu Ile Gly Asp Pro Ser Lys Gln Asn Ser Leu Leu Trp Arg
65 70 75 80

Ala Asn Thr Asp Arg Ala Phe Leu Gln Asp Gly Phe Ser Leu Ser Asn
85 90 95

Asn Ser Leu Leu Val Pro Thr Ser Gly Ile Tyr Phe Val Tyr Ser Gln
100 105 110

Val Val Phe Ser Gly Lys Ala Tyr Ser Pro Lys Ala Thr Ser Ser Pro
115 120 125

Leu Tyr Leu Ala His Glu Val Gln Leu Phe Ser Ser Gln Tyr Pro Phe
130 135 140

His Val Pro Leu Leu Ser Ser Gln Lys Met Val Tyr Pro Gly Leu Gln
145 150 155 160

Glu Pro Trp Leu His Ser Met Tyr His Gly Ala Ala Phe Gln Leu Thr
165 170 175

Gln Gly Asp Gln Leu Ser Thr His Thr Asp Gly Ile Pro His Leu Val
180 185 190

Leu Ser Pro Ser Thr Val Phe Phe Gly Ala Phe Ala Leu
195 200 205

<210> SEQ ID NO 2
<211> LENGTH: 233
<212> TYPE: PRT
<213> ORGANISM: Homo sapiens
<220> FEATURE:
<221> NAME/KEY: DOMAIN
<222> LOCATION: (86)..(233)
<223> OTHER INFORMATION: Preferred receptor binding domain
<300> PUBLICATION INFORMATION:
<308> DATABASE ACCESSION NUMBER: NP_000585
<309> DATABASE ENTRY DATE: 2008-12-28
<313> RELEVANT RESIDUES IN SEQ ID NO: (1)..(233)

<400> SEQUENCE: 2

Met Ser Thr Glu Ser Met Ile Arg Asp Val Glu Leu Ala Glu Glu Ala
1 5 10 15

Leu Pro Lys Lys Thr Gly Gly Pro Gln Gly Ser Arg Arg Cys Leu Phe
20 25 30

Leu Ser Leu Phe Ser Phe Leu Ile Val Ala Gly Ala Thr Thr Leu Phe
35 40 45

Cys Leu Leu His Phe Gly Val Ile Gly Pro Gln Arg Glu Glu Phe Pro
50 55 60

Arg Asp Leu Ser Leu Ile Ser Pro Leu Ala Gln Ala Val Arg Ser Ser

```
                65                  70                  75                  80
Ser Arg Thr Pro Ser Asp Lys Pro Val Ala His Val Val Ala Asn Pro
                        85                  90                  95

Gln Ala Glu Gly Gln Leu Gln Trp Leu Asn Arg Arg Ala Asn Ala Leu
                100                 105                 110

Leu Ala Asn Gly Val Glu Leu Arg Asp Asn Gln Leu Val Val Pro Ser
                115                 120                 125

Glu Gly Leu Tyr Leu Ile Tyr Ser Gln Val Leu Phe Lys Gly Gln Gly
                130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
                180                 185                 190

Pro Ile Tyr Leu Gly Gly Val Phe Gln Leu Glu Lys Gly Asp Arg Leu
                195                 200                 205

Ser Ala Glu Ile Asn Arg Pro Asp Tyr Leu Asp Phe Ala Glu Ser Gly
                210                 215                 220

Gln Val Tyr Phe Gly Ile Ile Ala Leu
225                 230

<210> SEQ ID NO 3
<211> LENGTH: 244
<212> TYPE: PRT
<213> ORGANISM: Homo sapiens
<220> FEATURE:
<221> NAME/KEY: DOMAIN
<222> LOCATION: (82)..(244)
<223> OTHER INFORMATION: Preferred receptor binding domain
<220> FEATURE:
<221> NAME/KEY: DOMAIN
<222> LOCATION: (86)..(244)
<223> OTHER INFORMATION: Preferred receptor binding domain
<300> PUBLICATION INFORMATION:
<308> DATABASE ACCESSION NUMBER: NP_002332
<309> DATABASE ENTRY DATE: 2008-12-21
<313> RELEVANT RESIDUES IN SEQ ID NO: (1)..(244)

<400> SEQUENCE: 3

Met Gly Ala Leu Gly Leu Glu Gly Arg Gly Gly Arg Leu Gln Gly Arg
1               5                   10                  15

Gly Ser Leu Leu Leu Ala Val Ala Gly Ala Thr Ser Leu Val Thr Leu
                20                  25                  30

Leu Leu Ala Val Pro Ile Thr Val Leu Ala Val Leu Ala Leu Val Pro
                35                  40                  45

Gln Asp Gln Gly Gly Leu Val Thr Glu Thr Ala Asp Pro Gly Ala Gln
                50                  55                  60

Ala Gln Gln Gly Leu Gly Phe Gln Lys Leu Pro Glu Glu Glu Pro Glu
65                  70                  75                  80

Thr Asp Leu Ser Pro Gly Leu Pro Ala Ala His Leu Ile Gly Ala Pro
                85                  90                  95

Leu Lys Gly Gln Gly Leu Gly Trp Glu Thr Thr Lys Glu Gln Ala Phe
                100                 105                 110

Leu Thr Ser Gly Thr Gln Phe Ser Asp Ala Glu Gly Leu Ala Leu Pro
                115                 120                 125

Gln Asp Gly Leu Tyr Tyr Leu Tyr Cys Leu Val Gly Tyr Arg Gly Arg
                130                 135                 140
```

```
Ala Pro Pro Gly Gly Gly Asp Pro Gln Gly Arg Ser Val Thr Leu Arg
145                 150                 155                 160

Ser Ser Leu Tyr Arg Ala Gly Gly Ala Tyr Gly Pro Gly Thr Pro Glu
            165                 170                 175

Leu Leu Leu Glu Gly Ala Glu Thr Val Thr Pro Val Leu Asp Pro Ala
            180                 185                 190

Arg Arg Gln Gly Tyr Gly Pro Leu Trp Tyr Thr Ser Val Gly Phe Gly
            195                 200                 205

Gly Leu Val Gln Leu Arg Arg Gly Glu Arg Val Tyr Val Asn Ile Ser
        210                 215                 220

His Pro Asp Met Val Asp Phe Ala Arg Gly Lys Thr Phe Phe Gly Ala
225                 230                 235                 240

Val Met Val Gly

<210> SEQ ID NO 4
<211> LENGTH: 183
<212> TYPE: PRT
<213> ORGANISM: Homo sapiens
<220> FEATURE:
<221> NAME/KEY: DOMAIN
<222> LOCATION: (52)..(183)
<220> FEATURE:
<221> NAME/KEY: DOMAIN
<222> LOCATION: (55)..(183)
<300> PUBLICATION INFORMATION:
<308> DATABASE ACCESSION NUMBER: NP_003317
<309> DATABASE ENTRY DATE: 2008-12-21
<313> RELEVANT RESIDUES IN SEQ ID NO: (1)..(183)

<400> SEQUENCE: 4

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

<210> SEQ ID NO 5
<211> LENGTH: 261
<212> TYPE: PRT
<213> ORGANISM: Homo sapiens
```

<220> FEATURE:
<221> NAME/KEY: DOMAIN
<222> LOCATION: (112)..(261)
<223> OTHER INFORMATION: Preferred receptor binding domain
<220> FEATURE:
<221> NAME/KEY: DOMAIN
<222> LOCATION: (117)..(261)
<223> OTHER INFORMATION: Preferred receptor binding domain
<300> PUBLICATION INFORMATION:
<308> DATABASE ACCESSION NUMBER: NP_000065
<309> DATABASE ENTRY DATE: 2008-12-28
<313> RELEVANT RESIDUES IN SEQ ID NO: (1)..(261)

<400> SEQUENCE: 5

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 6
<211> LENGTH: 281
<212> TYPE: PRT
<213> ORGANISM: Homo sapiens
<220> FEATURE:
<221> NAME/KEY: DOMAIN
<222> LOCATION: (142)..(281)
<223> OTHER INFORMATION: Preferred receptor binding domain
<220> FEATURE:
<221> NAME/KEY: DOMAIN
<222> LOCATION: (144)..(281)
<223> OTHER INFORMATION: Preferred receptor binding domain <300> PUBLICATION INFORMATION:
<308> DATABASE ACCESSION NUMBER: NP_000630
<309> DATABASE ENTRY DATE: 2008-12-21
<313> RELEVANT RESIDUES IN SEQ ID NO: (1)..(281)

<400> SEQUENCE: 6

Met Gln Gln Pro Phe Asn Tyr Pro Tyr Pro Gln Ile Tyr Trp Val Asp
1               5                   10                  15

Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Arg Pro Pro Pro Pro
        35                  40                  45

Pro Pro Pro Pro Pro Leu Pro Pro Pro Pro Pro Pro Pro Pro Leu Pro
    50                  55                  60

Pro Leu Pro Leu Pro Pro Leu Lys Lys Arg Gly Asn His Ser Thr Gly
65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
        115                 120                 125

Lys Gln Ile Gly His Pro Ser Pro Pro Pro Glu Lys Lys Glu Leu Arg
    130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
        195                 200                 205

His Lys Val Tyr Met Arg Asn Ser Lys Tyr Pro Gln Asp Leu Val Met
    210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
            260                 265                 270

Gln Thr Phe Phe Gly Leu Tyr Lys Leu
        275                 280

<210> SEQ ID NO 7
<211> LENGTH: 193
<212> TYPE: PRT
<213> ORGANISM: Homo sapiens
<220> FEATURE:
<221> NAME/KEY: DOMAIN
<222> LOCATION: (51)..(193)
<223> OTHER INFORMATION: Preferred receptor binding domain
<220> FEATURE:
<221> NAME/KEY: DOMAIN
<222> LOCATION: (56)..(193)
<223> OTHER INFORMATION: Preferred receptor binding domain
<300> PUBLICATION INFORMATION:
<308> DATABASE ACCESSION NUMBER: NP_001243
<309> DATABASE ENTRY DATE: 2008-12-14
<313> RELEVANT RESIDUES IN SEQ ID NO: (1)..(193)

<400> SEQUENCE: 7

| Met | Pro | Glu | Glu | Gly | Ser | Gly | Cys | Ser | Val | Arg | Arg | Pro | Tyr | Gly |
| 1 | | | | 5 | | | | | 10 | | | | | 15 |

| Cys | Val | Leu | Arg | Ala | Ala | Leu | Val | Pro | Leu | Val | Ala | Gly | Leu | Val | Ile |
| | | | 20 | | | | | 25 | | | | | 30 | | |

| Cys | Leu | Val | Val | Cys | Ile | Gln | Arg | Phe | Ala | Gln | Ala | Gln | Gln | Gln | Leu |
| | | 35 | | | | | 40 | | | | | 45 | | | |

| Pro | Leu | Glu | Ser | Leu | Gly | Trp | Asp | Val | Ala | Glu | Leu | Gln | Leu | Asn | His |
| | 50 | | | | | 55 | | | | | 60 | | | | |

| Thr | Gly | Pro | Gln | Gln | Asp | Pro | Arg | Leu | Tyr | Trp | Gln | Gly | Gly | Pro | Ala |
| 65 | | | | | 70 | | | | | 75 | | | | | 80 |

| Leu | Gly | Arg | Ser | Phe | Leu | His | Gly | Pro | Glu | Leu | Asp | Lys | Gly | Gln | Leu |
| | | | | 85 | | | | | 90 | | | | | 95 | |

| Arg | Ile | His | Arg | Asp | Gly | Ile | Tyr | Met | Val | His | Ile | Gln | Val | Thr | Leu |
| | | | 100 | | | | | 105 | | | | | 110 | | |

| Ala | Ile | Cys | Ser | Ser | Thr | Thr | Ala | Ser | Arg | His | His | Pro | Thr | Thr | Leu |
| | | 115 | | | | | 120 | | | | | 125 | | | |

| Ala | Val | Gly | Ile | Cys | Ser | Pro | Ala | Ser | Arg | Ser | Ile | Ser | Leu | Leu | Arg |
| | 130 | | | | | 135 | | | | | 140 | | | | |

| Leu | Ser | Phe | His | Gln | Gly | Cys | Thr | Ile | Ala | Ser | Gln | Arg | Leu | Thr | Pro |
| 145 | | | | | 150 | | | | | 155 | | | | | 160 |

| Leu | Ala | Arg | Gly | Asp | Thr | Leu | Cys | Thr | Asn | Leu | Thr | Gly | Thr | Leu | Leu |
| | | | | 165 | | | | | 170 | | | | | 175 | |

| Pro | Ser | Arg | Asn | Thr | Asp | Glu | Thr | Phe | Phe | Gly | Val | Gln | Trp | Val | Arg |
| | | | 180 | | | | | 185 | | | | | 190 | | |

Pro

<210> SEQ ID NO 8
<211> LENGTH: 234
<212> TYPE: PRT
<213> ORGANISM: Homo sapiens
<220> FEATURE:
<221> NAME/KEY: DOMAIN
<222> LOCATION: (97)..(234)
<223> OTHER INFORMATION: Preferred receptor binding domain
<220> FEATURE:
<221> NAME/KEY: DOMAIN
<222> LOCATION: (98)..(234)
<223> OTHER INFORMATION: Preferred receptor binding domain
<220> FEATURE:
<221> NAME/KEY: DOMAIN
<222> LOCATION: (102)..(234)
<223> OTHER INFORMATION: Preferred receptor binding domain
<300> PUBLICATION INFORMATION:
<308> DATABASE ACCESSION NUMBER: NP_001235
<309> DATABASE ENTRY DATE: 2008-09-28
<313> RELEVANT RESIDUES IN SEQ ID NO: (1)..(234)

<400> SEQUENCE: 8

| Met | Asp | Pro | Gly | Leu | Gln | Gln | Ala | Leu | Asn | Gly | Met | Ala | Pro | Pro | Gly |
| 1 | | | | 5 | | | | | 10 | | | | | 15 | |

| Asp | Thr | Ala | Met | His | Val | Pro | Ala | Gly | Ser | Val | Ala | Ser | His | Leu | Gly |
| | | | 20 | | | | | 25 | | | | | 30 | | |

| Thr | Thr | Ser | Arg | Ser | Tyr | Phe | Tyr | Leu | Thr | Thr | Ala | Thr | Leu | Ala | Leu |
| | | 35 | | | | | 40 | | | | | 45 | | | |

| Cys | Leu | Val | Phe | Thr | Val | Ala | Thr | Ile | Met | Val | Leu | Val | Val | Gln | Arg |
| | 50 | | | | | 55 | | | | | 60 | | | | |

| Thr | Asp | Ser | Ile | Pro | Asn | Ser | Pro | Asp | Asn | Val | Pro | Leu | Lys | Gly | Gly |
| 65 | | | | | 70 | | | | | 75 | | | | | 80 |

```
Asn Cys Ser Glu Asp Leu Leu Cys Ile Leu Lys Arg Ala Pro Phe Lys
             85                  90                  95

Lys Ser Trp Ala Tyr Leu Gln Val Ala Lys His Leu Asn Lys Thr Lys
            100                 105                 110

Leu Ser Trp Asn Lys Asp Gly Ile Leu His Gly Val Arg Tyr Gln Asp
            115                 120                 125

Gly Asn Leu Val Ile Gln Phe Pro Gly Leu Tyr Phe Ile Ile Cys Gln
130                 135                 140

Leu Gln Phe Leu Val Gln Cys Pro Asn Asn Ser Val Asp Leu Lys Leu
145                 150                 155                 160

Glu Leu Leu Ile Asn Lys His Ile Lys Lys Gln Ala Leu Val Thr Val
                165                 170                 175

Cys Glu Ser Gly Met Gln Thr Lys His Val Tyr Gln Asn Leu Ser Gln
            180                 185                 190

Phe Leu Leu Asp Tyr Leu Gln Val Asn Thr Thr Ile Ser Val Asn Val
            195                 200                 205

Asp Thr Phe Gln Tyr Ile Asp Thr Ser Thr Phe Pro Leu Glu Asn Val
210                 215                 220

Leu Ser Ile Phe Leu Tyr Ser Asn Ser Asp
225                 230

<210> SEQ ID NO 9
<211> LENGTH: 254
<212> TYPE: PRT
<213> ORGANISM: Homo sapiens
<220> FEATURE:
<221> NAME/KEY: DOMAIN
<222> LOCATION: (86)..(254)
<223> OTHER INFORMATION: Preferred receptor binding domain
<300> PUBLICATION INFORMATION:
<308> DATABASE ACCESSION NUMBER: NP_003802
<309> DATABASE ENTRY DATE: 2008-10-24
<313> RELEVANT RESIDUES IN SEQ ID NO: (1)..(254)

<400> SEQUENCE: 9

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
            20                  25                  30

Ala Gly Leu Leu Leu Leu Leu Leu Ala Ala Ala Cys Ala Val Phe
            35                  40                  45

Leu Ala Cys Pro Trp Ala Val Ser Gly Ala Arg Ala Ser Pro Gly Ser
50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
            115                 120                 125

Asp Thr Lys Glu Leu Val Val Ala Lys Ala Gly Val Tyr Tyr Val Phe
130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175
```

-continued

```
Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
    210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250
```

<210> SEQ ID NO 10
<211> LENGTH: 281
<212> TYPE: PRT
<213> ORGANISM: Homo sapiens
<220> FEATURE:
<221> NAME/KEY: DOMAIN
<222> LOCATION: (95)..(281)
<223> OTHER INFORMATION: Preferred receptor binding domain
<220> FEATURE:
<221> NAME/KEY: DOMAIN
<222> LOCATION: (116)..(281)
<223> OTHER INFORMATION: Preferred receptor binding domain
<220> FEATURE:
<221> NAME/KEY: DOMAIN
<222> LOCATION: (117)..(281)
<223> OTHER INFORMATION: Preferred receptor binding domain
<220> FEATURE:
<221> NAME/KEY: DOMAIN
<222> LOCATION: (118)..(281)
<223> OTHER INFORMATION: Preferred receptor binding domain
<220> FEATURE:
<221> NAME/KEY: DOMAIN
<222> LOCATION: (119)..(281)
<223> OTHER INFORMATION: Preferred receptor binding domain
<220> FEATURE:
<221> NAME/KEY: DOMAIN
<222> LOCATION: (120)..(281)
<223> OTHER INFORMATION: Preferred receptor binding domain
<300> PUBLICATION INFORMATION:
<308> DATABASE ACCESSION NUMBER: NP_003801
<309> DATABASE ENTRY DATE: 2008-12-28
<313> RELEVANT RESIDUES IN SEQ ID NO: (1)..(281)

<400> SEQUENCE: 10

```
Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
```

His Ser Phe Leu Ser Asn Leu His Leu Arg Asn Gly Glu Leu Val Ile
145                 150                 155                 160

His Glu Lys Gly Phe Tyr Tyr Ile Tyr Ser Gln Thr Tyr Phe Arg Phe
            165                 170                 175

Gln Glu Glu Ile Lys Glu Asn Thr Lys Asn Asp Lys Gln Met Val Gln
        180                 185                 190

Tyr Ile Tyr Lys Tyr Thr Ser Tyr Pro Asp Pro Ile Leu Leu Met Lys
    195                 200                 205

Ser Ala Arg Asn Ser Cys Trp Ser Lys Asp Ala Glu Tyr Gly Leu Tyr
210                 215                 220

Ser Ile Tyr Gln Gly Gly Ile Phe Glu Leu Lys Glu Asn Asp Arg Ile
225                 230                 235                 240

Phe Val Ser Val Thr Asn Glu His Leu Ile Asp Met Asp His Glu Ala
            245                 250                 255

Ser Phe Phe Gly Ala Phe Leu Val Gly
        260                 265

<210> SEQ ID NO 11
<211> LENGTH: 317
<212> TYPE: PRT
<213> ORGANISM: Homo sapiens
<220> FEATURE:
<221> NAME/KEY: DOMAIN
<222> LOCATION: (161)..(317)
<223> OTHER INFORMATION: Preferred receptor binding domain
<300> PUBLICATION INFORMATION:
<308> DATABASE ACCESSION NUMBER: NP_003692
<309> DATABASE ENTRY DATE: 2008-12-21
<313> RELEVANT RESIDUES IN SEQ ID NO: (1)..(317)

<400> SEQUENCE: 11

Met Arg Arg Ala Ser Arg Asp Tyr Thr Lys Tyr Leu Arg Gly Ser Glu
1               5                   10                  15

Glu Met Gly Gly Gly Pro Gly Ala Pro His Glu Gly Pro Leu His Ala
            20                  25                  30

Pro Pro Pro Pro Ala Pro His Gln Pro Pro Ala Ala Ser Arg Ser Met
        35                  40                  45

Phe Val Ala Leu Leu Gly Leu Gly Leu Gly Gln Val Val Cys Ser Val
    50                  55                  60

Ala Leu Phe Phe Tyr Phe Arg Ala Gln Met Asp Pro Asn Arg Ile Ser
65                  70                  75                  80

Glu Asp Gly Thr His Cys Ile Tyr Arg Ile Leu Arg Leu His Glu Asn
            85                  90                  95

Ala Asp Phe Gln Asp Thr Thr Leu Glu Ser Gln Asp Thr Lys Leu Ile
        100                 105                 110

Pro Asp Ser Cys Arg Arg Ile Lys Gln Ala Phe Gln Gly Ala Val Gln
    115                 120                 125

Lys Glu Leu Gln His Ile Val Gly Ser Gln His Ile Arg Ala Glu Lys
130                 135                 140

Ala Met Val Asp Gly Ser Trp Leu Asp Leu Ala Lys Arg Ser Lys Leu
145                 150                 155                 160

Glu Ala Gln Pro Phe Ala His Leu Thr Ile Asn Ala Thr Asp Ile Pro
            165                 170                 175

Ser Gly Ser His Lys Val Ser Leu Ser Ser Trp Tyr His Asp Arg Gly
        180                 185                 190

Trp Ala Lys Ile Ser Asn Met Thr Phe Ser Asn Gly Lys Leu Ile Val

```
                    195                 200                 205
Asn Gln Asp Gly Phe Tyr Tyr Leu Tyr Ala Asn Ile Cys Phe Arg His
        210                 215                 220

His Glu Thr Ser Gly Asp Leu Ala Thr Glu Tyr Leu Gln Leu Met Val
225                 230                 235                 240

Tyr Val Thr Lys Thr Ser Ile Lys Ile Pro Ser Ser His Thr Leu Met
                    245                 250                 255

Lys Gly Gly Ser Thr Lys Tyr Trp Ser Gly Asn Ser Glu Phe His Phe
                260                 265                 270

Tyr Ser Ile Asn Val Gly Gly Phe Phe Lys Leu Arg Ser Gly Glu Glu
                275                 280                 285

Ile Ser Ile Glu Val Ser Asn Pro Ser Leu Leu Asp Pro Asp Gln Asp
290                 295                 300

Ala Thr Tyr Phe Gly Ala Phe Lys Val Arg Asp Ile Asp
305                 310                 315

<210> SEQ ID NO 12
<211> LENGTH: 249
<212> TYPE: PRT
<213> ORGANISM: Homo sapiens
<220> FEATURE:
<221> NAME/KEY: DOMAIN
<222> LOCATION: (103)..(249)
<223> OTHER INFORMATION: Preferred receptor binding domain
<220> FEATURE:
<221> NAME/KEY: DOMAIN
<222> LOCATION: (104)..(249)
<223> OTHER INFORMATION: Preferred receptor binding domain
<220> FEATURE:
<221> NAME/KEY: DOMAIN
<222> LOCATION: (105)..(249)
<223> OTHER INFORMATION: Preferred receptor binding domain
<300> PUBLICATION INFORMATION:
<308> DATABASE ACCESSION NUMBER: NP_003800
<309> DATABASE ENTRY DATE: 2008-11-05
<313> RELEVANT RESIDUES IN SEQ ID NO: (1)..(249)

<400> SEQUENCE: 12

Met Ala Ala Arg Arg Ser Gln Arg Arg Gly Arg Gly Glu Pro
1               5                   10                  15

Gly Thr Ala Leu Leu Val Pro Leu Ala Leu Gly Leu Gly Leu Ala Leu
                20                  25                  30

Ala Cys Leu Gly Leu Leu Leu Ala Val Val Ser Leu Gly Ser Arg Ala
                35                  40                  45

Ser Leu Ser Ala Gln Glu Pro Ala Gln Glu Glu Leu Val Ala Glu Glu
            50                  55                  60

Asp Gln Asp Pro Ser Glu Leu Asn Pro Gln Thr Glu Glu Ser Gln Asp
65                  70                  75                  80

Pro Ala Pro Phe Leu Asn Arg Leu Val Arg Pro Arg Arg Ser Ala Pro
                85                  90                  95

Lys Gly Arg Lys Thr Arg Ala Arg Arg Ala Ile Ala Ala His Tyr Glu
                100                 105                 110

Val His Pro Arg Pro Gly Gln Asp Gly Ala Gln Ala Gly Val Asp Gly
            115                 120                 125

Thr Val Ser Gly Trp Glu Glu Ala Arg Ile Asn Ser Ser Ser Pro Leu
            130                 135                 140

Arg Tyr Asn Arg Gln Ile Gly Glu Phe Ile Val Thr Arg Ala Gly Leu
145                 150                 155                 160

Tyr Tyr Leu Tyr Cys Gln Val His Phe Asp Glu Gly Lys Ala Val Tyr
                165                 170                 175
```

```
Leu Lys Leu Asp Leu Leu Val Asp Gly Val Leu Ala Leu Arg Cys Leu
            180                 185                 190

Glu Glu Phe Ser Ala Thr Ala Ala Ser Ser Leu Gly Pro Gln Leu Arg
        195                 200                 205

Leu Cys Gln Val Ser Gly Leu Leu Ala Leu Arg Pro Gly Ser Ser Leu
210                 215                 220

Arg Ile Arg Thr Leu Pro Trp Ala His Leu Lys Ala Ala Pro Phe Leu
225                 230                 235                 240

Thr Tyr Phe Gly Leu Phe Gln Val His
                245

<210> SEQ ID NO 13
<211> LENGTH: 247
<212> TYPE: PRT
<213> ORGANISM: Homo sapiens
<220> FEATURE:
<221> NAME/KEY: DOMAIN
<222> LOCATION: (112)..(247)
<223> OTHER INFORMATION: Preferred receptor binding domain
<220> FEATURE:
<221> NAME/KEY: DOMAIN
<222> LOCATION: (113)..(247)
<223> OTHER INFORMATION: Preferred receptor binding domain
<300> PUBLICATION INFORMATION:
<308> DATABASE ACCESSION NUMBER: NP_742085
<309> DATABASE ENTRY DATE: 2008-11-05
<313> RELEVANT RESIDUES IN SEQ ID NO: (1)..(247)

<400> SEQUENCE: 13

Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
    50                  55                  60

Leu Gln Gly Thr Gly Gly Pro Ser Gln Asn Gly Glu Gly Tyr Pro Trp
65                  70                  75                  80

Gln Ser Leu Pro Glu Gln Ser Ser Asp Ala Leu Glu Ala Trp Glu Asn
                85                  90                  95

Gly Glu Arg Ser Arg Lys Arg Arg Ala Val Leu Thr Gln Lys Gln Lys
            100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
    210                 215                 220

Leu Ser Val Ile Ile Pro Arg Ala Arg Ala Lys Leu Asn Leu Ser Pro
```

```
                225                 230                 235                 240
His Gly Thr Phe Leu Gly Leu
                245

<210> SEQ ID NO 14
<211> LENGTH: 250
<212> TYPE: PRT
<213> ORGANISM: Homo sapiens
<220> FEATURE:
<221> NAME/KEY: DOMAIN
<222> LOCATION: (112)..(250)
<223> OTHER INFORMATION: Preferred receptor binding domain
<220> FEATURE:
<221> NAME/KEY: DOMAIN
<222> LOCATION: (113)..(250)
<223> OTHER INFORMATION: Preferred receptor binding domain
<300> PUBLICATION INFORMATION:
<308> DATABASE ACCESSION NUMBER: NP_003799
<309> DATABASE ENTRY DATE: 2008-11-05
<313> RELEVANT RESIDUES IN SEQ ID NO: (1)..(250)

<400> SEQUENCE: 14

Met Pro Ala Ser Ser Pro Phe Leu Leu Ala Pro Lys Gly Pro Pro Gly
  1               5                  10                  15

Asn Met Gly Gly Pro Val Arg Glu Pro Ala Leu Ser Val Ala Leu Trp
             20                  25                  30

Leu Ser Trp Gly Ala Ala Leu Gly Ala Val Ala Cys Ala Met Ala Leu
         35                  40                  45

Leu Thr Gln Gln Thr Glu Leu Gln Ser Leu Arg Arg Glu Val Ser Arg
     50                  55                  60

Leu Gln Gly Thr Gly Gly Pro Ser Gln Asn Gly Glu Gly Tyr Pro Trp
 65                  70                  75                  80

Gln Ser Leu Pro Glu Gln Ser Ser Asp Ala Leu Glu Ala Trp Glu Asn
                 85                  90                  95

Gly Glu Arg Ser Arg Lys Arg Arg Ala Val Leu Thr Gln Lys Gln Lys
            100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
    130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
    210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
                245                 250

<210> SEQ ID NO 15
<211> LENGTH: 285
<212> TYPE: PRT
<213> ORGANISM: Homo sapiens
<220> FEATURE:
```

<221> NAME/KEY: DOMAIN
<222> LOCATION: (140)..(285)
<223> OTHER INFORMATION: Preferred receptor binding domain
<300> PUBLICATION INFORMATION:
<308> DATABASE ACCESSION NUMBER: NP_006564
<309> DATABASE ENTRY DATE: 2008-02-11
<313> RELEVANT RESIDUES IN SEQ ID NO: (1)..(285)

<400> SEQUENCE: 15

```
Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
        195                 200                 205

Gly His Leu Ile Gln Arg Lys Lys Val His Val Phe Gly Asp Glu Leu
210                 215                 220

Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
                245                 250                 255

Asp Glu Leu Gln Leu Ala Ile Pro Arg Glu Asn Ala Gln Ile Ser Leu
            260                 265                 270

Asp Gly Asp Val Thr Phe Phe Gly Ala Leu Lys Leu Leu
        275                 280                 285
```

<210> SEQ ID NO 16
<211> LENGTH: 240
<212> TYPE: PRT
<213> ORGANISM: Homo sapiens
<220> FEATURE:
<221> NAME/KEY: DOMAIN
<222> LOCATION: (91)..(240)
<223> OTHER INFORMATION: Preferred receptor binding domain
<300> PUBLICATION INFORMATION:
<308> DATABASE ACCESSION NUMBER: NP_003798
<309> DATABASE ENTRY DATE: 2008-12-21
<313> RELEVANT RESIDUES IN SEQ ID NO: (1)..(240)

<400> SEQUENCE: 16

-continued

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Leu Met Gly
        35                  40                  45

Ala Gly Leu Ala Val Gln Gly Trp Phe Leu Leu Gln Leu His Trp Arg
50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Lys Val Val Val Arg Val Leu Asp Glu Arg Leu
210                 215                 220

Val Arg Leu Arg Asp Gly Thr Arg Ser Tyr Phe Gly Ala Phe Met Val
225                 230                 235                 240

<210> SEQ ID NO 17
<211> LENGTH: 251
<212> TYPE: PRT
<213> ORGANISM: Homo sapiens
<220> FEATURE:
<221> NAME/KEY: DOMAIN
<222> LOCATION: (91)..(251)
<223> OTHER INFORMATION: Preferred receptor binding domain
<220> FEATURE:
<221> NAME/KEY: DOMAIN
<222> LOCATION: (93)..(251)
<223> OTHER INFORMATION: Preferred receptor binding domain
<300> PUBLICATION INFORMATION:
<308> DATABASE ACCESSION NUMBER: NP_005109
<309> DATABASE ENTRY DATE: 2008-12-21
<313> RELEVANT RESIDUES IN SEQ ID NO: (1)..(251)

<400> SEQUENCE: 17

```
Met Ala Glu Asp Leu Gly Leu Ser Phe Gly Glu Thr Ala Ser Val Glu
1               5                   10                  15

Met Leu Pro Glu His Gly Ser Cys Arg Pro Lys Ala Arg Ser Ser Ser
            20                  25                  30

Ala Arg Trp Ala Leu Thr Cys Cys Leu Val Leu Leu Pro Phe Leu Ala
        35                  40                  45

Gly Leu Thr Thr Tyr Leu Leu Val Ser Gln Leu Arg Ala Gln Gly Glu
    50                  55                  60

Ala Cys Val Gln Phe Gln Ala Leu Lys Gly Gln Glu Phe Ala Pro Ser
```

```
                65                  70                  75                  80
His Gln Gln Val Tyr Ala Pro Leu Arg Ala Asp Gly Asp Lys Pro Arg
                    85                  90                  95

Ala His Leu Thr Val Val Arg Gln Thr Pro Thr Gln His Phe Lys Asn
                    100                 105                 110

Gln Phe Pro Ala Leu His Trp Glu His Glu Leu Gly Leu Ala Phe Thr
                    115                 120                 125

Lys Asn Arg Met Asn Tyr Thr Asn Lys Phe Leu Leu Ile Pro Glu Ser
130                 135                 140

Gly Asp Tyr Phe Ile Tyr Ser Gln Val Thr Phe Arg Gly Met Thr Ser
145                 150                 155                 160

Glu Cys Ser Glu Ile Arg Gln Ala Gly Arg Pro Asn Lys Pro Asp Ser
                    165                 170                 175

Ile Thr Val Val Ile Thr Lys Val Thr Asp Ser Tyr Pro Glu Pro Thr
                    180                 185                 190

Gln Leu Leu Met Gly Thr Lys Ser Val Cys Glu Val Gly Ser Asn Trp
                    195                 200                 205

Phe Gln Pro Ile Tyr Leu Gly Ala Met Phe Ser Leu Gln Glu Gly Asp
                    210                 215                 220

Lys Leu Met Val Asn Val Ser Asp Ile Ser Leu Val Asp Tyr Thr Lys
225                 230                 235                 240

Glu Asp Lys Thr Phe Phe Gly Ala Phe Leu Leu
                    245                 250

<210> SEQ ID NO 18
<211> LENGTH: 199
<212> TYPE: PRT
<213> ORGANISM: Homo sapiens
<220> FEATURE:
<221> NAME/KEY: DOMAIN
<222> LOCATION: (52)..(177)
<223> OTHER INFORMATION: Preferred receptor binding domain
<300> PUBLICATION INFORMATION:
<308> DATABASE ACCESSION NUMBER: NP_005083
<309> DATABASE ENTRY DATE: 2008-12-21
<313> RELEVANT RESIDUES IN SEQ ID NO: (1)..(199)

<400> SEQUENCE: 18

Met Thr Leu His Pro Ser Pro Ile Thr Cys Glu Phe Leu Phe Ser Thr
1               5                   10                  15

Ala Leu Ile Ser Pro Lys Met Cys Leu Ser His Leu Glu Asn Met Pro
                20                  25                  30

Leu Ser His Ser Arg Thr Gln Gly Ala Gln Arg Ser Ser Trp Lys Leu
            35                  40                  45

Trp Leu Phe Cys Ser Ile Val Met Leu Leu Phe Leu Cys Ser Phe Ser
        50                  55                  60

Trp Leu Ile Phe Ile Phe Leu Gln Leu Glu Thr Ala Lys Glu Pro Cys
65                  70                  75                  80

Met Ala Lys Phe Gly Pro Leu Pro Ser Lys Trp Gln Met Ala Ser Ser
                85                  90                  95

Glu Pro Pro Cys Val Asn Lys Val Ser Asp Trp Lys Leu Glu Ile Leu
                100                 105                 110

Gln Asn Gly Leu Tyr Leu Ile Tyr Gly Gln Val Ala Pro Asn Ala Asn
            115                 120                 125

Tyr Asn Asp Val Ala Pro Phe Glu Val Arg Leu Tyr Lys Asn Lys Asp
130                 135                 140

Met Ile Gln Thr Leu Thr Asn Lys Ser Lys Ile Gln Asn Val Gly Gly
```

```
                145                 150                 155                 160
Thr Tyr Glu Leu His Val Gly Asp Thr Ile Asp Leu Ile Phe Asn Ser
                    165                 170                 175

Glu His Gln Val Leu Lys Asn Asn Thr Tyr Trp Gly Ile Ile Leu Leu
                    180                 185                 190

Ala Asn Pro Gln Phe Ile Ser
                    195
```

<210> SEQ ID NO 19
<211> LENGTH: 391
<212> TYPE: PRT
<213> ORGANISM: Homo sapiens
<220> FEATURE:
<221> NAME/KEY: DOMAIN
<222> LOCATION: (245)..(391)
<223> OTHER INFORMATION: Preferred receptor binding domain
<300> PUBLICATION INFORMATION:
<308> DATABASE ACCESSION NUMBER: NP_001390
<309> DATABASE ENTRY DATE: 2008-12-21
<313> RELEVANT RESIDUES IN SEQ ID NO: (1)..(391)

<400> SEQUENCE: 19

```
Met Gly Tyr Pro Glu Val Glu Arg Arg Glu Leu Leu Pro Ala Ala Ala
1                   5                   10                  15

Pro Arg Glu Arg Gly Ser Gln Gly Cys Gly Cys Gly Gly Ala Pro Ala
                    20                  25                  30

Arg Ala Gly Glu Gly Asn Ser Cys Leu Leu Phe Leu Gly Phe Phe Gly
                35                  40                  45

Leu Ser Leu Ala Leu His Leu Leu Thr Leu Cys Cys Tyr Leu Glu Leu
    50                  55                  60

Arg Ser Glu Leu Arg Arg Glu Arg Gly Ala Glu Ser Arg Leu Gly Gly
65                  70                  75                  80

Ser Gly Thr Pro Gly Thr Ser Gly Thr Leu Ser Ser Leu Gly Gly Leu
                    85                  90                  95

Asp Pro Asp Ser Pro Ile Thr Ser His Leu Gly Gln Pro Ser Pro Lys
                100                 105                 110

Gln Gln Pro Leu Glu Pro Gly Glu Ala Ala Leu His Ser Asp Ser Gln
            115                 120                 125

Asp Gly His Gln Met Ala Leu Leu Asn Phe Phe Phe Pro Asp Glu Lys
        130                 135                 140

Pro Tyr Ser Glu Glu Glu Ser Arg Arg Val Arg Arg Asn Lys Arg Ser
145                 150                 155                 160

Lys Ser Asn Glu Gly Ala Asp Gly Pro Val Lys Asn Lys Lys Lys Gly
                    165                 170                 175

Lys Lys Ala Gly Pro Pro Gly Pro Asn Gly Pro Pro Gly Pro Pro Gly
                180                 185                 190

Pro Pro Gly Pro Gln Gly Pro Pro Gly Ile Pro Gly Ile Pro Gly Ile
            195                 200                 205

Pro Gly Thr Thr Val Met Gly Pro Pro Gly Pro Pro Gly Pro Pro Gly
        210                 215                 220

Pro Gln Gly Pro Pro Gly Leu Gln Gly Pro Ser Gly Ala Ala Asp Lys
225                 230                 235                 240

Ala Gly Thr Arg Glu Asn Gln Pro Ala Val Val His Leu Gln Gly Gln
                    245                 250                 255

Gly Ser Ala Ile Gln Val Lys Asn Asp Leu Ser Gly Gly Val Leu Asn
                260                 265                 270

Asp Trp Ser Arg Ile Thr Met Asn Pro Lys Val Phe Lys Leu His Pro
```

```
            275                 280                 285
Arg Ser Gly Glu Leu Glu Val Leu Val Asp Gly Thr Tyr Phe Ile Tyr
290                 295                 300

Ser Gln Val Glu Val Tyr Tyr Ile Asn Phe Thr Asp Phe Ala Ser Tyr
305                 310                 315                 320

Glu Val Val Val Asp Glu Lys Pro Phe Leu Gln Cys Thr Arg Ser Ile
                325                 330                 335

Glu Thr Gly Lys Thr Asn Tyr Asn Thr Cys Tyr Thr Ala Gly Val Cys
            340                 345                 350

Leu Leu Lys Ala Arg Gln Lys Ile Ala Val Lys Met Val His Ala Asp
        355                 360                 365

Ile Ser Ile Asn Met Ser Lys His Thr Thr Phe Phe Gly Ala Ile Arg
370                 375                 380

Leu Gly Glu Ala Pro Ala Ser
385                 390

<210> SEQ ID NO 20
<211> LENGTH: 389
<212> TYPE: PRT
<213> ORGANISM: Homo sapiens
<220> FEATURE:
<221> NAME/KEY: DOMAIN
<222> LOCATION: (245)..(389)
<223> OTHER INFORMATION: Preferred receptor binding domain
<300> PUBLICATION INFORMATION:
<308> DATABASE ACCESSION NUMBER: NP_001005609
<309> DATABASE ENTRY DATE: 2008-12-21
<313> RELEVANT RESIDUES IN SEQ ID NO: (1)..(389)

<400> SEQUENCE: 20

Met Gly Tyr Pro Glu Val Glu Arg Arg Glu Leu Leu Pro Ala Ala Ala
1               5                   10                  15

Pro Arg Glu Arg Gly Ser Gln Gly Cys Gly Cys Gly Gly Ala Pro Ala
            20                  25                  30

Arg Ala Gly Glu Gly Asn Ser Cys Leu Leu Phe Leu Gly Phe Phe Gly
        35                  40                  45

Leu Ser Leu Ala Leu His Leu Leu Thr Leu Cys Cys Tyr Leu Glu Leu
50                  55                  60

Arg Ser Glu Leu Arg Arg Glu Arg Gly Ala Glu Ser Arg Leu Gly Gly
65                  70                  75                  80

Ser Gly Thr Pro Gly Thr Ser Gly Thr Leu Ser Ser Leu Gly Gly Leu
                85                  90                  95

Asp Pro Asp Ser Pro Ile Thr Ser His Leu Gly Gln Pro Ser Pro Lys
            100                 105                 110

Gln Gln Pro Leu Glu Pro Gly Glu Ala Ala Leu His Ser Asp Ser Gln
        115                 120                 125

Asp Gly His Gln Met Ala Leu Leu Asn Phe Phe Pro Asp Glu Lys
130                 135                 140

Pro Tyr Ser Glu Glu Ser Arg Arg Val Arg Arg Asn Lys Arg Ser
145                 150                 155                 160

Lys Ser Asn Glu Gly Ala Asp Gly Pro Val Lys Asn Lys Lys Gly
                165                 170                 175

Lys Lys Ala Gly Pro Pro Gly Pro Asn Gly Pro Pro Gly Pro Pro Gly
            180                 185                 190

Pro Pro Gly Pro Gln Gly Pro Pro Gly Ile Pro Gly Ile Pro Gly Ile
        195                 200                 205

Pro Gly Thr Thr Val Met Gly Pro Pro Gly Pro Pro Gly Pro Pro Gly
```

```
                 210                 215                 220

Pro Gln Gly Pro Pro Gly Leu Gln Gly Pro Ser Gly Ala Ala Asp Lys
225                 230                 235                 240

Ala Gly Thr Arg Glu Asn Gln Pro Ala Val Val His Leu Gln Gly Gln
                245                 250                 255

Gly Ser Ala Ile Gln Val Lys Asn Asp Leu Ser Gly Gly Val Leu Asn
            260                 265                 270

Asp Trp Ser Arg Ile Thr Met Asn Pro Lys Val Phe Lys Leu His Pro
        275                 280                 285

Arg Ser Gly Glu Leu Glu Val Leu Val Asp Gly Thr Tyr Phe Ile Tyr
    290                 295                 300

Ser Gln Val Tyr Tyr Ile Asn Phe Thr Asp Phe Ala Ser Tyr Glu Val
305                 310                 315                 320

Val Val Asp Glu Lys Pro Phe Leu Gln Cys Thr Arg Ser Ile Glu Thr
                325                 330                 335

Gly Lys Thr Asn Tyr Asn Thr Cys Tyr Thr Ala Gly Val Cys Leu Leu
            340                 345                 350

Lys Ala Arg Gln Lys Ile Ala Val Lys Met Val His Ala Asp Ile Ser
        355                 360                 365

Ile Asn Met Ser Lys His Thr Thr Phe Phe Gly Ala Ile Arg Leu Gly
    370                 375                 380

Glu Ala Pro Ala Ser
385

<210> SEQ ID NO 21
<211> LENGTH: 375
<212> TYPE: PRT
<213> ORGANISM: Homo sapiens
<220> FEATURE:
<221> NAME/KEY: DOMAIN
<222> LOCATION: (217)..(375)
<223> OTHER INFORMATION: Preferred collectin trimerization domain
<220> FEATURE:
<221> NAME/KEY: DOMAIN
<222> LOCATION: (217)..(257)
<223> OTHER INFORMATION: Preferred neck domain
<220> FEATURE:
<221> NAME/KEY: DOMAIN
<222> LOCATION: (218)..(375)
<223> OTHER INFORMATION: Preferred collectin trimerization domain
<220> FEATURE:
<221> NAME/KEY: DOMAIN
<222> LOCATION: (218)..(257)
<223> OTHER INFORMATION: Preferred neck domain
<220> FEATURE:
<221> NAME/KEY: DOMAIN
<222> LOCATION: (219)..(375)
<223> OTHER INFORMATION: Preferred collectin trimerization domain
<220> FEATURE:
<221> NAME/KEY: DOMAIN
<222> LOCATION: (219)..(257)
<223> OTHER INFORMATION: Preferred neck domain
<220> FEATURE:
<221> NAME/KEY: DOMAIN
<222> LOCATION: (220)..(375)
<223> OTHER INFORMATION: Preferred collectin trimerization domain
<220> FEATURE:
<221> NAME/KEY: DOMAIN
<222> LOCATION: (220)..(257)
<223> OTHER INFORMATION: Preferred neck domain
<220> FEATURE:
<221> NAME/KEY: DOMAIN
<222> LOCATION: (221)..(375)
<223> OTHER INFORMATION: Preferred collectin trimerization domain
<220> FEATURE:
<221> NAME/KEY: DOMAIN
<222> LOCATION: (221)..(257)
```

<223> OTHER INFORMATION: Preferred neck domain
<220> FEATURE:
<221> NAME/KEY: DOMAIN
<222> LOCATION: (222)..(375)
<223> OTHER INFORMATION: Preferred collectin trimerization domain
<220> FEATURE:
<221> NAME/KEY: DOMAIN
<222> LOCATION: (222)..(257)
<223> OTHER INFORMATION: Preferred neck domain
<220> FEATURE:
<221> NAME/KEY: DOMAIN
<222> LOCATION: (223)..(375)
<223> OTHER INFORMATION: Preferred collectin trimerization domain
<220> FEATURE:
<221> NAME/KEY: DOMAIN
<222> LOCATION: (223)..(257)
<223> OTHER INFORMATION: Preferred neck domain
<220> FEATURE:
<221> NAME/KEY: DOMAIN
<222> LOCATION: (224)..(375)
<223> OTHER INFORMATION: Preferred collectin trimerization domain
<220> FEATURE:
<221> NAME/KEY: DOMAIN
<222> LOCATION: (224)..(257)
<223> OTHER INFORMATION: Preferred neck domain
<220> FEATURE:
<221> NAME/KEY: DOMAIN
<222> LOCATION: (225)..(375)
<223> OTHER INFORMATION: Preferred collectin trimerization domain
<220> FEATURE:
<221> NAME/KEY: DOMAIN
<222> LOCATION: (225)..(257)
<223> OTHER INFORMATION: Preferred neck domain
<220> FEATURE:
<221> NAME/KEY: DOMAIN
<222> LOCATION: (258)..(375)
<223> OTHER INFORMATION: Preferred carbohydrate recognition domain
<300> PUBLICATION INFORMATION:
<308> DATABASE ACCESSION NUMBER: P35247
<309> DATABASE ENTRY DATE: 2008-12-16
<313> RELEVANT RESIDUES IN SEQ ID NO: (1)..(375)

<400> SEQUENCE: 21

Met Leu Leu Phe Leu Leu Ser Ala Leu Val Leu Leu Thr Gln Pro Leu
1               5                   10                  15

Gly Tyr Leu Glu Ala Glu Met Lys Thr Tyr Ser His Arg Thr Met Pro
            20                  25                  30

Ser Ala Cys Thr Leu Val Met Cys Ser Ser Val Glu Ser Gly Leu Pro
        35                  40                  45

Gly Arg Asp Gly Arg Asp Gly Arg Glu Gly Pro Arg Gly Glu Lys Gly
    50                  55                  60

Asp Pro Gly Leu Pro Gly Ala Ala Gly Gln Ala Gly Met Pro Gly Gln
65                  70                  75                  80

Ala Gly Pro Val Gly Pro Lys Gly Asp Asn Gly Ser Val Gly Glu Pro
                85                  90                  95

Gly Pro Lys Gly Asp Thr Gly Pro Ser Gly Pro Pro Gly Pro Pro Gly
            100                 105                 110

Val Pro Gly Pro Ala Gly Arg Glu Gly Pro Leu Gly Lys Gln Gly Asn
        115                 120                 125

Ile Gly Pro Gln Gly Lys Pro Gly Pro Lys Gly Glu Ala Gly Pro Lys
    130                 135                 140

Gly Glu Val Gly Ala Pro Gly Met Gln Gly Ser Ala Gly Ala Arg Gly
145                 150                 155                 160

Leu Ala Gly Pro Lys Gly Glu Arg Gly Val Pro Gly Glu Arg Gly Val
                165                 170                 175

Pro Gly Asn Ala Gly Ala Ala Gly Ser Ala Gly Ala Met Gly Pro Gln
            180                 185                 190

```
Gly Ser Pro Gly Ala Arg Gly Pro Gly Leu Lys Gly Asp Lys Gly
            195                 200                 205
Ile Pro Gly Asp Lys Gly Ala Lys Gly Glu Ser Gly Leu Pro Asp Val
210                 215                 220
Ala Ser Leu Arg Gln Gln Val Glu Ala Leu Gln Gly Gln Val Gln His
225                 230                 235                 240
Leu Gln Ala Ala Phe Ser Gln Tyr Lys Lys Val Glu Leu Phe Pro Asn
            245                 250                 255
Gly Gln Ser Val Gly Glu Lys Ile Phe Lys Thr Ala Gly Phe Val Lys
            260                 265                 270
Pro Phe Thr Glu Ala Gln Leu Leu Cys Thr Gln Ala Gly Gly Gln Leu
            275                 280                 285
Ala Ser Pro Arg Ser Ala Glu Asn Ala Ala Leu Gln Gln Leu Val
290                 295                 300
Val Ala Lys Asn Glu Ala Ala Phe Leu Ser Met Thr Asp Ser Lys Thr
305                 310                 315                 320
Glu Gly Lys Phe Thr Tyr Pro Thr Gly Glu Ser Leu Val Tyr Ser Asn
            325                 330                 335
Trp Ala Pro Gly Glu Pro Asn Asp Asp Gly Gly Ser Glu Asp Cys Val
            340                 345                 350
Glu Ile Phe Thr Asn Gly Lys Trp Asn Asp Arg Ala Cys Gly Glu Lys
            355                 360                 365
Arg Leu Val Val Cys Glu Phe
            370                 375

<210> SEQ ID NO 22
<211> LENGTH: 271
<212> TYPE: PRT
<213> ORGANISM: Homo sapiens
<220> FEATURE:
<221> NAME/KEY: DOMAIN
<222> LOCATION: (110)..(147)
<223> OTHER INFORMATION: Preferred neck domain
<220> FEATURE:
<221> NAME/KEY: DOMAIN
<222> LOCATION: (110)..(148)
<223> OTHER INFORMATION: Preferred neck domain
<220> FEATURE:
<221> NAME/KEY: DOMAIN
<222> LOCATION: (110)..(149)
<223> OTHER INFORMATION: Preferred neck domain
<220> FEATURE:
<221> NAME/KEY: DOMAIN
<222> LOCATION: (110)..(150)
<223> OTHER INFORMATION: Preferred neck domain
<220> FEATURE:
<221> NAME/KEY: DOMAIN
<222> LOCATION: (110)..(151)
<223> OTHER INFORMATION: Preferred neck domain
<220> FEATURE:
<221> NAME/KEY: DOMAIN
<222> LOCATION: (116)..(147)
<223> OTHER INFORMATION: Preferred neck domain
<220> FEATURE:
<221> NAME/KEY: DOMAIN
<222> LOCATION: (116)..(148)
<223> OTHER INFORMATION: Preferred neck domain
<220> FEATURE:
<221> NAME/KEY: DOMAIN
<222> LOCATION: (116)..(149)
<223> OTHER INFORMATION: Preferred neck domain
<220> FEATURE:
<221> NAME/KEY: DOMAIN
<222> LOCATION: (116)..(150)
<223> OTHER INFORMATION: Preferred neck domain
<220> FEATURE:
```

```
<221> NAME/KEY: DOMAIN
<222> LOCATION: (116)..(151)
<223> OTHER INFORMATION: Preferred neck domain
<220> FEATURE:
<221> NAME/KEY: DOMAIN
<222> LOCATION: (121)..(147)
<223> OTHER INFORMATION: Preferred neck domain
<220> FEATURE:
<221> NAME/KEY: DOMAIN
<222> LOCATION: (121)..(148)
<223> OTHER INFORMATION: Preferred neck domain
<220> FEATURE:
<221> NAME/KEY: DOMAIN
<222> LOCATION: (121)..(149)
<223> OTHER INFORMATION: Preferred neck domain
<220> FEATURE:
<221> NAME/KEY: DOMAIN
<222> LOCATION: (121)..(150)
<223> OTHER INFORMATION: Preferred neck domain
<220> FEATURE:
<221> NAME/KEY: DOMAIN
<222> LOCATION: (121)..(151)
<223> OTHER INFORMATION: Preferred neck domain
<220> FEATURE:
<221> NAME/KEY: DOMAIN
<222> LOCATION: (149)..(271)
<223> OTHER INFORMATION: Preferred carbohydrate recognition domain
<220> FEATURE:
<221> NAME/KEY: DOMAIN
<222> LOCATION: (152)..(271)
<223> OTHER INFORMATION: Preferred carbohydrate recognition domain
<300> PUBLICATION INFORMATION:
<308> DATABASE ACCESSION NUMBER: Q9BWP8
<309> DATABASE ENTRY DATE: 2008-12-16
<313> RELEVANT RESIDUES IN SEQ ID NO: (1)..(271)

<400> SEQUENCE: 22

Met Arg Gly Asn Leu Ala Leu Val Gly Val Leu Ile Ser Leu Ala Phe
1               5                   10                  15

Leu Ser Leu Leu Pro Ser Gly His Pro Gln Pro Ala Gly Asp Asp Ala
            20                  25                  30

Cys Ser Val Gln Ile Leu Val Pro Gly Leu Lys Gly Asp Ala Gly Glu
        35                  40                  45

Lys Gly Asp Lys Gly Ala Pro Gly Arg Pro Gly Arg Val Gly Pro Thr
    50                  55                  60

Gly Glu Lys Gly Asp Met Gly Asp Lys Gly Gln Lys Gly Ser Val Gly
65                  70                  75                  80

Arg His Gly Lys Ile Gly Pro Ile Gly Ser Lys Gly Glu Lys Gly Asp
                85                  90                  95

Ser Gly Asp Ile Gly Pro Pro Gly Pro Asn Gly Glu Pro Gly Leu Pro
            100                 105                 110

Cys Glu Cys Ser Gln Leu Arg Lys Ala Ile Gly Glu Met Asp Asn Gln
        115                 120                 125

Val Ser Gln Leu Thr Ser Glu Leu Lys Phe Ile Lys Asn Ala Val Ala
    130                 135                 140

Gly Val Arg Glu Thr Glu Ser Lys Ile Tyr Leu Leu Val Lys Glu Glu
145                 150                 155                 160

Lys Arg Tyr Ala Asp Ala Gln Leu Ser Cys Gln Gly Arg Gly Gly Thr
                165                 170                 175

Leu Ser Met Pro Lys Asp Glu Ala Ala Asn Gly Leu Met Ala Ala Tyr
            180                 185                 190

Leu Ala Gln Ala Gly Leu Ala Arg Val Phe Ile Gly Ile Asn Asp Leu
        195                 200                 205

Glu Lys Glu Gly Ala Phe Val Tyr Ser Asp His Ser Pro Met Arg Thr
    210                 215                 220
```

```
Phe Asn Lys Trp Arg Ser Gly Glu Pro Asn Asn Ala Tyr Asp Glu Glu
225                 230                 235                 240

Asp Cys Val Glu Met Val Ala Ser Gly Gly Trp Asn Asp Val Ala Cys
            245                 250                 255

His Thr Thr Met Tyr Phe Met Cys Glu Phe Asp Lys Glu Asn Met
        260                 265                 270

<210> SEQ ID NO 23
<211> LENGTH: 19
<212> TYPE: PRT
<213> ORGANISM: Artificial Sequence
<220> FEATURE:
<223> OTHER INFORMATION: Signal peptide

<400> SEQUENCE: 23

Met Asn Phe Gly Phe Ser Leu Ile Phe Leu Val Leu Val Leu Lys Gly
1               5                   10                  15

Val Gln Cys

<210> SEQ ID NO 24
<211> LENGTH: 20
<212> TYPE: PRT
<213> ORGANISM: Artificial Sequence
<220> FEATURE:
<223> OTHER INFORMATION: Signal peptide

<400> SEQUENCE: 24

Met Glu Thr Asp Thr Leu Leu Leu Trp Val Leu Leu Leu Trp Val Pro
1               5                   10                  15

Gly Ser Thr Gly
            20

<210> SEQ ID NO 25
<211> LENGTH: 20
<212> TYPE: PRT
<213> ORGANISM: Artificial Sequence
<220> FEATURE:
<223> OTHER INFORMATION: Signal peptide

<400> SEQUENCE: 25

Met Glu Thr Asp Thr Leu Leu Leu Trp Val Leu Leu Leu Trp Val Pro
1               5                   10                  15

Ala Gly Asn Gly
            20

<210> SEQ ID NO 26
<211> LENGTH: 339
<212> TYPE: PRT
<213> ORGANISM: Artificial Sequence
<220> FEATURE:
<223> OTHER INFORMATION: Fusion protein
<220> FEATURE:
<221> NAME/KEY: MISC_FEATURE
<222> LOCATION: (1)..(20)
<223> OTHER INFORMATION: Signal peptide 3 (SEQ ID NO:25)
<220> FEATURE:
<221> NAME/KEY: MISC_FEATURE
<222> LOCATION: (21)..(182)
<223> OTHER INFORMATION: TRAIL receptor binding domain (residues 120-281
      of SEQ ID NO:10)
<220> FEATURE:
<221> NAME/KEY: MISC_FEATURE
<222> LOCATION: (183)..(339)
<223> OTHER INFORMATION: SP-D collectin trimerization domain (residues
      219-375 of SEQ ID NO:21)
<220> FEATURE:
```

```
<221> NAME/KEY: MISC_FEATURE
<222> LOCATION: (183)..(221)
<223> OTHER INFORMATION: SP-D neck region (residues 219-257 of SEQ ID
      NO:21)
<220> FEATURE:
<221> NAME/KEY: MISC_FEATURE
<222> LOCATION: (222)..(339)
<223> OTHER INFORMATION: SP-D CRD (residues 258-375 of SEQ ID NO:21)

<400> SEQUENCE: 26
```

Met Glu Thr Asp Thr Leu Leu Leu Trp Val Leu Leu Leu Trp Val Pro
1               5                   10                  15

Ala Gly Asn Gly Gln Arg Val Ala Ala His Ile Thr Gly Thr Arg Gly
            20                  25                  30

Arg Ser Asn Thr Leu Ser Ser Pro Asn Ser Lys Asn Glu Lys Ala Leu
        35                  40                  45

Gly Arg Lys Ile Asn Ser Trp Glu Ser Ser Arg Ser Gly His Ser Phe
    50                  55                  60

Leu Ser Asn Leu His Leu Arg Asn Gly Glu Leu Val Ile His Glu Lys
65                  70                  75                  80

Gly Phe Tyr Tyr Ile Tyr Ser Gln Thr Tyr Phe Arg Phe Gln Glu Glu
                85                  90                  95

Ile Lys Glu Asn Thr Lys Asn Asp Lys Gln Met Val Gln Tyr Ile Tyr
            100                 105                 110

Lys Tyr Thr Ser Tyr Pro Asp Pro Ile Leu Leu Met Lys Ser Ala Arg
        115                 120                 125

Asn Ser Cys Trp Ser Lys Asp Ala Glu Tyr Gly Leu Tyr Ser Ile Tyr
    130                 135                 140

Gln Gly Gly Ile Phe Glu Leu Lys Glu Asn Asp Arg Ile Phe Val Ser
145                 150                 155                 160

Val Thr Asn Glu His Leu Ile Asp Met Asp His Glu Ala Ser Phe Phe
                165                 170                 175

Gly Ala Phe Leu Val Gly Ser Gly Leu Pro Asp Val Ala Ser Leu Arg
            180                 185                 190

Gln Gln Val Glu Ala Leu Gln Gly Gln Val Gln His Leu Gln Ala Ala
        195                 200                 205

Phe Ser Gln Tyr Lys Lys Val Glu Leu Phe Pro Asn Gly Gln Ser Val
    210                 215                 220

Gly Glu Lys Ile Phe Lys Thr Ala Gly Phe Val Lys Pro Phe Thr Glu
225                 230                 235                 240

Ala Gln Leu Leu Cys Thr Gln Ala Gly Gly Gln Leu Ala Ser Pro Arg
                245                 250                 255

Ser Ala Ala Glu Asn Ala Ala Leu Gln Gln Leu Val Val Ala Lys Asn
            260                 265                 270

Glu Ala Ala Phe Leu Ser Met Thr Asp Ser Lys Thr Glu Gly Lys Phe
        275                 280                 285

Thr Tyr Pro Thr Gly Glu Ser Leu Val Tyr Ser Asn Trp Ala Pro Gly
    290                 295                 300

Glu Pro Asn Asp Asp Gly Gly Ser Glu Asp Cys Val Glu Ile Phe Thr
305                 310                 315                 320

Asn Gly Lys Trp Asn Asp Arg Ala Cys Gly Glu Lys Arg Leu Val Val
                325                 330                 335

Cys Glu Phe

```
<210> SEQ ID NO 27
<211> LENGTH: 343
```

```
<212> TYPE: PRT
<213> ORGANISM: Artificial Sequence
<220> FEATURE:
<223> OTHER INFORMATION: Fusion protein
<220> FEATURE:
<221> NAME/KEY: MISC_FEATURE
<222> LOCATION: (1)..(20)
<223> OTHER INFORMATION: Signal peptide 2 (SEQ ID NO:24)
<220> FEATURE:
<221> NAME/KEY: MISC_FEATURE
<222> LOCATION: (21)..(186)
<223> OTHER INFORMATION: TRAIL receptor binding domain (residues 116-281
      of SEQ ID NO:10)
<220> FEATURE:
<221> NAME/KEY: MISC_FEATURE
<222> LOCATION: (187)..(343)
<223> OTHER INFORMATION: SP-D collectin trimerization domain (residues
      219-375 of SEQ ID NO:21)
<220> FEATURE:
<221> NAME/KEY: MISC_FEATURE
<222> LOCATION: (187)..(225)
<223> OTHER INFORMATION: SP-D neck region (residues 219-257 of SEQ ID
      NO:21)
<220> FEATURE:
<221> NAME/KEY: MISC_FEATURE
<222> LOCATION: (226)..(343)
<223> OTHER INFORMATION: SP-D CRD (residues 258-375 of SEQ ID NO:21)

<400> SEQUENCE: 27

Met Glu Thr Asp Thr Leu Leu Leu Trp Val Leu Leu Leu Trp Val Pro
1               5                   10                  15

Gly Ser Thr Gly Glu Arg Gly Pro Gln Arg Val Ala Ala His Ile Thr
            20                  25                  30

Gly Thr Arg Gly Arg Ser Asn Thr Leu Ser Ser Pro Asn Ser Lys Asn
        35                  40                  45

Glu Lys Ala Leu Gly Arg Lys Ile Asn Ser Trp Glu Ser Ser Arg Ser
    50                  55                  60

Gly His Ser Phe Leu Ser Asn Leu His Leu Arg Asn Gly Glu Leu Val
65                  70                  75                  80

Ile His Glu Lys Gly Phe Tyr Tyr Ile Tyr Ser Gln Thr Tyr Phe Arg
                85                  90                  95

Phe Gln Glu Glu Ile Lys Glu Asn Thr Lys Asn Asp Lys Gln Met Val
            100                 105                 110

Gln Tyr Ile Tyr Lys Tyr Thr Ser Tyr Pro Asp Pro Ile Leu Leu Met
        115                 120                 125

Lys Ser Ala Arg Asn Ser Cys Trp Ser Lys Asp Ala Glu Tyr Gly Leu
    130                 135                 140

Tyr Ser Ile Tyr Gln Gly Gly Ile Phe Glu Leu Lys Glu Asn Asp Arg
145                 150                 155                 160

Ile Phe Val Ser Val Thr Asn Glu His Leu Ile Asp Met Asp His Glu
                165                 170                 175

Ala Ser Phe Phe Gly Ala Phe Leu Val Gly Ser Gly Leu Pro Asp Val
            180                 185                 190

Ala Ser Leu Arg Gln Gln Val Glu Ala Leu Gln Gly Gln Val Gln His
        195                 200                 205

Leu Gln Ala Ala Phe Ser Gln Tyr Lys Lys Val Glu Leu Phe Pro Asn
    210                 215                 220

Gly Gln Ser Val Gly Glu Lys Ile Phe Lys Thr Ala Gly Phe Val Lys
225                 230                 235                 240

Pro Phe Thr Glu Ala Gln Leu Leu Cys Thr Gln Ala Gly Gly Gln Leu
                245                 250                 255

Ala Ser Pro Arg Ser Ala Ala Glu Asn Ala Ala Leu Gln Gln Leu Val
```

```
                260                 265                 270
Val Ala Lys Asn Glu Ala Ala Phe Leu Ser Met Thr Asp Ser Lys Thr
            275                 280                 285

Glu Gly Lys Phe Thr Tyr Pro Thr Gly Glu Ser Leu Val Tyr Ser Asn
        290                 295                 300

Trp Ala Pro Gly Glu Pro Asn Asp Asp Gly Ser Glu Asp Cys Val
305                 310                 315                 320

Glu Ile Phe Thr Asn Gly Lys Trp Asn Asp Arg Ala Cys Gly Glu Lys
                325                 330                 335

Arg Leu Val Val Cys Glu Phe
            340

<210> SEQ ID NO 28
<211> LENGTH: 225
<212> TYPE: PRT
<213> ORGANISM: Artificial Sequence
<220> FEATURE:
<223> OTHER INFORMATION: Fusion protein
<220> FEATURE:
<221> NAME/KEY: MISC_FEATURE
<222> LOCATION: (1)..(20)
<223> OTHER INFORMATION: Signal peptide 2 (SEQ ID NO:24)
<220> FEATURE:
<221> NAME/KEY: MISC_FEATURE
<222> LOCATION: (21)..(186)
<223> OTHER INFORMATION: TRAIL receptor binding domain (residues 116-281
      of SEQ ID NO:10)
<220> FEATURE:
<221> NAME/KEY: MISC_FEATURE
<222> LOCATION: (187)..(225)
<223> OTHER INFORMATION: SP-D neck region (residues 219-257 of SEQ ID
      NO:21)

<400> SEQUENCE: 28

Met Glu Thr Asp Thr Leu Leu Leu Trp Val Leu Leu Leu Trp Val Pro
1               5                   10                  15

Gly Ser Thr Gly Glu Arg Gly Pro Gln Arg Val Ala Ala His Ile Thr
            20                  25                  30

Gly Thr Arg Gly Arg Ser Asn Thr Leu Ser Ser Pro Asn Ser Lys Asn
        35                  40                  45

Glu Lys Ala Leu Gly Arg Lys Ile Asn Ser Trp Glu Ser Ser Arg Ser
    50                  55                  60

Gly His Ser Phe Leu Ser Asn Leu His Leu Arg Asn Gly Glu Leu Val
65                  70                  75                  80

Ile His Glu Lys Gly Phe Tyr Tyr Ile Tyr Ser Gln Thr Tyr Phe Arg
                85                  90                  95

Phe Gln Glu Glu Ile Lys Glu Asn Thr Lys Asn Asp Lys Gln Met Val
            100                 105                 110

Gln Tyr Ile Tyr Lys Tyr Thr Ser Tyr Pro Asp Pro Ile Leu Leu Met
        115                 120                 125

Lys Ser Ala Arg Asn Ser Cys Trp Ser Lys Asp Ala Glu Tyr Gly Leu
    130                 135                 140

Tyr Ser Ile Tyr Gln Gly Gly Ile Phe Glu Leu Lys Glu Asn Asp Arg
145                 150                 155                 160

Ile Phe Val Ser Val Thr Asn Glu His Leu Ile Asp Met Asp His Glu
                165                 170                 175

Ala Ser Phe Phe Gly Ala Phe Leu Val Gly Ser Gly Leu Pro Asp Val
            180                 185                 190

Ala Ser Leu Arg Gln Gln Val Glu Ala Leu Gln Gly Gln Val Gln His
        195                 200                 205
```

Leu Gln Ala Ala Phe Ser Gln Tyr Lys Lys Val Glu Leu Phe Pro Asn
            210                 215                 220

Gly
225

<210> SEQ ID NO 29
<211> LENGTH: 338
<212> TYPE: PRT
<213> ORGANISM: Artificial Sequence
<220> FEATURE:
<223> OTHER INFORMATION: Fusion protein
<220> FEATURE:
<221> NAME/KEY: MISC_FEATURE
<222> LOCATION: (1)..(20)
<223> OTHER INFORMATION: Signal peptide 3 (SEQ ID NO:25)
<220> FEATURE:
<221> NAME/KEY: MISC_FEATURE
<222> LOCATION: (21)..(182)
<223> OTHER INFORMATION: TRAIL receptor binding domain (residues 120-281
      of SEQ ID NO:10)
<220> FEATURE:
<221> NAME/KEY: MISC_FEATURE
<222> LOCATION: (183)..(338)
<223> OTHER INFORMATION: Collectin-11 collectin trimerization domain
      (residues 116-271 of SEQ ID NO:22)
<220> FEATURE:
<221> NAME/KEY: MISC_FEATURE
<222> LOCATION: (183)..(218)
<223> OTHER INFORMATION: Collectin-11 neck region (residues 116-151 of
      SEQ ID NO:22)
<220> FEATURE:
<221> NAME/KEY: MISC_FEATURE
<222> LOCATION: (219)..(338)
<223> OTHER INFORMATION: Collectin-11 CRD (residues 152-271 of SEQ ID
      NO:22)

<400> SEQUENCE: 29

Met Glu Thr Asp Thr Leu Leu Leu Trp Val Leu Leu Leu Trp Val Pro
1               5                   10                  15

Ala Gly Asn Gly Gln Arg Val Ala Ala His Ile Thr Gly Thr Arg Gly
            20                  25                  30

Arg Ser Asn Thr Leu Ser Ser Pro Asn Ser Lys Asn Glu Lys Ala Leu
        35                  40                  45

Gly Arg Lys Ile Asn Ser Trp Glu Ser Ser Arg Ser Gly His Ser Phe
    50                  55                  60

Leu Ser Asn Leu His Leu Arg Asn Gly Glu Leu Val Ile His Glu Lys
65                  70                  75                  80

Gly Phe Tyr Tyr Ile Tyr Ser Gln Thr Tyr Phe Arg Phe Gln Glu Glu
                85                  90                  95

Ile Lys Glu Asn Thr Lys Asn Asp Lys Gln Met Val Gln Tyr Ile Tyr
            100                 105                 110

Lys Tyr Thr Ser Tyr Pro Asp Pro Ile Leu Leu Met Lys Ser Ala Arg
        115                 120                 125

Asn Ser Cys Trp Ser Lys Asp Ala Glu Tyr Gly Leu Tyr Ser Ile Tyr
    130                 135                 140

Gln Gly Gly Ile Phe Glu Leu Lys Glu Asn Asp Arg Ile Phe Val Ser
145                 150                 155                 160

Val Thr Asn Glu His Leu Ile Asp Met Asp His Glu Ala Ser Phe Phe
                165                 170                 175

Gly Ala Phe Leu Val Gly Ser Gln Leu Arg Lys Ala Ile Gly Glu Met
            180                 185                 190

Asp Asn Gln Val Ser Gln Leu Thr Ser Glu Leu Lys Phe Ile Lys Asn
        195                 200                 205

```
Ala Val Ala Gly Val Arg Glu Thr Glu Ser Lys Ile Tyr Leu Leu Val
    210                 215                 220

Lys Glu Glu Lys Arg Tyr Ala Asp Ala Gln Leu Ser Cys Gln Gly Arg
225                 230                 235                 240

Gly Gly Thr Leu Ser Met Pro Lys Asp Glu Ala Ala Asn Gly Leu Met
                245                 250                 255

Ala Ala Tyr Leu Ala Gln Ala Gly Leu Ala Arg Val Phe Ile Gly Ile
            260                 265                 270

Asn Asp Leu Glu Lys Glu Gly Ala Phe Val Tyr Ser Asp His Ser Pro
        275                 280                 285

Met Arg Thr Phe Asn Lys Trp Arg Ser Gly Glu Pro Asn Asn Ala Tyr
    290                 295                 300

Asp Glu Glu Asp Cys Val Glu Met Val Ala Ser Gly Gly Trp Asn Asp
305                 310                 315                 320

Val Ala Cys His Thr Thr Met Tyr Phe Met Cys Glu Phe Asp Lys Glu
                325                 330                 335

Asn Met

<210> SEQ ID NO 30
<211> LENGTH: 342
<212> TYPE: PRT
<213> ORGANISM: Artificial Sequence
<220> FEATURE:
<223> OTHER INFORMATION: Fusion protein
<220> FEATURE:
<221> NAME/KEY: MISC_FEATURE
<222> LOCATION: (1)..(20)
<223> OTHER INFORMATION: Signal peptide 2 (SEQ ID NO:24)
<220> FEATURE:
<221> NAME/KEY: MISC_FEATURE
<222> LOCATION: (21)..(186)
<223> OTHER INFORMATION: TRAIL receptor binding domain (residues 116-281
      of SEQ ID NO:10)
<220> FEATURE:
<221> NAME/KEY: MISC_FEATURE
<222> LOCATION: (187)..(342)
<223> OTHER INFORMATION: Collectin-11 collectin trimerization domain
      (residues 116-271 of SEQ ID NO:22)
<220> FEATURE:
<221> NAME/KEY: MISC_FEATURE
<222> LOCATION: (187)..(222)
<223> OTHER INFORMATION: Collectin-11 neck region (residues 116-151 of
      SEQ ID NO:22)
<220> FEATURE:
<221> NAME/KEY: MISC_FEATURE
<222> LOCATION: (223)..(342)
<223> OTHER INFORMATION: Collectin-11 CRD (residues 152-271 of SEQ ID
      NO:22)

<400> SEQUENCE: 30

Met Glu Thr Asp Thr Leu Leu Leu Trp Val Leu Leu Leu Trp Val Pro
1               5                   10                  15

Gly Ser Thr Gly Glu Arg Gly Pro Gln Arg Val Ala Ala His Ile Thr
            20                  25                  30

Gly Thr Arg Gly Arg Ser Asn Thr Leu Ser Ser Pro Asn Ser Lys Asn
        35                  40                  45

Glu Lys Ala Leu Gly Arg Lys Ile Asn Ser Trp Glu Ser Ser Arg Ser
    50                  55                  60

Gly His Ser Phe Leu Ser Asn Leu His Leu Arg Asn Gly Glu Leu Val
65                  70                  75                  80

Ile His Glu Lys Gly Phe Tyr Tyr Ile Tyr Ser Gln Thr Tyr Phe Arg
                85                  90                  95
```

```
Phe Gln Glu Glu Ile Lys Glu Asn Thr Lys Asn Asp Lys Gln Met Val
                100                 105                 110
Gln Tyr Ile Tyr Lys Tyr Thr Ser Tyr Pro Asp Pro Ile Leu Leu Met
            115                 120                 125
Lys Ser Ala Arg Asn Ser Cys Trp Ser Lys Asp Ala Glu Tyr Gly Leu
        130                 135                 140
Tyr Ser Ile Tyr Gln Gly Gly Ile Phe Glu Leu Lys Glu Asn Asp Arg
145                 150                 155                 160
Ile Phe Val Ser Val Thr Asn Glu His Leu Ile Asp Met Asp His Glu
                165                 170                 175
Ala Ser Phe Phe Gly Ala Phe Leu Val Gly Ser Gln Leu Arg Lys Ala
            180                 185                 190
Ile Gly Glu Met Asp Asn Gln Val Ser Gln Leu Thr Ser Glu Leu Lys
        195                 200                 205
Phe Ile Lys Asn Ala Val Ala Gly Val Arg Glu Thr Glu Ser Lys Ile
210                 215                 220
Tyr Leu Leu Val Lys Glu Glu Lys Arg Tyr Ala Asp Ala Gln Leu Ser
225                 230                 235                 240
Cys Gln Gly Arg Gly Gly Thr Leu Ser Met Pro Lys Asp Glu Ala Ala
                245                 250                 255
Asn Gly Leu Met Ala Ala Tyr Leu Ala Gln Ala Gly Leu Ala Arg Val
            260                 265                 270
Phe Ile Gly Ile Asn Asp Leu Glu Lys Glu Gly Ala Phe Val Tyr Ser
        275                 280                 285
Asp His Ser Pro Met Arg Thr Phe Asn Lys Trp Arg Ser Gly Glu Pro
290                 295                 300
Asn Asn Ala Tyr Asp Glu Glu Asp Cys Val Glu Met Val Ala Ser Gly
305                 310                 315                 320
Gly Trp Asn Asp Val Ala Cys His Thr Thr Met Tyr Phe Met Cys Glu
                325                 330                 335
Phe Asp Lys Glu Asn Met
            340

<210> SEQ ID NO 31
<211> LENGTH: 222
<212> TYPE: PRT
<213> ORGANISM: Artificial Sequence
<220> FEATURE:
<223> OTHER INFORMATION: Fusion protein
<220> FEATURE:
<221> NAME/KEY: MISC_FEATURE
<222> LOCATION: (1)..(20)
<223> OTHER INFORMATION: Signal peptide (SEQ ID NO:24)
<220> FEATURE:
<221> NAME/KEY: MISC_FEATURE
<222> LOCATION: (21)..(186)
<223> OTHER INFORMATION: TRAIL receptor binding domain (residues 116-281
      of SEQ ID NO:10)
<220> FEATURE:
<221> NAME/KEY: MISC_FEATURE
<222> LOCATION: (187)..(222)
<223> OTHER INFORMATION: Collectin-11 neck region (residues 116-151 of
      SEQ ID NO:22)

<400> SEQUENCE: 31

Met Glu Thr Asp Thr Leu Leu Leu Trp Val Leu Leu Leu Trp Val Pro
1               5                   10                  15
Gly Ser Thr Gly Glu Arg Gly Pro Gln Arg Val Ala Ala His Ile Thr
            20                  25                  30
Gly Thr Arg Gly Arg Ser Asn Thr Leu Ser Ser Pro Asn Ser Lys Asn
```

```
                35                  40                  45
Glu Lys Ala Leu Gly Arg Lys Ile Asn Ser Trp Glu Ser Ser Arg Ser
 50                  55                  60

Gly His Ser Phe Leu Ser Asn Leu His Leu Arg Asn Gly Glu Leu Val
 65                  70                  75                  80

Ile His Glu Lys Gly Phe Tyr Tyr Ile Tyr Ser Gln Thr Tyr Phe Arg
                 85                  90                  95

Phe Gln Glu Glu Ile Lys Glu Asn Thr Lys Asn Asp Lys Gln Met Val
                100                 105                 110

Gln Tyr Ile Tyr Lys Tyr Thr Ser Tyr Pro Asp Pro Ile Leu Leu Met
            115                 120                 125

Lys Ser Ala Arg Asn Ser Cys Trp Ser Lys Asp Ala Glu Tyr Gly Leu
130                 135                 140

Tyr Ser Ile Tyr Gln Gly Gly Ile Phe Glu Leu Lys Gly Asn Asp Arg
145                 150                 155                 160

Ile Phe Val Ser Val Thr Asn Glu His Leu Ile Asp Met Asp His Glu
                165                 170                 175

Ala Ser Phe Phe Gly Ala Phe Leu Val Gly Ser Gln Leu Arg Lys Ala
            180                 185                 190

Ile Gly Glu Met Asp Asn Gln Val Ser Gln Leu Thr Ser Glu Leu Lys
        195                 200                 205

Phe Ile Lys Asn Ala Val Ala Gly Val Arg Glu Thr Glu Ser
    210                 215                 220

<210> SEQ ID NO 32
<211> LENGTH: 9
<212> TYPE: PRT
<213> ORGANISM: Artificial Sequence
<220> FEATURE:
<223> OTHER INFORMATION: Flag-epitope/enterokinase processing site

<400> SEQUENCE: 32

Asp Tyr Lys Asp Asp Asp Asp Lys Asp
1               5

<210> SEQ ID NO 33
<211> LENGTH: 54
<212> TYPE: PRT
<213> ORGANISM: Artificial Sequence
<220> FEATURE:
<223> OTHER INFORMATION: Flexible linker element
<220> FEATURE:
<221> NAME/KEY: MISC_FEATURE
<222> LOCATION: (1)..(1)
<223> OTHER INFORMATION: Gly (when a=1, 2, 3, 4, 5, or 6) or absent
      (when a=0)
<220> FEATURE:
<221> NAME/KEY: MISC_FEATURE
<222> LOCATION: (2)..(2)
<223> OTHER INFORMATION: Ser (when a=1, 2, 3, 4, 5, or 6) or absent
      (when a=0)
<220> FEATURE:
<221> NAME/KEY: MISC_FEATURE
<222> LOCATION: (3)..(3)
<223> OTHER INFORMATION: Ser (when a=1, 2, 3, 4, 5, or 6) or absent
      (when a=0)
<220> FEATURE:
<221> NAME/KEY: MISC_FEATURE
<222> LOCATION: (4)..(4)
<223> OTHER INFORMATION: Gly (when a=2, 3, 4, 5, or 6) or absent (when
      a=0 or 1)
<220> FEATURE:
<221> NAME/KEY: MISC_FEATURE
<222> LOCATION: (5)..(5)
<223> OTHER INFORMATION: Ser (when a=2, 3, 4, 5, or 6) or absent (when
```

```
      a=0 or 1)
<220> FEATURE:
<221> NAME/KEY: MISC_FEATURE
<222> LOCATION: (6)..(6)
<223> OTHER INFORMATION: Ser (when a=2, 3, 4, 5, or 6) or absent (when
      a=0 or 1)
<220> FEATURE:
<221> NAME/KEY: MISC_FEATURE
<222> LOCATION: (7)..(7)
<223> OTHER INFORMATION: Gly (when a=3, 4, 5, or 6) or absent (when
      a=0, 1, or 2)
<220> FEATURE:
<221> NAME/KEY: MISC_FEATURE
<222> LOCATION: (8)..(8)
<223> OTHER INFORMATION: Ser (when a=3, 4, 5, or 6) or absent (when
      a=0, 1, or 2)
<220> FEATURE:
<221> NAME/KEY: MISC_FEATURE
<222> LOCATION: (9)..(9)
<223> OTHER INFORMATION: Ser (when a=3, 4, 5, or 6) or absent (when
      a=0, 1, or 2)
<220> FEATURE:
<221> NAME/KEY: MISC_FEATURE
<222> LOCATION: (10)..(10)
<223> OTHER INFORMATION: Gly (when a=4, 5, or 6) or absent (when
      a=0, 1, 2, or 3)
<220> FEATURE:
<221> NAME/KEY: MISC_FEATURE
<222> LOCATION: (11)..(11)
<223> OTHER INFORMATION: Ser (when a=4, 5, or 6) or absent (when
      a=0, 1, 2, or 3)
<220> FEATURE:
<221> NAME/KEY: MISC_FEATURE
<222> LOCATION: (12)..(12)
<223> OTHER INFORMATION: Ser (when a=4, 5, or 6) or absent (when
      a=0, 1, 2, or 3)
<220> FEATURE:
<221> NAME/KEY: MISC_FEATURE
<222> LOCATION: (13)..(13)
<223> OTHER INFORMATION: Gly (when a=5 or 6) or absent (when
      a=0, 1, 2, 3, or 4)
<220> FEATURE:
<221> NAME/KEY: MISC_FEATURE
<222> LOCATION: (14)..(14)
<223> OTHER INFORMATION: Ser (when a=5 or 6) or absent (when
      a=0, 1, 2, 3, or 4)
<220> FEATURE:
<221> NAME/KEY: MISC_FEATURE
<222> LOCATION: (15)..(15)
<223> OTHER INFORMATION: Ser (when a=5 or 6) or absent (when
      a=0, 1, 2, 3, or 4)
<220> FEATURE:
<221> NAME/KEY: MISC_FEATURE
<222> LOCATION: (16)..(16)
<223> OTHER INFORMATION: Gly (when a=6) or absent (when a=0, 1, 2, 3,
      4, or 5)
<220> FEATURE:
<221> NAME/KEY: MISC_FEATURE
<222> LOCATION: (17)..(17)
<223> OTHER INFORMATION: Ser (when a=6) or absent (when a=0, 1, 2, 3,
      4, or 5)
<220> FEATURE:
<221> NAME/KEY: MISC_FEATURE
<222> LOCATION: (18)..(18)
<223> OTHER INFORMATION: Ser (when a=6) or absent (when a=0, 1, 2, 3,
      4, or 5)
<220> FEATURE:
<221> NAME/KEY: MISC_FEATURE
<222> LOCATION: (19)..(19)
<223> OTHER INFORMATION: Ser (when b=1, 2, 3, 4, 5, or 6) or absent
      (when b=0)
<220> FEATURE:
<221> NAME/KEY: MISC_FEATURE
<222> LOCATION: (20)..(20)
<223> OTHER INFORMATION: Ser (when b=1, 2, 3, 4, 5, or 6) or absent
      (when b=0)
<220> FEATURE:
<221> NAME/KEY: MISC_FEATURE
<222> LOCATION: (21)..(21)
```

-continued

```
<223> OTHER INFORMATION: Gly (when b=1, 2, 3, 4, 5, or 6) or absent
      (when b=0)
<220> FEATURE:
<221> NAME/KEY: MISC_FEATURE
<222> LOCATION: (22)..(22)
<223> OTHER INFORMATION: Ser (when b=2, 3, 4, 5, or 6) or absent (when
      b=0 or 1)
<220> FEATURE:
<221> NAME/KEY: MISC_FEATURE
<222> LOCATION: (23)..(23)
<223> OTHER INFORMATION: Ser (when b=2, 3, 4, 5, or 6) or absent (when
      b=0 or 1)
<220> FEATURE:
<221> NAME/KEY: MISC_FEATURE
<222> LOCATION: (24)..(24)
<223> OTHER INFORMATION: Gly (when b=2, 3, 4, 5, or 6) or absent (when
      b=0 or 1)
<220> FEATURE:
<221> NAME/KEY: MISC_FEATURE
<222> LOCATION: (25)..(25)
<223> OTHER INFORMATION: Ser (when b=3, 4, 5, or 6) or absent (when
      b=0, 1, or 2)
<220> FEATURE:
<221> NAME/KEY: MISC_FEATURE
<222> LOCATION: (26)..(26)
<223> OTHER INFORMATION: Ser (when b=3, 4, 5, or 6) or absent (when
      b=0, 1, or 2)
<220> FEATURE:
<221> NAME/KEY: MISC_FEATURE
<222> LOCATION: (27)..(27)
<223> OTHER INFORMATION: Gly (when b=3, 4, 5, or 6) or absent (when
      b=0, 1, or 2)
<220> FEATURE:
<221> NAME/KEY: MISC_FEATURE
<222> LOCATION: (28)..(28)
<223> OTHER INFORMATION: Ser (when b=4, 5, or 6) or absent (when
      b=0, 1, 2, or 3)
<220> FEATURE:
<221> NAME/KEY: MISC_FEATURE
<222> LOCATION: (29)..(29)
<223> OTHER INFORMATION: Ser (when b=4, 5, or 6) or absent (when
      b=0, 1, 2, or 3)
<220> FEATURE:
<221> NAME/KEY: MISC_FEATURE
<222> LOCATION: (30)..(30)
<223> OTHER INFORMATION: Gly (when b=4, 5, or 6) or absent (when
      b=0, 1, 2, or 3)
<220> FEATURE:
<221> NAME/KEY: MISC_FEATURE
<222> LOCATION: (31)..(31)
<223> OTHER INFORMATION: Ser (when b=5 or 6) or absent (when b=0, 1, 2,
      3, or 4)
<220> FEATURE:
<221> NAME/KEY: MISC_FEATURE
<222> LOCATION: (32)..(32)
<223> OTHER INFORMATION: Ser (when b=5 or 6) or absent (when b=0, 1, 2,
      3, or 4)
<220> FEATURE:
<221> NAME/KEY: MISC_FEATURE
<222> LOCATION: (33)..(33)
<223> OTHER INFORMATION: Gly (when b=5 or 6) or absent (when b=0, 1, 2,
      3, or 4)
<220> FEATURE:
<221> NAME/KEY: MISC_FEATURE
<222> LOCATION: (34)..(34)
<223> OTHER INFORMATION: Ser (when b=6) or absent (when b=0, 1, 2, 3,
      4, or 5)
<220> FEATURE:
<221> NAME/KEY: MISC_FEATURE
<222> LOCATION: (35)..(35)
<223> OTHER INFORMATION: Ser (when b=6) or absent (when b=0, 1, 2, 3,
      4, or 5)
<220> FEATURE:
<221> NAME/KEY: MISC_FEATURE
<222> LOCATION: (36)..(36)
<223> OTHER INFORMATION: Gly (when b=6) or absent (when b=0, 1, 2, 3,
      4, or 5)
<220> FEATURE:
<221> NAME/KEY: MISC_FEATURE
```

<222> LOCATION: (37)..(37)
<223> OTHER INFORMATION: Gly (when c=1, 2, 3, 4, 5, or 6) or absent
      (when c=0)
<220> FEATURE:
<221> NAME/KEY: MISC_FEATURE
<222> LOCATION: (38)..(38)
<223> OTHER INFORMATION: Ser (when c=1, 2, 3, 4, 5, or 6) or absent
      (when c=0)
<220> FEATURE:
<221> NAME/KEY: MISC_FEATURE
<222> LOCATION: (39)..(39)
<223> OTHER INFORMATION: Gly (when c=1, 2, 3, 4, 5, or 6) or absent
      (when c=0)
<220> FEATURE:
<221> NAME/KEY: MISC_FEATURE
<222> LOCATION: (40)..(40)
<223> OTHER INFORMATION: Gly (when c=2, 3, 4, 5, or 6) or absent (when
      c=0 or 1)
<220> FEATURE:
<221> NAME/KEY: MISC_FEATURE
<222> LOCATION: (41)..(41)
<223> OTHER INFORMATION: Ser (when c=2, 3, 4, 5, or 6) or absent (when
      c=0 or 1)
<220> FEATURE:
<221> NAME/KEY: MISC_FEATURE
<222> LOCATION: (42)..(42)
<223> OTHER INFORMATION: Gly (when c=2, 3, 4, 5, or 6) or absent (when
      c=0 or 1)
<220> FEATURE:
<221> NAME/KEY: MISC_FEATURE
<222> LOCATION: (43)..(43)
<223> OTHER INFORMATION: Gly (when c=3, 4, 5, or 6) or absent (when
      c=0, 1, or 2)
<220> FEATURE:
<221> NAME/KEY: MISC_FEATURE
<222> LOCATION: (44)..(44)
<223> OTHER INFORMATION: Ser (when c=3, 4, 5, or 6) or absent (when
      c=0, 1, or 2)
<220> FEATURE:
<221> NAME/KEY: MISC_FEATURE
<222> LOCATION: (45)..(45)
<223> OTHER INFORMATION: Gly (when c=3, 4, 5, or 6) or absent (when
      c=0, 1, or 2)
<220> FEATURE:
<221> NAME/KEY: MISC_FEATURE
<222> LOCATION: (46)..(46)
<223> OTHER INFORMATION: Gly (when c=4, 5, or 6) or absent (when
      c=0, 1, 2, or 3)
<220> FEATURE:
<221> NAME/KEY: MISC_FEATURE
<222> LOCATION: (47)..(47)
<223> OTHER INFORMATION: Ser (when c=4, 5, or 6) or absent (when
      c=0, 1, 2, or 3)
<220> FEATURE:
<221> NAME/KEY: MISC_FEATURE
<222> LOCATION: (48)..(48)
<223> OTHER INFORMATION: Gly (when c=4, 5, or 6) or absent (when
      c=0, 1, 2, or 3)
<220> FEATURE:
<221> NAME/KEY: MISC_FEATURE
<222> LOCATION: (49)..(49)
<223> OTHER INFORMATION: Gly (when c=5 or 6) or absent (when c=0, 1, 2,
      3, or 4)
<220> FEATURE:
<221> NAME/KEY: MISC_FEATURE
<222> LOCATION: (50)..(50)
<223> OTHER INFORMATION: Ser (when c=5 or 6) or absent (when c=0, 1, 2,
      3, or 4)
<220> FEATURE:
<221> NAME/KEY: MISC_FEATURE
<222> LOCATION: (51)..(51)
<223> OTHER INFORMATION: Gly (when c=5 or 6) or absent (when c=0, 1, 2,
      3, or 4)
<220> FEATURE:
<221> NAME/KEY: MISC_FEATURE
<222> LOCATION: (52)..(52)
<223> OTHER INFORMATION: Gly (when c=6) or absent (when c=0, 1, 2, 3,
      4, or 5)
<220> FEATURE:

```
<221> NAME/KEY: MISC_FEATURE
<222> LOCATION: (53)..(53)
<223> OTHER INFORMATION: Ser (when c=6) or absent (when c=0, 1, 2, 3,
      4, or 5)
<220> FEATURE:
<221> NAME/KEY: MISC_FEATURE
<222> LOCATION: (54)..(54)
<223> OTHER INFORMATION: Gly (when c=6) or absent (when c=0, 1, 2, 3,
      4, or 5)

<400> SEQUENCE: 33

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa
    50

<210> SEQ ID NO 34
<211> LENGTH: 11
<212> TYPE: PRT
<213> ORGANISM: Artificial Sequence
<220> FEATURE:
<223> OTHER INFORMATION: Flexible linker element

<400> SEQUENCE: 34

Gly Ser Ser Gly Ser Ser Gly Ser Ser Gly Ser
1               5                   10

<210> SEQ ID NO 35
<211> LENGTH: 8
<212> TYPE: PRT
<213> ORGANISM: Artificial Sequence
<220> FEATURE:
<223> OTHER INFORMATION: Flexible linker element

<400> SEQUENCE: 35

Gly Ser Ser Gly Ser Ser Gly Ser
1               5

<210> SEQ ID NO 36
<211> LENGTH: 5
<212> TYPE: PRT
<213> ORGANISM: Artificial Sequence
<220> FEATURE:
<223> OTHER INFORMATION: Flexible linker element

<400> SEQUENCE: 36

Gly Ser Ser Gly Ser
1               5

<210> SEQ ID NO 37
<211> LENGTH: 825
<212> TYPE: PRT
<213> ORGANISM: Homo sapiens
<300> PUBLICATION INFORMATION:
<308> DATABASE ACCESSION NUMBER: P24394
<309> DATABASE ENTRY DATE: 2008-12-16
<313> RELEVANT RESIDUES IN SEQ ID NO: (1)..(825)

<400> SEQUENCE: 37

Met Gly Trp Leu Cys Ser Gly Leu Leu Phe Pro Val Ser Cys Leu Val
1               5                   10                  15

Leu Leu Gln Val Ala Ser Ser Gly Asn Met Lys Val Leu Gln Glu Pro
```

```
            20                  25                  30
Thr Cys Val Ser Asp Tyr Met Ser Ile Ser Thr Cys Glu Trp Lys Met
            35                  40                  45

Asn Gly Pro Thr Asn Cys Ser Thr Glu Leu Arg Leu Leu Tyr Gln Leu
 50                  55                  60

Val Phe Leu Leu Ser Glu Ala His Thr Cys Ile Pro Glu Asn Asn Gly
 65                  70                  75                  80

Gly Ala Gly Cys Val Cys His Leu Leu Met Asp Asp Val Val Ser Ala
                85                  90                  95

Asp Asn Tyr Thr Leu Asp Leu Trp Ala Gly Gln Gln Leu Leu Trp Lys
                100                 105                 110

Gly Ser Phe Lys Pro Ser Glu His Val Lys Pro Arg Ala Pro Gly Asn
                115                 120                 125

Leu Thr Val His Thr Asn Val Ser Asp Thr Leu Leu Thr Trp Ser
                130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
                165                 170                 175

Val Thr Tyr Leu Glu Pro Ser Leu Arg Ile Ala Ala Ser Thr Leu Lys
                180                 185                 190

Ser Gly Ile Ser Tyr Arg Ala Arg Val Arg Ala Trp Ala Gln Cys Tyr
                195                 200                 205

Asn Thr Thr Trp Ser Glu Trp Ser Pro Ser Thr Lys Trp His Asn Ser
                210                 215                 220

Tyr Arg Glu Pro Phe Glu Gln His Leu Leu Leu Gly Val Ser Val Ser
225                 230                 235                 240

Cys Ile Val Ile Leu Ala Val Cys Leu Leu Cys Tyr Val Ser Ile Thr
                245                 250                 255

Lys Ile Lys Lys Glu Trp Trp Asp Gln Ile Pro Asn Pro Ala Arg Ser
                260                 265                 270

Arg Leu Val Ala Ile Ile Ile Gln Asp Ala Gln Gly Ser Gln Trp Glu
                275                 280                 285

Lys Arg Ser Arg Gly Gln Glu Pro Ala Lys Cys Pro His Trp Lys Asn
                290                 295                 300

Cys Leu Thr Lys Leu Leu Pro Cys Phe Leu Glu His Asn Met Lys Arg
305                 310                 315                 320

Asp Glu Asp Pro His Lys Ala Ala Lys Glu Met Pro Phe Gln Gly Ser
                325                 330                 335

Gly Lys Ser Ala Trp Cys Pro Val Glu Ile Ser Lys Thr Val Leu Trp
                340                 345                 350

Pro Glu Ser Ile Ser Val Val Arg Cys Val Glu Leu Phe Glu Ala Pro
                355                 360                 365

Val Glu Cys Glu Glu Glu Glu Val Glu Glu Lys Gly Ser Phe
                370                 375                 380

Cys Ala Ser Pro Glu Ser Ser Arg Asp Asp Phe Gln Glu Gly Arg Glu
385                 390                 395                 400

Gly Ile Val Ala Arg Leu Thr Glu Ser Leu Phe Leu Asp Leu Leu Gly
                405                 410                 415

Glu Glu Asn Gly Gly Phe Cys Gln Gln Asp Met Gly Glu Ser Cys Leu
                420                 425                 430

Leu Pro Pro Ser Gly Ser Thr Ser Ala His Met Pro Trp Asp Glu Phe
                435                 440                 445
```

```
Pro Ser Ala Gly Pro Lys Glu Ala Pro Pro Trp Gly Lys Glu Gln Pro
    450                 455                 460
Leu His Leu Glu Pro Ser Pro Ala Ser Pro Thr Gln Ser Pro Asp
465                 470                 475                 480
Asn Leu Thr Cys Thr Glu Thr Pro Leu Val Ile Ala Gly Asn Pro Ala
                485                 490                 495
Tyr Arg Ser Phe Ser Asn Ser Leu Ser Gln Ser Pro Cys Pro Arg Glu
                500                 505                 510
Leu Gly Pro Asp Pro Leu Leu Ala Arg His Leu Glu Glu Val Glu Pro
            515                 520                 525
Glu Met Pro Cys Val Pro Gln Leu Ser Glu Pro Thr Thr Val Pro Gln
    530                 535                 540
Pro Glu Pro Glu Thr Trp Glu Gln Ile Leu Arg Arg Asn Val Leu Gln
545                 550                 555                 560
His Gly Ala Ala Ala Pro Val Ser Ala Pro Thr Ser Gly Tyr Gln
                565                 570                 575
Glu Phe Val His Ala Val Glu Gln Gly Gly Thr Gln Ala Ser Ala Val
                580                 585                 590
Val Gly Leu Gly Pro Pro Gly Glu Ala Gly Tyr Lys Ala Phe Ser Ser
            595                 600                 605
Leu Leu Ala Ser Ser Ala Val Ser Pro Glu Lys Cys Gly Phe Gly Ala
        610                 615                 620
Ser Ser Gly Glu Glu Gly Tyr Lys Pro Phe Gln Asp Leu Ile Pro Gly
625                 630                 635                 640
Cys Pro Gly Asp Pro Ala Pro Val Pro Val Pro Leu Phe Thr Phe Gly
                645                 650                 655
Leu Asp Arg Glu Pro Pro Arg Ser Pro Gln Ser Ser His Leu Pro Ser
                660                 665                 670
Ser Ser Pro Glu His Leu Gly Leu Glu Pro Gly Glu Lys Val Glu Asp
            675                 680                 685
Met Pro Lys Pro Pro Leu Pro Gln Glu Gln Ala Thr Asp Pro Leu Val
    690                 695                 700
Asp Ser Leu Gly Ser Gly Ile Val Tyr Ser Ala Leu Thr Cys His Leu
705                 710                 715                 720
Cys Gly His Leu Lys Gln Cys His Gly Gln Glu Asp Gly Gly Gln Thr
                725                 730                 735
Pro Val Met Ala Ser Pro Cys Cys Gly Cys Cys Gly Asp Arg Ser
                740                 745                 750
Ser Pro Pro Thr Thr Pro Leu Arg Ala Pro Asp Pro Ser Pro Gly Gly
            755                 760                 765
Val Pro Leu Glu Ala Ser Leu Cys Pro Ala Ser Leu Ala Pro Ser Gly
770                 775                 780
Ile Ser Glu Lys Ser Lys Ser Ser Ser Phe His Pro Ala Pro Gly
785                 790                 795                 800
Asn Ala Gln Ser Ser Ser Gln Thr Pro Lys Ile Val Asn Phe Val Ser
                805                 810                 815
Val Gly Pro Thr Tyr Met Arg Val Ser
            820                 825

<210> SEQ ID NO 38
<211> LENGTH: 8
<212> TYPE: PRT
<213> ORGANISM: Artificial Sequence
<220> FEATURE:
```

<223> OTHER INFORMATION: Strep-tag II

<400> SEQUENCE: 38

Trp Ser His Pro Gln Phe Glu Lys
1               5

<210> SEQ ID NO 39
<211> LENGTH: 8
<212> TYPE: PRT
<213> ORGANISM: Artificial Sequence
<220> FEATURE:
<223> OTHER INFORMATION: Affinity tag linker element

<400> SEQUENCE: 39

Pro Ser Ser Ser Ser Ser Ser Ala
1               5

<210> SEQ ID NO 40
<211> LENGTH: 346
<212> TYPE: PRT
<213> ORGANISM: Artificial Sequence
<220> FEATURE:
<223> OTHER INFORMATION: Fusion protein
<220> FEATURE:
<221> NAME/KEY: MISC_FEATURE
<222> LOCATION: (1)..(20)
<223> OTHER INFORMATION: Signal peptide (SEQ ID NO:24)
<220> FEATURE:
<221> NAME/KEY: MISC_FEATURE
<222> LOCATION: (21)..(160)
<223> OTHER INFORMATION: CD95L receptor binding domain (residues 142-281
      of SEQ ID NO:6)
<220> FEATURE:
<221> NAME/KEY: MISC_FEATURE
<222> LOCATION: (161)..(171)
<223> OTHER INFORMATION: Flexible linker A (SEQ ID NO:34)
<220> FEATURE:
<221> NAME/KEY: MISC_FEATURE
<222> LOCATION: (172)..(327)
<223> OTHER INFORMATION: SP-D collectin trimerization domain (residues
      220-375 of SEQ ID NO:21)
<220> FEATURE:
<221> NAME/KEY: MISC_FEATURE
<222> LOCATION: (172)..(209)
<223> OTHER INFORMATION: SP-D neck region (residues 220-257 of SEQ ID
      NO:21)
<220> FEATURE:
<221> NAME/KEY: MISC_FEATURE
<222> LOCATION: (210)..(327)
<223> OTHER INFORMATION: SP-D CRD (residues 258-375 of SEQ ID NO:21)
<220> FEATURE:
<221> NAME/KEY: MISC_FEATURE
<222> LOCATION: (328)..(338)
<223> OTHER INFORMATION: Affinity tag linker element (SEQ ID NO:54)
<220> FEATURE:
<221> NAME/KEY: MISC_FEATURE
<222> LOCATION: (339)..(346)
<223> OTHER INFORMATION: Strep-tag II (SEQ ID NO:38)

<400> SEQUENCE: 40

Met Glu Thr Asp Thr Leu Leu Leu Trp Val Leu Leu Leu Trp Val Pro
1               5                   10                  15

Gly Ser Thr Gly Glu Leu Arg Lys Val Ala His Leu Thr Gly Lys Ser
            20                  25                  30

Asn Ser Arg Ser Met Pro Leu Glu Trp Glu Asp Thr Tyr Gly Ile Val
        35                  40                  45

Leu Leu Ser Gly Val Lys Tyr Lys Lys Gly Gly Leu Val Ile Asn Glu
    50                  55                  60

Thr Gly Leu Tyr Phe Val Tyr Ser Lys Val Tyr Phe Arg Gly Gln Ser
65                  70                  75                  80

```
Cys Asn Asn Leu Pro Leu Ser His Lys Val Tyr Met Arg Asn Ser Lys
                 85                  90                  95

Tyr Pro Gln Asp Leu Val Met Met Glu Gly Lys Met Met Ser Tyr Cys
            100                 105                 110

Thr Thr Gly Gln Met Trp Ala Arg Ser Ser Tyr Val Gly Ala Val Phe
        115                 120                 125

Asn Leu Thr Ser Ala Asp His Leu Tyr Val Asn Val Ser Glu Leu Ser
    130                 135                 140

Leu Val Asn Phe Glu Glu Ser Gln Thr Phe Phe Gly Leu Tyr Lys Leu
145                 150                 155                 160

Gly Ser Ser Gly Ser Ser Gly Ser Ser Gly Ser Gly Leu Pro Asp Val
                165                 170                 175

Ala Ser Leu Arg Gln Gln Val Glu Ala Leu Gln Gly Gln Val Gln His
            180                 185                 190

Leu Gln Ala Ala Phe Ser Gln Tyr Lys Lys Val Glu Leu Phe Pro Asn
        195                 200                 205

Gly Gln Ser Val Gly Glu Lys Ile Phe Lys Thr Ala Gly Phe Val Lys
    210                 215                 220

Pro Phe Thr Glu Ala Gln Leu Leu Cys Thr Gln Ala Gly Gly Gln Leu
225                 230                 235                 240

Ala Ser Pro Arg Ser Ala Ala Glu Asn Ala Ala Leu Gln Gln Leu Val
                245                 250                 255

Val Ala Lys Asn Glu Ala Ala Phe Leu Ser Met Thr Asp Ser Lys Thr
            260                 265                 270

Glu Gly Lys Phe Thr Tyr Pro Thr Gly Glu Ser Leu Val Tyr Ser Asn
        275                 280                 285

Trp Ala Pro Gly Glu Pro Asn Asp Asp Gly Gly Ser Glu Asp Cys Val
    290                 295                 300

Glu Ile Phe Thr Asn Gly Lys Trp Asn Asp Arg Ala Cys Gly Glu Lys
305                 310                 315                 320

Arg Leu Val Val Cys Glu Phe Gly Gly Ser Pro Ser Ser Ser Ser Ser
                325                 330                 335

Ser Ala Trp Ser His Pro Gln Phe Glu Lys
                340                 345

<210> SEQ ID NO 41
<211> LENGTH: 356
<212> TYPE: PRT
<213> ORGANISM: Artificial Sequence
<220> FEATURE:
<223> OTHER INFORMATION: Fusion protein
<220> FEATURE:
<221> NAME/KEY: MISC_FEATURE
<222> LOCATION: (1)..(20)
<223> OTHER INFORMATION: Signal peptide 2 (SEQ ID NO:24)
<220> FEATURE:
<221> NAME/KEY: MISC_FEATURE
<222> LOCATION: (21)..(170)
<223> OTHER INFORMATION: LIGHT receptor binding domain (residues 91-240
      of SEQ ID NO:16)
<220> FEATURE:
<221> NAME/KEY: MISC_FEATURE
<222> LOCATION: (171)..(181)
<223> OTHER INFORMATION: Flexible linker A (SEQ ID NO:34)
<220> FEATURE:
<221> NAME/KEY: MISC_FEATURE
<222> LOCATION: (182)..(337)
<223> OTHER INFORMATION: SP-D collectin trimerization domain (residues
      220-375 of SEQ ID NO:21)
<220> FEATURE:
<221> NAME/KEY: MISC_FEATURE
```

-continued

```
<222> LOCATION: (182)..(219)
<223> OTHER INFORMATION: SP-D neck region (residues 220-257 of SEQ ID
      NO:21)
<220> FEATURE:
<221> NAME/KEY: MISC_FEATURE
<222> LOCATION: (220)..(337)
<223> OTHER INFORMATION: SP-D CRD (residues 258-375 of SEQ ID NO:21)
<220> FEATURE:
<221> NAME/KEY: MISC_FEATURE
<222> LOCATION: (338)..(348)
<223> OTHER INFORMATION: Affinity tag linker element 2 (SEQ ID NO:54)
<220> FEATURE:
<221> NAME/KEY: MISC_FEATURE
<222> LOCATION: (349)..(356)
<223> OTHER INFORMATION: Strep-tag II (SEQ ID NO:38)

<400> SEQUENCE: 41

Met Glu Thr Asp Thr Leu Leu Leu Trp Val Leu Leu Leu Trp Val Pro
1               5                   10                  15

Gly Ser Thr Gly Glu Val Asn Pro Ala Ala His Leu Thr Gly Ala Asn
            20                  25                  30

Ser Ser Leu Thr Gly Ser Gly Pro Leu Leu Trp Glu Thr Gln Leu
        35                  40                  45

Gly Leu Ala Phe Leu Arg Gly Leu Ser Tyr His Asp Gly Ala Leu Val
50                  55                  60

Val Thr Lys Ala Gly Tyr Tyr Tyr Ile Tyr Ser Lys Val Gln Leu Gly
65                  70                  75                  80

Gly Val Gly Cys Pro Leu Gly Leu Ala Ser Thr Ile Thr His Gly Leu
                85                  90                  95

Tyr Lys Arg Thr Pro Arg Tyr Pro Glu Glu Leu Glu Leu Leu Val Ser
            100                 105                 110

Gln Gln Ser Pro Cys Gly Arg Ala Thr Ser Ser Ser Arg Val Trp Trp
        115                 120                 125

Asp Ser Ser Phe Leu Gly Gly Val Val His Leu Glu Ala Gly Glu Glu
130                 135                 140

Val Val Val Arg Val Leu Asp Glu Arg Leu Val Arg Leu Arg Asp Gly
145                 150                 155                 160

Thr Arg Ser Tyr Phe Gly Ala Phe Met Val Gly Ser Ser Gly Ser Ser
                165                 170                 175

Gly Ser Ser Gly Ser Gly Leu Pro Asp Val Ala Ser Leu Arg Gln Gln
            180                 185                 190

Val Glu Ala Leu Gln Gly Gln Val Gln His Leu Gln Ala Ala Phe Ser
        195                 200                 205

Gln Tyr Lys Lys Val Glu Leu Phe Pro Asn Gly Gln Ser Val Gly Glu
    210                 215                 220

Lys Ile Phe Lys Thr Ala Gly Phe Val Lys Pro Phe Thr Glu Ala Gln
225                 230                 235                 240

Leu Leu Cys Thr Gln Ala Gly Gly Gln Leu Ala Ser Pro Arg Ser Ala
                245                 250                 255

Ala Glu Asn Ala Ala Leu Gln Gln Leu Val Val Ala Lys Asn Glu Ala
            260                 265                 270

Ala Phe Leu Ser Met Thr Asp Ser Lys Thr Glu Gly Lys Phe Thr Tyr
        275                 280                 285

Pro Thr Gly Glu Ser Leu Val Tyr Ser Asn Trp Ala Pro Gly Glu Pro
    290                 295                 300

Asn Asp Asp Gly Gly Ser Glu Asp Cys Val Glu Ile Phe Thr Asn Gly
305                 310                 315                 320

Lys Trp Asn Asp Arg Ala Cys Gly Glu Lys Arg Leu Val Val Cys Glu
```

Phe Gly Gly Ser Pro Ser Ser Ser Ser Ala Trp Ser His Pro
            325                 330                 335
Gln Phe Glu Lys
        355

<210> SEQ ID NO 42
<211> LENGTH: 1129
<212> TYPE: DNA
<213> ORGANISM: Artificial Sequence
<220> FEATURE:
<223> OTHER INFORMATION: Expression cassette for TRAIL-SPD fusion
      protein 3 (SEQ ID NO:43)
<220> FEATURE:
<221> NAME/KEY: misc_feature
<222> LOCATION: (1)..(6)
<223> OTHER INFORMATION: HindIII restriction site
<220> FEATURE:
<221> NAME/KEY: misc_feature
<222> LOCATION: (16)..(18)
<223> OTHER INFORMATION: Start codon
<220> FEATURE:
<221> NAME/KEY: misc_feature
<222> LOCATION: (559)..(564)
<223> OTHER INFORMATION: BamHI restriction site
<220> FEATURE:
<221> NAME/KEY: misc_feature
<222> LOCATION: (1122)..(1129)
<223> OTHER INFORMATION: NotI restriction site

<400> SEQUENCE: 42
aagcttgccg ccaccatgga gaccgataca ctgctcttgt gggtgctctt gctgtgggtt      60
cctgcaggta atggtcaaag agtcgcagct cacatcactg ggactagagg caggagtaac     120
accctgagtt ctcccaattc caagaacgag aaagccctgg gtaggaagat caactcctgg     180
gaaagctcca gaagcggcca tagctttctt agcaacctcc acttgaggaa tggcgaactt     240
gtgatccatg agaagggctt ctactacatc tacagccaga cgtacttcag gttccaggag     300
gaaatcaagg agaacaccaa gaacgacaag cagatggtgc aatacatcta caagtacacg     360 tcatacccctg atcctatact gctgatgaag tccgccagaa acagttgctg gagcaaagac     420
gctgaatacg gcctgtattc catctatcag ggcggtatct ttgaactcaa ggagaacgac     480
aggatcttcg tgtctgtgac aaacgagcat ctgatcgaca tggaccatga agcgtctttc     540
ttcggtgcct tcttggtggg atcctctggt tcgagtggtt cgagtggttc tggattgcca     600
gacgttgctt ctttgagaca acaggttgag gctttgcagg tcaagtcca gcacttgcag     660 gctgcttttct ctcaatacaa gaaggttgag ttgttcccaa acggtcaatc tgttggcgaa     720
aagattttca agactgctgg tttcgtcaaa ccattcacgg aggcacaatt attgtgtact     780
caggctggtg gacagttggc ctctccacgt tctgccgctg agaacgccgc cttgcaacag     840
ttggtcgtag ctaagaacga ggctgctttc ttgagcatga ctgattccaa gacagagggc     900
aagttcacct acccaacagg agaatccttg gtctattcta attgggcacc tggagagccc     960
aacgatgatg gcggctcaga ggactgtgtg gaaatcttca ccaatggcaa gtggaatgac    1020
agagcttgtg gagagaagcg tttggtggtc tgtgagttcg gaggcagtcc ttcatcttca    1080
tctagctctc cctggtcgca tccacaattc gagaaataat agcggccgc                1129

<210> SEQ ID NO 43
<211> LENGTH: 367
<212> TYPE: PRT
<213> ORGANISM: Artificial Sequence
<220> FEATURE:

<223> OTHER INFORMATION: Fusion protein
<220> FEATURE:
<221> NAME/KEY: MISC_FEATURE
<222> LOCATION: (1)..(20)
<223> OTHER INFORMATION: Signal peptide 3 (SEQ ID NO:25)
<220> FEATURE:
<221> NAME/KEY: MISC_FEATURE
<222> LOCATION: (21)..(181)
<223> OTHER INFORMATION: TRAIL receptor binding domain (residues 120-280 of SEQ ID NO:10)
<220> FEATURE:
<221> NAME/KEY: MISC_FEATURE
<222> LOCATION: (182)..(192)
<223> OTHER INFORMATION: Flexible linker A (SEQ ID NO:34)
<220> FEATURE:
<221> NAME/KEY: MISC_FEATURE
<222> LOCATION: (193)..(348)
<223> OTHER INFORMATION: SP-D collectin trimerization domain (residues 220-375 of SEQ ID NO:21)
<220> FEATURE:
<221> NAME/KEY: MISC_FEATURE
<222> LOCATION: (193)..(230)
<223> OTHER INFORMATION: SP-D neck region (residues 220-257 of SEQ ID NO:21)
<220> FEATURE:
<221> NAME/KEY: MISC_FEATURE
<222> LOCATION: (231)..(348)
<223> OTHER INFORMATION: SP-D CRD (residues 258-375 of SEQ ID NO:21)
<220> FEATURE:
<221> NAME/KEY: MISC_FEATURE
<222> LOCATION: (349)..(359)
<223> OTHER INFORMATION: Affinity tag linker element 2 (SEQ ID NO:54)
<220> FEATURE:
<221> NAME/KEY: MISC_FEATURE
<222> LOCATION: (360)..(367)
<223> OTHER INFORMATION: Strep-tag II (SEQ ID NO:38)

<400> SEQUENCE: 43

Met Glu Thr Asp Thr Leu Leu Leu Trp Val Leu Leu Leu Trp Val Pro
1               5                   10                  15

Ala Gly Asn Gly Gln Arg Val Ala Ala His Ile Thr Gly Thr Arg Gly
            20                  25                  30

Arg Ser Asn Thr Leu Ser Ser Pro Asn Ser Lys Asn Glu Lys Ala Leu
        35                  40                  45

Gly Arg Lys Ile Asn Ser Trp Glu Ser Ser Arg Ser Gly His Ser Phe
    50                  55                  60

Leu Ser Asn Leu His Leu Arg Asn Gly Glu Leu Val Ile His Glu Lys
65                  70                  75                  80

Gly Phe Tyr Tyr Ile Tyr Ser Gln Thr Tyr Phe Arg Phe Gln Glu Glu
                85                  90                  95

Ile Lys Glu Asn Thr Lys Asn Asp Lys Gln Met Val Gln Tyr Ile Tyr
            100                 105                 110

Lys Tyr Thr Ser Tyr Pro Asp Pro Ile Leu Leu Met Lys Ser Ala Arg
        115                 120                 125

Asn Ser Cys Trp Ser Lys Asp Ala Glu Tyr Gly Leu Tyr Ser Ile Tyr
    130                 135                 140

Gln Gly Gly Ile Phe Glu Leu Lys Glu Asn Asp Arg Ile Phe Val Ser
145                 150                 155                 160

Val Thr Asn Glu His Leu Ile Asp Met Asp His Glu Ala Ser Phe Phe
                165                 170                 175

Gly Ala Phe Leu Val Gly Ser Ser Gly Ser Ser Gly Ser Gly Ser
            180                 185                 190

Gly Leu Pro Asp Val Ala Ser Leu Arg Gln Gln Val Glu Ala Leu Gln
        195                 200                 205

Gly Gln Val Gln His Leu Gln Ala Ala Phe Ser Gln Tyr Lys Lys Val

```
            210                 215                 220
Glu Leu Phe Pro Asn Gly Gln Ser Val Gly Glu Lys Ile Phe Lys Thr
225                 230                 235                 240

Ala Gly Phe Val Lys Pro Phe Thr Glu Ala Gln Leu Leu Cys Thr Gln
                245                 250                 255

Ala Gly Gly Gln Leu Ala Ser Pro Arg Ser Ala Ala Glu Asn Ala Ala
            260                 265                 270

Leu Gln Gln Leu Val Val Ala Lys Asn Glu Ala Ala Phe Leu Ser Met
        275                 280                 285

Thr Asp Ser Lys Thr Glu Gly Lys Phe Thr Tyr Pro Thr Gly Glu Ser
    290                 295                 300

Leu Val Tyr Ser Asn Trp Ala Pro Gly Glu Pro Asn Asp Asp Gly Gly
305                 310                 315                 320

Ser Glu Asp Cys Val Glu Ile Phe Thr Asn Gly Lys Trp Asn Asp Arg
                325                 330                 335

Ala Cys Gly Glu Lys Arg Leu Val Val Cys Glu Phe Gly Gly Ser Pro
            340                 345                 350

Ser Ser Ser Ser Ser Ser Ala Trp Ser His Pro Gln Phe Glu Lys
        355                 360                 365
```

<210> SEQ ID NO 44
<211> LENGTH: 246
<212> TYPE: PRT
<213> ORGANISM: Artificial Sequence
<220> FEATURE:
<223> OTHER INFORMATION: Fusion protein
<220> FEATURE:
<221> NAME/KEY: MISC_FEATURE
<222> LOCATION: (1)..(20)
<223> OTHER INFORMATION: Signal peptide 3 (SEQ ID NO:25)
<220> FEATURE:
<221> NAME/KEY: MISC_FEATURE
<222> LOCATION: (21)..(181)
<223> OTHER INFORMATION: TRAIL receptor binding domain (residues 120-280
      of SEQ ID NO:10)
<220> FEATURE:
<221> NAME/KEY: MISC_FEATURE
<222> LOCATION: (182)..(192)
<223> OTHER INFORMATION: Flexible linker A (SEQ ID NO:34)
<220> FEATURE:
<221> NAME/KEY: MISC_FEATURE
<222> LOCATION: (193)..(230)
<223> OTHER INFORMATION: SP-D neck region (residues 220-257 of SEQ ID
      NO:21)
<220> FEATURE:
<221> NAME/KEY: MISC_FEATURE
<222> LOCATION: (231)..(238)
<223> OTHER INFORMATION: Affinity tag linker element (SEQ ID NO:39)
<220> FEATURE:
<221> NAME/KEY: MISC_FEATURE
<222> LOCATION: (239)..(246)
<223> OTHER INFORMATION: Strep-tag II (SEQ ID NO:38)

<400> SEQUENCE: 44

```
Met Glu Thr Asp Thr Leu Leu Leu Trp Val Leu Leu Leu Trp Val Pro
1               5                   10                  15

Ala Gly Asn Gly Gln Arg Val Ala Ala His Ile Thr Gly Thr Arg Gly
                20                  25                  30

Arg Ser Asn Thr Leu Ser Ser Pro Asn Ser Lys Asn Glu Lys Ala Leu
            35                  40                  45

Gly Arg Lys Ile Asn Ser Trp Glu Ser Ser Arg Ser Gly His Ser Phe
        50                  55                  60

Leu Ser Asn Leu His Leu Arg Asn Gly Glu Leu Val Ile His Glu Lys
65                  70                  75                  80
```

```
Gly Phe Tyr Tyr Ile Tyr Ser Gln Thr Tyr Phe Arg Phe Gln Glu Glu
                85                  90                  95

Ile Lys Glu Asn Thr Lys Asn Asp Lys Gln Met Val Gln Tyr Ile Tyr
            100                 105                 110

Lys Tyr Thr Ser Tyr Pro Asp Pro Ile Leu Leu Met Lys Ser Ala Arg
        115                 120                 125

Asn Ser Cys Trp Ser Lys Asp Ala Glu Tyr Gly Leu Tyr Ser Ile Tyr
130                 135                 140

Gln Gly Gly Ile Phe Glu Leu Lys Glu Asn Asp Arg Ile Phe Val Ser
145                 150                 155                 160

Val Thr Asn Glu His Leu Ile Asp Met Asp His Glu Ala Ser Phe Phe
                165                 170                 175

Gly Ala Phe Leu Val Gly Ser Ser Gly Ser Ser Gly Ser Ser Gly Ser
            180                 185                 190

Gly Leu Pro Asp Val Ala Ser Leu Arg Gln Gln Val Glu Ala Leu Gln
        195                 200                 205

Gly Gln Val Gln His Leu Gln Ala Ala Phe Ser Gln Tyr Lys Lys Val
    210                 215                 220

Glu Leu Phe Pro Asn Gly Pro Ser Ser Ser Ser Ser Ala Trp Ser
225                 230                 235                 240

His Pro Gln Phe Glu Lys
                245

<210> SEQ ID NO 45
<211> LENGTH: 365
<212> TYPE: PRT
<213> ORGANISM: Artificial Sequence
<220> FEATURE:
<223> OTHER INFORMATION: Fusion protein
<220> FEATURE:
<221> NAME/KEY: MISC_FEATURE
<222> LOCATION: (1)..(20)
<223> OTHER INFORMATION: Signal peptide 3 (SEQ ID NO:25)
<220> FEATURE:
<221> NAME/KEY: MISC_FEATURE
<222> LOCATION: (21)..(181)
<223> OTHER INFORMATION: TRAIL receptor binding domain (residues 120-280
      of SEQ ID NO:10)
<220> FEATURE:
<221> NAME/KEY: MISC_FEATURE
<222> LOCATION: (182)..(192)
<223> OTHER INFORMATION: Flexible linker A (SEQ ID NO:34)
<220> FEATURE:
<221> NAME/KEY: MISC_FEATURE
<222> LOCATION: (193)..(347)
<223> OTHER INFORMATION: Collectin-11 colletin trimerization domain
      (residues 117-271 of SEQ ID NO:22)
<220> FEATURE:
<221> NAME/KEY: MISC_FEATURE
<222> LOCATION: (193)..(224)
<223> OTHER INFORMATION: Collectin-11 neck region (residues 117-148 of
      SEQ ID NO:22)
<220> FEATURE:
<221> NAME/KEY: MISC_FEATURE
<222> LOCATION: (225)..(347)
<223> OTHER INFORMATION: Collectin-11 CRD (residues 149-271 of SEQ ID
      NO:22)
<220> FEATURE:
<221> NAME/KEY: MISC_FEATURE
<222> LOCATION: (348)..(357)
<223> OTHER INFORMATION: Affinity tag linker element 3 (SEQ ID NO:55)
<220> FEATURE:
<221> NAME/KEY: MISC_FEATURE
<222> LOCATION: (358)..(365)
<223> OTHER INFORMATION: Strep-tag II (SEQ ID NO:38)

<400> SEQUENCE: 45
```

```
Met Glu Thr Asp Thr Leu Leu Leu Trp Val Leu Leu Leu Trp Val Pro
1               5                   10                  15

Ala Gly Asn Gly Gln Arg Val Ala Ala His Ile Thr Gly Thr Arg Gly
            20                  25                  30

Arg Ser Asn Thr Leu Ser Ser Pro Asn Ser Lys Asn Glu Lys Ala Leu
        35                  40                  45

Gly Arg Lys Ile Asn Ser Trp Glu Ser Ser Arg Ser Gly His Ser Phe
    50                  55                  60

Leu Ser Asn Leu His Leu Arg Asn Gly Glu Leu Val Ile His Glu Lys
65                  70                  75                  80

Gly Phe Tyr Tyr Ile Tyr Ser Gln Thr Tyr Phe Arg Phe Gln Glu Glu
                85                  90                  95

Ile Lys Glu Asn Thr Lys Asn Asp Lys Gln Met Val Gln Tyr Ile Tyr
                100                 105                 110

Lys Tyr Thr Ser Tyr Pro Asp Pro Ile Leu Leu Met Lys Ser Ala Arg
            115                 120                 125

Asn Ser Cys Trp Ser Lys Asp Ala Glu Tyr Gly Leu Tyr Ser Ile Tyr
        130                 135                 140

Gln Gly Gly Ile Phe Glu Leu Lys Glu Asn Asp Arg Ile Phe Val Ser
145                 150                 155                 160

Val Thr Asn Glu His Leu Ile Asp Met Asp His Glu Ala Ser Phe Phe
                165                 170                 175

Gly Ala Phe Leu Val Gly Ser Ser Gly Ser Ser Gly Ser Ser Gly Ser
                180                 185                 190

Gln Leu Arg Lys Ala Ile Gly Glu Met Asp Asn Gln Val Ser Gln Leu
        195                 200                 205

Thr Ser Glu Leu Lys Phe Ile Lys Asn Ala Val Ala Gly Val Arg Glu
210                 215                 220

Thr Glu Ser Lys Ile Tyr Leu Leu Val Lys Glu Lys Arg Tyr Ala
225                 230                 235                 240

Asp Ala Gln Leu Ser Cys Gln Gly Arg Gly Thr Leu Ser Met Pro
                245                 250                 255

Lys Asp Glu Ala Ala Asn Gly Leu Met Ala Ala Tyr Leu Ala Gln Ala
            260                 265                 270

Gly Leu Ala Arg Val Phe Ile Gly Ile Asn Asp Leu Glu Lys Glu Gly
            275                 280                 285

Ala Phe Val Tyr Ser Asp His Ser Pro Met Arg Thr Phe Asn Lys Trp
    290                 295                 300

Arg Ser Gly Glu Pro Asn Asn Ala Tyr Asp Glu Asp Cys Val Glu
305                 310                 315                 320

Met Val Ala Ser Gly Gly Trp Asn Asp Val Ala Cys His Thr Thr Met
                325                 330                 335

Tyr Phe Met Cys Glu Phe Asp Lys Glu Asn Met Gly Ser Pro Ser Ser
                340                 345                 350

Ser Ser Ser Ser Ala Trp Ser His Pro Gln Phe Glu Lys
                355                 360                 365

<210> SEQ ID NO 46
<211> LENGTH: 246
<212> TYPE: PRT
<213> ORGANISM: Artificial Sequence
<220> FEATURE:
<223> OTHER INFORMATION: Fusion protein
<220> FEATURE:
<221> NAME/KEY: MISC_FEATURE
```

```
<222> LOCATION: (1)..(20)
<223> OTHER INFORMATION: Signal peptide 3 (SEQ ID NO:25)
<220> FEATURE:
<221> NAME/KEY: MISC_FEATURE
<222> LOCATION: (21)..(181)
<223> OTHER INFORMATION: TRAIL receptor binding domain (residues 120-280
      of SEQ ID NO:10)
<220> FEATURE:
<221> NAME/KEY: MISC_FEATURE
<222> LOCATION: (182)..(193)
<223> OTHER INFORMATION: Flexible linker E (SEQ ID NO:56)
<220> FEATURE:
<221> NAME/KEY: MISC_FEATURE
<222> LOCATION: (194)..(229)
<223> OTHER INFORMATION: Collectin-11 neck region (residues 116-151 of
      SEQ ID NO:22)
<220> FEATURE:
<221> NAME/KEY: MISC_FEATURE
<222> LOCATION: (230)..(238)
<223> OTHER INFORMATION: Affinity tag linker element 4 (SEQ ID NO:57)
<220> FEATURE:
<221> NAME/KEY: MISC_FEATURE
<222> LOCATION: (239)..(246)
<223> OTHER INFORMATION: Strep-tag II (SEQ ID NO:38)

<400> SEQUENCE: 46

Met Glu Thr Asp Thr Leu Leu Leu Trp Val Leu Leu Trp Val Pro
 1               5                  10                  15

Ala Gly Asn Gly Gln Arg Val Ala Ala His Ile Thr Gly Thr Arg Gly
                 20                  25                  30

Arg Ser Asn Thr Leu Ser Ser Pro Asn Ser Lys Asn Glu Lys Ala Leu
             35                  40                  45

Gly Arg Lys Ile Asn Ser Trp Glu Ser Ser Arg Ser Gly His Ser Phe
     50                  55                  60

Leu Ser Asn Leu His Leu Arg Asn Gly Glu Leu Val Ile His Glu Lys
65                  70                  75                  80

Gly Phe Tyr Tyr Ile Tyr Ser Gln Thr Tyr Phe Arg Phe Gln Glu Glu
                 85                  90                  95

Ile Lys Glu Asn Thr Lys Asn Asp Lys Gln Met Val Gln Tyr Ile Tyr
            100                 105                 110

Lys Tyr Thr Ser Tyr Pro Asp Pro Ile Leu Leu Met Lys Ser Ala Arg
        115                 120                 125

Asn Ser Cys Trp Ser Lys Asp Ala Glu Tyr Gly Leu Tyr Ser Ile Tyr
130                 135                 140

Gln Gly Gly Ile Phe Glu Leu Lys Glu Asn Asp Arg Ile Phe Val Ser
145                 150                 155                 160

Val Thr Asn Glu His Leu Ile Asp Met Asp His Glu Ala Ser Phe Phe
                165                 170                 175

Gly Ala Phe Leu Val Gly Ser Ser Gly Ser Ser Gly Ser Ser Gly Ser
            180                 185                 190

Gly Ser Gln Leu Arg Lys Ala Ile Gly Glu Met Asp Asn Gln Val Ser
        195                 200                 205

Gln Leu Thr Ser Glu Leu Lys Phe Ile Lys Asn Ala Val Ala Gly Val
    210                 215                 220

Arg Glu Thr Glu Ser Gly Pro Ser Ser Ser Ser Ser Ala Trp Ser
225                 230                 235                 240

His Pro Gln Phe Glu Lys
                245

<210> SEQ ID NO 47
<211> LENGTH: 367
<212> TYPE: PRT
```

```
<213> ORGANISM: Artificial Sequence
<220> FEATURE:
<223> OTHER INFORMATION: Fusion protein
<220> FEATURE:
<221> NAME/KEY: MISC_FEATURE
<222> LOCATION: (1)..(20)
<223> OTHER INFORMATION: Signal peptide 3 (SEQ ID NO:25)
<220> FEATURE:
<221> NAME/KEY: MISC_FEATURE
<222> LOCATION: (21)..(181)
<223> OTHER INFORMATION: TRAIL mutant 1 receptor binding domain
      (residues 120-280 of SEQ ID NO:10 with Y189A, Q193S, N199V, K201R,
      Y213W, S215D)
<220> FEATURE:
<221> NAME/KEY: MISC_FEATURE
<222> LOCATION: (182)..(192)
<223> OTHER INFORMATION: Flexible linker A (SEQ ID NO:34)
<220> FEATURE:
<221> NAME/KEY: MISC_FEATURE
<222> LOCATION: (193)..(348)
<223> OTHER INFORMATION: SP-D collectin trimerization domain (residues
      220-375 of SEQ ID NO:21)
<220> FEATURE:
<221> NAME/KEY: MISC_FEATURE
<222> LOCATION: (193)..(230)
<223> OTHER INFORMATION: SP-D neck region (residues 220-257 of SEQ ID
      NO:21)
<220> FEATURE:
<221> NAME/KEY: MISC_FEATURE
<222> LOCATION: (231)..(348)
<223> OTHER INFORMATION: SP-D CRD (residues 258-375 of SEQ ID NO:21)
<220> FEATURE:
<221> NAME/KEY: MISC_FEATURE
<222> LOCATION: (349)..(359)
<223> OTHER INFORMATION: Affinity tag linker element 2 (SEQ ID NO:54)
<220> FEATURE:
<221> NAME/KEY: MISC_FEATURE
<222> LOCATION: (360)..(367)
<223> OTHER INFORMATION: Strep-tag II (SEQ ID NO:38)

<400> SEQUENCE: 47

Met Glu Thr Asp Thr Leu Leu Leu Trp Val Leu Leu Leu Trp Val Pro
1               5                   10                  15

Ala Gly Asn Gly Gln Arg Val Ala Ala His Ile Thr Gly Thr Arg Gly
            20                  25                  30

Arg Ser Asn Thr Leu Ser Ser Pro Asn Ser Lys Asn Glu Lys Ala Leu
        35                  40                  45

Gly Arg Lys Ile Asn Ser Trp Glu Ser Ser Arg Ser Gly His Ser Phe
    50                  55                  60

Leu Ser Asn Leu His Leu Arg Asn Gly Glu Leu Val Ile His Glu Lys
65                  70                  75                  80

Gly Phe Tyr Tyr Ile Tyr Ser Gln Thr Ala Phe Arg Phe Ser Glu Glu
                85                  90                  95

Ile Lys Glu Val Thr Arg Asn Asp Lys Gln Met Val Gln Tyr Ile Tyr
            100                 105                 110

Lys Trp Thr Asp Tyr Pro Asp Pro Ile Leu Leu Met Lys Ser Ala Arg
        115                 120                 125

Asn Ser Cys Trp Ser Lys Asp Ala Glu Tyr Gly Leu Tyr Ser Ile Tyr
    130                 135                 140

Gln Gly Gly Ile Phe Glu Leu Lys Glu Asn Asp Arg Ile Phe Val Ser
145                 150                 155                 160

Val Thr Asn Glu His Leu Ile Asp Met Asp His Glu Ala Ser Phe Phe
                165                 170                 175

Gly Ala Phe Leu Val Gly Ser Ser Gly Ser Ser Gly Ser Ser Gly Ser
            180                 185                 190

Gly Leu Pro Asp Val Ala Ser Leu Arg Gln Gln Val Glu Ala Leu Gln
```

```
              195                 200                 205
Gly Gln Val Gln His Leu Gln Ala Ala Phe Ser Gln Tyr Lys Lys Val
        210                 215                 220
Glu Leu Phe Pro Asn Gly Gln Ser Val Gly Glu Lys Ile Phe Lys Thr
225                 230                 235                 240
Ala Gly Phe Val Lys Pro Phe Thr Glu Ala Gln Leu Leu Cys Thr Gln
                    245                 250                 255
Ala Gly Gly Gln Leu Ala Ser Pro Arg Ser Ala Glu Asn Ala Ala
                260                 265                 270
Leu Gln Gln Leu Val Val Ala Lys Asn Glu Ala Ala Phe Leu Ser Met
            275                 280                 285
Thr Asp Ser Lys Thr Glu Gly Lys Phe Thr Tyr Pro Thr Gly Glu Ser
290                 295                 300
Leu Val Tyr Ser Asn Trp Ala Pro Gly Glu Pro Asn Asp Asp Gly Gly
305                 310                 315                 320
Ser Glu Asp Cys Val Glu Ile Phe Thr Asn Gly Lys Trp Asn Asp Arg
                325                 330                 335
Ala Cys Gly Glu Lys Arg Leu Val Val Cys Glu Phe Gly Gly Ser Pro
                340                 345                 350
Ser Ser Ser Ser Ser Ser Ala Trp Ser His Pro Gln Phe Glu Lys
            355                 360                 365
```

<210> SEQ ID NO 48
<211> LENGTH: 367
<212> TYPE: PRT
<213> ORGANISM: Artificial Sequence
<220> FEATURE:
<223> OTHER INFORMATION: Fusion protein
<220> FEATURE:
<221> NAME/KEY: MISC_FEATURE
<222> LOCATION: (1)..(20)
<223> OTHER INFORMATION: Signal peptide 3 (SEQ ID NO:25)
<220> FEATURE:
<221> NAME/KEY: MISC_FEATURE
<222> LOCATION: (21)..(181)
<223> OTHER INFORMATION: TRAIL mutant 2 receptor binding domain
    (residues 120-280 of SEQ ID NO:10 with Y189Q, R191K, Q193R, H264R,
    I266L, D267Q)
<220> FEATURE:
<221> NAME/KEY: MISC_FEATURE
<222> LOCATION: (182)..(192)
<223> OTHER INFORMATION: Flexible linker A (SEQ ID NO:34)
<220> FEATURE:
<221> NAME/KEY: MISC_FEATURE
<222> LOCATION: (193)..(348)
<223> OTHER INFORMATION: SP-D collectin trimerization domain (residues
    220-375 of SEQ ID NO:21)
<220> FEATURE:
<221> NAME/KEY: MISC_FEATURE
<222> LOCATION: (193)..(230)
<223> OTHER INFORMATION: SP-D neck region (residues 220-257 of SEQ ID
    NO:21)
<220> FEATURE:
<221> NAME/KEY: MISC_FEATURE
<222> LOCATION: (231)..(348)
<223> OTHER INFORMATION: SP-D CRD (residues 258-375 of SEQ ID NO:21)
<220> FEATURE:
<221> NAME/KEY: MISC_FEATURE
<222> LOCATION: (349)..(359)
<223> OTHER INFORMATION: Affinity tag linker element 2 (SEQ ID NO:54)
<220> FEATURE:
<221> NAME/KEY: MISC_FEATURE
<222> LOCATION: (360)..(367)
<223> OTHER INFORMATION: Strep-tag II (SEQ ID NO:38)

<400> SEQUENCE: 48

Met Glu Thr Asp Thr Leu Leu Leu Trp Val Leu Leu Leu Trp Val Pro

```
  1               5                  10                 15
Ala Gly Asn Gly Gln Arg Val Ala Ala His Ile Thr Gly Thr Arg Gly
             20                 25                 30

Arg Ser Asn Thr Leu Ser Ser Pro Asn Ser Lys Asn Glu Lys Ala Leu
             35                 40                 45

Gly Arg Lys Ile Asn Ser Trp Glu Ser Ser Arg Ser Gly His Ser Phe
             50                 55                 60

Leu Ser Asn Leu His Leu Arg Asn Gly Glu Leu Val Ile His Glu Lys
 65                 70                 75                 80

Gly Phe Tyr Tyr Ile Tyr Ser Gln Thr Gln Phe Lys Phe Arg Glu Glu
                 85                 90                 95

Ile Lys Glu Asn Thr Lys Asn Asp Lys Gln Met Val Gln Tyr Ile Tyr
            100                105                110

Lys Tyr Thr Ser Tyr Pro Asp Pro Ile Leu Leu Met Lys Ser Ala Arg
            115                120                125

Asn Ser Cys Trp Ser Lys Asp Ala Glu Tyr Gly Leu Tyr Ser Ile Tyr
            130                135                140

Gln Gly Gly Ile Phe Glu Leu Lys Glu Asn Asp Arg Ile Phe Val Ser
145                150                155                160

Val Thr Asn Glu Arg Leu Leu Gln Met Asp His Glu Ala Ser Phe Phe
                165                170                175

Gly Ala Phe Leu Val Gly Ser Ser Gly Ser Ser Gly Ser Ser Gly Ser
                180                185                190

Gly Leu Pro Asp Val Ala Ser Leu Arg Gln Gln Val Glu Ala Leu Gln
                195                200                205

Gly Gln Val Gln His Leu Gln Ala Ala Phe Ser Gln Tyr Lys Lys Val
            210                215                220

Glu Leu Phe Pro Asn Gly Gln Ser Val Gly Glu Lys Ile Phe Lys Thr
225                230                235                240

Ala Gly Phe Val Lys Pro Phe Thr Glu Ala Gln Leu Leu Cys Thr Gln
                245                250                255

Ala Gly Gly Gln Leu Ala Ser Pro Arg Ser Ala Ala Glu Asn Ala Ala
            260                265                270

Leu Gln Gln Leu Val Val Ala Lys Asn Glu Ala Ala Phe Leu Ser Met
            275                280                285

Thr Asp Ser Lys Thr Glu Gly Lys Phe Thr Tyr Pro Thr Gly Glu Ser
            290                295                300

Leu Val Tyr Ser Asn Trp Ala Pro Gly Glu Pro Asn Asp Asp Gly Gly
305                310                315                320

Ser Glu Asp Cys Val Glu Ile Phe Thr Asn Gly Lys Trp Asn Asp Arg
                325                330                335

Ala Cys Gly Glu Lys Arg Leu Val Val Cys Glu Phe Gly Gly Ser Pro
            340                345                350

Ser Ser Ser Ser Ser Ser Ala Trp Ser His Pro Gln Phe Glu Lys
            355                360                365

<210> SEQ ID NO 49
<211> LENGTH: 367
<212> TYPE: PRT
<213> ORGANISM: Artificial Sequence
<220> FEATURE:
<223> OTHER INFORMATION: Fusion protein
<220> FEATURE:
<221> NAME/KEY: MISC_FEATURE
<222> LOCATION: (1)..(20)
<223> OTHER INFORMATION: Signal peptide 3 (SEQ ID NO:25)
```

```
<220> FEATURE:
<221> NAME/KEY: MISC_FEATURE
<222> LOCATION: (21)..(181)
<223> OTHER INFORMATION: TRAIL receptor binding domain (residues 120-280
      of SEQ ID NO:10)
<220> FEATURE:
<221> NAME/KEY: MISC_FEATURE
<222> LOCATION: (182)..(192)
<223> OTHER INFORMATION: Flexible linker A (SEQ ID NO:34)
<220> FEATURE:
<221> NAME/KEY: MISC_FEATURE
<222> LOCATION: (193)..(348)
<223> OTHER INFORMATION: SP-D mutant 1 collectin trimerization domain
      (residues 220-375 of SEQ ID NO:21 with F355A)
<220> FEATURE:
<221> NAME/KEY: MISC_FEATURE
<222> LOCATION: (193)..(230)
<223> OTHER INFORMATION: SP-D mutant 1 neck region (residues 220-257 of
      SEQ ID NO:21)
<220> FEATURE:
<221> NAME/KEY: MISC_FEATURE
<222> LOCATION: (231)..(348)
<223> OTHER INFORMATION: SP-D mutant 1 CRD (residues 258-375 of SEQ ID
      NO:21 with F355A)
<220> FEATURE:
<221> NAME/KEY: MISC_FEATURE
<222> LOCATION: (349)..(359)
<223> OTHER INFORMATION: Affinity tag linker element 2 (SEQ ID NO:54)
<220> FEATURE:
<221> NAME/KEY: MISC_FEATURE
<222> LOCATION: (360)..(367)
<223> OTHER INFORMATION: Strep-tag II (SEQ ID NO:38)

<400> SEQUENCE: 49

Met Glu Thr Asp Thr Leu Leu Leu Trp Val Leu Leu Leu Trp Val Pro
1               5                   10                  15

Ala Gly Asn Gly Gln Arg Val Ala Ala His Ile Thr Gly Thr Arg Gly
            20                  25                  30

Arg Ser Asn Thr Leu Ser Ser Pro Asn Ser Lys Asn Glu Lys Ala Leu
        35                  40                  45

Gly Arg Lys Ile Asn Ser Trp Glu Ser Ser Arg Ser Gly His Ser Phe
50                  55                  60

Leu Ser Asn Leu His Leu Arg Asn Gly Glu Leu Val Ile His Glu Lys
65                  70                  75                  80

Gly Phe Tyr Tyr Ile Tyr Ser Gln Thr Tyr Phe Arg Phe Gln Glu Glu
                85                  90                  95

Ile Lys Glu Asn Thr Lys Asn Asp Lys Gln Met Val Gln Tyr Ile Tyr
            100                 105                 110

Lys Tyr Thr Ser Tyr Pro Asp Pro Ile Leu Leu Met Lys Ser Ala Arg
        115                 120                 125

Asn Ser Cys Trp Ser Lys Asp Ala Glu Tyr Gly Leu Tyr Ser Ile Tyr
130                 135                 140

Gln Gly Gly Ile Phe Glu Leu Lys Glu Asn Asp Arg Ile Phe Val Ser
145                 150                 155                 160

Val Thr Asn Glu His Leu Ile Asp Met Asp His Glu Ala Ser Phe Phe
                165                 170                 175

Gly Ala Phe Leu Val Gly Ser Ser Gly Ser Ser Gly Ser
            180                 185                 190

Gly Leu Pro Asp Val Ala Ser Leu Arg Gln Gln Val Glu Ala Leu Gln
        195                 200                 205

Gly Gln Val Gln His Leu Gln Ala Ala Phe Ser Gln Tyr Lys Lys Val
210                 215                 220

Glu Leu Phe Pro Asn Gly Gln Ser Val Gly Glu Lys Ile Phe Lys Thr
225                 230                 235                 240
```

-continued

```
Ala Gly Phe Val Lys Pro Phe Thr Glu Ala Gln Leu Leu Cys Thr Gln
            245                 250                 255

Ala Gly Gly Gln Leu Ala Ser Pro Arg Ser Ala Ala Glu Asn Ala Ala
        260                 265                 270

Leu Gln Gln Leu Val Val Ala Lys Asn Glu Ala Ala Phe Leu Ser Met
        275                 280                 285

Thr Asp Ser Lys Thr Glu Gly Lys Phe Thr Tyr Pro Thr Gly Glu Ser
        290                 295                 300

Leu Val Tyr Ser Asn Trp Ala Pro Gly Glu Pro Asn Asp Asp Gly Gly
305                 310                 315                 320

Ser Glu Asp Cys Val Glu Ile Ala Thr Asn Gly Lys Trp Asn Asp Arg
                325                 330                 335

Ala Cys Gly Glu Lys Arg Leu Val Val Cys Glu Phe Gly Gly Ser Pro
            340                 345                 350

Ser Ser Ser Ser Ser Ala Trp Ser His Pro Gln Phe Glu Lys
        355                 360                 365
```

<210> SEQ ID NO 50
<211> LENGTH: 367
<212> TYPE: PRT
<213> ORGANISM: Artificial Sequence
<220> FEATURE:
<223> OTHER INFORMATION: Fusion protein
<220> FEATURE:
<221> NAME/KEY: MISC_FEATURE
<222> LOCATION: (1)..(20)
<223> OTHER INFORMATION: Signal peptide 3 (SEQ ID NO:25)
<220> FEATURE:
<221> NAME/KEY: MISC_FEATURE
<222> LOCATION: (21)..(181)
<223> OTHER INFORMATION: TRAIL receptor binding domain (residues 120-280
    of SEQ ID NO:10)
<220> FEATURE:
<221> NAME/KEY: MISC_FEATURE
<222> LOCATION: (182)..(192)
<223> OTHER INFORMATION: Flexible linker A (SEQ ID NO:34)
<220> FEATURE:
<221> NAME/KEY: MISC_FEATURE
<222> LOCATION: (193)..(348)
<223> OTHER INFORMATION: SP-D mutant 2 collectin trimerization domain
    (residues 220-375 of SEQ ID NO:21 with F355D)
<220> FEATURE:
<221> NAME/KEY: MISC_FEATURE
<222> LOCATION: (193)..(230)
<223> OTHER INFORMATION: SP-D mutant 2 neck region (residues 220-257 of
    SEQ ID NO:21)
<220> FEATURE:
<221> NAME/KEY: MISC_FEATURE
<222> LOCATION: (231)..(348)
<223> OTHER INFORMATION: SP-D mutant 2 CRD (residues 258-375 of SEQ ID
    NO:21 with F355D)
<220> FEATURE:
<221> NAME/KEY: MISC_FEATURE
<222> LOCATION: (349)..(359)
<223> OTHER INFORMATION: Affinity tag linker element 2 (SEQ ID NO:54)
<220> FEATURE:
<221> NAME/KEY: MISC_FEATURE
<222> LOCATION: (360)..(367)
<223> OTHER INFORMATION: Strep-tag II (SEQ ID NO:38)

<400> SEQUENCE: 50

```
Met Glu Thr Asp Thr Leu Leu Leu Trp Val Leu Leu Leu Trp Val Pro
1               5                   10                  15

Ala Gly Asn Gly Gln Arg Val Ala Ala His Ile Thr Gly Thr Arg Gly
            20                  25                  30

Arg Ser Asn Thr Leu Ser Ser Pro Asn Ser Lys Asn Glu Lys Ala Leu
        35                  40                  45
```

Gly Arg Lys Ile Asn Ser Trp Glu Ser Ser Arg Ser Gly His Ser Phe
 50                  55                  60

Leu Ser Asn Leu His Leu Arg Asn Gly Glu Leu Val Ile His Glu Lys
 65                  70                  75                  80

Gly Phe Tyr Tyr Ile Tyr Ser Gln Thr Tyr Phe Arg Phe Gln Glu Glu
                 85                  90                  95

Ile Lys Glu Asn Thr Lys Asn Asp Lys Gln Met Val Gln Tyr Ile Tyr
            100                 105                 110

Lys Tyr Thr Ser Tyr Pro Asp Pro Ile Leu Leu Met Lys Ser Ala Arg
        115                 120                 125

Asn Ser Cys Trp Ser Lys Asp Ala Glu Tyr Gly Leu Tyr Ser Ile Tyr
    130                 135                 140

Gln Gly Gly Ile Phe Glu Leu Lys Glu Asn Asp Arg Ile Phe Val Ser
145                 150                 155                 160

Val Thr Asn Glu His Leu Ile Asp Met Asp His Glu Ala Ser Phe Phe
                165                 170                 175

Gly Ala Phe Leu Val Gly Ser Ser Gly Ser Ser Gly Ser Ser Gly Ser
            180                 185                 190

Gly Leu Pro Asp Val Ala Ser Leu Arg Gln Gln Val Glu Ala Leu Gln
        195                 200                 205

Gly Gln Val Gln His Leu Gln Ala Ala Phe Ser Gln Tyr Lys Lys Val
    210                 215                 220

Glu Leu Phe Pro Asn Gly Gln Ser Val Gly Glu Lys Ile Phe Lys Thr
225                 230                 235                 240

Ala Gly Phe Val Lys Pro Phe Thr Glu Ala Gln Leu Leu Cys Thr Gln
                245                 250                 255

Ala Gly Gly Gln Leu Ala Ser Pro Arg Ser Ala Ala Glu Asn Ala Ala
            260                 265                 270

Leu Gln Gln Leu Val Val Ala Lys Asn Glu Ala Ala Phe Leu Ser Met
        275                 280                 285

Thr Asp Ser Lys Thr Glu Gly Lys Phe Thr Tyr Pro Thr Gly Glu Ser
    290                 295                 300

Leu Val Tyr Ser Asn Trp Ala Pro Gly Glu Pro Asn Asp Asp Gly Gly
305                 310                 315                 320

Ser Glu Asp Cys Val Glu Ile Asp Thr Asn Gly Lys Trp Asn Asp Arg
                325                 330                 335

Ala Cys Gly Glu Lys Arg Leu Val Val Cys Glu Phe Gly Gly Ser Pro
            340                 345                 350

Ser Ser Ser Ser Ser Ala Trp Ser His Pro Gln Phe Glu Lys
        355                 360                 365

<210> SEQ ID NO 51
<211> LENGTH: 344
<212> TYPE: PRT
<213> ORGANISM: Artificial Sequence
<220> FEATURE:
<223> OTHER INFORMATION: Fusion protein
<220> FEATURE:
<221> NAME/KEY: MISC_FEATURE
<222> LOCATION: (1)..(20)
<223> OTHER INFORMATION: Signal peptide 3 (SEQ ID NO:25)
<220> FEATURE:
<221> NAME/KEY: MISC_FEATURE
<222> LOCATION: (21)..(158)
<223> OTHER INFORMATION: APRIL version 2 receptor binding domain
      (residues 113-250 of SEQ ID NO:14)
<220> FEATURE:
<221> NAME/KEY: MISC_FEATURE

```
<222> LOCATION: (159)..(169)
<223> OTHER INFORMATION: Flexible linker A (SEQ ID NO:34)
<220> FEATURE:
<221> NAME/KEY: MISC_FEATURE
<222> LOCATION: (170)..(325)
<223> OTHER INFORMATION: SP-D collectin trimerization domain (residues
      220-375 of SEQ ID NO:21)
<220> FEATURE:
<221> NAME/KEY: MISC_FEATURE
<222> LOCATION: (170)..(207)
<223> OTHER INFORMATION: SP-D neck region (residues 220-257 of SEQ ID
      NO:21)
<220> FEATURE:
<221> NAME/KEY: MISC_FEATURE
<222> LOCATION: (208)..(325)
<223> OTHER INFORMATION: SP-D CRD (residues 258-375 of SEQ ID NO:21)
<220> FEATURE:
<221> NAME/KEY: MISC_FEATURE
<222> LOCATION: (326)..(336)
<223> OTHER INFORMATION: Affinity tag linker element 2 (SEQ ID NO:54)
<220> FEATURE:
<221> NAME/KEY: MISC_FEATURE
<222> LOCATION: (337)..(344)
<223> OTHER INFORMATION: Strep-tag II (SEQ ID NO:38)

<400> SEQUENCE: 51
```

Met Glu Thr Asp Thr Leu Leu Leu Trp Val Leu Leu Trp Val Pro
1               5                   10                  15

Ala Gly Asn Gly Lys Gln His Ser Val Leu His Leu Val Pro Ile Asn
            20                  25                  30

Ala Thr Ser Lys Asp Asp Ser Asp Val Thr Glu Val Met Trp Gln Pro
        35                  40                  45

Ala Leu Arg Arg Gly Arg Gly Leu Gln Ala Gln Gly Tyr Gly Val Arg
    50                  55                  60

Ile Gln Asp Ala Gly Val Tyr Leu Leu Tyr Ser Gln Val Leu Phe Gln
65                  70                  75                  80

Asp Val Thr Phe Thr Met Gly Gln Val Val Ser Arg Glu Gly Gln Gly
                85                  90                  95

Arg Gln Glu Thr Leu Phe Arg Cys Ile Arg Ser Met Pro Ser His Pro
            100                 105                 110

Asp Arg Ala Tyr Asn Ser Cys Tyr Ser Ala Gly Val Phe His Leu His
        115                 120                 125

Gln Gly Asp Ile Leu Ser Val Ile Ile Pro Arg Ala Arg Ala Lys Leu
    130                 135                 140

Asn Leu Ser Pro His Gly Thr Phe Leu Gly Phe Val Lys Leu Gly Ser
145                 150                 155                 160

Ser Gly Ser Ser Gly Ser Ser Gly Ser Gly Leu Pro Asp Val Ala Ser
                165                 170                 175

Leu Arg Gln Gln Val Glu Ala Leu Gln Gly Gln Val Gln His Leu Gln
            180                 185                 190

Ala Ala Phe Ser Gln Tyr Lys Lys Val Glu Leu Phe Pro Asn Gly Gln
        195                 200                 205

Ser Val Gly Glu Lys Ile Phe Lys Thr Ala Gly Phe Val Lys Pro Phe
    210                 215                 220

Thr Glu Ala Gln Leu Leu Cys Thr Gln Ala Gly Gly Gln Leu Ala Ser
225                 230                 235                 240

Pro Arg Ser Ala Ala Glu Asn Ala Ala Leu Gln Gln Leu Val Val Ala
                245                 250                 255

Lys Asn Glu Ala Ala Phe Leu Ser Met Thr Asp Ser Lys Thr Glu Gly
            260                 265                 270

Lys Phe Thr Tyr Pro Thr Gly Glu Ser Leu Val Tyr Ser Asn Trp Ala

-continued

```
                275                 280                 285
Pro Gly Glu Pro Asn Asp Asp Gly Gly Ser Glu Asp Cys Val Glu Ile
        290                 295                 300

Phe Thr Asn Gly Lys Trp Asn Asp Arg Ala Cys Gly Glu Lys Arg Leu
305                 310                 315                 320

Val Val Cys Glu Phe Gly Gly Ser Pro Ser Ser Ser Ser Ser Ser Ala
                325                 330                 335

Trp Ser His Pro Gln Phe Glu Lys
            340
```

<210> SEQ ID NO 52
<211> LENGTH: 450
<212> TYPE: PRT
<213> ORGANISM: Artificial Sequence
<220> FEATURE:
<223> OTHER INFORMATION: Fusion protein
<220> FEATURE:
<221> NAME/KEY: MISC_FEATURE
<222> LOCATION: (1)..(20)
<223> OTHER INFORMATION: Signal peptide 3 (SEQ ID NO:25)
<220> FEATURE:
<221> NAME/KEY: MISC_FEATURE
<222> LOCATION: (21)..(140)
<223> OTHER INFORMATION: Variable domain heavy chain
<220> FEATURE:
<221> NAME/KEY: MISC_FEATURE
<222> LOCATION: (141)..(155)
<223> OTHER INFORMATION: Flexible linker element F (SEQ ID NO:58)
<220> FEATURE:
<221> NAME/KEY: MISC_FEATURE
<222> LOCATION: (156)..(264)
<223> OTHER INFORMATION: Variable domain light chain
<220> FEATURE:
<221> NAME/KEY: MISC_FEATURE
<222> LOCATION: (265)..(275)
<223> OTHER INFORMATION: Flexible linker A (SEQ ID NO:34)
<220> FEATURE:
<221> NAME/KEY: MISC_FEATURE
<222> LOCATION: (276)..(431)
<223> OTHER INFORMATION: SP-D collectin trimerization domain (residues
      220-375 of SEQ ID NO:21)
<220> FEATURE:
<221> NAME/KEY: MISC_FEATURE
<222> LOCATION: (432)..(441)
<223> OTHER INFORMATION: Affinity tag linker element 2 (SEQ ID NO:54)
<220> FEATURE:
<221> NAME/KEY: MISC_FEATURE
<222> LOCATION: (442)..(450)
<223> OTHER INFORMATION: Strep-tag II (SEQ ID NO:38)

<400> SEQUENCE: 52

```
Met Glu Thr Asp Thr Leu Leu Leu Trp Val Leu Leu Leu Trp Val Pro
1               5                   10                  15

Ala Gly Asn Gly Glu Val Gln Leu Val Glu Ser Gly Gly Gly Leu Val
            20                  25                  30

Lys Pro Gly Gly Ser Leu Arg Leu Ser Cys Ala Ala Ser Gly Phe Thr
        35                  40                  45

Phe Asn Thr Asn Ala Met Asn Trp Val Arg Gln Ala Pro Gly Lys Gly
    50                  55                  60

Leu Glu Trp Val Ala Arg Ile Arg Ser Lys Ser Asn Asn Tyr Ala Thr
65                  70                  75                  80

Tyr Tyr Ala Asp Ser Val Lys Asp Arg Phe Thr Leu Ser Arg Asp Asp
                85                  90                  95

Ser Lys Asn Thr Leu Tyr Leu Gln Met Asn Ser Leu Lys Thr Glu Asp
            100                 105                 110

Thr Ala Val Tyr Tyr Cys Thr Arg Asp Arg Gly Trp Gly Ala Met Asp
```

```
                    115                 120                 125
Tyr Trp Gly Gln Gly Thr Thr Val Thr Val Ser Ser Gly Gly Gly Gly
            130                 135                 140

Ser Gly Gly Gly Gly Ser Gly Gly Gly Thr Gly Asp Ile Gln Met Thr
145                 150                 155                 160

Gln Ser Pro Ser Ser Leu Ser Ala Ser Val Gly Asp Arg Val Thr Ile
                165                 170                 175

Thr Cys Ser Ala Ser Gln Asp Ile Asn Asn Tyr Leu Asn Trp Tyr Gln
            180                 185                 190

Gln Lys Pro Gly Lys Ala Pro Lys Leu Leu Ile Tyr Tyr Thr Ser Ser
        195                 200                 205

Leu His Ser Gly Val Pro Ser Arg Phe Ser Gly Ser Gly Ser Gly Thr
        210                 215                 220

Asp Phe Thr Leu Thr Ile Ser Ser Leu Gln Pro Glu Asp Phe Ala Thr
225                 230                 235                 240

Tyr Tyr Cys Gln Gln Phe Ser Asn Leu Pro Trp Thr Phe Gly Gly Gly
                245                 250                 255

Thr Lys Leu Glu Ile Lys Arg Thr Gly Ser Ser Gly Ser Ser Gly Ser
            260                 265                 270

Ser Gly Ser Gly Leu Pro Asp Val Ala Ser Leu Arg Gln Gln Val Glu
        275                 280                 285

Ala Leu Gln Gly Gln Val Gln His Leu Gln Ala Ala Phe Ser Gln Tyr
290                 295                 300

Lys Lys Val Glu Leu Phe Pro Asn Gly Gln Ser Val Gly Glu Lys Ile
305                 310                 315                 320

Phe Lys Thr Ala Gly Phe Val Lys Pro Phe Thr Glu Ala Gln Leu Leu
                325                 330                 335

Cys Thr Gln Ala Gly Gly Gln Leu Ala Ser Pro Arg Ser Ala Ala Glu
            340                 345                 350

Asn Ala Ala Leu Gln Gln Leu Val Val Ala Lys Asn Glu Ala Ala Phe
        355                 360                 365

Leu Ser Met Thr Asp Ser Lys Thr Glu Gly Lys Phe Thr Tyr Pro Thr
        370                 375                 380

Gly Glu Ser Leu Val Tyr Ser Asn Trp Ala Pro Gly Glu Pro Asn Asp
385                 390                 395                 400

Asp Gly Gly Ser Glu Asp Cys Val Glu Ile Phe Thr Asn Gly Lys Trp
                405                 410                 415

Asn Asp Arg Ala Cys Gly Glu Lys Arg Leu Val Val Cys Glu Phe Gly
            420                 425                 430

Gly Ser Pro Ser Ser Ser Ser Ser Ala Trp Ser His Pro Gln Phe
        435                 440                 445

Glu Lys
    450

<210> SEQ ID NO 53
<211> LENGTH: 450
<212> TYPE: PRT
<213> ORGANISM: Artificial Sequence
<220> FEATURE:
<223> OTHER INFORMATION: Fusion protein
<220> FEATURE:
<221> NAME/KEY: MISC_FEATURE
<222> LOCATION: (1)..(20)
<223> OTHER INFORMATION: Signal peptide 3 (SEQ ID NO:25)
<220> FEATURE:
<221> NAME/KEY: MISC_FEATURE
<222> LOCATION: (21)..(140)
```

```
<223> OTHER INFORMATION: Variable domain heavy chain
<220> FEATURE:
<221> NAME/KEY: MISC_FEATURE
<222> LOCATION: (141)..(155)
<223> OTHER INFORMATION: Flexible linker element F (SEQ ID NO:58)
<220> FEATURE:
<221> NAME/KEY: MISC_FEATURE
<222> LOCATION: (156)..(264)
<223> OTHER INFORMATION: Variable domain light chain
<220> FEATURE:
<221> NAME/KEY: MISC_FEATURE
<222> LOCATION: (265)..(275)
<223> OTHER INFORMATION: Flexible linker A (SEQ ID NO:34)
<220> FEATURE:
<221> NAME/KEY: MISC_FEATURE
<222> LOCATION: (276)..(431)
<223> OTHER INFORMATION: SP-D mutant collectin trimerization domain
      (residues 220-375 of SEQ ID NO:21 with F355D)
<220> FEATURE:
<221> NAME/KEY: MISC_FEATURE
<222> LOCATION: (432)..(441)
<223> OTHER INFORMATION: Affinity tag linker element (SEQ ID NO:54)
<220> FEATURE:
<221> NAME/KEY: MISC_FEATURE
<222> LOCATION: (442)..(450)
<223> OTHER INFORMATION: Strep-tag II (SEQ ID NO:38)

<400> SEQUENCE: 53

Met Glu Thr Asp Thr Leu Leu Leu Trp Val Leu Leu Leu Trp Val Pro
1               5                   10                  15

Ala Gly Asn Gly Glu Val Gln Leu Val Glu Ser Gly Gly Gly Leu Val
            20                  25                  30

Lys Pro Gly Gly Ser Leu Arg Leu Ser Cys Ala Ala Ser Gly Phe Thr
        35                  40                  45

Phe Asn Thr Asn Ala Met Asn Trp Val Arg Gln Ala Pro Gly Lys Gly
    50                  55                  60

Leu Glu Trp Val Ala Arg Ile Arg Ser Lys Ser Asn Asn Tyr Ala Thr
65                  70                  75                  80

Tyr Tyr Ala Asp Ser Val Lys Asp Arg Phe Thr Leu Ser Arg Asp Asp
                85                  90                  95

Ser Lys Asn Thr Leu Tyr Leu Gln Met Asn Ser Leu Lys Thr Glu Asp
            100                 105                 110

Thr Ala Val Tyr Tyr Cys Thr Arg Asp Arg Gly Trp Gly Ala Met Asp
        115                 120                 125

Tyr Trp Gly Gln Gly Thr Thr Val Thr Val Ser Ser Gly Gly Gly Gly
    130                 135                 140

Ser Gly Gly Gly Gly Ser Gly Gly Thr Gly Asp Ile Gln Met Thr
145                 150                 155                 160

Gln Ser Pro Ser Ser Leu Ser Ala Ser Val Gly Asp Arg Val Thr Ile
                165                 170                 175

Thr Cys Ser Ala Ser Gln Asp Ile Asn Asn Tyr Leu Asn Trp Tyr Gln
            180                 185                 190

Gln Lys Pro Gly Lys Ala Pro Lys Leu Leu Ile Tyr Tyr Thr Ser Ser
        195                 200                 205

Leu His Ser Gly Val Pro Ser Arg Phe Ser Gly Ser Gly Ser Gly Thr
    210                 215                 220

Asp Phe Thr Leu Thr Ile Ser Ser Leu Gln Pro Glu Asp Phe Ala Thr
225                 230                 235                 240

Tyr Tyr Cys Gln Gln Phe Ser Asn Leu Pro Trp Thr Phe Gly Gly Gly
                245                 250                 255

Thr Lys Leu Glu Ile Lys Arg Thr Gly Ser Ser Gly Ser Gly Ser
            260                 265                 270
```

-continued

```
Ser Gly Ser Gly Leu Pro Asp Val Ala Ser Leu Arg Gln Gln Val Glu
        275                 280                 285

Ala Leu Gln Gly Gln Val Gln His Leu Gln Ala Ala Phe Ser Gln Tyr
    290                 295                 300

Lys Lys Val Glu Leu Phe Pro Asn Gly Gln Ser Val Gly Glu Lys Ile
305                 310                 315                 320

Phe Lys Thr Ala Gly Phe Val Lys Pro Phe Thr Glu Ala Gln Leu Leu
                325                 330                 335

Cys Thr Gln Ala Gly Gly Gln Leu Ala Ser Pro Arg Ser Ala Ala Glu
            340                 345                 350

Asn Ala Ala Leu Gln Gln Leu Val Val Ala Lys Asn Glu Ala Ala Phe
        355                 360                 365

Leu Ser Met Thr Asp Ser Lys Thr Glu Gly Lys Phe Thr Tyr Pro Thr
    370                 375                 380

Gly Glu Ser Leu Val Tyr Ser Asn Trp Ala Pro Gly Glu Pro Asn Asp
385                 390                 395                 400

Asp Gly Gly Ser Glu Asp Cys Val Glu Ile Asp Thr Asn Gly Lys Trp
                405                 410                 415

Asn Asp Arg Ala Cys Gly Glu Lys Arg Leu Val Val Cys Glu Phe Gly
            420                 425                 430

Gly Ser Pro Ser Ser Ser Ser Ala Trp Ser His Pro Gln Phe
        435                 440                 445

Glu Lys
    450

<210> SEQ ID NO 54
<211> LENGTH: 11
<212> TYPE: PRT
<213> ORGANISM: Artificial Sequence
<220> FEATURE:
<223> OTHER INFORMATION: Affinity tag linker element

<400> SEQUENCE: 54

Gly Gly Ser Pro Ser Ser Ser Ser Ser Ala
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Affinity tag linker element

<400> SEQUENCE: 55

Gly Ser Pro Ser Ser Ser Ser Ser Ala
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Flexible linker element

<400> SEQUENCE: 56

Gly Ser Ser Gly Ser Ser Gly Ser Ser Gly Ser Gly
1               5                   10

<210> SEQ ID NO 57
<211> LENGTH: 9
```

```
<212> TYPE: PRT
<213> ORGANISM: Artificial Sequence
<220> FEATURE:
<223> OTHER INFORMATION: Affinity tag linker element

<400> SEQUENCE: 57

Gly Pro Ser Ser Ser Ser Ser Ala
1               5

<210> SEQ ID NO 58
<211> LENGTH: 15
<212> TYPE: PRT
<213> ORGANISM: Artificial Sequence
<220> FEATURE:
<223> OTHER INFORMATION: Flexible linker element

<400> SEQUENCE: 58

Gly Gly Gly Gly Ser Gly Gly Gly Gly Ser Gly Gly Gly Thr Gly
1               5                   10                  15

<210> SEQ ID NO 59
<211> LENGTH: 248
<212> TYPE: PRT
<213> ORGANISM: Homo sapiens
<300> PUBLICATION INFORMATION:
<308> DATABASE ACCESSION NUMBER: Q8IWL2
<309> DATABASE ENTRY DATE: 2008-12-16
<313> RELEVANT RESIDUES IN SEQ ID NO: (1)..(248)

<400> SEQUENCE: 59

Met Trp Leu Cys Pro Leu Ala Leu Asn Leu Ile Leu Met Ala Ala Ser
1               5                   10                  15

Gly Ala Val Cys Glu Val Lys Asp Val Cys Val Gly Ser Pro Gly Ile
                20                  25                  30

Pro Gly Thr Pro Gly Ser His Gly Leu Pro Gly Arg Asp Gly Arg Asp
            35                  40                  45

Gly Leu Lys Gly Asp Pro Gly Pro Pro Gly Pro Met Gly Pro Pro Gly
        50                  55                  60

Glu Met Pro Cys Pro Pro Gly Asn Asp Gly Leu Pro Gly Ala Pro Gly
65                  70                  75                  80

Ile Pro Gly Glu Cys Gly Glu Lys Gly Glu Pro Gly Glu Arg Gly Pro
                85                  90                  95

Pro Gly Leu Pro Ala His Leu Asp Glu Glu Leu Gln Ala Thr Leu His
            100                 105                 110

Asp Phe Arg His Gln Ile Leu Gln Thr Arg Gly Ala Leu Ser Leu Gln
        115                 120                 125

Gly Ser Ile Met Thr Val Gly Glu Lys Val Phe Ser Ser Asn Gly Gln
130                 135                 140

Ser Ile Thr Phe Asp Ala Ile Gln Glu Ala Cys Ala Arg Ala Gly Gly
145                 150                 155                 160

Arg Ile Ala Val Pro Arg Asn Pro Glu Glu Asn Glu Ala Ile Ala Ser
                165                 170                 175

Phe Val Lys Lys Tyr Asn Thr Tyr Ala Tyr Val Gly Leu Thr Glu Gly
            180                 185                 190

Pro Ser Pro Gly Asp Phe Arg Tyr Ser Asp Gly Thr Pro Val Asn Tyr
        195                 200                 205

Thr Asn Trp Tyr Arg Gly Glu Pro Ala Gly Arg Gly Lys Glu Gln Cys
    210                 215                 220

Val Glu Met Tyr Thr Asp Gly Gln Trp Asn Asp Arg Asn Cys Leu Tyr
225                 230                 235                 240
```

Ser Arg Leu Thr Ile Cys Glu Phe
            245

<210> SEQ ID NO 60
<211> LENGTH: 248
<212> TYPE: PRT
<213> ORGANISM: Homo sapiens
<300> PUBLICATION INFORMATION:
<308> DATABASE ACCESSION NUMBER: Q8IWL1
<309> DATABASE ENTRY DATE: 2008-12-16
<313> RELEVANT RESIDUES IN SEQ ID NO: (1)..(248)

<400> SEQUENCE: 60

Met Trp Leu Cys Pro Leu Ala Leu Asn Leu Ile Leu Met Ala Ala Ser
1               5                   10                  15

Gly Ala Ala Cys Glu Val Lys Asp Val Cys Val Gly Ser Pro Gly Ile
            20                  25                  30

Pro Gly Thr Pro Gly Ser His Gly Leu Pro Gly Arg Asp Gly Arg Asp
        35                  40                  45

Gly Val Lys Gly Asp Pro Gly Pro Pro Gly Pro Met Gly Pro Pro Gly
    50                  55                  60

Glu Thr Pro Cys Pro Pro Gly Asn Asn Gly Leu Pro Gly Ala Pro Gly
65                  70                  75                  80

Val Pro Gly Glu Arg Gly Glu Lys Gly Glu Ala Gly Glu Arg Gly Pro
                85                  90                  95

Pro Gly Leu Pro Ala His Leu Asp Glu Glu Leu Gln Ala Thr Leu His
            100                 105                 110

Asp Phe Arg His Gln Ile Leu Gln Thr Arg Gly Ala Leu Ser Leu Gln
        115                 120                 125

Gly Ser Ile Met Thr Val Gly Glu Lys Val Phe Ser Ser Asn Gly Gln
    130                 135                 140

Ser Ile Thr Phe Asp Ala Ile Gln Glu Ala Cys Ala Arg Ala Gly Gly
145                 150                 155                 160

Arg Ile Ala Val Pro Arg Asn Pro Glu Glu Asn Glu Ala Ile Ala Ser
                165                 170                 175

Phe Val Lys Lys Tyr Asn Thr Tyr Ala Tyr Val Gly Leu Thr Glu Gly
            180                 185                 190

Pro Ser Pro Gly Asp Phe Arg Tyr Ser Asp Gly Thr Pro Val Asn Tyr
        195                 200                 205

Thr Asn Trp Tyr Arg Gly Glu Pro Ala Gly Arg Gly Lys Glu Gln Cys
    210                 215                 220

Val Glu Met Tyr Thr Asp Gly Gln Trp Asn Asp Arg Asn Cys Leu Tyr
225                 230                 235                 240

Ser Arg Leu Thr Ile Cys Glu Phe
            245

<210> SEQ ID NO 61
<211> LENGTH: 248
<212> TYPE: PRT
<213> ORGANISM: Homo sapiens
<300> PUBLICATION INFORMATION:
<308> DATABASE ACCESSION NUMBER: P11226
<309> DATABASE ENTRY DATE: 2008-12-16
<313> RELEVANT RESIDUES IN SEQ ID NO: (1)..(248)

<400> SEQUENCE: 61

Met Ser Leu Phe Pro Ser Leu Pro Leu Leu Leu Leu Ser Met Val Ala
1               5                   10                  15

-continued

```
Ala Ser Tyr Ser Glu Thr Val Thr Cys Glu Asp Ala Gln Lys Thr Cys
             20                  25                  30

Pro Ala Val Ile Ala Cys Ser Ser Pro Gly Ile Asn Gly Phe Pro Gly
             35                  40                  45

Lys Asp Gly Arg Asp Gly Thr Lys Gly Glu Lys Gly Glu Pro Gly Gln
 50                  55                  60

Gly Leu Arg Gly Leu Gln Gly Pro Pro Gly Lys Leu Gly Pro Pro Gly
65                  70                  75                  80

Asn Pro Gly Pro Ser Gly Ser Pro Gly Pro Lys Gly Gln Lys Gly Asp
                 85                  90                  95

Pro Gly Lys Ser Pro Asp Gly Asp Ser Ser Leu Ala Ala Ser Glu Arg
            100                 105                 110

Lys Ala Leu Gln Thr Glu Met Ala Arg Ile Lys Lys Trp Leu Thr Phe
            115                 120                 125

Ser Leu Gly Lys Gln Val Gly Asn Lys Phe Phe Leu Thr Asn Gly Glu
            130                 135                 140

Ile Met Thr Phe Glu Lys Val Lys Ala Leu Cys Val Lys Phe Gln Ala
145                 150                 155                 160

Ser Val Ala Thr Pro Arg Asn Ala Ala Glu Asn Gly Ala Ile Gln Asn
                165                 170                 175

Leu Ile Lys Glu Glu Ala Phe Leu Gly Ile Thr Asp Glu Lys Thr Glu
            180                 185                 190

Gly Gln Phe Val Asp Leu Thr Gly Asn Arg Leu Thr Tyr Thr Asn Trp
            195                 200                 205

Asn Glu Gly Glu Pro Asn Asn Ala Gly Ser Asp Glu Asp Cys Val Leu
        210                 215                 220

Leu Leu Lys Asn Gly Gln Trp Asn Asp Val Pro Cys Ser Thr Ser His
225                 230                 235                 240

Leu Ala Val Cys Glu Phe Pro Ile
                245

<210> SEQ ID NO 62
<211> LENGTH: 277
<212> TYPE: PRT
<213> ORGANISM: Homo sapiens
<300> PUBLICATION INFORMATION:
<308> DATABASE ACCESSION NUMBER: Q9Y6Z7
<309> DATABASE ENTRY DATE: 2008-12-16
<313> RELEVANT RESIDUES IN SEQ ID NO: (1)..(277)

<400> SEQUENCE: 62

Met Asn Gly Phe Ala Ser Leu Leu Arg Arg Asn Gln Phe Ile Leu Leu
1               5                  10                  15

Val Leu Phe Leu Leu Gln Ile Gln Ser Leu Gly Leu Asp Ile Asp Ser
             20                  25                  30

Arg Pro Thr Ala Glu Val Cys Ala Thr His Thr Ile Ser Pro Gly Pro
             35                  40                  45

Lys Gly Asp Asp Gly Glu Lys Gly Asp Pro Gly Glu Glu Gly Lys His
 50                  55                  60

Gly Lys Val Gly Arg Met Gly Pro Lys Gly Ile Lys Gly Glu Leu Gly
65                  70                  75                  80

Asp Met Gly Asp Gln Gly Asn Ile Gly Lys Thr Gly Pro Ile Gly Lys
                 85                  90                  95

Lys Gly Asp Lys Gly Glu Lys Gly Leu Leu Gly Ile Pro Gly Glu Lys
            100                 105                 110

Gly Lys Ala Gly Thr Val Cys Asp Cys Gly Arg Tyr Arg Lys Phe Val
```

```
            115                 120                 125
Gly Gln Leu Asp Ile Ser Ile Ala Arg Leu Lys Thr Ser Met Lys Phe
    130                 135                 140

Val Lys Asn Val Ile Ala Gly Ile Arg Glu Thr Glu Lys Phe Tyr
145                 150                 155                 160

Tyr Ile Val Gln Glu Lys Asn Tyr Arg Glu Ser Leu Thr His Cys
                165                 170                 175

Arg Ile Arg Gly Gly Met Leu Ala Met Pro Lys Asp Glu Ala Ala Asn
            180                 185                 190

Thr Leu Ile Ala Asp Tyr Val Ala Lys Ser Gly Phe Phe Arg Val Phe
        195                 200                 205

Ile Gly Val Asn Asp Leu Glu Arg Glu Gly Gln Tyr Met Phe Thr Asp
    210                 215                 220

Asn Thr Pro Leu Gln Asn Tyr Ser Asn Trp Asn Glu Gly Glu Pro Ser
225                 230                 235                 240

Asp Pro Tyr Gly His Glu Asp Cys Val Glu Met Leu Ser Ser Gly Arg
                245                 250                 255

Trp Asn Asp Thr Glu Cys His Leu Thr Met Tyr Phe Val Cys Glu Phe
            260                 265                 270

Ile Lys Lys Lys Lys
            275

<210> SEQ ID NO 63
<211> LENGTH: 742
<212> TYPE: PRT
<213> ORGANISM: Homo sapiens
<300> PUBLICATION INFORMATION:
<308> DATABASE ACCESSION NUMBER: Q5KU26
<309> DATABASE ENTRY DATE: 2008-12-16
<313> RELEVANT RESIDUES IN SEQ ID NO: (1)..(742)

<400> SEQUENCE: 63

Met Lys Asp Asp Phe Ala Glu Glu Glu Val Gln Ser Phe Gly Tyr
1               5                   10                  15

Lys Arg Phe Gly Ile Gln Glu Gly Thr Gln Cys Thr Lys Cys Lys Asn
            20                  25                  30

Asn Trp Ala Leu Lys Phe Ser Ile Ile Leu Tyr Ile Leu Cys Ala
        35                  40                  45

Leu Leu Thr Ile Thr Val Ala Ile Leu Gly Tyr Lys Val Val Glu Lys
    50                  55                  60

Met Asp Asn Val Thr Gly Gly Met Glu Thr Ser Arg Gln Thr Tyr Asp
65                  70                  75                  80

Asp Lys Leu Thr Ala Val Glu Ser Asp Leu Lys Lys Leu Gly Asp Gln
                85                  90                  95

Thr Gly Lys Lys Ala Ile Ser Thr Asn Ser Glu Leu Ser Thr Phe Arg
            100                 105                 110

Ser Asp Ile Leu Asp Leu Arg Gln Gln Leu Arg Glu Ile Thr Glu Lys
        115                 120                 125

Thr Ser Lys Asn Lys Asp Thr Leu Glu Lys Leu Gln Ala Ser Gly Asp
    130                 135                 140

Ala Leu Val Asp Arg Gln Ser Gln Leu Lys Glu Thr Leu Glu Asn Asn
145                 150                 155                 160

Ser Phe Leu Ile Thr Thr Val Asn Lys Thr Leu Gln Ala Tyr Asn Gly
                165                 170                 175

Tyr Val Thr Asn Leu Gln Gln Asp Thr Ser Val Leu Gln Gly Asn Leu
            180                 185                 190
```

```
Gln Asn Gln Met Tyr Ser His Asn Val Val Ile Met Asn Leu Asn Asn
            195                 200                 205

Leu Asn Leu Thr Gln Val Gln Gln Arg Asn Leu Ile Thr Asn Leu Gln
        210                 215                 220

Arg Ser Val Asp Asp Thr Ser Gln Ala Ile Gln Arg Ile Lys Asn Asp
225                 230                 235                 240

Phe Gln Asn Leu Gln Gln Val Phe Leu Gln Ala Lys Lys Asp Thr Asp
                245                 250                 255

Trp Leu Lys Glu Lys Val Gln Ser Leu Gln Thr Leu Ala Ala Asn Asn
            260                 265                 270

Ser Ala Leu Ala Lys Ala Asn Asn Asp Thr Leu Glu Asp Met Asn Ser
        275                 280                 285

Gln Leu Asn Ser Phe Thr Gly Gln Met Glu Asn Ile Thr Thr Ile Ser
    290                 295                 300

Gln Ala Asn Glu Gln Asn Leu Lys Asp Leu Gln Asp Leu His Lys Asp
305                 310                 315                 320

Ala Glu Asn Arg Thr Ala Ile Lys Phe Asn Gln Leu Glu Glu Arg Phe
                325                 330                 335

Gln Leu Phe Glu Thr Asp Ile Val Asn Ile Ile Ser Asn Ile Ser Tyr
            340                 345                 350

Thr Ala His His Leu Arg Thr Leu Thr Ser Asn Leu Asn Glu Val Arg
        355                 360                 365

Thr Thr Cys Thr Asp Thr Leu Thr Lys His Thr Asp Asp Leu Thr Ser
    370                 375                 380

Leu Asn Asn Thr Leu Ala Asn Ile Arg Leu Asp Ser Val Ser Leu Arg
385                 390                 395                 400

Met Gln Gln Asp Leu Met Arg Ser Arg Leu Asp Thr Glu Val Ala Asn
                405                 410                 415

Leu Ser Val Ile Met Glu Glu Met Lys Leu Val Asp Ser Lys His Gly
            420                 425                 430

Gln Leu Ile Lys Asn Phe Thr Ile Leu Gln Gly Pro Pro Gly Pro Arg
        435                 440                 445

Gly Pro Arg Gly Asp Arg Gly Ser Gln Gly Pro Pro Gly Pro Thr Gly
    450                 455                 460

Asn Lys Gly Gln Lys Gly Glu Lys Gly Glu Pro Gly Pro Pro Gly Pro
465                 470                 475                 480

Ala Gly Glu Arg Gly Pro Ile Gly Pro Ala Gly Pro Pro Gly Glu Arg
                485                 490                 495

Gly Gly Lys Gly Ser Lys Gly Ser Gln Gly Pro Lys Gly Ser Arg Gly
            500                 505                 510

Ser Pro Gly Lys Pro Gly Pro Gln Gly Pro Ser Gly Asp Pro Gly Pro
        515                 520                 525

Pro Gly Pro Pro Gly Lys Glu Gly Leu Pro Gly Pro Gln Gly Pro Pro
    530                 535                 540

Gly Phe Gln Gly Leu Gln Gly Thr Val Gly Glu Pro Gly Val Pro Gly
545                 550                 555                 560

Pro Arg Gly Leu Pro Gly Leu Pro Gly Val Pro Gly Met Pro Gly Pro
                565                 570                 575

Lys Gly Pro Pro Gly Pro Gly Pro Ser Gly Ala Val Val Pro Leu
            580                 585                 590

Ala Leu Gln Asn Glu Pro Thr Pro Ala Pro Glu Asp Asn Gly Cys Pro
        595                 600                 605
```

-continued

```
Pro His Trp Lys Asn Phe Thr Asp Lys Cys Tyr Tyr Phe Ser Val Glu
    610             615             620

Lys Glu Ile Phe Glu Asp Ala Lys Leu Phe Cys Glu Asp Lys Ser Ser
625             630             635             640

His Leu Val Phe Ile Asn Thr Arg Glu Glu Gln Gln Trp Ile Lys Lys
            645             650             655

Gln Met Val Gly Arg Glu Ser His Trp Ile Gly Leu Thr Asp Ser Glu
            660             665             670

Arg Glu Asn Glu Trp Lys Trp Leu Asp Gly Thr Ser Pro Asp Tyr Lys
        675             680             685

Asn Trp Lys Ala Gly Gln Pro Asp Asn Trp Gly His Gly His Gly Pro
    690             695             700

Gly Glu Asp Cys Ala Gly Leu Ile Tyr Ala Gly Gln Trp Asn Asp Phe
705             710             715             720

Gln Cys Glu Asp Val Asn Asn Phe Ile Cys Glu Lys Asp Arg Glu Thr
                725             730             735

Val Leu Ser Ser Ala Leu
            740
```

FUSION PROTEINS FORMING TRIMERS

This application is a continuation of U.S. application Ser. No. 13/143,531, filed Sep. 6, 2011; which is a National Stage of International Application PCT/EP2009/050233, filed Jan. 9, 2009, published Jul. 15, 2010, under PCT Article 21(2) in English. The contents of the above-identified applications are incorporated herein by reference in their entireties.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence_Listing.txt with a creation date of Oct. 17, 2011, and a size of 160 kilobytes. The Sequence Listing filed via EFS-Web is part of the specification and is hereby incorporated in its entirety by reference herein.

DESCRIPTION

1. Field of Invention

The present invention refers to fusion proteins comprising a neck region and carbohydrate recognition domain of a collectin trimerization domain, a linker element and an effector polypeptide. Further the invention refers to a nucleic acid encoding the said fusion protein. The fusion proteins, the nucleic acid, and the cell are suitable as pharmaceutical composition or for therapeutic, diagnostic and/or research applications as described herein.

2. Background

Collectin proteins are known to form stable oligomers. Collectins are one of 18 group members building the protein lectin superfamily containing a structural protein fold called C-type lectin domain (Zelensky et al., FEBS Journal 2005, Vol 272, p 6179-6217). Lectins are proteins that bind to carbohydrates and C-type lectins require calcium for binding. As the C-type lectin domain is involved in carbohydrate binding, this domain is also called the carbohydrate recognition domain (CRD). Collectins belong to the innate immunity and among other functions neutralize pathogens by binding to the carbohydrates e.g. present on viruses and bacteria. In addition, collectins regulate immune functions such as activation of complement and influencing inflammation. The basic structural features of collectins are a collageneous and a lectin domain which are the name giving components of collectins. Some members have been shown to contain additional structural features, thus they contain the following components: i) an N-terminal collagen domain connected to ii) an alpha-helical segment that is also referred to as the neck-region and iii) the CRD at the C-terminus (FIG. 35). Collectins trimerize non-covalently via the "triplehelical collagen", the "coiled coil neck" and CRD regions. In humans, the collectin group contains serum mannose binding protein(s), collectins of the liver, kidneys, placenta and lung. Four lung collectins are known including pulmonary surfactant protein-A and -D (SP-A and SP-D) which contain N-terminal cysteines that are involved in the disulfide-mediatet oligomerization of pre-formed trimers. For instance, SP-D forms tetramers of trimers and SP-A forms hexamers of trimers (Kishore et al, Mol. Immunol. 2006, Vol. 43, 1293-1315)

In the attempt to provide trimeric complexes of TNF superfamily cytokines recombinant fusion proteins comprising a TNF cytokine and a multimerization component have been suggested as one possible approach (e.g. WO 0149866). The disclosed constructs however exhibited trimerization domains with a large molecular weight and with inefficient trimerization properties.

Schneider et al. (J Exp Med 187 (1989), 1205-1213) describes that trimers of TNF cytokines are stabilized by N-terminally positioned stabilization motifs. In CD95L, the stabilization of the CD95L-receptor binding domain trimer is presumably caused by N-terminal amino acid domains which are located near the cytoplasmic membrane.

Shiraishi et al. (Biochem Biophys Res Commun 322 (2004), 197-202) describes that the receptor binding domain of CD95L may be stabilized by N-terminally positioned artificial α-helical coiled-coil (leucine zipper) motifs. It was found, however, that the orientation of the polypeptide chains to each other, e.g. parallel or antiparallel orientation, can hardly be predicted. Further, the optimal number of hepta-d-repeats in the coiled-coil zipper motif are difficult to determine. In addition, coiled-coil structures have the tendency to form macromolecular aggregates after alteration of pH and/or ionic strength.

Mc Alinden et al. (J of Biol Chem, 2002, 277(43):41274-41281) discloses the preparation of a fusion protein between a human type IIA procollagen amino acid sequence and a 14 amino acid sequence corresponding to the first two heptad repeats of the rat surfactant protein's (SP-D) neck domain.

WO 01/42298 discloses the preparation of a fusion protein between surfactant protein-D comprising the signal sequence, the collagen domain and the neck domain and CD40L. The disadvantage of those fusion proteins is that they lead to multimeric aggregates that are highly immunogenic and that they do not produce biochemically defined trimeric ligands.

To circumvent the named problems existing in the art could be achieved by using collectin trimerization domains as a tool for forming controlled trimers. In the art attempts for this have been performed. However only the coiled-coil neck region of collectin trimerization domains (CRD) have been used in such attempts. The coiled-coil like neck-region of SP-D itself can be used as trimerisation domain, either N- or C-terminal fused to protein domains as described in WO95/31540.

However if using solely the coiled-coil neck region the optimal number of hepta-d-repeats to achieve a stable trimer (the overall length) are difficult to determine. The presented part of the SP-D neck region does not form sufficiently stable trimeres itself and needs to be optimized with respect to its length or repetition grade to generate stabilised trimeric fusion proteins. In addition, coiled-coil structures tend to form macromolecular aggregates after alteration of pH and/or ionic strength. Accordingly a collectin neck-region α-helical bundle exists only as a trimeric molecule in conditions which mimic or approximate physiological conditions. This implicates, that purification strategies employing pH-shifts and/or the alteration of the ionic strength might have a negative effect on the trimeric state of the neck solely based fusion proteins.

Also oligomerization of antibody fragments have been attempted by using collectin trimerization domains. E.g. fusion proteins comprising an anti-CD89-Fab or an anti-CD64-Fab fused to recombinant human fragment SP-D (neck+CRD-domain) have been investigated and found to be effective in targeting pathogens towards neutrophils. The fusion proteins presented had been generated by chemical crosslinking resulting in a mixture of protein products with the necessity of a complex purification regime to achieve the wanted protein species.

For human SP-D a mutant has been described in which amino acid phenylalanine 335 (corresponding to amino acid 355 of SEQ ID NO:21) has been mutated to alanine (SPD_F335A, Crouch et al., *JBC* 281: 18008-18014). This mutant showed very weak carbohydrate binding.

To allow for an efficient manufacturing process for Fab-SP-D based fusion proteins a process would be desirable that does not necessitate laborious purification procedures but allows for controlled production of defined products instead of crude mixtures.

The inventors found that the fusion proteins disclosed herein overcome the problems present in the art and allow for controlled generation of trimers of different effector polypeptides such as cytokines of the TNF superfamily or also of antibody fragments or single chain antibodies.

It was an object of the present invention to provide fusion proteins forming trimers which allow efficient recombinant manufacture combined with good trimerization properties and improved pharmaceutical properties.

SUMMARY OF THE INVENTION

The present invention relates to a fusion protein comprising
(i) a collectin family trimerization domain comprising
   a. a collectin family Carbohydrate Recognition Domain; and
   b. a collectin family neck region;
(ii) a linker element; and
(iii) an effector polypeptide, wherein the effector polypeptide is located N-terminally of the collectin family neck region.

The invention further relates to a nucleic acid molecule encoding a fusion protein as described herein and to a cell or a non-human organism transformed or transfected with a nucleic acid molecule as described herein.

The invention also relates to a fusion protein, a nucleic acid molecule, or a cell as described herein for use as a medicament.

The invention further related to the fusion protein, nucleic acid molecule, or cell as described herein for us in therapy and/or prophylaxis of neoplastic, inflammatory, infectious, degenerative, genetic, proliferative and vascular diseases, and of premalignant and malignant cancerous conditions, cancer and inborn errors.

The invention also relates to a pharmaceutical or diagnostic composition comprising as an active agent a fusion protein, a nucleic acid molecule, or a cell as described herein. The fusion protein, nucleic acid molecule, or cell as described herein may be used for the preparation of a pharmaceutical composition in the prophylaxis and/or treatment of neoplastic, inflammatory, infectious, degenerative, genetic, proliferative and vascular diseases, and of premalignant and malignant cancerous conditions, cancer and inborn errors.

BRIEF DESCRIPTION OF THE DRAWINGS

FIG. 18: Caspase activity of SEC fractions A1-A14 from affinity purified TRAILR1 mut-ASPD on Jurkat cells

FIG. 38: Schematic picture representing the modification introduced to minimize the TNF-SF-RBD. The N-terminal stalk is deleted. 1. anti-parallel β-fold of receptor-binding domain (RBD), 2. interface of RBD and cell membrane

DETAILED DESCRIPTION OF THE INVENTION

Figure 1:
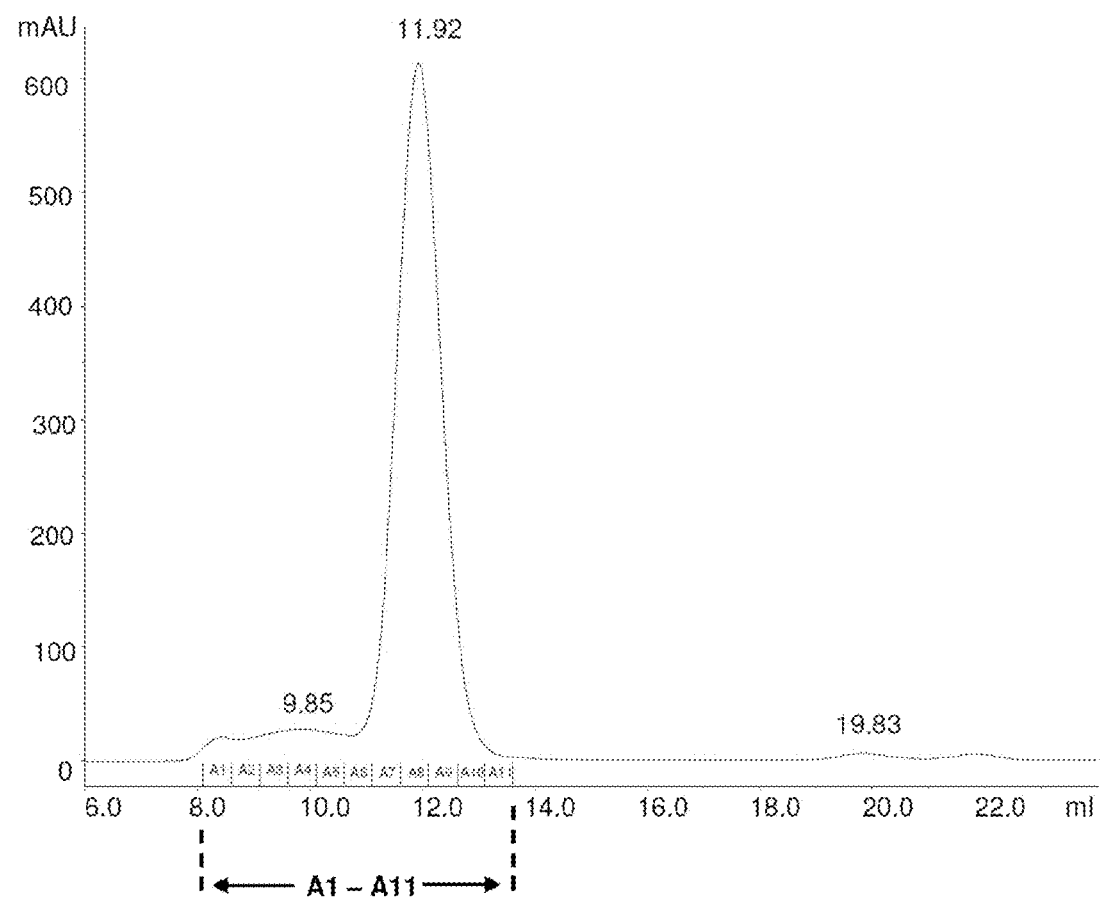
FIG. 1: SEC of affinity purified CD95L-ASPD

The fusion protein as disclosed herein may be a monomeric protein or a multimeric protein. Preferably, the fusion protein is present as a trimeric complex consisting of three monomeric units which may be identical or different. Preferably, a trimeric complex consists of three identical fusion proteins. In a further preferred embodiment, the complex is formed by covalent linkage between three of the fusion proteins described herein, e.g., a covalent linkage of disulfide bridges between cysteines of the collectin trimerization domain as described herein.

The trimeric complex as such shows biological activity. It was found, however, that oligomers of the trimeric complex, e.g. defined complexes wherein the basic trimeric structure is present 2, 3 or 4 times, also have biological activity. Thus, also preferred is an oligomer of the trimeric complex.

The fusion protein comprises the following elements:
(i) a collectin family trimerization domain comprising
   a. a collectin family Carbohydrate Recognition Domain; and
   b. a collectin family neck region;]
(ii) a linker element; and
(iii) an effector polypeptide, wherein the effector polypeptide is located N-terminally of the collectin family neck region.

A collectin trimerization domain as used herein is generally derived from the C-terminal part of Collectin polypeptides. The trimerization domain as used herein comprises a coiled-coil region (in certain embodiments referred to as neck region) and a Carbohydrate Recognition Domain (referred to herein also as CRD).

The collectin trimerization domain may comprise any collectin family member. Such members and their structures are summarized in, e.g., Hakansson et al. (Protein Science, 2000, 9:1607-1617) and may comprise surfactant protein-D (acc. No.: P35247; SEQ ID NO:21), surfactant protein-A 1 (acc. No.: Q8IWL2; SEQ ID NO:59), surfactant protein-A 2 (acc. No.: Q8IWL1; SEQ ID NO:60), mannan-binding-protein-C (accession No.: P11226; SEQ ID NO:61), collectin liver 1 (acc. No.: Q9Y6Z7; SEQ ID NO:62), collectin placenta 1 (acc. No.: Q5KU26; SEQ ID NO:63), or collectin-11 (acc. No.: Q9BWP8; SEQ ID NO:22). As well the coiled-coil region (neck region) as the CRD may be selected from the above mentioned collectins. It must be understood that coiled-coil (neck region) and CRD may but need not be from the same collectin.

The collectin trimerization domain as described herein may be from a different species than the cytokine of the TNF superfamily or a receptor binding domain thereof as described herein. Alternatively, the collectin trimerization domain as described herein may be from the same species than the cytokine of the TNF superfamily or a receptor binding domain thereof described herein. In a preferred embodiment, the collectin domain as described herein is from human and the cytokine of the TNF superfamily or a receptor binding domain thereof as described herein is from human.

The CRD may comprise a mutant, e.g., a mutant of surfactant protein-D or collectin-11, which does not bind to mannose. Such mutants may be identified by methods known to the skilled person, e.g., the methods disclosed in Crouch et al. (J Biol Chem, 2006, 281(26):18008-18014). The collectin trimerization domain (ii) may further comprise a mutant which comprise at least one amino acid substitution as is described herein and may be generated as described herein. Such amino acid substitutions may modify the binding of the collectin trimerization domain to its ligand mannose and lead to an alteration of the clearance rate of a fusion protein as described herein when used in therapy and/or as pharmaceutical composition. The modification may result in a decreased or no binding to mannose and a low clearance rate. Such modifications may be achieved by, e.g., amino acid substitution that affect amino acid position F355 of human surfactant protein-D of SEQ ID NO:21, particularly by the amino acid substitutions F355A, F355S, F355T, F355E, F355D, F355K, or F355R. Especially preferred is the substitution F355D. Alternatively, the modification may result in an increased binding to mannose and a high clearance rate. Such modifications may be achieved by, e.g., amino acid substitution that affect amino acid position F355 of human surfactant protein-D of SEQ ID NO:21, particularly by the amino acid substitutions F355L, F355Y, or F355W.

A neck region as used herein may comprise a coiled-coil structure. The neck may be located adjacent to the CRD of collectins or may in certain cases be located remote from the CRD.

In a preferred embodiment, the collectin trimerization domain comprises the neck and carbohydrate binding domain (CRD) domain of the surfactant protein-D, particularly amino acids 217-375, 218-375, 219-375, 220-375, 221-375, 222-375, 223-375, 224-375, 225-375 from human surfactant protein-D of SEQ ID NO:21. In another preferred embodiment, the collectin trimerization domain comprises the neck domain of the surfactant protein-D, particularly amino acids 217-257, 218-257, 219-257, 220-257, 221-257, 222-257, 223-257, 224-257, or 225-257 from human surfactant protein-D of SEQ ID NO:21. In another preferred embodiment, the collectin trimerization domain comprises the neck and carbohydrate binding domain (CRD) domain of collectin-11, particularly amino acids 110-271, 116-271, or 121-271 of human collectin-11 of SEQ ID NO:22. In another preferred embodiment, the collectin trimerization domain comprises the neck domain of collectin-11, particularly amino acids 110-147, 110-148, 110-149, 110-150, 110-151, 116-147, 116-148, 116-149, 116-150, 116-151, 121-147, 121-148, 121-149, 121-150, or 121-151 of human collectin-11 of SEQ ID NO:22.

A flexible linker element is located between the collectin trimerization domain as described herein and the effector polypeptide. The flexible linker element preferably has a length of 25 amino acids or less. In certain embodiments the linker element has a length of 3-30 amino acids, particularly a length of 3, 4, 5, 6, 7, 8, 9, 10, 11, 12, 13, 14, 15, 16, 17, 18, 19 20, 21, 22, 23, 24, 25, 26, 27, 28 or 30 amino acids. In one embodiment the length of the linker element is 5-25 amino acids, 8-20 amino acids or 10-20 amino acids. More preferably, the length of the linker is 9-15 amino acids. Generally the linker element used herein may be composed of any known amino acids or of artificial amino acid derivatives. In certain embodiments the linker elements are built of small and hydrophilic non-charged amino acids. Generally the linker element according to the invention may comprise amino acids selected from G, S, A and T. The linker element is preferably a glycine/serine linker, i.e., a peptide linker substantially consisting of the amino acids glycine and serine. In an especially preferred embodiment, the linker has the amino acid sequence $(GSS)_a(SSG)_b(GSG)_c$, SEQ ID NO:33, wherein a, b, c is each 0, 1, 2, 3, 4, 5 or 6. It is clear to the skilled person that in cases in which the cytokine of the TNF superfamily or a receptor binding domain thereof already terminates with a G, e.g. human TRAIL (SEQ ID NO:10) such a G may form the first G of the linker in the linker sequence $(GSS)_a(SSG)_b(GSG)_c$, SEQ ID NO:33. It must be understood that in principle the building blocks for the linker elements may be composed of 1, 2, 3, 4 or more amino acids so that the linkers useful herein are not restricted to linkers made of building blocks of 3 elements. Generally a linker element as used herein may be composed of building blocks or also from a sequence of amino acids.

The effector polypeptide as used herein is an extracellular polypeptide or a fragment of a protein comprising extracellular portions of such protein. Generally proteins or fragments thereof may be used as effector polypeptides. Effector polypeptides may be polypeptides of any origin and may be selected from e.g. mammalian polypeptides, vertebrate polypeptides, insect polypeptides, bacterial polypeptides, plant polypeptides, yeast polypeptides. Mammalian polypeptides may comprise mouse, rat, human, horse, goat, dog, rabbit, cat, sheep, hamster, donkey, monkey and other polypeptides. In certain embodiments the polypeptides are human polypeptides or humanized polypeptides. Such extracellular proteins or extracellular portions of proteins may for example be selected from cell surface proteins, secreted extracellular proteins, extracellular regions of transmembrane proteins etc. In certain embodiments of the invention the effector polypeptide is selected from a group consisting of a cytokine of the TNF superfamily, a receptor binding domain thereof, a receptor for a cytokine and/or an antibody or fragments thereof.

In one embodiment the effector polypeptide is a cytokine of the TNF superfamily or a receptor binding domain thereof. Preferably, the cytokine is a mammalian, particularly human cytokine or a receptor binding domain thereof including allelic variants and/or derivatives thereof. Further, it is preferred that the TNF cytokine is a receptor binding domain thereof capable of binding to the corresponding cytokine receptor and preferably capable of receptor activation, whereby apoptotic or proliferative activity may be caused. The cytokine may e.g. be selected from TNF superfamily members, e.g. human TNFSF-1 to -18 as indicated in Table 1, preferably from LTA (SEQ ID NO:1), TNFα (SEQ ID NO:2), LTB (SEQ ID NO:3), OX40L (SEQ ID NO:4), CD40L (SEQ ID NO:5), CD95L (SEQ ID NO:6), CD27L (SEQ ID NO:7), CD30L (SEQ ID NO:8), CD137L (SEQ ID NO:9), TRAIL (SEQ ID NO:10), RANKL (SEQ ID NO:11), TWEAK (SEQ ID NO:12), APRIL 1 (SEQ ID NO:13), APRIL 2 (SEQ ID NO:14), BAFF (SEQ ID NO:15), LIGHT (SEQ ID NO:16), TL1A (SEQ ID NO:17), GITRL (SEQ ID NO:18), EDA-A1 (SEQ ID NO:19), EDA-A2 (SEQ ID NO:20), or a receptor binding domain thereof. Preferred receptor binding domains of the respective proteins are indicated in Table 1 ($NH_2$-aa to COOH-aa) and comprise, e.g., comprises amino acids 59-205 or 60-205 of LTA (SEQ ID NO:1), 86-233 of TNFα (SEQ ID NO:2), 82-244 or 86-244 of LTB (SEQ ID NO:3), 52-183 or 55-183 of OX40L (SEQ ID NO:4), 112-261 or 117-261 of CD40L (SEQ ID NO:5), 51-193 or 56-193 of CD27L (SEQ ID NO:7), 97-234, 98-234 or 102-234 of CD30L (SEQ ID NO:8), 86-254 of CD137L (SEQ ID NO:9), 161-317 of RANKL (SEQ ID NO:11), 103-249, 104-249 or 105-249 of TWEAK (SEQ ID NO:12), 112-247 or 113-247 of APRIL 1 (SEQ ID NO:13), 112-250 or 113-250 of APRIL 2 (SEQ ID NO:14), 140-285 of BAFF (SEQ ID NO:15), 91-240 of LIGHT (SEQ ID NO:16), 91-251 or 93-251 of TL1A (SEQ ID NO:17), 52-177 of GITRL (SEQ ID NO:18), 245-391 of EDA-A1 (SEQ ID NO:19), 245-389 of EDA-A2 (SEQ ID NO:20).

In one embodiment the effector polypeptide may be IL4R-alpha (acc. No.: P24394, SEQ ID NO:37)

More preferably, the cytokine of the TNF superfamily or a receptor binding domain thereof is selected from CD95L or TRAIL or a receptor binding domain thereof. In an especially preferred embodiment, the cytokine of the TNF superfamily or a receptor binding domain thereof comprises the extracellular portion of a TNF cytokine including the receptor binding domain without membrane located domains.

In a preferred embodiment, the cytokine of the TNF superfamily or a receptor binding domain thereof of the fusion protein is selected from human CD95L (SEQ ID NO:6), particularly amino acids 142-281 or 144-281 of human CD95L.

In a further preferred embodiment, the cytokine of the TNF superfamily or a receptor binding domain thereof of the fusion protein is human TRAIL (SEQ ID NO:10), particularly amino acids 95-281, 116-281, 117-281, 118-281, 119-281 or 120-281 of human TRAIL. In another preferred embodiment human TRAIL comprise any amino acid from 95-120 as initial amino acid-amino acid 281 of SEQ ID NO:10.

In a further preferred embodiment of the invention, the cytokine of the TNF superfamily or a receptor binding domain thereof of the fusion protein as described herein comprises a mutant of the cytokine of the TNF superfamily or a receptor binding domain thereof which binds and/or activates TRAIL-receptor 1 (TRAILR1) and/or TRAIL-receptor 2 (TRAILR2). The binding and/or activity of the mutant may be, e.g., determined by the assays as disclosed herein, e.g., in the Examples or by the assays disclosed in van der Sloot et al. (PNAS, 2006, 103:8634-8639), Kelley et al. (J. Biol. Chem., 2005, 280:2205-2215), or MacFarlane et al. (Cancer Res., 2005, 65: 11265-11270).

The mutant may be generated by any technique and is known by the skilled person, e.g., the techniques disclosed in an der Sloot et al. (PNAS, 2006, 103:8634-8639), Kelley et al. (J. Biol. Chem., 2005, 280:2205-2215), or MacFarlane et al. (Cancer Res., 2005, 65: 11265-11270) any may comprise any type of structural mutations, e.g., substitution, deletion, duplication and/or insertion of an amino acid. A preferred embodiment is the generation of substitutions. The substitution may affect at least one amino acid of the cytokine of the TNF superfamily or a receptor binding domain thereof as described herein. In a preferred embodiment, the substitution may affect at least one of the amino acids of TRAIL, e.g., human TRAIL (e.g., SEQ ID NO:10). Preferred substitutions in this regard affect at least one of the following amino acids of human TRAIL of SEQ ID NO:10: R130, G160, Y189, R191, Q193, E195, N199, K201, Y213, T214, S215, H264, I266, D267, D269. Preferred amino acid substitutions of human TRAIL of SEQ ID NO:10 are at least one of the following substitutions: R130E, 0160M, Y189A, Y189Q, R191K, Q193S, Q193R, E195R, N199V, N199R, K201R, Y213W, T214R, S215D, H264R, I266L, D267Q, D269H, D269R, or D269K.

The amino acid substitution(s) may affect the binding and/or activity of TRAIL, e.g., human TRAIL, to or on either the TRAILR1 or the TRAILR2. Alternatively, the amino acid substitution(s) may affect the binding and/or activity of TRAIL, e.g., human TRAIL, to or on both, the TRAILR1 and the TRAILR2. The binding and/or activity of the TRAILR1 and/or TRAILR2 may be affected positively, i.e., stronger, more selective or specific binding and/or more activation of the receptor. Alternatively, the binding and/or activity of the TRAILR1 and/or TRAILR2 may be affected negatively, i.e., weaker, less selective or specific binding and/or less or no activation of the receptor.

Examples of mutants of TRAIL with amino acid substitution(s) that affect binding and/or activity of both TRAILR1 and TRAILR2 may be found, e.g., in Table 1 of MacFarlane et al. (cf. above) and may comprise human TRAIL mutants with the following two amino acid substitutions of SEQ ID NO:10 Y213W and S215D or the following single amino acid substitution Y189A.

Examples of mutants of TRAIL with amino acid substitution(s) that affect binding and/or activity of TRAILR1 may be found, e.g., in Table 1 of MacFarlane et al. (cf. above) and may comprise human TRAIL mutants with the following four amino acid substitutions of SEQ ID NO:10 N199V, K201R, Y213W and S215D or the following five amino acid substitutions Q193S, N199V, K201R, Y213W and S215D or in Table 2 of Kelley et al. (cf. above) and may comprise human TRAIL mutants with the following six amino acid substitutions Y213W, S215D, Y189A, Q193S, N199V, and K201R or Y213W, S215D, Y189A, Q193S, N199R, and K201R.

Examples of mutants of TRAIL with amino acid substitution(s) that affect binding and/or activity of TRAILR2 may be found, e.g., in Table 1 of MacFarlane et al. (cf. above) or in Table 2 of Kelley et al. (cf. above) and may comprise human TRAIL mutants with the following six amino acid substitutions of SEQ ID NO:10: Y189Q, R191K, Q193R, H264R, I266L, and D267Q, or in Table 2 of van der Sloot et al. (cf. above), and may comprise human TRAIL mutants with the following single amino acid substitution D269H, the following two amino acid substitutions D269H and E195R or D269H and T214R.

In a further preferred embodiment, the cytokine portion of the fusion protein is derived from human LIGHT (SEQ ID NO:16), particularly amino acids 91-240 of SEQ ID NO:16. LIGHT is a member of TNF superfamily, and its receptors have been identified as lymphotoxin-beta receptor (LTbetaR) and the herpesvirus entry mediator (HVEM)/ATAR/TR2, both of which lack the cytoplasmic sequence termed the 'death domain'. Since LIGHT engages LTbetaR and HVEM as the cellular receptors, it is expected to have biological functions similar to those of LTalpha and LTbeta. As previous studies have shown, LIGHT induces cell death in HT-29 cells as does LTalpha (Harrop, J. A et al. (1998) J. Biol. Chem. 273, 27548-27556; Zhai, Y., et al. (1998) J. Clin. Invest. 102, 1142-1151 and Rooney, I. A. et al. (2000) J. Biol. Chem. 275, 14307-14315), it causes growth arrest in RD cells following the developmental changes to smooth muscles cells, and it stimulates secretion of IL-8 and RANTES from the cells (Hikichi, Y., et al. (2001) Biochem. Biophys. Res. Commun. 289, 670-677). It has also been reported that LIGHT is one of the CD28-independent co-stimulatory molecules in T cells (Tamada, K., et al. (2000) J. Immunol. 164, 4105-4110).

In one embodiment the cytokine of the TNF superfamily is RANK-L. Human RANK Ligand (RANK-L) is a member of the tumor necrosis factor superfamily of proteins known to be key regulators of the immune system, bone development and homeostasis (Anderson, et al., Nature 390: 175-179, 1997). This ligand is also designated Tumor Necrosis Factor Related Activation-Induced Cytokine (TRANCE) (Wong, et al., J. Exp. Med. 186: 2075, 1997), Osteoprotegerin Ligand (OPGL) (Lacey, et al., Cell 93: 165, 1998), and Osteoclast Differentiation Factor (ODF) (Yasuda, et al., Proc. Natl. Acad. Sci. 95: 3597, 1998). Members of the tumor necrosis family mediate diverse and sometimes opposite biological responses such as proliferation, apoptosis, cell survival, and differentiation.

In a further embodiment the cytokine of the TNF superfamily is TWEAK. TWEAK (TNFLSF member 12) was recently found to be a direct and strong inducer of angiogenesis (formation and growth of blood vessels) as it was observed that picomolar concentrations of TWEAK promote proliferation of normal endothelial cells and that TWEAK induces angiogenesis in an in vivo rat cornea model (Lynch et al., 1999, The Journal of Biological Chemistry, 274(13) pp. 8455-8459).

In a still further preferred embodiment, the cytokine portion of the fusion protein is derived from human APRIL (SEQ ID NO:13 or 14), particularly amino acids 112-247 or 113-247 of SEQ ID NO:13, or 112-250 or 113-250 of SEQ ID NO:14. APRIL (TNFLS member 13) is a trimeric cytokine that binds to the receptor TNFRSF13B and to TNFRSF17. It has recently been shown that the addition of recombinant APRIL to various tumor cells stimulates their proliferation and hence APRIL may be implicated in the regulation of tumor cell growth (Hahne M., et al, 1998; J. Exp. Med. 188:1185-1190). It has also been suggested that APRIL may be involved in monocyte/macrophage-mediated immunological processes.

The TNF superfamily cytokines used as effector polypeptides herein may in certain embodiments be truncated at the N-terminal side. Truncation as used in this respect shall refer to omission of all amino acids of the stalk region, or to omission of part of the amino acids of the stalk region.

Proteins of the TNF superfamily are anchored to the membrane via an N-terminal proportion of 15-30 amino acids, the so-called stalk-region. The stalk-region contributes to trimerization and provides for a certain distance to the cell membrane. However, the stalk-region does not form part of the receptor binding domain (RBD).

Figure 36:
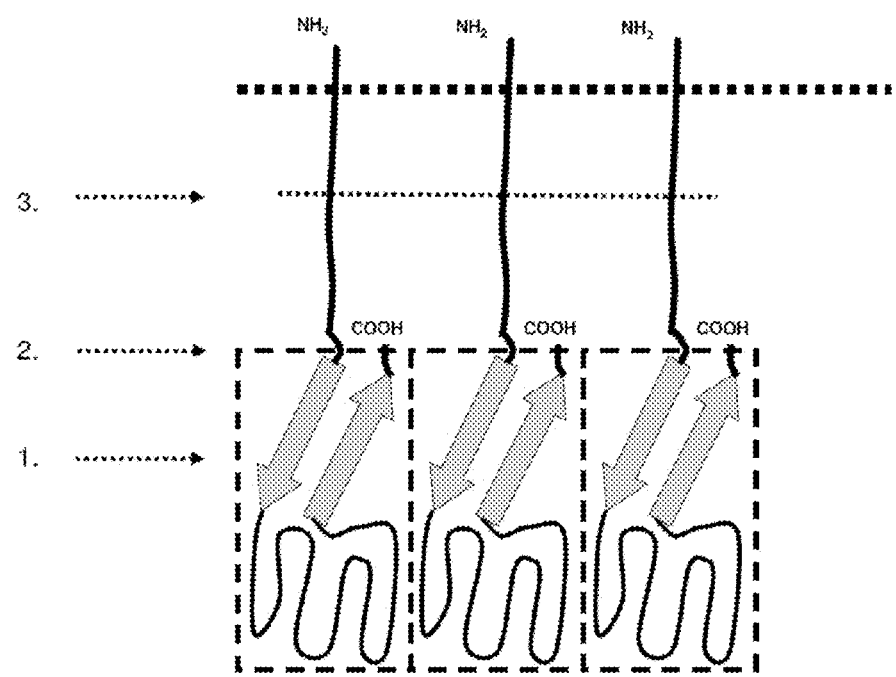
FIG. 36: Schematic picture representing the general structure of TNF-SFproteins. "■ ■ ■" designates cell membrane; N-terminus located within the cell, 1. anti-parallel β-fold of receptor-binding domain (RBD), 2. interface of RBD and cell membrane, 3. protease cleavage site.
Figure 37:
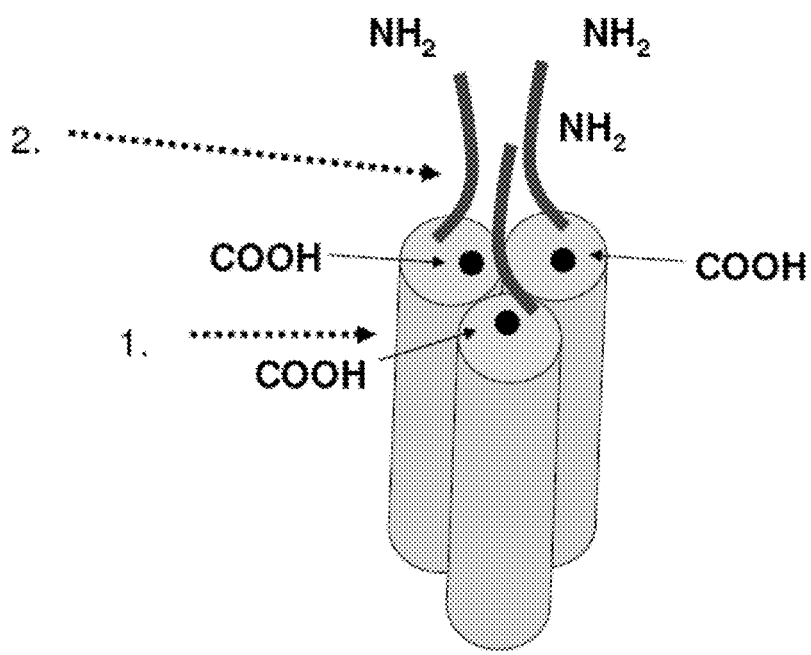
FIG. 37: Schematic picture representing the structure of the native TNF-SF trimer. Cylindric structures (1) represent RBDs, N-termini (2) forming the stalk and connecting the RBD with the cell membrane.

Importantly, the RBD is characterized by a particular localization of its N- and C-terminal amino acids. Said amino acids are immediately adjacent and are located central to the axes of the trimers. The first N-terminal amino acids of the RBD form an anti-parallel beta-strand with the C-terminal amino acids of the RBD (FIGS. 36 and 38).

Thus, the anti-parallel beta-strand of the RBD forms an interface with the cell membrane, which is connected to and anchored within the cell membrane via the amino acids of the stalk-region. In certain embodiments of the invention the stalk region of the TNF superfamily cytokine used as an effector polypeptide is omitted. This has the particular advantage that steric hindrance between the stalk region and the linker-collectin can be avoided. Otherwise, the linker connecting the C-terminus of one of the TNF-SF-RBD domain with the N-terminus of the collectin domain would be sterically hindered by the stalk, which might result in instability and/or formation of aggregates.

In certain embodiments truncating the TNF superfamily cytokine by omitting the stalk region of the N-terminus is a prerequisite for C-terminal positioning of the collectin trimerization domain. In certain embodiments it is highly preferred that the collectin based trimeric fusion protein comprises a receptor binding domain of the TNF-SF cytokine lacking any amino acids from the stalk-region.

The ability of the collectin based trimeric TNF-SF fusion polypeptide, wherein the effector TNF superfamily cytokine is positioned N-terminally of the collectin trimerization domain, of forming an ordered trimeric structure comprising at least one functional binding site for the respective cytokine receptor, is in certain embodiments of the invention crucially associated with total or partial omission of the stalk region of the TNF superfamily cytokine.

In the fusion protein of the invention as described herein, the collectin trimerization domain is located C-terminally of the effector polypeptide. Thus, the fusion protein may comprise a effector polypeptide as described herein and a collectin trimerization domain that comprises a collectin family neck domain and a collectin family CRD domain, e.g., the neck domain and the CRD and/or neck domain of surfactant protein-D or the neck domain and the CRD and/or neck domain of collectin-11 both as described herein wherein those domains are located C-terminally of the effector polypeptide. In this embodiment, it is preferred that the collectin trimerization domain comprises the neck domain and the CRD.

The fusion proteins disclosed herein comprise the effector polypeptide N-terminally to the collectin trimerization domain. The inventors found that controlled formation of trimers may only be effective if this orientation is obeyed. Only constructs having the effector polypeptide N-terminally of the collectin trimerization domain do lead to controlled stable trimers and are minimally prone to form larger aggregates during handling and purification. From the published crystal structure (Shrive, A. K., et al., 2003, J. Mol. Biol. 331: 509-523) of the neck-CRD part of recombinant human SP-D, the relative position of the N- and C-terminal amino acid of each monomer can be derived. Whereas the amino-terminal amino-acids (A205[A225]*) of the trimers are solvent exposed and located in direct proximity at the beginning of the parallel coiled-coil structure, the side-chain of the C-terminal (F355[F375]*) amino-acids of the trimers are buried within the CRD-domain and positioned in a triangular distant symmetry to each other. The COOH groups of F355[F375]* are forming an isosceles triangle with approx. 23 angstrom side length. Importantly, the protein-core of the neck-CRD trimers is within this triangle, thus only the space radially to the neck-CRD core is accessible for fusion partners.

It can be concluded, that by their relative position to each other, the N- and the C-terminal amino acids in the neck-CRD part of the SP-D trimere are not equivalent with respect to their use as joining point for the construction of fusion proteins.

As a disadvantage in the case of the TNF-SF proteins, a C-terminal fusion (this means, fusing the TNF-SF-fragment towards the C-terminal amino-acid of the neck-CRD; F355 [F375]*) comprising the extracellular region with the stalk region would result in an large molecular aggregate due to the trimerisation force of the TNF-SF fragment itself.

*The numbers given in [ ] refer to Seq ID 21.

Therefore, fusing an TNF-SF-RBD domain with its endogenous stalk C-terminal to the neck-CRD construct would not result in an defined trimeric assembly. Accordingly in certain embodiments of the invention truncated polypeptides of the TNF-SF-RBD (TNF superfamily receptor binding domain) lacking the stalk region are used as effector polypeptides.

In a preferred embodiment, the fusion protein comprises TRAIL, particularly human TRAIL or a receptor binding domain thereof or a mutant of TRAIL as described herein, preferably 95-281, 116-281, 117-281, 118-281, 119-281 or 120-281 of human TRAIL (SEQ ID NO:10) and a collectin trimerization domain or mutant thereof as described herein, particularly the CRD and neck domain of surfactant protein-D, preferably amino acids 217-375, 218-375, 219-375, 220-375, 221-375, 222-375, 223-375, 224-375, 225-375 of human surfactant protein-D of SEQ ID NO:21 wherein the collectin trimerization domain is located C-terminally of TRAIL or mutant TRAIL as described herein. Preferred fusion proteins in this regard are SEQ ID Nos:26 or 27. Alternatively, the above fusion protein may additionally comprise a linker as described herein, e.g., a linker with the amino acid sequence (GSS)a(SSG)b(GSG)c, SEQ ID NO: 33, wherein a, b, c is each 0, 1, 2, 3, 4, 5 or 6. Preferably, the linker has a length of 9-15 amino acids.

In a preferred embodiment, the fusion protein comprises TRAIL, particularly human TRAIL or a receptor binding domain thereof or a mutant of TRAIL as described herein, preferably 95-281, 116-281, 117-281, 118-281, 119-281 or 120-281 of human TRAIL (SEQ ID NO:10) and a collectin trimerization domain or mutant thereof as described herein, particularly the neck domain of surfactant protein-D, preferably amino acids 217-257, 218-257, 219-257, 220-257, 221-257, 222-257, 223-257, 224-257, or 225-257 of human surfactant protein-D of SEQ ID NO:21 wherein the collectin trimerization domain is located C-terminally of TRAIL or mutant TRAIL as described herein. A preferred fusion protein in this regard is SEQ ID NO:28. Alternatively, the above fusion protein may additionally comprise a linker as described herein, e.g., a linker with the amino acid sequence (GSS)a(SSG)b(GSG)c, SEQ ID NO: 33, wherein a, b, c is each 0, 1, 2, 3, 4, 5 or 6.

In another preferred embodiment, the fusion protein comprises TRAIL, particularly human TRAIL or a receptor binding domain thereof or a mutant of TRAIL as described herein, preferably 95-281, 116-281, 117-281, 118-281, 119-281 or 120-281 of human TRAIL (SEQ ID NO:10) and a collectin trimerization domain or mutant thereof as described herein, particularly the CRD and neck domain of collectin-11, preferably amino acids 110-271, 116-271, or 121-271 of human collectin-11 of SEQ ID NO:22 wherein the collectin trimerization domain is located C-terminally of TRAIL or mutant TRAIL as described herein. Preferred fusion proteins in this regard are SEQ ID Nos:29 and 30. Alternatively, the above fusion protein may additionally comprise a linker as described herein, e.g., a linker with the amino acid sequence (GSS)a(SSG)b(GSG)c, SEQ ID NO: 33, wherein a, b, c is each 0, 1, 2, 3, 4, 5 or 6. Preferably, the linker has a length of 9-15 amino acids.

In another preferred embodiment, the fusion protein comprises TRAIL, particularly human TRAIL or a receptor binding domain thereof or a mutant of TRAIL as described herein, preferably 95-281, 116-281, 117-281, 118-281, 119-281 or 120-281 of human TRAIL (SEQ ID NO:10) and a collectin trimerization domain or mutant thereof as described herein, particularly the neck domain of collectin-11, preferably amino acids 110-147, 110-148, 110-149, 110-150, 110-151, 116-147, 116-148, 116-149, 116-150, 116-151, 121-147, 121-148, 121-149, 121-150, or 121-151 of human collectin-11 of SEQ ID NO:22 wherein the collectin trimerization domain is located C-terminally of TRAIL or mutant TRAIL as described herein. A preferred fusion protein in this regard is SEQ ID NO:31. Alternatively, the above fusion protein may additionally comprise a linker as described herein, e.g., a linker with the amino acid sequence (GSS)a(SSG)b(GSG)c, SEQ ID NO: 33, wherein a, b, c is each 0, 1, 2, 3, 4, 5 or 6.

In another preferred embodiment, the fusion protein comprises CD95L, particularly human CD95L, or a receptor binding domain thereof as described herein, e.g. amino acids 21-160 of SEQ ID NO:40, and a collectin trimerization domain comprising the neck domain and the CRD of human SP-D, e.g. amino acids 172-209 and 210-327 of SEQ ID NO:40, respectively, or a mutant thereof as described herein. The fusion protein may comprise a linker, e.g. a flexible linker, more preferably a glycine/serine linker as described herein having a length of preferably 9-15 amino acids. A preferred fusion protein in this regard comprises SEQ ID NO:40, particularly amino acids 21-327 of SEQ ID NO:40.

In another preferred embodiment, the fusion protein comprises LIGHT, particularly human LIGHT or a receptor binding domain thereof as described herein, preferably amino acids 21-170 of SEQ ID NO:41, and a collectin trimerization domain comprising the neck domain and the CRD of human SP-D, e.g. amino acids 182-219, and 220-337 of SEQ ID NO:41, respectively, or a mutant thereof as described herein. The cytokine and the collectin domain are connected by a linker, e.g. a glycine/serine linker as described herein, having a length of preferably 9-15 amino acids. A preferred fusion protein in this regard comprises SEQ ID NO:41, particularly amino acids 21-327 of SEQ ID NO:41.

In another preferred embodiment, the fusion protein comprises TRAIL, particularly human TRAIL or a receptor binding domain thereof or mutant of TRAIL as described herein, e.g. amino acids 21-181 of SEQ ID NO:43 (wild type TRAIL), amino acids 21-181 of SEQ ID NO:47 (TRAILR1mut) or amino acids 21-181 of SEQ ID NO:48 (TRAILR2mut). Further, the fusion protein comprises a collectin trimerization domain selected from the neck domain and optionally the CRD of human SP-D, e.g. amino acids 193-230, and 231-384 of SEQ ID NO:43, respectively, or a mutant thereof as described herein, e.g. mutants as shown in SEQ ID NO:49 or 50. The fusion polypeptide comprises both the neck region and the CRD of human SP-D. The cytokine and collectin domain are connected by a linker, e.g. a glycine/serine linker as described herein. Preferably, the linker has a length of 9-15 amino acids. Preferred fusion proteins in this regard comprise (i) SEQ ID NO:43, particularly amino acids 21-348 of SEQ ID NO:43, (ii) SEQ ID NO:44, particularly amino acids 21-230 of SEQ ID NO:44, (iii) SEQ ID NO:47, particularly amino acids 21-348 of SEQ ID NO:47, (iv) SEQ ID NO:48, particularly amino acids 21-348 of SEQ ID NO:48, (v) SEQ ID NO: 49, particularly amino acids 21-348 of SEQ ID NO:49 or (vi) SEQ ID NO:50, particularly amino acids 21-348 of SEQ ID NO:50.

In another preferred embodiment, the fusion protein comprises TRAIL, particularly human TRAIL or receptor-binding domain thereof or a mutant of TRAIL as described herein above, and a collectin trimerization domain, which is the neck domain of human collectin 11, and the CRD of human collectin 11, e.g. amino acids 193-224 and 225-347 of SEQ ID NO:45, respectively. The cytokine and the collectin domain are connected by a linker, e.g. a glycine/serine linker as described above herein, preferably having a length of 9-15 amino acids. Preferred fusion proteins in this regard comprise SEQ ID NO:45 and SEQ ID NO:46, particularly, amino acids 21-347 of SEQ ID NO:45 or amino acids 21-229 of SEQ ID NO:46.

In another preferred embodiment, the fusion protein comprises APRIL, particularly human APRIL or a receptor binding domain thereof as described herein, e.g. amino acids 21-158 of SEQ ID NO:51 and a collectin trimerization domain as described herein, particularly the neck domain and the CRD of human SP-D or a mutant thereof, as described herein, e.g. amino acids 170-207 and 208-325 of SEQ ID NO:51, respectively. The cytokine and the collectin domain are connected by a linker, e.g. a glycine/serine linker as described herein, preferably having a length of 9-15 amino acids. The preferred fusion protein in this regard comprises SEQ ID NO:51, particularly amino acids 21-325 of SEQ ID NO:51.

In certain embodiments the effector polypeptide is an antibody. An antibody as used herein may comprise conventional wild type antibodies, as well as modified and altered antibodies. Such modifications may comprise generation of single chain antibodies, antibody fragments, humanized antibodies etc. Generally antibodies or antigen binding amino acid sequences (complementary determining regions, CDRs) may be antibodies or CDRs from any species as well as antibodies or CDRs recombinantly produced.

The antibody may be a complete antibody from human class A, E, D, M or G and preferably from IgG, or an antigen binding fragment thereof. Preferably, the antibody or an antigen binding fragment thereof is a chimeric or humanized antibody which has human constant regions, preferably IgG1, IgG2, IgG3 or IgG4 subclass or combinations thereof or engineered variants that have altered effector functions. Effector functions may by antibody dependent cellular toxicity (ADCC) and complement dependent cytotoxicity (CDC). Engineered Fc parts may also have altered pharmacokinetic properties. Further, a fully human antibody or antigen binding fragment thereof is preferred. More preferably the antibody is a humanized or human antibody or a fragment thereof which additionally comprises human or substantially human framework regions. Also preferred are antibody fragments, e.g. divalent or monovalent antibody fragments such as F(ab)2 or Fab fragments. On the other hand, the antibody may be a recombinant antibody, e.g. a single chain antibody or a fragment thereof, e.g. an scFv fragment where the Fv fragments are connected by any amino acid sequence, preferably by small polar amino acids and more preferably composed of glycine and/or serine and/or threonine. Further, the recombinant antibody may be a multimeric scFv assembly, e.g. two or more scFv-fragments linked together on a single polypeptide.

In certain embodiments the antibodies, single chain antibody or a fragment of an antibody or a single chain antibody are directed against a cytokine of the TNF superfamily, a receptor binding domain thereof or a receptor for a cytokine. In a special embodiment the antibodies are directed against is IL4R-alpha.

In certain embodiments the antibody is an antibody or an antibody fragment, e.g. chimeric or humanized antibody derived from the murine antibody X2/45 (Tony et al., 1994) produced by the hybridoma cell line DSM ACC2882. The hybridoma cell line DSM ACC2882 was deposited under the Budapest Treaty for the Deposit of Microorganisms on Jan. 29, 2008 at Deutsche Sammlung von Mikroorganismen and Zellkulturen GmbH (DSZM), Mascheroder Weg 1 b, 38124 Braunschweig, Germany. Inn certain special embodiments the antibody or antibody fragment recognizes human IL4Ra-Receptor extracellular domain. In a further embodiment, the complementary determining regions of heavy and light chain of murine X2/45 have been used to generate an human or humanized antibody or a recombinant humanized antibody fragment recognizing human IL4Ra. In a preferred embodiment, an humanized scFv antibody fragment as depicted in SEQ ID: 52, position 21-264, is used as an effector polypeptide.

The fusion protein as described herein may additionally comprise an N-terminal signal peptide domain, which allows processing, e.g., extracellular secretion, in a suitable host cell. Preferably, the N-terminal signal peptide domain comprises a protease, e.g., a signal peptidase cleavage site and thus may be removed after or during expression to obtain the mature protein. In a preferred embodiment, the N-terminal signal peptide domain comprises the sequence SEQ ID NO:23, SEQ ID NO:24, or SEQ ID NO:25.

Further, the fusion protein may comprise comprises a recognition/purification domain, e.g., a Strep-tag domain and/or a poly-His domain, which may be located at the N-terminus or at the C-terminus.

The fusion protein may additionally comprise a C-terminal flexible element, having a length of, e.g., 1-50, preferably 10-30 amino acids which may include and/or connect to a recognition/purification domain as described herein.

In certain embodiments the fusion protein may additionally comprise an antibody, a single chain antibody or a fragment of an antibody or single chain antibody fused to the C-terminal end of the CRD. Such antibody may in certain embodiment serve e.g. for targeting the fusion protein to certain molecules or sites. Also may such constructs offer an opportunity to create fusion polypeptides with at least two different antigen specificities.

A further aspect of the present invention relates to a nucleic acid molecule encoding a fusion protein as described herein. The nucleic acid molecule may be a DNA molecule, e.g., a double-stranded or single-stranded DNA molecule, or an RNA molecule. The nucleic acid molecule may encode the fusion protein or a precursor thereof, e.g., a pro- or pre-proform of the fusion protein which may comprise a signal sequence as described herein or other heterologous amino acid portions for secretion or purification which are preferably located at the N- and/or C-terminus of the fusion protein as described herein. The nucleic acid molecule may encode the fusion protein wherein the heterologous amino acid portions may be linked to the first and/or second domain via a protease cleavage site, e.g., a Factor $X_a$, thrombin or IgA protease cleavage site.

The nucleic acid molecule may be operatively linked to an expression control sequence, e.g. an expression control sequence which allows expression of the nucleic acid molecule in a desired host cell. The nucleic acid molecule may be located on a vector, e.g. a plasmid, a bacteriophage, a viral vector, a chromosal integration vector, etc. Examples of suitable expression control sequences and vectors are described for example by Sambrook et al. (1989) *Molecular Cloning, A Laboratory Manual*, Cold Spring Harbor Press, and Ausubel et al. (1989), *Current Protocols in Molecular Biology*, John Wiley & Sons or more recent editions thereof.

Various expression vector/host cell systems may be used to express the nucleic acid sequences encoding the fusion proteins of the present invention. Suitable host cells include, but are not limited to, prokaryotic cells such as bacteria, e.g. *E. coli*, eukaryotic host cells such as yeast cells, insect cells, plant cells or animal cells, preferably mammalian cells and, more preferably, human cells. The nucleic acid molecule encoding the fusion protein as described herein may be optimized in view of its codon-usage for the expression in suitable host cells, e.g. *E. coli*, yeast cells, plant cells, insect cells, animal cells, e.g., mammalian cells or human cells.

Further, the invention relates to a non-human organism, e.g., mouse or rat, transformed or transfected with a nucleic acid molecule as described herein. Such organisms may be comprise knock-out organisms, generated by known methods of genetic transfer including homologous recombination. Alternatively, such organisms may comprise transgenic organisms which comprise several copies of the nucleic acid molecule as described herein. The generation of transgenic organisms is known in the art.

The fusion protein, the nucleic acid coding therefore, the transformed or transfected cell as well as the trimeric complexes or oligomers of the trimeric complexes, all as described herein may be used for pharmaceutical, diagnostic and/or research applications. For these applications it is preferred to use fusion proteins in which both the effector polypeptide as described herein and the collectin trimerization domain as described herein are from the same species in order to minimize immunological effects, e.g., from human when applying such proteins to humans. In addition, the fusion of an effector polypeptide as described herein to a neck-collectin trimerization domain as described herein, e.g., neck domain from surfactant protein-D or collectin-11, may lead to fast clearance. Alternatively, the fusion of a TNF-superfamily cytokine or receptor binding domain thereof as described herein to a neck and CRD-collectin trimerization domain as described herein, e.g., neck and CRD domain from surfactant protein-D or collectin-11, may lead to low clearance. The use of mutants of the collectin trimerization domain as described herein may modify the clearance rate of the fusion protein in a way as described herein.

A further aspect of the present invention relates to a pharmaceutical or diagnostic composition comprising as an active agent at least one fusion protein, the nucleic acid coding therefore, the transformed or transfected cell as well as the trimeric complexes or oligomers of the trimeric complexes, all as described herein.

At least one fusion protein, the nucleic acid coding therefore, the transformed or transfected cell as well as the trimeric complexes or oligomers of the trimeric complexes, all as described herein may be used in therapy, e.g., in the prophylaxis and/or treatment of disorders selected from proliferative disorders, particularly disorders caused by, associated with and/or accompanied by dysfunction of TNF cytokines, such as tumors, e.g. solid or lymphatic tumors, infectious diseases, inflammatory diseases, metabolic diseases, autoimmune disorders, e.g. rheumatoid and/or arthritic diseases, degenerative diseases, e.g. neurodegenerative diseases such as multiple sclerosis, apoptosis-associated diseases and transplant rejections.

The fusion protein, a nucleic acid molecule, or a cell as described herein may be used in therapy of diseases, e.g. as a medicament or for the preparation of a pharmaceutical composition in the prophylaxis and/or treatment of neoplastic, inflammatory, infectious, degenerative, genetic, proliferative and vascular diseases, and of premalignant and malignant cancerous conditions, cancer and inborn errors.

In certain embodiments of the invention degenerative diseases may comprise degenerative diseases of different tissues or organs such as neurodegenerative diseases, degenerative diseases of bones and the skeleton, degenerative diseases of the skin, of mucosal epithelia and may comprise e.g. osteoporesis, osteopenia, Alzheimer disease and the like.

In one embodiment, the proliferative diseases are tumors. Tumors may comprise tumors of the head and the neck, tumors of the respiratory tract, tumors of the anogenital tract, tumors of the gastrointestinal tract, tumors of the urinary system, tumors of the reproductive system, tumors of the endocrine system, tumors of the central and peripheral nervous system, tumors of the skin and its appendages, tumors of the soft tissues and bones, tumors of the lymphopoietic and hematopoietic system, etc. Tumors may comprise for example neoplasms such as benign and malignant tumors, carcinomas, sarcomas, leukemias, lymphomas or dysplasias. In a particular embodiment, the tumor is for example cancer of the head and the neck, cancer of the respiratory tract, cancer of the anogenital tract, cancer of the gastrointestinal tract, cancer of the skin and its appendages, cancer of the central and peripheral nervous system, cancer of the urinary system, cancer of the reproductive system, cancer of the endocrine system, cancer of the soft tissues and bone, cancer of the hematopoietic and lymphopoietic system.

In certain embodiments where the effector polypeptide is selected from a group consisting of a TNSF polypeptide or a cytokine Receptor polypeptide the invention also relates to a fusion protein, a nucleic acid molecule, or a cell as described herein for use in therapy, e.g., the use of a fusion protein, a nucleic acid molecule, or a cell as described herein for the preparation of a pharmaceutical composition in the prophylaxis and/or treatment of proliferative disorders, particularly disorders caused by, associated with and/or accompanied by dysfunction of TNF cytokines, such as tumors, e.g. solid or lymphatic tumors, infectious diseases, inflammatory diseases, metabolic diseases, autoimmune disorders, e.g. rheumatoid and/or arthritic diseases, degenerative diseases, e.g. neurodegenerative diseases such as multiple sclerosis, apoptosis-associated diseases and transplant rejections.

In certain embodiments where the effector polypeptide is an antibody, a single chain antibody or a fragment of an antibody or a single chain antibody the invention also relates to a fusion protein, a nucleic acid molecule, or a cell as described herein for use in therapy, e.g., the use of a fusion protein, a nucleic acid molecule, or a cell as described herein for the preparation of a pharmaceutical composition in the prophylaxis and/or treatment of proliferative disorders, immunologic disorders, autoimmune disorders, inflammatory disease, lymphatic tumors, infectious diseases, metabolic diseases, autoimmune disorders, e.g. rheumatoid and/or arthritic diseases, degenerative diseases, e.g. neurodegenerative diseases such as multiple sclerosis, apoptosis-associated diseases and transplant rejections.

The composition may be administered as monotherapy or as combination therapy with further medicaments, e.g. cytostatic or chemotherapeutic agents, corticosteroids and/or antibiotics. Preferably, the composition is administered together with tumor-selective apoptosis sensitizing and/or inducing agents, e.g. as described in Example 2.8.

The fusion protein is administered to a subject in need thereof, particularly a human patient, in a sufficient dose for the treatment of the specific conditions by suitable means. For example, the fusion protein may be formulated as a pharmaceutical composition together with pharmaceutically acceptable carriers, diluents and/or adjuvants. Therapeutic efficacy and toxicity may be determined according to standard protocols. The pharmaceutical composition may be administered systemically, e.g. intraperitoneally, intramuscularly or intravenously or locally, e.g. intranasally, subcutaneously or intrathecally. Preferred is intravenous administration.

The dose of the fusion protein administered will of course be dependent on the subject to be treated, on the subject's weight, the type and severity of the disease, the manner of administration and the judgement of the prescribing physician. For the administration of fusion proteins, a daily dose of 0.001 to 100 mg/kg is suitable.

REFERENCES

1. Locksley R M, Killeen N and Lenardo M J (2001) Cell 104: 487-501
2. Bodmer J L, Schneider P and Tschopp J (2002) Trends Biochem. Sci. 27: 19-26
3. Grell M, Douni E, Wajant H, Lohden M., Clauss M, Maxeiner B, Georgopoulos S, Lesslauer W, Kollias G, Pfizenmaier K and Scheurich P (1995) Cell 83: 793-802
4. Schneider P, Holler N, Bodmer J L, Hahne M, Frei K, Fontana A and Tschopp J (1998) J. Exp. Med. 187: 1205-1213
5. Wajant H, Moosmayer D, Wuest T, Bartke T, Gerlach E, Schonherr U, Peters N, Scheurich P and Pfizenmaier K (2001) Oncogene 20: 4101-4106
6. Haswell L E, Glennie M J and Al-Shamkhani A (2001) Eur. J. Immunol. 31: 3094-31008
7. Holler N, Tardivel A, Kovacsovics-Bankowski M, Hertig S, Gaide O, Martinon F, Tinel A, Deperthes D, Calderara S, Schulthess T, Engel J, Schneider P and Tschopp J (2003) Mol. Cell. Biol. 23: 1428-1440
8. Stone G W, Barzee S, Snarsky V, Kee K, Spina C A, Yu X F and Kornbluth R S (2006) J. Virol. 80: 1762-177216
9. Mundle S D and Raza A (2002) Trends Immunol. 23: 187-194
10. Siegel R M, Muppidi J R, Sarker M, Lobito A, Jen M, Martin D, Straus S E and Lenardo M J (2004) J. Cell Biol. 167: 735-744
11. Henkler F, Behrle E, Dennehy K M, Wicovsky A, Peters N, Warnke C, Pfizenmaier K and Wajant H (2005) J. Cell Biol. 168: 1087-1098

Basic Structure of a Fusion Protein

In the following, the basic structure of the recombinant proteins of the invention is shown exemplified for the TNF-superfamily cytokines as described herein. This exemplification is not intended to limit the general scope of the invention but to give a general impression of the components present in the fusion protein.

As a basic structure the fusion protein comprises the following elements:
 (i) a collectin family trimerization domain comprising
   a. a collectin family Carbohydrate Recognition Domain; and
   b. a collectin family neck region;
 (ii) a linker element; and
 (iii) an effector polypeptide, wherein the effector polypeptide is located N-terminally of the collectin family neck region.

1.1 Sequences of the Signal Peptides

```
                                        (SEQ ID NO: 23)
            MNFGFSLIFLVLVLKGVQC (SEQ ID NO: 24)
            METDTLLLWVLLLWVPGSTG (SEQ ID NO: 25)
            METDTLLLWVLLLWVPAGNG
```

1.2 Flag-Epitope/Enterokinase-Processing Site

```
                                              (SEQ ID NO: 31)
            DYKDDDDKD
                                                      5
```

1.3 Human Collectins

```
Surfactant Protein-D
                                                              (SEQ ID NO: 21)
   1 MLLFLLSALV LLTQPLGYLE AEMKTYSHRT TPSACTLVMC SSVESGLPGR DGRDGREGPR

61 GEKGDPGLPG AAGQAGMPGQ AGPVGPKGDN GSVGEPGPKG DTGPSGPPGP PGVPGPAGRE

121 GPLGKQGNIG PQGKPGPKGE AGPKGEVGAP GMQGSAGARG LAGPKGERGV PGERGVPGNA

181 GAAGSAGAMG PQGSPGARGP PGLKGDKGIP GDKGAKGESG LPDVASLRQQ VEALQGQVQH

241 LQAAFSQYKK VELFPNGQSV GEKIFKTAGF VKPFTEAQLL CTQAGGQLAS PRSAAENAAL

301 QQLVVAKNEA AFLSMTDSKT EGKFTYPTGE SLVYSNWAPG EPNDDGGSED CVEIFTNGKW

361 NDRACGEKRL VVCEF

Collectin-11
                                                              (SEQ ID NO: 22)
   1 MRGNLALVGV LISLAFLSLL PSGHPQPAGD DACSVQILVP GLKGDAGEKG DKGAPGRPGR

61 VGPTGEKGDM GDKGQKGSVG RHGKIGPIGS KGEKGDSGDI GPPGPNGEPG LPCECSQLRK

121 AIGEMDNQVS QLTSELKFIK NAVAGVRETE SKIYLLVKEE KRYADAQLSC QGRGGTLSMP

181 KDEAANGLMA AYLAQAGLAR VFIGINDLEK EGAFVYSDHS PMRTFNKWRS GEPNNAYDEE

241 DCVEMVASGG WNDVACHTTM YFMCEFDKEN M
```

Various fragments of the human collectins Surfactant protein-D and collectin-11 are conceivable as trimerization domains as described herein.

1.4 Flexible Linker Element (GSS)a(SSG)b(GSG)c, SEQ ID NO: 33, wherein a, b, c are each 0, 1, 2, 3, 4, 5 or 6.

1.5 TNF-Superfamily Cytokine/Receptor Binding Domain Thereof (See Also Table 1)

```
SEQ NP_000586_TNFSF1_LTA
KEYWORD PROTEIN
FEATURES
ORIGIN
                                                                    SEQ-ID-01
   1 MTPPERLFLP RVCGTTLHLL LLGLLLVLLP GAQGLPGVGL TPSAAQTARQ HPKMHLAHST

61 LKPAAHLIGD PSKQNSLLWR ANTDRAFLQD GFSLSNNSLL VPTSGIYFVY SQVVFSGKAY

121 SPKATSSPLY LAHEVQLFSS QYPFHVPLLS SQKMVYPGLQ EPWLHSMYHG AAFQLTQGDQ

181 LSTHTDGIPH LVLSPSTVFF GAFAL

SEQ NP_000585_TNFSF2_TNFa
KEYWORD PROTEIN
ORIGIN
                                                                    SEQ-ID-02
   1 MSTESMIRDV ELAEEALPKK TGGPQGSRRC LFLSLFSFLI VAGATTLFCL LHFGVIGPQR

61 EEFPRDLSLI SPLAQAVRSS SRTPSDKPVA HVVANPQAEG QLQWLNRRAN ALLANGVELR

121 DNQLVVPSEG LYLIYSQVLF KGQGCPSTHV LLTHTISRIA VSYQTKVNLL SAIKSPCQRE

181 TPEGAEAKPW YEPIYLGGVF QLEKGDRLSA EINRPDYLDF AESGQVYFGI IAL

SEQ NP_002332_TNFSF3_LTB
KEYWORD PROTEIN
ORIGIN
                                                                    SEQ-ID-03
   1 MGALGLEGRG GRLQGRGSLL LAVAGATSLV TLLLAVPITV LAVLALVPQD QGGLVTETAD

61 PGAQAQQGLG FQKLPEEEPE TDLSPGLPAA HLIGAPLKGQ GLGWETTKEQ AFLTSGTQFS
```

```
121 DAEGLALPQD GLYYLYCLVG YRGRAPPGGG DPQGRSVTLR SSLYRAGGAY GPGTPELLLE

181 GAETVTPVLD PARRQGYGPL WYTSVGFGGL VQLRRGERVY VNISHPDMVD FARGKTFFGA

241 VMVG

SEQ NP_003317_TNFSF4_OX40L
KEYWORD PROTEIN
ORIGIN
                                                                 SEQ-ID-04
  1 MERVQPLEEN VGNAARPRFE RNKLLLVASV IQGLGLLLCF TYICLHFSAL QVSHRYPRIQ

61 SIKVQFTEYK KEKGFILTSQ KEDEIMKVQN NSVIINCDGF YLISLKGYFS QEVNISLHYQ

121 KDEEPLFQLK KVRSVNSLMV ASLTYKDKVY LNVTTDNTSL DDFHVNGGEL ILIHQNPGEF

181 CVL

SEQ NP_000065_TNFSF5_CD40L
KEYWORD PROTEIN
ORIGIN
                                                                 SEQ-ID-05
  1 MIETYNQTSP RSAATGLPIS MKIFMYLLTV FLITQMIGSA LFAVYLHRRL DKIEDERNLH

61 EDFVFMKTIQ RCNTGERSLS LLNCEEIKSQ FEGFVKDIML NKEETKKENS FEMQKGDQNP

121 QIAAHVISEA SSKTTSVLQW AEKGYYTMSN NLVTLENGKQ LTVKRQGLYY IYAQVTFCSN

181 REASSQAPFI ASLCLKSPGR FERILLRAAN THSSAKPCGQ QSIHLGGVFE LQPGASVFVN

241 VTDPSQVSHG TGFTSFGLLK L

SEQ NP_000630_TNFSF6_CD95L
KEYWORD PROTEIN
ORIGIN
                                                                 SEQ-ID-06
  1 MQQPFNYPYP QIYWVDSSAS SPWAPPGTVL PCPTSVPRRP GQRRPPPPPP PPPLPPPPPP

61 PPLPPLPLPP LKKRGNHSTG LCLLVMFFMV LVALVGLGLG MFQLFHLQKE LAELRESTSQ

121 MHTASSLEKQ IGHPSPPPEK KELRKVAHLT GKSNSRSMPL EWEDTYGIVL LSGVKYKKGG

181 LVINETGLYF VYSKVYFRGQ SCNNLPLSHK VYMRNSKYPQ DLVMMEGKMM SYCTTGQMWA

241 RSSYLGAVFN LTSADHLYVN VSELSLVNFE ESQTFFGLYK L

SEQ NP_001243_TNFSF7_CD27L
KEYWORD PROTEIN
ORIGIN
                                                                 SEQ-ID-07
  1 MPEEGSGCSV RRRPYGCVLR AALVPLVAGL VICLVVCIQR FAQAQQQLPL ESLGWDVAEL

61 QLNHTGPQQD PRLYWQGGPA LGRSFLHGPE LDKGQLRIHR DGIYMVHIQV TLAICSSTTA

121 SRHHPTTLAV GICSPASRSI SLLRLSFHQG CTIASQRLTP LARGDTLCTN LTGTLLPSRN

181 TDETFFGVQW VRP

SEQ NP_001235_TNFSF8_CD30L
KEYWORD PROTEIN
ORIGIN
                                                                 SEQ-ID-08
  1 MDPGLQQALN GMAPPGDTAM HVPAGSVASH LGTTSRSYFY LTTATLALCL VFTVATIMVL

61 VVQRTDSIPN SPDNVPLKGG NCSEDLLCIL KRAPFKKSWA YLQVAKHLNK TKLSWNKDGI

121 LHGVRYQDGN LVIQFPGLYF IICQLQFLVQ CPNNSVDLKL ELLINKHIKK QALVTCESG

181 MQTKHVYQNL SQFLLDYLQV NTTISVNVDT FQYIDTSTFP LENVLSIFLY SNSD

SEQ NP_003802_TNFSF9_CD137L
KEYWORD PROTEIN
ORIGIN
                                                                 SEQ-ID-09
  1 MEYASDASLD PEAPWPPAPR ARACRVLPWA LVAGLLLLLL LAAACAVFLA CPWAVSGARA

61 SPGSAASPRL REGPELSPDD PAGLLDLRQG MFAQLVAQNV LLIDGPLSWY SDPGLAGVSL

121 TGGLSYKEDT KELVVAKAGV YYVFFQLELR RVVAGEGSGS VSLALHLQPL RSAAGAAALA
```

-continued

```
181 LTVDLPPASS EARNSAFGFQ GRLLHLSAGQ RLGVHLHTEA RARHAWQLTQ GATVLGLFRV

241 TPEIPAGLPS PRSE
```

SEQ NP_003801_TNFSF10_TRAIL
KEYWORD PROTEIN
ORIGIN
```
                                                                SEQ-ID-10
  1 MAMMEVQGGP SLGQTCVLIV IFTVLLQSLC VAVTYVYFTN ELKQMQDKYS KSGIACFLKE

61 DDSYWDPNDE ESMNSPCWQV KWQLRQLVRK MILRTSEETI STVQEKQQNI SPLVRERGPQ

121 RVAAHITGTR GRSNTLSSPN SKNEKALGRK INSWESSRSG HSFLSNLHLR NGELVIHEKG

181 FYYIYSQTYF RFQEEIKENT KNDKQMVQYI YKYTSYPDPI LLMKSARNSC WSKDAEYGLY

241 SIYQGGIFEL KENDRIFVSV TNEHLIDMDH EASFFGAFLV G
```

SEQ NP_003692_TNFSF11_a_RANKL
KEYWORD PROTEIN
ORIGIN
```
                                                                SEQ-ID-11
  1 MRRASRDYTK YLRGSEEMGG GPGAPHEGPL HAPPPPAPHQ PPAASRSMFV ALLGLGLGQV

61 VCSVALFFYF RAQMDPNRIS EDGTHCIYRI LRLHENADFQ DTTLESQDTK LIPDSCRRIK

121 QAFQGAVQKE LQHIVGSQHI RAEKAMVDGS WLDLAKRSKL EAQPFAHLTI NATDIPSGSH

181 KVSLSSWYHD RGWAKISNMT FSNGKLIVNQ DGFYYLYANI CFRHHETSGD LATEYLQLMV

241 YVTKTSIKIP SSHTLMKGGS TKYWSGNSEF HFYSINVGGF FKLRSGEEIS IEVSNPSLLD

301 PDQDATYFGA FKVRDID
```

SEQ NP_003800_TNFSF12_TWEAK
KEYWORD PROTEIN
ORIGIN
```
                                                                SEQ-ID-12
  1 MAARRSQRRR GRRGEPGTAL LVPLALGLGL ALACLGLLLA VVSLGSRASL SAQEPAQEEL

61 VAEEDQDPSE LNPQTEESQD PAPFLNRLVR PRRSAPKGRK TRARRAIAAH YEVHPRPGQD

121 GAQAGVDGTV SGWEEARINS SSPLRYNRQI GEFIVTRAGL YYLYCQVHFD EGKAVYLKLD

181 LLVDGVLALR CLEEFSATAA SSLGPQLRLC QVSGLLALRP GSSLRIRTLP WAHLKAAPFL

241 TYFGLFQVH
```

SEQ NP_742085_TNFSF13_APRIL_ver1
KEYWORD PROTEIN
ORIGIN
```
                                                                SEQ-ID-13
  1 MPASSPFLLA PKGPPGNMGG PVREPALSVA LWLSWGAALG AVACAMALLT QQTELQSLRR

61 EVSRLQGTGG PSQNGEGYPW QSLPEQSSDA LEAWENGERS RKRRAVLTQK QKKQHSVLHL

121 VPINATSKDD SDVTEVMWQP ALRRGRGLQA QGYGVRIQDA GVYLLYSQVL FQDVTFTMGQ

181 VVSREGQGRQ ETLFRCIRSM PSHPDRAYNS CYSAGVFHLH QGDILSVIIP RARAKLNLSP

241 HGTFLGL
```

SEQ NP_003799_TNFSF13_APRIL_ver2
KEYWORD PROTEIN
ORIGIN
```
                                                                SEQ-ID-14
  1 MPASSPFLLA PKGPPGNMGG PVREPALSVA LWLSWGAALG AVACAMALLT QQTELQSLRR

61 EVSRLQGTGG PSQNGEGYPW QSLPEQSSDA LEAWENGERS RKRRAVLTQK QKKQHSVLHL

121 VPINATSKDD SDVTEVMWQP ALRRGRGLQA QGYGVRIQDA GVYLLYSQVL FQDVTFTMGQ

181 VVSREGQGRQ ETLFRCIRSM PSHPDRAYNS CYSAGVFHLH QGDILSVIIP RARAKLNLSP

241 HGTFLGFVKL
```

```
SEQ NP_006564_TNFSF13b_BAFF
KEYWORD PROTEIN
ORIGIN
                                                                       SEQ-ID-15
   1 MDDSTEREQS RLTSCLKKRE EMKLKECVSI LPRKESPSVR SSKDGKLLAA TLLLALLSCC

61 LTVVSFYQVA ALQGDLASLR AELQGHHAEK LPAGAGAPKA GLEEAPAVTA GLKIFEPPAP

121 GEGNSSQNSR NKRAVQGPEE TVTQDCLQLI ADSETPTIQK GSYTFVPWLL SFKRGSALEE

181 KENKILVKET GYFFIYGQVL YTDKTYAMGH LIQRKKVHVF GDELSLVTLF RCIQNMPETL

241 PNNSCYSAGI AKLEEGDELQ LAIPRENAQI SLDGDVTFFG ALKLL

SEQ NP_003798_TNFSF14_LIGHT
KEYWORD PROTEIN
ORIGIN
                                                                       SEQ-ID-16
   1 MEESVVRPSV FVVDGQTDIP FTRLGRSHRR QSCSVARVGL GLLLLLMGAG LAVQGWFLLQ

61 LHWRLGEMVT RLPDGPAGSW EQLIQERRSH EVNPAAHLTG ANSSLTGSGG PLLWETQLGL

121 AFLRGLSYHD GALVVTKAGY YYIYSKVQLG GVGCPLGLAS TITHGLYKRT PRYPEELELL

181 VSQQSPCGRA TSSSRVWWDS SFLGGVVHLE AGEKVVVRVL DERLVRLRDG TRSYFGAFMV

SEQ NP_005109_TNFSF15_TL1A
KEYWORD PROTEIN
ORIGIN
                                                                       SEQ-ID-17
   1 MAEDLGLSFG ETASVEMLPE HGSCRPKARS SSARWALTCC LVLLPFLAGL TTYLLVSQLR

61 AQGEACVQFQ ALKGQEFAPS HQQVYAPLRA DGDKPRAHLT VVRQTPTQHF KNQFPALHWE

121 HELGLAFTKN RMNYTNKFLL IPESGDYFIY SQVTFRGMTS ECSEIRQAGR PNKPDSITVV

181 ITKVTDSYPE PTQLLMGTKS VCEVGSNWFQ PIYLGAMFSL QEGDKLMVNV SDISLVDYTK

241 EDKTFFGAFL L

SEQ NP_005083_TNFSF18_GITRL
KEYWORD PROTEIN
ORIGIN
                                                                       SEQ-ID-18
   1 MCLSHLENMP LSHSRTQGAQ RSSWKLWLFC SIVMLLFLCS FSWLIFIFLQ LETAKEPCMA

61 KFGPLPSKWQ MASSEPPCVN KVSDWKLEIL QNGLYLIYGQ VAPNANYNDV APFEVRLYKN

121 KDMIQTLTNK SKIQNVGGTY ELHVGDTIDL IFNSEHQVLK NNTYWGIILL ANPQFIS

SEQ NP_001390_EDA-A1
KEYWORD PROTEIN
ORIGIN
                                                                       SEQ-ID-19
   1 MGYPEVERRE LLPAAAPRER GSQGCGCGGA PARAGEGNSC LLFLGFFGLS LALHLLTLCC

61 YLELRSELRR ERGAESRLGG SGTPGTSGTL SSLGGLDPDS PITSHLGQPS PKQQPLEPGE

121 AALHSDSQDG HQMALLNFFF PDEKPYSEEE SRRVRRNKRS KSNEGADGPV KNKKKGKKAG

181 PPGPNGPPGP PGPPGPQGPP GIPGIPGIPG TTVMGPPGPP GPPGPQGPPG LQGPSGAADK

241 AGTRENQPAV VHLQGQGSAI QVKNDLSGGV LNDWSRITMN PKVFKLHPRS GELEVLVDGT

301 YFIYSQVEVY YINFTDFASY EVVVDEKPFL QCTRSIETGK TNYNTCYTAG VCLLKARQKI

361 AVKMVHADIS INMSKHTTFF GAIRLGEAPA S

SEQ NP_001005609_EDA-A2
KEYWORD PROTEIN
ORIGIN
                                                                       SEQ-ID-20
   1 MGYPEVERRE LLPAAAPRER GSQGCGCGGA PARAGEGNSC LLFLGFFGLS LALHLLTLCC

61 YLELRSELRR ERGAESRLGG SGTPGTSGTL SSLGGLDPDS PITSHLGQPS PKQQPLEPGE

121 AALHSDSQDG HQMALLNFFF PDEKPYSEEE SRRVRRNKRS KSNEGADGPV KNKKKGKKAG

181 PPGPNGPPGP PGPPGPQGPP GIPGIPGIPG TTVMGPPGPP GPPGPQGPPG LQGPSGAADK
```

```
241 AGTRENQPAV VHLQGQGSAI QVKNDLSGGV LNDWSRITMN PKVFKLHPRS GELEVLVDGT

301 YFIYSQVYYI NFTDFASYEV VVDEKPFLQC TRSIETGKTN YNTCYTAGVC LLKARQKIAV

361 KMVHADISIN MSKHTTFFGA IRLGEAPAS
```

Various fragments, e.g., receptor binding domains, of TNF-superfamily cytokines are conceivable as described herein.

1.6 Examples of Fusion Proteins

```
SP-hsTrailsyn-SPD-Konstrukt-1_PRO.PRO
KEYWORD PROTEIN
ORIGIN
                                                        SEQ ID NO: 26
  1 METDTLLLWV LLLWVPAGNG QRVAAHITGT RGRSNTLSSP NSKNEKALGR KINSWESSRS

61 GHSFLSNLHL RNGELVIHEK GFYYIYSQTY FRFQEEIKEN TKNDKQMVQY IYKYTSYPDP

121 ILLMKSARNS CWSKDAEYGL YSIYQGGIFE LKENDRIFVS VTNEHLIDMD HEASFFGAFL

181 VGSGLPDVAS LRQQVEALQG QVQHLQAAFS QYKKVELFPN GQSVGEKIFK TAGFVKPFTE

241 AQLLCTQAGG QLASPRSAAE NAALQQLVVA KNEAAFLSMT DSKTEGKFTY PTGESLVYSN

301 WAPGEPNDDG GSEDCVEIFT NGKWNDRACG EKRLVVCEF

SP-hsTrailsyn-SPD-Konstrukt-2_PRO.PRO
KEYWORD PROTEIN
ORIGIN
                                                        SEQ ID NO: 27
  1 METDTLLLWV LLLWVPGSTG ERGPQRVAAH ITGTRGRSNT LSSPNSKNEK ALGRKINSWE

61 SSRSGHSFLS NLHLRNGELV IHEKGFYYIY SQTYFRFQEE IKENTKNDKQ MVQYIYKYTS

121 YPDPILLMKS ARNSCWSKDA EYGLYSIYQG GIFELKENDR IFVSVTNEHL IDMDHEASFF

181 GAFLVGSGLP DVASLRQQVE ALQGQVQHLQ AAFSQYKKVE LFPNGQSVGE KIFKTAGFVK

241 PFTEAQLLCT QAGGQLASPR SAAENAALQQ LVVAKNEAAF LSMTDSKTEG KFTYPTGESL

301 VYSNWAPGEP NDDGGSEDCV EIFTNGKWND RACGEKRLVV CEF

ORIGIN
                                                        SEQ ID NO: 28
  1 METDTLLLWV LLLWVPGSTG ERGPQRVAAH ITGTRGRSNT LSSPNSKNEK ALGRKINSWE

61 SSRSGHSFLS NLHLRNGELV IHEKGFYYIY SQTYFRFQEE IKENTKNDKQ MVQYIYKYTS

121 YPDPILLMKS ARNSCWSKDA EYGLYSIYQG GIFELKENDR IFVSVTNEHL IDMDHEASFF

181 GAFLVGSGLP DVASLRQQVE ALQGQVQHLQ AAFSQYKKVE LFPNG

SP-hsTrailsyn-coll11-Konstrukt-1.pro
KEYWORD PROTEIN
ORIGIN
                                                        SEQ ID NO: 29
  1 METDTLLLWV LLLWVPAGNG QRVAAHITGT RGRSNTLSSP NSKNEKALGR KINSWESSRS

61 GHSFLSNLHL RNGELVIHEK GFYYIYSQTY FRFQEEIKEN TKNDKQMVQY IYKYTSYPDP

121 ILLMKSARNS CWSKDAEYGL YSIYQGGIFE LKENDRIFVS VTNEHLIDMD HEASFFGAFL

181 VGSQLRKAIG EMDNQVSQLT SELKFIKNAV AGVRETESKI YLLVKEEKRY ADAQLSCQGR

241 GGTLSMPKDE AANGLMAAYL AQAGLARVFI GINDLEKEGA FVYSDHSPMR TFNKWRSGEP

301 NNAYDEEDCV EMVASGGWND VACHTTMYFM CEFDKENM

SP-hsTrailsyn-coll-11-Konstrukt-2.pro
KEYWORD PROTEIN
ORIGIN
                                                        SEQ ID NO: 30
  1 METDTLLLWV LLLWVPGSTG ERGPQRVAAH ITGTRGRSNT LSSPNSKNEK ALGRKINSWE

61 SSRSGHSFLS NLHLRNGELV IHEKGFYYIY SQTYFRFQEE IKENTKNDKQ MVQYIYKYTS

121 YPDPILLMKS ARNSCWSKDA EYGLYSIYQG GIFELKENDR IFVSVTNEHL IDMDHEASFF
```

-continued

```
181 GAFLVGSQLR KAIGEMDNQV SQLTSELKFI KNAVAGVRET ESKIYLLVKE EKRYADAQLS

241 CQGRGGTLSM PKDEAANGLM AAYLAQAGLA RVFIGINDLE KEGAFVYSDH SPMRTFNKWR

301 SGEPNNAYDE EDCVEMVASG GWNDVACHTT MYFMCEFDKE NM

SP-hsTrailsyn-coll-11-Konstrukt-3.pro
KEYWORD PROTEIN
ORIGIN
                                                           SEQ ID NO: 31
  1 METDTLLLWV LLLWVPGSTG ERGPQRVAAH ITGTRGRSNT LSSPNSKNEK ALGRKINSWE

61 SSRSGHSFLS NLHLRNGELV IHEKGFYYIY SQTYFRFQEE IKENTKNDKQ MVQYIYKYTS

121 YPDPILLMKS ARNSCWSKDA EYGLYSIYQG GIFELKENDR IFVSVTNEHL IDMDHEASFF

181 GAFLVGSQLR KAIGEMDNQV SQLTSELKFI KNAVAGVRET ES
```

Examples

1.1 Construction of TNF-SF-Proteins Stabilised by a C-Terminal Positioned Collectin Derived Trimerization Domain The trimerization motifs (Tables 2. and 3) derived from human Collectin-11 (Col11), the "coiled coil" of Collectin-11 (CC11), human pulmonary surfactant protein-D (SP-D), the "coiled coil" of SP-D (CCSPD) were fused C-terminally to the human receptor binding domain (RBD) of CD95L ("CD95L-RBD"; Glu142-Leu281), human TRAIL-RBD (Gln120-Gly281), human LIGHT-RBD (Glu91-Val240) and human APRIL-RBD (Lys113-Leu250), respectively.

TABLE 2

List of the used regions from wild type (wt) sequences for the construction of trimerizing motifs.

| Trimerization motif | Amino acids of the unprocessed wt sequences used for motif construction | Swiss-Prot entry |
|---|---|---|
| SPD | 220-375 | P35247 |
| SPD_F335A | 220-375; Phe355 -> Ala355 | P35247 |
| SPD_F335D | 220-375; Phe355 -> Asp355 | P35247 |
| CCSPD | 220-257 | P35247 |
| Col11 | 117-271 | Q9BWP8 |
| CC11 | 116-151 | Q9BWP8 |

TABLE 3

Explanation of C-terminal trimerization motifs used to generate stable TNFSF fusion proteins.

| Trimerization motif | Explanation |
|---|---|
| SPD | human Surfactant protein-D (coiled-coiled "neck" + Carbohydrate Recognition Domain, CRD) |
| SPD_F335A | as in 1, but with the mutation Phe -> Ala at position 335 (numbering referring to processed wild type SP-D) |
| SPD_F335D | as in 1, but with the mutation Phe -> Asp at position 335 (numbering referring to processed wild type SP-D) |
| CCSPD | coiled-coiled "neck" of human SP-D |
| Col11 | human Collectin-11 (coiled-coiled "neck" + CRD of human Collectin-11) |
| CC11 | coiled-coiled "neck" of human Collectin-11 |
| T4 | Bacteriophage T4 Whisker protein (WO2008025516) |
| 69 | Bacteriophage 69 Whisker protein (WO2008025516) |

Between the TNFSF-RBD and the trimerization domain, a flexible linker element was placed with varying lengths (Table 4):

TABLE 4

Linker names and amino acid sequence (G = glycine; S = serine)

| Linker name | Amino-acid sequence |
|---|---|
| A | GSS GSS GSS GS (SEQ ID NO: 34) |
| B | GSS GSS GS (SEQ ID NO: 35) |
| C | GSS GS (SEQ ID NO: 36) |
| D | GS |

1.2 Generation of Expression Constructs

The nucleic acid molecule encoding the fusion protein as described herein may be cloned into a suitable vector for expressing the fusion protein. The molecular tools necessary in order to generate such a vector are known to the skilled person and comprise restriction enzymes, vectors, and suitable host for propagating the vectors.

For purification and analytical strategies, a Strep-tag II (amino acid sequence WSHPQFEK, SEQ ID NO: 38) was added C-terminally. This affinity tag was linked to the trimerization domain by a flexible linker element (amino acid sequence PSSSSSSA, SEQ ID NO: 39). To allow for secretory based expression, signal peptides derived from human Igκ were fused to the N-termini of said proteins. The amino acid sequences of the fusion proteins were backtranslated and their codon usage optimised for mammalian cell-based expression. Gene synthesis was done by ENTELECHON GmbH (Regensburg, Germany). The final expression cassettes were subcloned into pCDNA4-His-Max-backbone, using unique Hind-III- and Not-I-sites of the plasmid. All expression cassettes were routinely verified by DNA sequencing.

Data will be presented herein for the following constructs (Table 5a and 5b):

TABLE 5a

Overview of TRAIL fusion proteins with shown data.

| Motif | TRAIL (wild-type) | | | | TRAIL Mutein (R1-specific) Linker: | | | | TRAIL Mutein (R2-specific) | | | |
|---|---|---|---|---|---|---|---|---|---|---|---|---|
| | A | B | C | D | A | B | C | D | A | B | C | D |
| SPD | • | • | • | • | • | n.s. | n.s. | • | • | n.s. | n.s. | • |
| SPD_F335A | • | n.s. | n.s. | n.s. | n.s. | n.s. | n.s. | n.s. | n.s. | n.s. | n.s. | n.s. |
| SPD_F335D | • | n.s. | n.s. | n.s. | n.s. | n.s. | n.s. | n.s. | n.s. | n.s. | n.s. | n.s. |
| CCSPD | • | • | • | • | • | n.s. | n.s. | • | • | n.s. | n.s. | • |
| Col11 | • | • | • | • | n.s. | n.s. | n.s. | n.s. | n.s. | n.s. | n.s. | n.s. |
| CC11 | • | • | • | • | n.s. | n.s. | n.s. | n.s. | n.s. | n.s. | n.s. | n.s. |
| T4 | • | • | • | • | n.s. | n.s. | n.s. | n.s. | n.s. | n.s. | n.s. | n.s. |
| 69 | • | • | • | • | n.s. | n.s. | n.s. | n.s. | n.s. | n.s. | n.s. | n.s. |

Filled circles indicate that data are presented.
n.s., not shown.

TABLE 1

5b: Overview of LIGHT-, APRIL-, and CD95L-constructs with shown data.

| Motif | LIGHT | APRIL Linker: | CD95L |
|---|---|---|---|
| | A | A | A |
| SPD | • | • | • |
| CCSPD | • | • | n.s. |
| Col11 | • | • | n.s. |
| 69 | • | • | n.s. |

Filled circles indicate that data are presented. N.s., not shown.

1.3 Expression and Purification of Engineered Ligands of the TNF Superfamily Hek 293T cells grown in DMEM+GlutaMAX (GibCo) supplemented with 10% FBS, 100 units/ml Penicillin and 100 μg/ml Streptomycin were transiently transfected with plasmids encoding a fusion protein as described herein. Cell culture supernatant containing recombinant proteins were harvested three days post transfection and clarified by centrifugation at 300×g followed by filtration through a 0.22 μm sterile filter. For affinity purification, 4 ml of 50% Streptactin Sepharose (IBA GmbH, Göttingen, Germany) were packed to a 2 ml column and equilibrated with 30 ml phosphate buffered saline, pH 7.4 (PBS; Invitrogen Cat. 10010) or buffer W (100 mM Tris-HCl, 150 mM NaCl pH 8.0). The cell culture supernatant was applied to the column at 4° C. with a flow rate of 2 ml/min. Subsequently, the column was washed with PBS or buffer W and specifically bound proteins were eluted stepwise by addition of 5×2 ml buffer E (PBS or buffer W with 2.5 mM Desthiobiotin, pH 7.4). The protein content of the eluate fractions was analysed by absorption spectroscopy and by silver-stained SDS-PAGE. Positive fractions were subsequently concentrated by ultrafiltration (Sartorius, Vivaspin, 10,000 Da cut-off) and further analysed by size exclusion chromatography (SEC).

SEC was performed on a Superdex 200 column using an Äkta chromatography system (GE-Healthcare). The column was equilibrated with PBS (Invitrogen Cat. 10010) and the concentrated, streptactin purified proteins were loaded onto the SEC column at a flow rate of 0.5 ml/min. The elution of was monitored by absorbance at 280 nm. The apparent molecular weight of purified proteins were determined based on calibration of the Superdex 200 column with gel filtration standard proteins (Bio-Rad GmbH, München, Germany).

1.4. Cell Death Assays

To analyze caspase activation, a cellular assay with the Jurkat A3 permanent human T-cell line (cat. no. CRL2570, ATCC) was used. Jurkat cells were grown in flasks with RPMI 1640-medium+GlutaMAX (GibCo) supplemented with 10% FBS (Biochrom), 100 units/ml Penicillin and 100 μl/ml Streptomycin (GibCo). Prior to the assay, 100,000 cells were seeded per well into a 96-well microtiterplate. The addition of different solutions containing the protein with or without a crosslinking antibody to the wells (final volume: 200 μl) was followed by a 3 hour incubation at 37° C. Cells were lysed by adding 20 μl lysis buffer (250 mM HEPES, 50 mM $MgCl_2$, 10 mM EGTA, 5% Triton-X-100, 100 mM DTT, 10 mM AEBSF, pH 7.5) and plates were incubated on ice for 30 minutes to 2 hours. Apoptosis is paralleled by an increased activity of Caspases. Hence, cleavage of the specific Caspase substrate Ac-DEVD-AFC (Biomol) was used to determine the extent of apoptosis. For the Caspase activity assay, 20 μl cell lysate was transferred to a black 96-well microtiterplate. After the addition of 80 μl buffer containing 50 mM HEPES, 1% Sucrose, 0.1% CHAPS, 50 μM Ac-DEVD-AFC, and 25 mM DTT, pH 7.5, the plate was transferred to a Tecan Infinite F500 microtiterplate reader and the increase in fluorescence intensity was monitored (excitation wavelength 400 nm, emission wavelength 505 nm).

For the determination of cell death in HT1080 fibrosarcoma, HeLa cervix carcinoma and WM35 melanoma cells, 15,000 cells were plated in 96-well plates over night in RPMI 1640-medium+GlutaMAX (GibCo) supplemented with 10% FBS (Biochrom). For Colo205 cells, 50,000 cells were plated over night. Cells were stimulated the following day with indicated ligand and incubated for an additional 18 hours. For HeLa and HT1080 cells, cycloheximide (Sigma) at a final concentration of 2.5 μg/ml was used during stimulation with ligands. Cell death of HT1080, HeLa and WM35 was quantified by staining with buffer KV (0.5% crystal violet, 20% methanol). After staining, the wells were washed with water and air-dried. The dye was eluted with methanol and optical density at 595 nm was measured with an ELISA reader. Viability of Colo205 cells was quantified by MTS assay (Promega).

1.5 Hepatocellular Cytotoxicity Assay

To determine the effect of TRAIL fusion proteins, primary human hepatocytes were prepared from healthy donors and cultured in Williams E medium using 25,000 cells per well in 96-well plates. At day two, medium was changed to DMEM-F12 supplemented with 10% FCS, human insulin, Pen/Strep, minimum essential medium (MEM), sodium pyruvate and 10 mM Hepes and cultured for another day. Cells were stimulated at day three with varying concentrations of indicated proteins in presence or absence of cross-linking antibodies (StrepMabImmo, IBA GmbH). To evaluate the potential hepatotoxic effect of a cotreatment of ligands with chemotherapeutic agents, TRAIL-ASPD_F335D was coincubated at varying concentrations together with 5 mM of doxorubicin or 5 mM gemcitabine. Cells were incubated for 5 or 24 hours at 37° C. and 5% $CO_2$ and were then lysed for determination of caspase activity as described in section "Cell death assays".

1.6 Streptactin-ELISA

To determine the binding of receptors to constructed ligands, streptactin-coated 96-well microplates were used. Therefore, supernatants from transiently transfected HEK293 cells, mouse sera or purified proteins were immobilized on streptactin-plates (IBA GmbH) for 1-3 hours in PBS. Samples were diluted in ELISA binding/blocking buffer (PBS, 0.1% Tween-20, 20% SuperBlock T20-PBS (Pierce)). Plates were washed with PBS+0.1% Tween-20 and incubated with mouse-anti-TRAIL antibody (Pharmingen, clone RIK-2), TRAIL-Receptor 1-Fc (R&D Systems), TRAIL-Receptor 2-Fc (R&D Systems), TACI-Fc (R&D Systems) or HVEM-Fc (R&D Systems) for one hour at room temperature. Plates were again washed and Fc-proteins were detected with anti-human- or anti-mouse-Fc-specific peroxidase-conjugated antibodies (Sigma). Colour reaction was done by addition of 100 µl per well of TMB substrate (Kem-En-Tec Diagnostics) and the absorbance at 450 nm and 630 nm was determined with an ELISA reader after addition of 25 µl of 25% $H_2SO_4$ as stop-solution. Values were calculated as 450 nm-630 nm with MS Excel.

1.7 Mannan-Binding Assay

ELISA plates (Nunc Maxisorp) were incubated over night at 4° C. with 10 µg/well of yeast mannan (Sigma) in sterile coating buffer (15 mM $Na_2CO_3$, 35 mM $NaHCO_3$, 0.025% $NaN_3$, pH 9.6). Plates were first incubated for one hour at room temperature with buffer BB (20 mM Tris, 140 mM NaCl, 5 mM $CaCl_2$, 0.1% BSA and 20% SuperBlock T20-PBS (Pierce)) and secondly for additional 90 minutes with varying concentrations of indicated ligands in buffer BB. Plates were washed with buffer WB (20 mM Tris, 140 mM NaCl, 5 mM $CaCl_2$, 0.05% Tween-20) and detection was done by using streptactin-HRP (IBA GmbH) in buffer BB. Plates were washed and developed with TMB substrate (Kem-En-Tec Diagnostics). The absorption at 450 nm and 630 nm was determined with an ELISA reader after addition of 25 µl of 25% $H_2SO_4$ as stop-solution. Values were calculated as 450 nm-630 nm with MS Excel.

1.8 Pharmacokinetics of TRAIL-SPD Fusion Proteins

Male CD1 mice (Charles River) were intravenously injected with 10 µg protein dissolved in 300 µl PBS (Invitrogen). Blood was collected after 0 min (predose), 5 min, 30 min, 2 hours, 6 hours and 24 hours. For each time point, two samples were collected. Blood samples were processed to obtain serum and were stored at −15° C. The concentration of TRAIL-fusion proteins was determined using an ELISA as described below (chapter 1.9) and half-lives were calculated (GraphPad Prism v4.0).

1.9 ELISA for the Quantitation of TRAIL-Constructs in Mouse Sera

To quantitate the concentration of TRAIL proteins in mouse sera (originating from pharmacokinetic studies), an ELISA method employing 96-well microplates was used.

ELISA plates were coated for 1 h at 37° C. with 2 µg/ml mouse-anti-TRAIL (clone RIK-2; Pharmingen). After washing with PBS+0.1% Tween-20 and blocking the plate for 30 min at 37° C. with StartingBlock™ (Pierce), serum samples at a concentration of 0.2% and 5%, calibration samples and control samples were added and incubated for 1 h at 37° C. Calibration and control samples were prepared from the respective TRAIL batch (TRAIL-ASPD or TRAIL-ASPD-F335A or TRAIL-ASPD-F335D) and were supplemented with 0.2% or 5% non-treated pooled CD1-mouse serum to account for potential matrix effects. Control samples (high, medium and low concentration of the TRAIL-construct) were added as quality controls to ensure precision and accuracy of the TRAIL-quantitation in the given assay window. Plates were again washed and the StrepTag-containing TRAIL-constructs were detected with 1:1000 diluted StrepTactin-POD (IBA). All samples and proteins were diluted with ELISA buffer (PBS, 0.1% Tween-20, 5% StartingBlock (Pierce)). The colour reaction started after addition of 100 µl per well TMB substrate (Kem-En-Tec Diagnostics). the absorbance at 450 nm and 630 nm was determined with an ELISA reader after addition of 25 µl of 25% H2SO4 as stop-solution. Values were calculated as 450 nm-630 nm with MS Excel.

2. Results

2.1 Characterization of CD95L Fusion Protein (CD95L-ASPD)

From the Streptactin-affinity purified CD95L-ASPD 0.5 ml (0.86 mg protein) were loaded with a flow rate of 0.5 ml/min onto a Superdex200 column using PBS as running buffer. Fractions of 0.5 ml were collected (A1 to A11 are indicated). The retention volume of the major peak at 11.92 ml corresponded to 170 kDa as determined from size exclusion standard. This indicated that the protein is a trimer composed of glycosylated monomers. The calculated molecular weight of the monomeric polypeptide is 38 kDa. An aliquot of fractions A1 to A11 was used for SDS-PAGE and caspase activity. Only the defined trimeric peak (fractions A7 to A10) was used for final analyses. The results are shown in FIG. 1.

Figure 2:
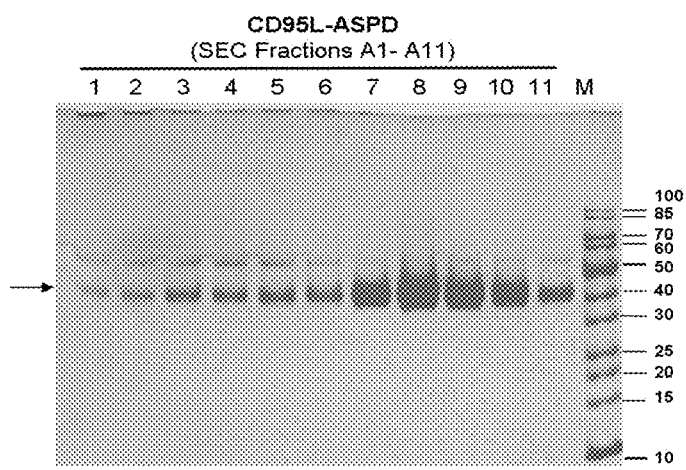
FIG. 2: Silver gel of SEC fractions A1-A11 from affinity purified CD95L-ASPD

An aliquot from size exclusion chromatography of affinity purified CD95L-ASPD was used for reducing SDS-PAGE followed by silver staining. The band detected at approximately 40-45 kDa (indicated by an arrow) corresponded to CD95L-ASPD. The trimeric species was present in fractions A7 to A10. The results are shown in FIG. 2.

Figure 3:
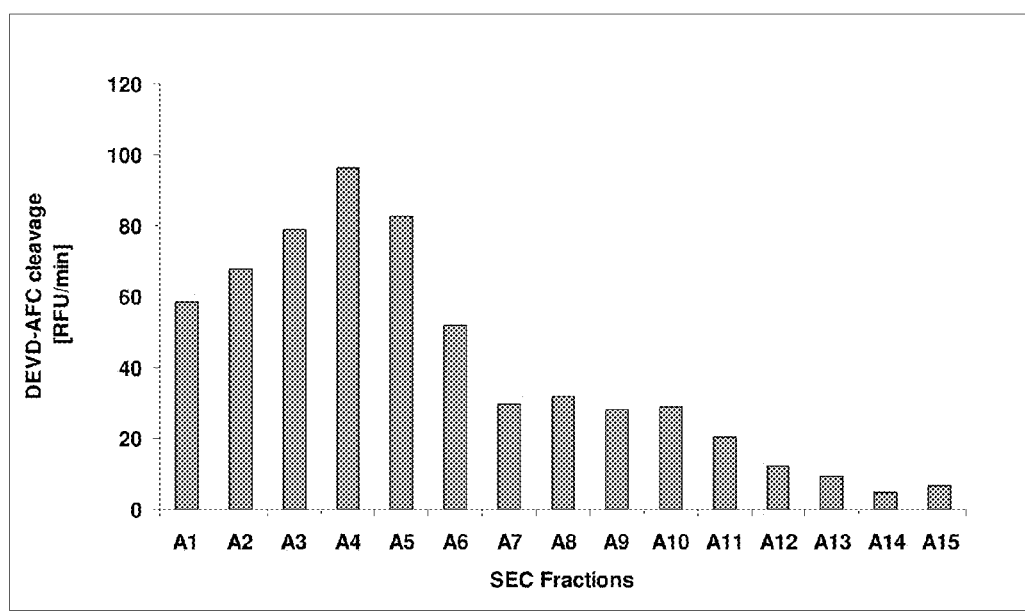
FIG. 3: Caspase activity on Jurkat cells induced by SEC fractions A1-A15 from affinity purified CD95L-ASPD

Jurkat cells were incubated with aliquots at a final 8-fold dilution from fractions A1 to A15 from SEC with affinity purified CD95L-ASPD. Cells were lysed after 3 h incubation and the caspase activity was determined with a fluorogenic assay. The fractions corresponding to the trimeric peak (fractions A7-A10) induced clear but weak caspase activity in Jurkat as these cells are known to require extensively cross-linked ligand. The aggregated and undefined species in fractions A1-A6 is therefore a potent inducer of caspase activation (not used further). Importantly, only the defined trimeric species (A7 to A10) was collected and used for final analyses. The results are shown in FIG. 3.

Figure 4:
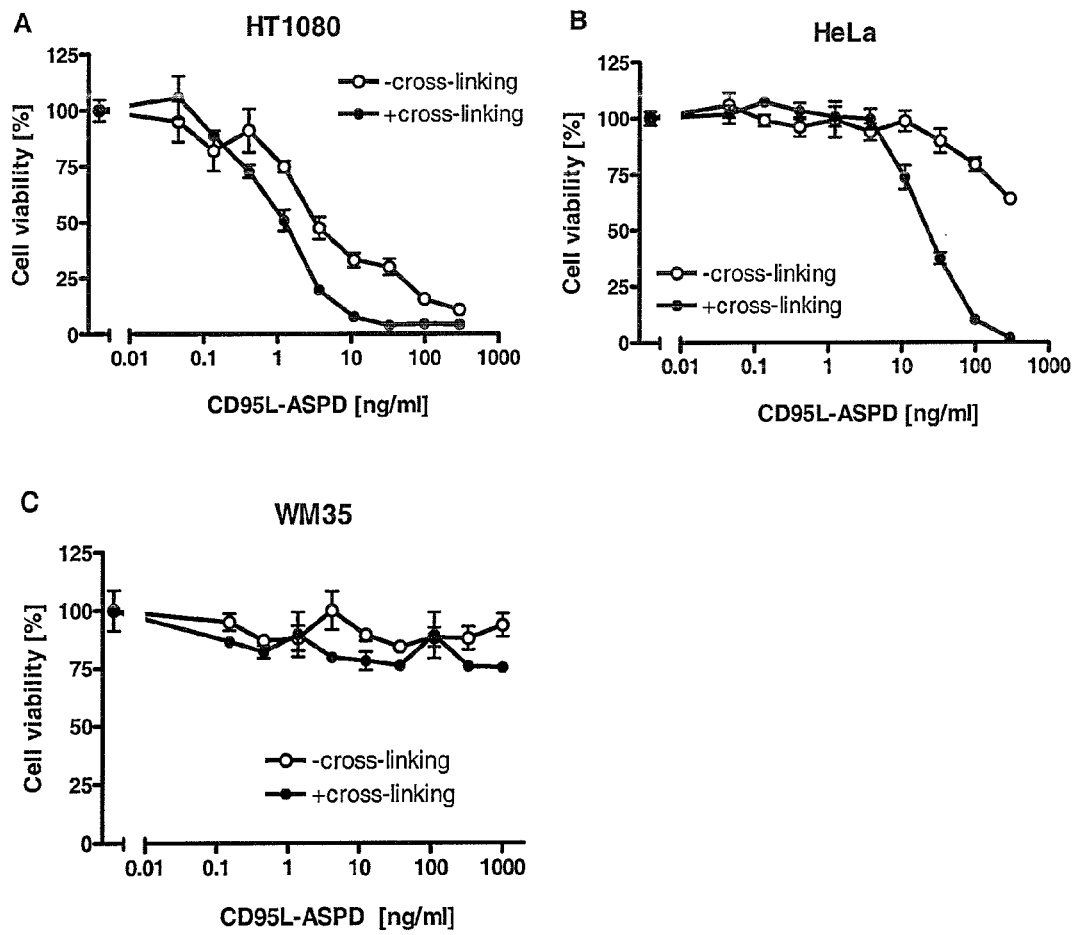
FIG. 4: Cytotoxicity of CD95L-ASPD on WM35, HT1080 and HeLa cells

The human cancer cell lines HT1080 (A), HeLa (B) or WM35 (C) were incubated with indicated concentrations of purified, trimeric CD95L-ASPD in the presence or absence of cross-linking antibody (2.5 microgram/ml of anti-Strep-tag II). Cells were incubated for 18 h and cytotoxicity was analyzed by crystal violet staining. As a result, CD95L-ASPD induced cell death in HeLa cervix carcinoma and HT1080 fibrosarcoma, but not in WM35 melanoma cells. The results are shown in FIG. 4.

The amino acid sequence of CD95L-ASPD is shown below.

```
Sp-CD95L-ASPD
Total amino acid number: 346, MW = 37682
ORIGIN
                                                         SEQ ID 40
  1 METDTLLLWV LLLWVPGSTG ELRKVAHLTG KSNSRSMPLE WEDTYGIVLL SGVKYKKGGL

61 VINETGLYFV YSKVYFRGQS CNNLPLSHKV YMRNSKYPQD LVMMEGKMMS YCTTGQMWAR

121 SSYVGAVFNL TSADHLYVNV SELSLVNFEE SQTFFGLYKL GSSGSSGSSG SGLPDVASLR

181 QQVEALQGQV QHLQAAFSQY KKVELFPNGQ SVGEKIFKTA GFVKPFTEAQ LLCTQAGGQL

241 ASPRSAAENA ALQQLVVAKN EAAFLSMTDS KTEGKFTYPT GESLVYSNWA PGEPNDDGGS

301 EDCVEIFTNG KWNDRACGEK RLVVCEFGGS PSSSSSSAWS HPQFEK
1-20:    Secretion signal peptide (Sp; underlined)
21-160:  CD95L-receptor binding domain
161-171: Flexible linker element (A-linker; italic)
172-209: Coiled coil "neck" region of human SP-D
210-327: C-type lectin domain of human SP-D
328-338: Linker element (GGSPSSSSSSA)

339-346: Strep-tag II (WSHPQFEK)
```

2.2 Characterization of LIGHT Fusion Proteins (LIGHT-ASPD)

Figure 5:
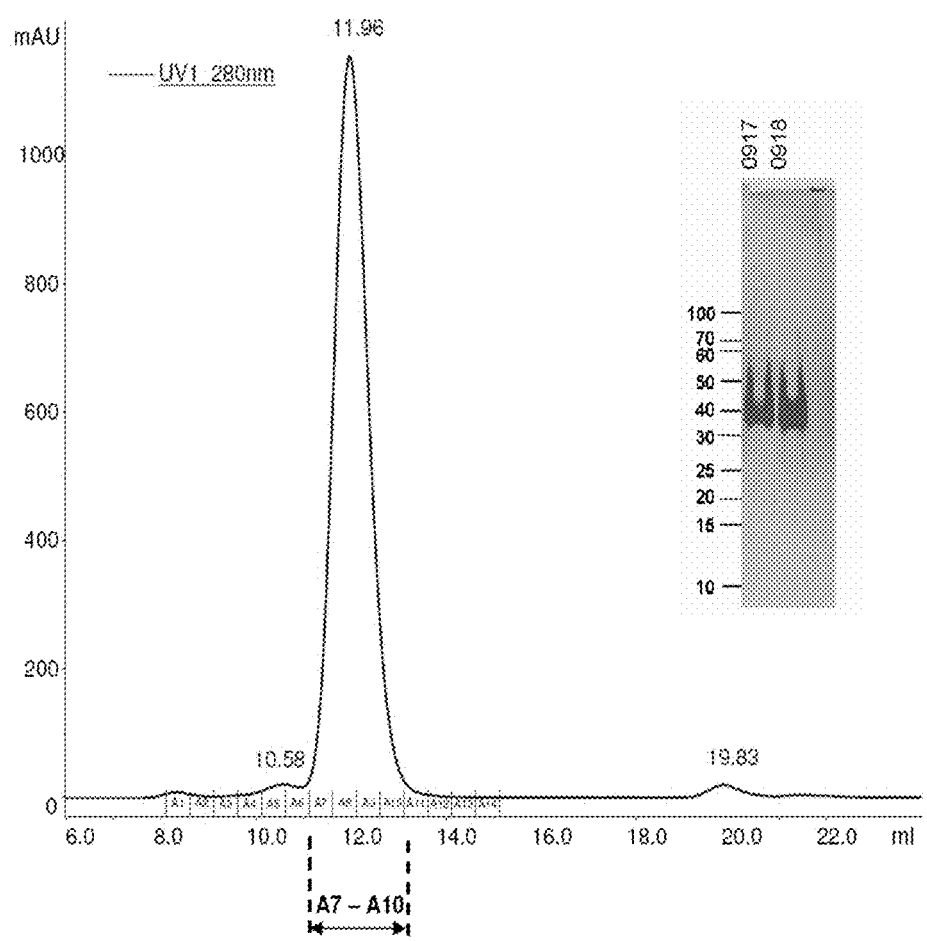
FIG. 5: SEC of affinity purified LIGHT-ASPD

From affinity purified LIGHT-ASPD 0.5 ml (1.56 mg) were loaded onto a Superdex 200 column and resolved at 0.5 ml/min using PBS as running buffer. The major peak detected at 11.96 ml corresponded to a size of 170-180 kDa indicating that LIGHT-ASPD is a trimer composed of three glycosylated monomers. The trimeric peak (fractions A7 to A10) was collected and used for final analyses. The inset shows the silver stained SDS-PAGE of two independent purified and trimeric LIGHT-ASPD batches (designated 0917 and 0918). The results are shown in FIG. 5.

Figure 6:
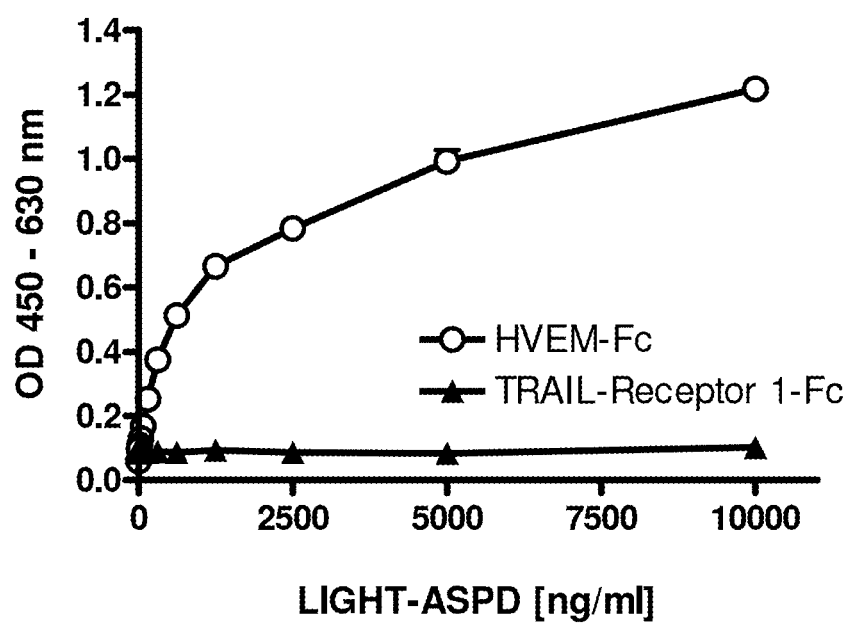
FIG. 6: Binding of HVEM-Fc to immobilized LIGHT-ASPD

Varying concentrations (0-10 microgram/ml) of affinity and SEC purified, trimeric LIGHT-ASPD were used for immobilized via the Strep-tag II on Streptactin-coated microplates. LIGHT-ASPD was then detected in a ELISA set-up using 100 ng/ml of Fc-fusion proteins of the receptors HVEM and TRAIL-Receptor 1, respectively. Whereas the ELISA signal increased for HVEM-Fc with increasing amounts of immobilized ligand, no signal was detected for TRAIL-Receptor 1-Fc over the whole range analyzed. This indicated that LIGHT-ASPD is a functional molecule that could bind to its receptor HVEM. The results are shown in FIG. 6.

The amino acid sequence of the LIGHT-ASPD fusion protein is shown below:

```
Sp-LIGHT-ASPD
Total amino acid number: 356, MW = 37931
ORIGIN
                                                         SEQ ID 41
  1 METDTLLLWV LLLWVPGSTG EVNPAAHLTG ANSSLTGSGG PLLWETQLGL AFLRGLSYHD

61 GALVVTKAGY YYIYSKVQLG GVGCPLGLAS TITHGLYKRT PRYPEELELL VSQQSPCGRA

121 TSSSRVWWDS SFLGGVVHLE AGEEVVVRVL DERLVRLRDG TRSYFGAFMV GSSGSSGSSG

181 SGLPDVASLR QQVEALQGQV QHLQAAFSQY KKVELFPNGQ SVGEKIFKTA GFVKPFTEAQ

241 LLCTQAGGQL ASPRSAAENA ALQQLVVAKN EAAFLSMTDS KTEGKFTYPT GESLVYSNWA

301 PGEPNDDGGS EDCVEIFTNG KWNDRACGEK RLVVCEFGGS PSSSSSSAWS HPQFEK
1-20:    Secretion signal peptide (Sp; underlined)
21-170:  LIGHT-receptor binding domain
171-181: Flexible linker element (A-linker; italic)
182-219: Coiled coil "neck" region of human SP-D
220-337: C-type lectin domain of human SP-D
338-348: Linker element (GGSPSSSSSSA)

349-356: Strep-tag II (WSHPQFEK)
```

2.3 Characterization of TRAIL Fusion Proteins

HEK293 cells were transiently transfected with 24 different expression vectors encoding for TRAIL fusion proteins (Table 6).

TABLE 6

Overview fusion proteins produced by transient transfection of expression vecors. The ligand TRAIL was transfected as fusion proteins comprising one of six stabilzing trimerization motifs and the linker element (A, B, C and D linker).

| No | Ligand | Linker | Trimerization motif |
|---|---|---|---|
| 1 | TRAIL | A/B/C/D | 69 |
| 2 | TRAIL | A/B/C/D | T4 |
| 3 | TRAIL | A/B/C/D | SPD |
| 4 | TRAIL | A/B/C/D | CCSPD |
| 5 | TRAIL | A/B/C/D | Col11 |
| 6 | TRAIL | A/B/C/D | CC11 |

Supernatants were used for SDS-PAGE and TRAIL-constructs were detected by Western Blot analysis employing an antibody specific for Strep-tag II.

Figure 7:
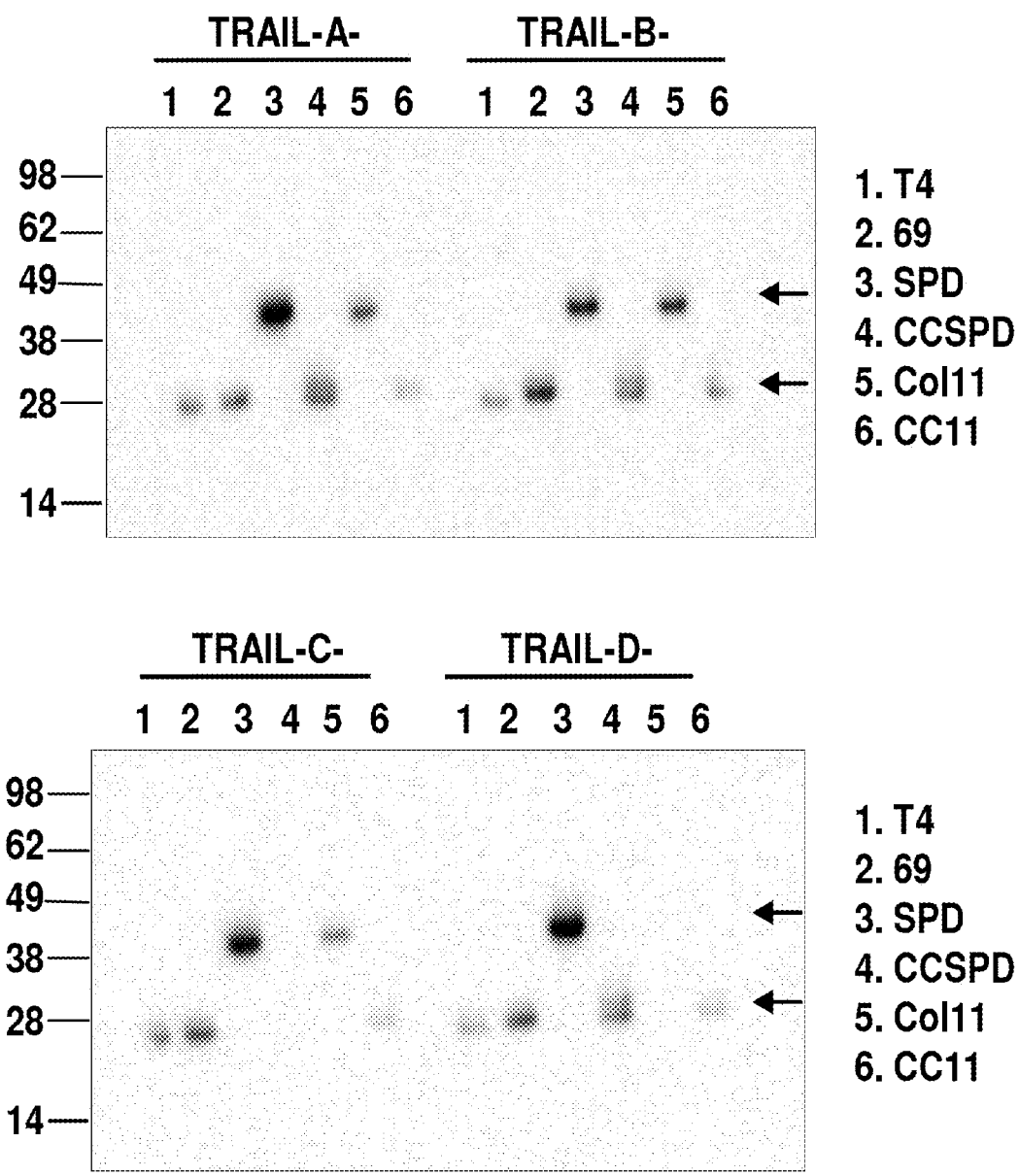
FIG. 7: Western blot from HEK cells transiently transfected with TRAIL-constructs

Specific bands detected are indicated by an arrow. The expression strength depended on the type of the trimerization motif employed for construction, (SPD>69/T4/Collectin11/CCSPD/CC11) as well as on the length of the linker element (A>B>C>D). The results are shown in FIG. 7.

Jurkat cells were incubated for three hours in the presence (filled bars, anti-Strep-tag II) or absence (clear bars) of a cross-linking antibody (2.5 micrograms/ml anti-Strep-tag II) with supernatants from transiently transfected HEK cells. Supernatants contained TRAIL-fusion proteins with different trimerization motifs (T4, 69, SPD, CCSPD, Col11, CC11) fused through varying linker elements (A, B, C and D linker). As negative control, cell supernatant from untransfected cells was used. Jurkat cells were lysed and analyzed for caspase activity with a fluorogenic assay.

Figure 8:
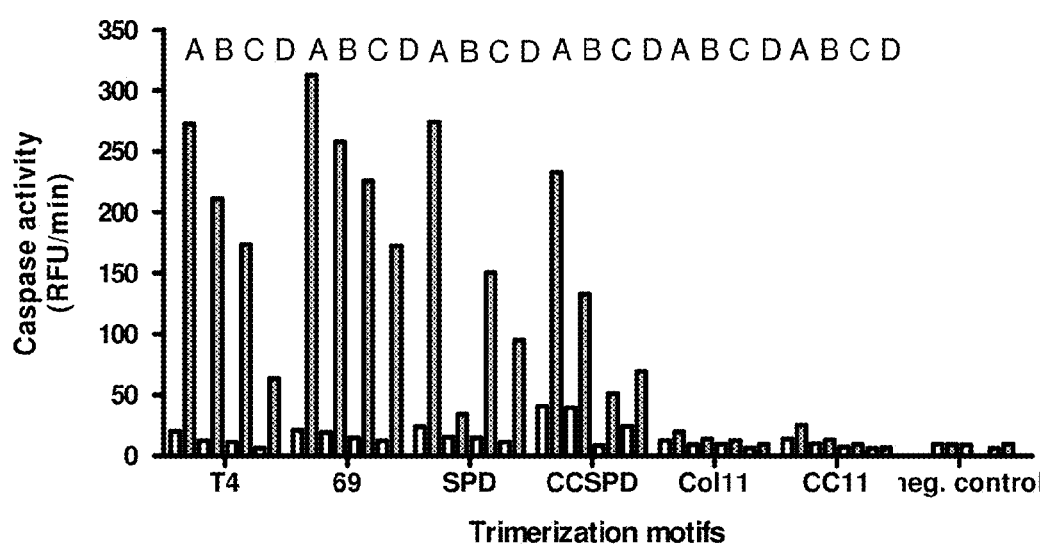
FIG. 8: Caspase activity in Jurkat T-cells

As a result, the caspase activity decreased with the type of linker element employed (A>B>C>D) and on the Fold-On employed. Collectin-11 or coiled coil of Collectin-11 (CCCol11) containing TRAIL constructs are expressed (shown by Western Blot analyses), however were not functional, whereas SPD-derived fold-on motifs yielded functional TRAIL-ligands. The results are shown in FIG. 8.

Figure 9:
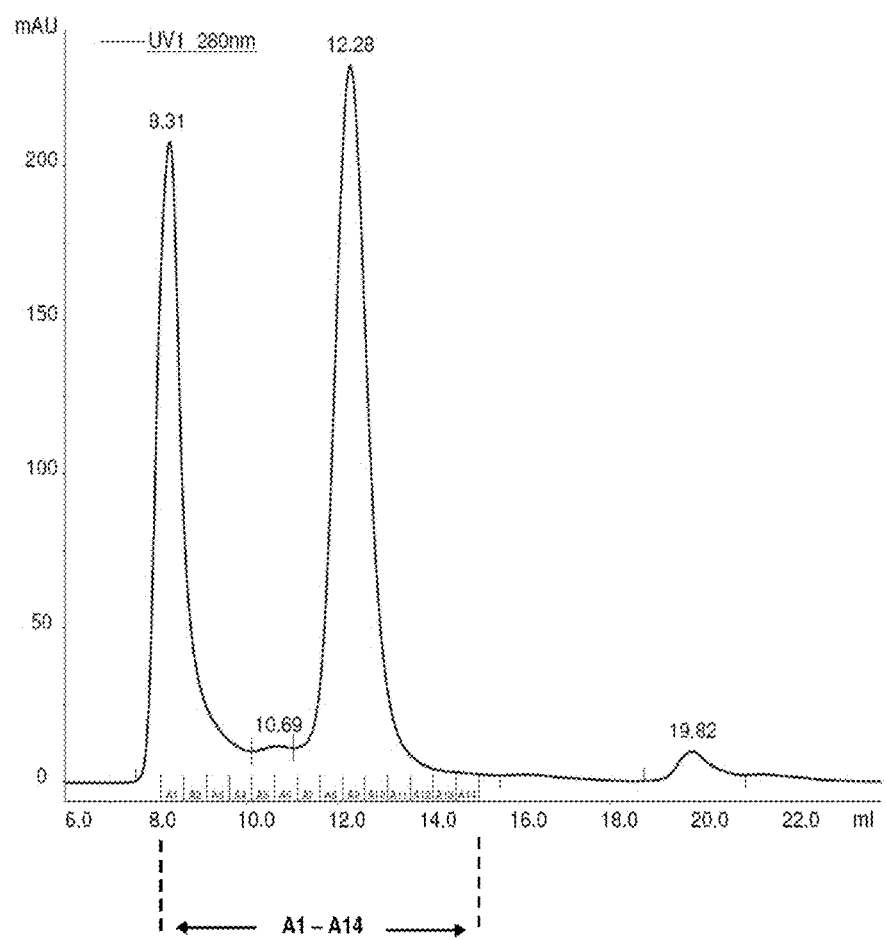
FIG. 9: Size exclusion chromatography of TRAIL-ASPD

Affinity purified TRAIL-ASPD was subjected to SEC by loading 0.5 ml (0.4 mg protein) to a Superdex200 column at 0.5 ml/min with PBS as running buffer. Protein elution was monitored by absorption at 280 nm and 0.5 ml fractions were collected. The retention volume of 12.28 ml corresponds to 135-140 kDa as determined from size exclusion standard. This indicated that TRAIL-ASPD is a homotrimer, as the calculated molecular weight of the monomeric polypeptide is 40 kDa. Importantly, for all fusion proteins analyzed by SEC consisting of the wild-type TRAIL-RBD sequence, an additional peak at around 8 ml corresponding to aggregated and non-active TRAIL-fusion protein was observed. From the collected fractions A1-A14 only the trimeric peak (A8-A10) was used for further analyses. The results are shown in FIG. 9.

Figure 10:
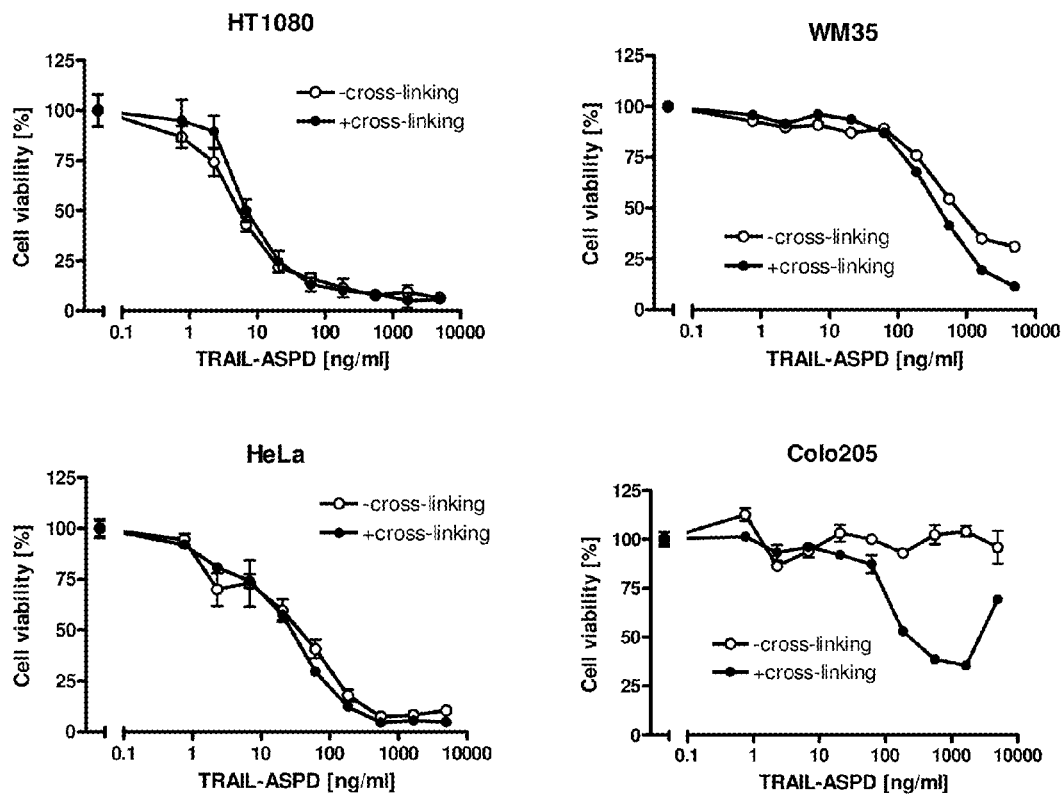
FIG. 10: Cytotoxic activity of TRAIL-ASPD against human cancer cells

The human cancer cell lines HeLa, HT1080, Colo205 or WM35 were incubated for 18 hours with indicated concentrations of purified, trimeric TRAIL-ASPD in the presence or absence of cross-linking antibody (2.5 microgram/ml of anti-Strep-tag II). Cell death was quantified by crystal violet staining (HeLa, WM35 and HT1080) or by MTS assay (Colo205). The rise in the viability of Colo205 cells at high ligand concentration is likely due to limitation of cross-linking antibody. The results are shown in FIG. 10.

Figure 11:
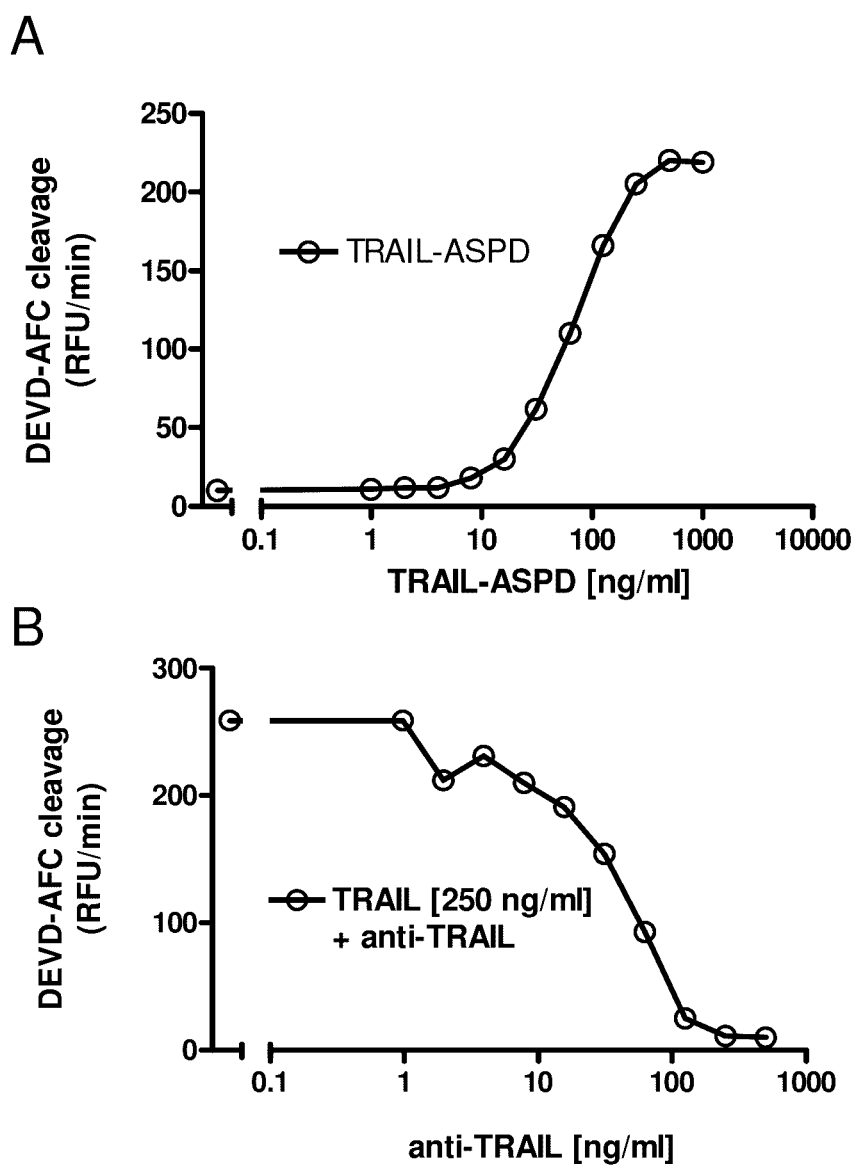
FIG. 11: TRAIL-ASPD induced caspase activity in Jurkat

Varying (A) or a constant (B) concentration of affinity and SEC purified, trimeric TRAIL-ASPD was used for immobilization on Streptactin-coated 96-well plates. Plates were then incubated for 5 h with 100,000 Jurkat cells per well at 37° C., 5% CO2 and the caspase activity was determined with a fluorogenic assay. To analyze specificity, plate (B) was incubated for 30 minutes with indicated varying concentrations of an antagonistic anti-TRAIL antibody (clone RIK-2, Pharmingen) prior addition of cells. The results are shown in FIG. 11.

Figure 12:
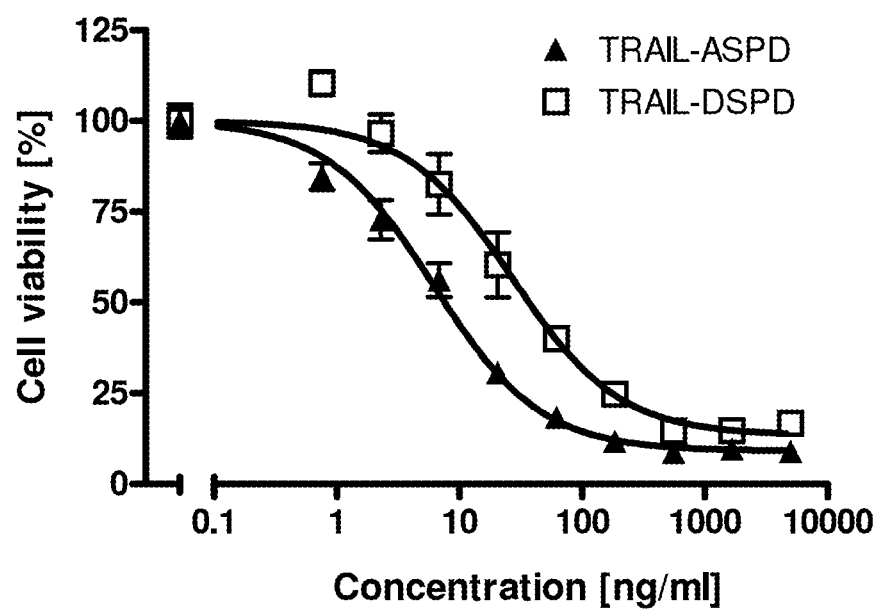
FIG. 12: Cytotoxicity assay with TRAIL-ASPD or TRAIL-DSPD on HT1080 cells
Figure 13:
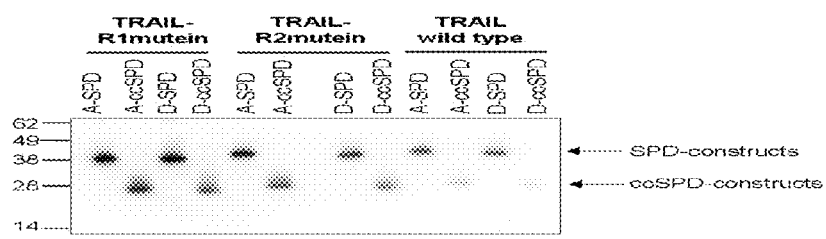
FIG. 13: Western blot from transiently transfected HEK cells transiently transfected with TRAIL-SPD-constructs or TRAIL-receptor selective SPD constructs.
Figure 14:
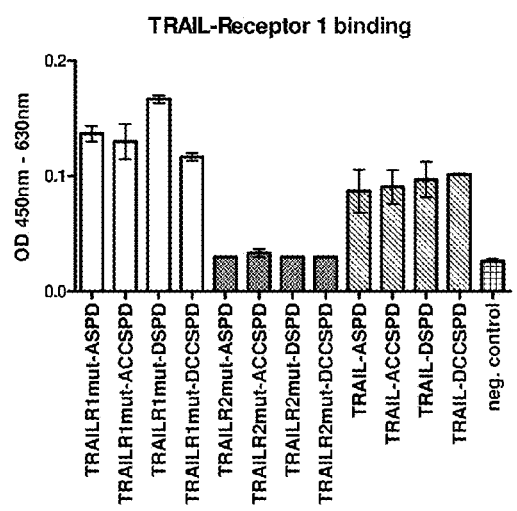
FIG. 14: TRAIL-Receptor selective ligands (TRAILR1mut and TRAILR2mut) immobilized on Streptactin plates, are differentially detected by TRAIL-Receptor 1-Fc or TRAIL-Receptor 2-Fc
Figure 14:
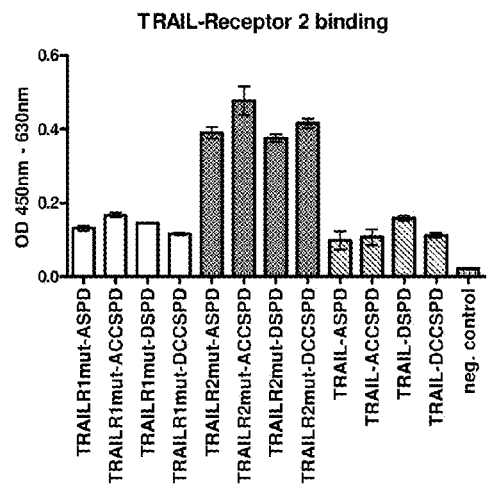
Figure 14:
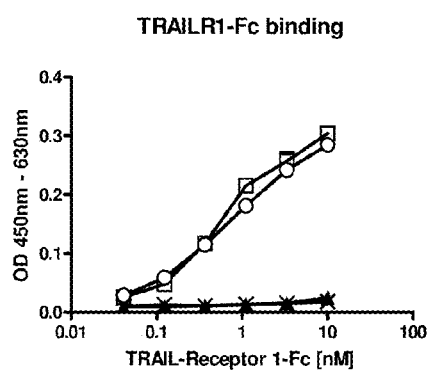
Figure 14:
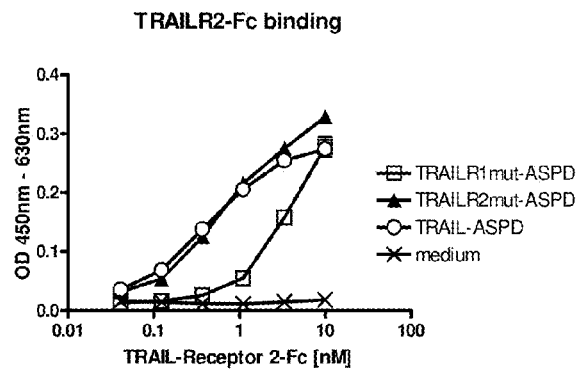
Figure 15:
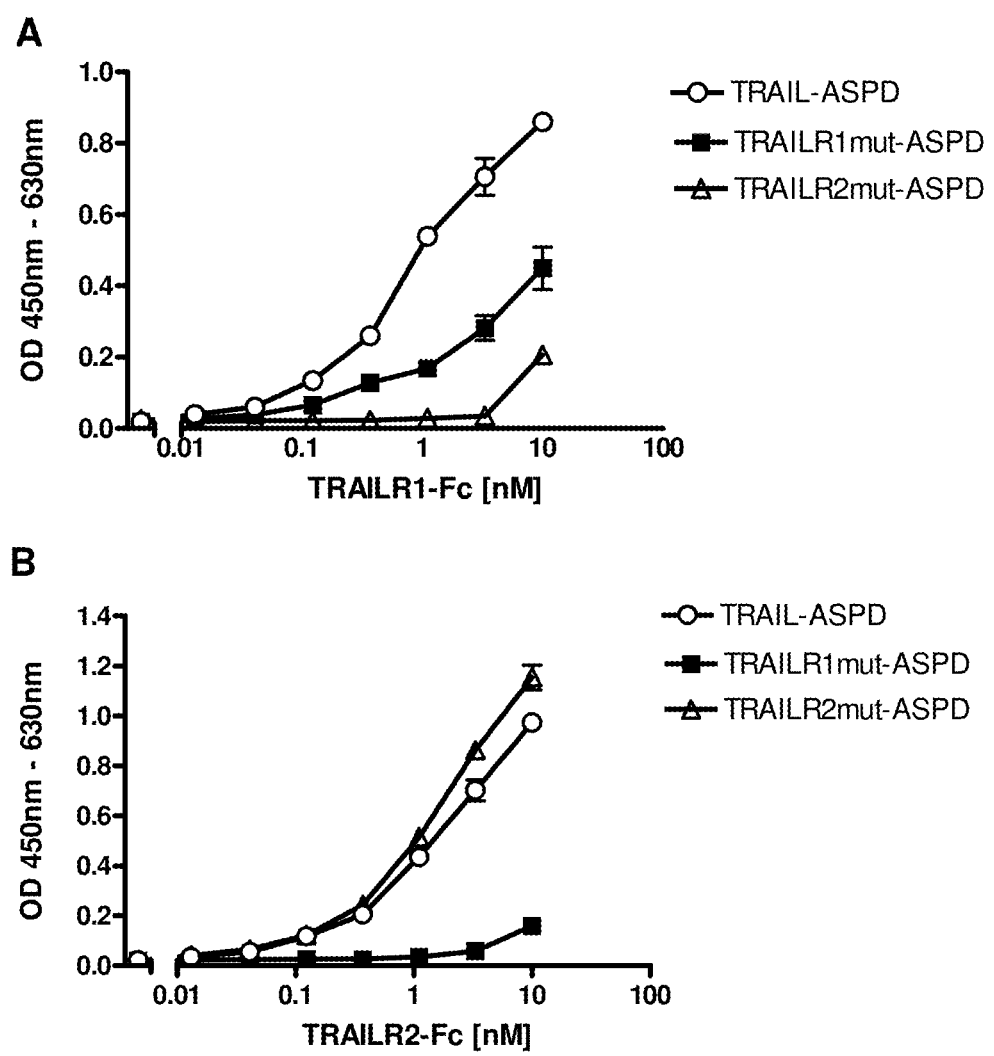
FIG. 15: Binding of TRAIL-Receptors to Receptor-selective "mutein" ligands
Figure 16:
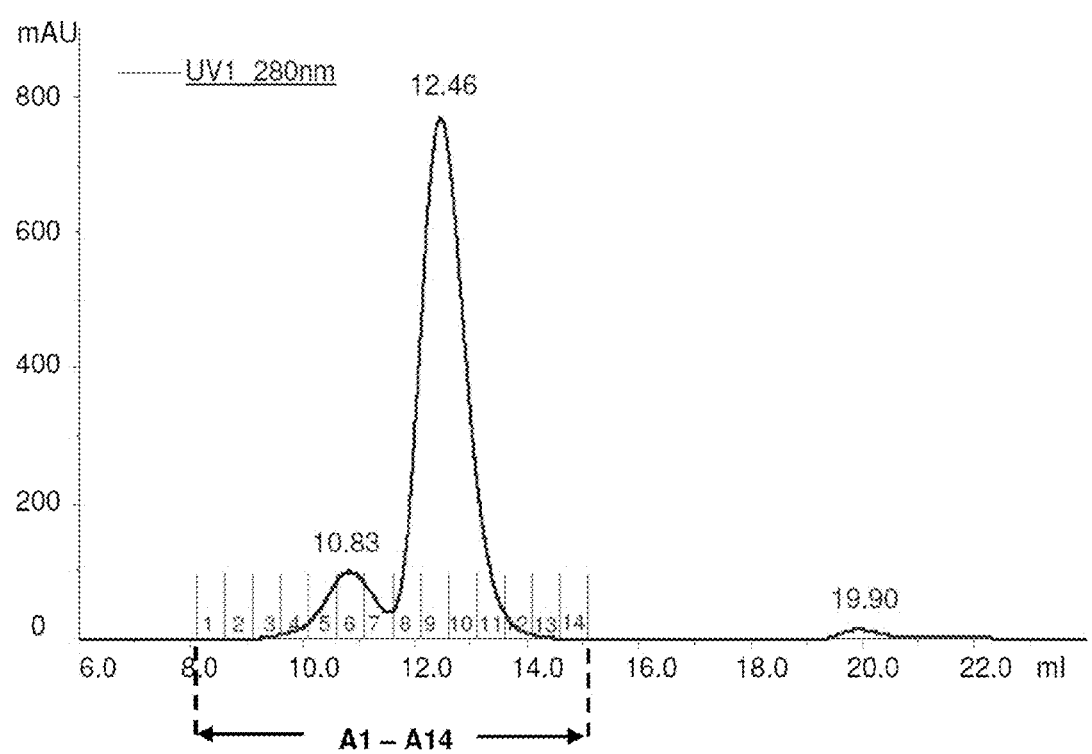
FIG. 16: Size exclusion chromatography of affinity purified TRAILR1 mut-ASPD
Figure 17:
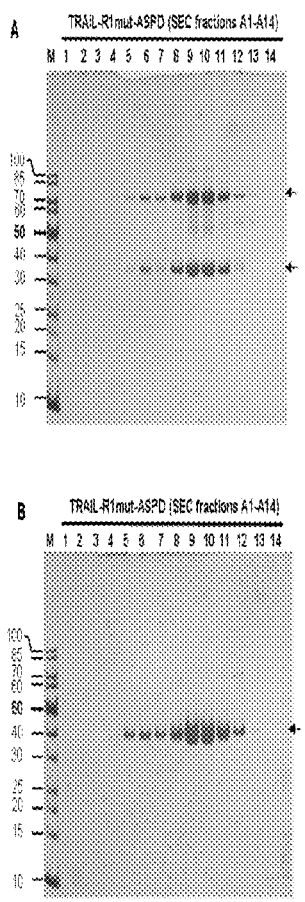
FIG. 17: Silver stained SDS-PAGE of SEC fractions A1-A14 from affinity purified TRAILR1 mut-ASPD

HT1080 cells were incubated on the same 96-well plate with purified and trimeric TRAIL-ASPD or TRAIL-DSPD at indicated concentrations. Cell death was quantified the following day by crystal violet staining. The use of the D-linker reduced the bioactivity approximately 4.5-fold, as indicated by the EC50 values of 27 ng/ml and 6 ng/ml for TRAIL-DSPD and TRAIL-ASPD, respectively. The results are shown in FIG. 12.

The nucleic acid and amino sequences of TRAIL fusion polypeptides are shown below.

```
SEQ ID 42: Expression cassette of Sp-TRAIL-ASPD
Endonuclease restriction sites are underlined (HindIII, AAGCTT; BamHI,
GGATCC; NotI, GCGGCCGC). The translational start codon is in boldface.
ORIGIN
    1 AAGCTTGCCG CCACCATGGA GACCGATACA CTGCTCTTGT GGGTGCTCTT GCTGTGGGTT

61 CCTGCAGGTA ATGGTCAAAG AGTCGCAGCT CACATCACTG GGACTAGAGG CAGGAGTAAC

121 ACCCTGAGTT CTCCCAATTC CAAGAACGAG AAAGCCCTGG GTAGGAAGAT CAACTCCTGG

181 GAAAGCTCCA GAAGCGGCCA TAGCTTTCTT AGCAACCTCC ACTTGAGGAA TGGCGAACTT

241 GTGATCCATG AGAAGGGCTT CTACTACATC TACAGCCAGA CGTACTTCAG GTTCCAGGAG

301 GAAATCAAGG AGAACACCAA GAACGACAAG CAGATGGTGC AATACATCTA CAAGTACACG

361 TCATACCCTG ATCCTATACT GCTGATGAAG TCCGCCAGAA ACAGTTGCTG GAGCAAAGAC

421 GCTGAATACG GCCTGTATTC CATCTATCAG GGCGGTATCT TTGAACTCAA GGAGAACGAC

481 AGGATCTTCG TGTCTGTGAC AAACGAGCAT CTGATCGACA TGGACCATGA AGCGTCTTTC

541 TTCGGTGCCT TCTTGGTGGG ATCCTCTGGT TCGAGTGGTT CGAGTGGTTC TGGATTGCCA

601 GACGTTGCTT CTTTGAGACA ACAGGTTGAG GCTTTGCAGG GTCAAGTCCA GCACTTGCAG

661 GCTGCTTTCT CTCAATACAA GAAGGTTGAG TTGTTCCCAA ACGGTCAATC TGTTGGCGAA
```

```
 721 AAGATTTTCA AGACTGCTGG TTTCGTCAAA CCATTCACGG AGGCACAATT ATTGTGTACT

781 CAGGCTGGTG GACAGTTGGC CTCTCCACGT TCTGCCGCTG AGAACGCCGC CTTGCAACAG

841 TTGGTCGTAG CTAAGAACGA GGCTGCTTTC TTGAGCATGA CTGATTCCAA GACAGAGGGC

901 AAGTTCACCT ACCCAACAGG AGAATCCTTG GTCTATTCTA ATTGGGCACC TGGAGAGCCC

961 AACGATGATG GCGGCTCAGA GGACTGTGTG GAAATCTTCA CCAATGGCAA GTGGAATGAC

1021 AGAGCTTGTG GAGAGAAGCG TTTGGTGGTC TGTGAGTTCG GAGGCAGTCC TTCATCTTCA

1081 TCTAGCTCTG CCTGGTCGCA TCCACAATTC GAGAAATAAT AGCGGCCGC
```

SEQ ID 43 Sp-TRAIL-ASPD
Total amino acid number: 367, MW = 40404
ORIGIN
```
   1 METDTLLLWV LLLWVPAGNG QRVAAHITGT RGRSNTLSSP NSKNEKALGR KINSWESSRS

61 GHSFLSNLHL RNGELVIHEK GFYYIYSQTY FRFQEEIKEN TKNDKQMVQY IYKYTSYPDP

121 ILLMKSARNS CWSKDAEYGL YSIYQGGIFE LKENDRIFVS VTNEHLIDMD HEASFFGAFL

181 VGSSGSSGSS GSGLPDVASL RQQVEALQGQ VQHLQAAFSQ YKKVELFPNG QSVGEKIFKT

241 AGFVKPFTEA QLLCTQAGGQ LASPRSAAEN AALQQLVVAK NEAAFLSMTD SKTEGKFTYP

301 TGESLVYSNW APGEPNDDGG SEDCVEIFTN GKWNDRACGE KRLVVCEFGG SPSSSSSSAW

361 SHPQFEK
```
1-20: Secretion signal peptide (Sp; underlined)
21-181: TRAIL-receptor binding domain
182-192: Flexible linker element (A-linker; italic)
193-230: Coiled coil "neck" region of human SP-D
231-348: C-type lectin domain of human SP-D
349-359: Linker element (GGSPSSSSSSA)
360-367: Strep-tag II (WSHPQFEK)

SEQ ID 44 Sp-TRAIL-ACCSPD
Total amino acid number: 246, MW = 27534
ORIGIN
```
   1 METDTLLLWV LLLWVPAGNG QRVAAHITGT RGRSNTLSSP NSKNEKALGR KINSWESSRS

61 GHSFLSNLHL RNGELVIHEK GFYYIYSQTY FRFQEEIKEN TKNDKQMVQY IYKYTSYPDP

121 ILLMKSARNS CWSKDAEYGL YSIYQGGIFE LKENDRIFVS VTNEHLIDMD HEASFFGAFL

181 VGSSGSSGSS GSGLPDVASL RQQVEALQGQ VQHLQAAFSQ YKKVELFPNG PSSSSSSAWS

241 HPQFEK
```
1-20: Secretion signal peptide (Sp; underlined)
21-181: TRAIL-receptor binding domain
182-192: Flexible linker element (A-linker; italic)
193-230: Coiled coil "neck" region of human SP-D
231-238: Linker element (PSSSSSSA)
239-246: Strep-tag II (WSHPQFEK)

SEQ ID 45 Sp-TRAIL-AColl1
Total amino acid number: 365, MW = 40806
ORIGIN
```
   1 METDTLLLWV LLLWVPAGNG QRVAAHITGT RGRSNTLSSP NSKNEKALGR KINSWESSRS

61 GHSFLSNLHL RNGELVIHEK GFYYIYSQTY FRFQEEIKEN TKNDKQMVQY IYKYTSYPDP

121 ILLMKSARNS CWSKDAEYGL YSIYQGGIFE LKENDRIFVS VTNEHLIDMD HEASFFGAFL

181 VGSSGSSGSS GSQLRKAIGE MDNQVSQLTS ELKFIKNAVA GVRETESKIY LLVKEEKRYA

241 DAQLSCQGRG GTLSMPKDEA ANGLMAAYLA QAGLARVFIG INDLEKEGAF VYSDHSPMRT

301 FNKWRSGEPN NAYDEEDCVE MVASGGWNDV ACHTTMYFMC EFDKENMGSP SSSSSSAWSH

361 PQFEK
```
1-20: Secretion signal peptide (Sp; underlined)
21-181: TRAIL-receptor binding domain
182-192: Flexible linker element (A-linker; italic)
193-224: Coiled coil "neck" region of human Collectin-11
225-347: C-type lectin domain of human Collectin-11
348-357: Linker element (GSPSSSSSSA)
358-365: Strep-tag II (WSHPQFEK)

-continued
```
SEQ ID 46 Sp-TRAIL-ACC11
Total amino acid number: 246, MW = 27431
ORIGIN
    1 METDTLLLWV LLLWVPAGNG QRVAAHITGT RGRSNTLSSP NSKNEKALGR KINSWESSRS

61 GHSFLSNLHL RNGELVIHEK GFYYIYSQTY FRFQEEIKEN TKNDKQMVQY IYKYTSYPDP

121 ILLMKSARNS CWSKDAEYGL YSIYQGGIFE LKENDRIFVS VTNEHLIDMD HEASFFGAFL

181 VGSSGSSGSS GSGSQLRKAI GEMDNQVSQL TSELKFIKNA VAGVRETESG PSSSSSSAWS

241 HPQFEK
1-20: Secretion signal peptide (underlined)
21-181: TRAIL-receptor binding domain
182-193: Flexible linker element (A-linker; GSS GSS GSS GSG italic)
194-229: Coiled coil "neck" region of human Collectin-11
230-238: Linker element (GPSSSSSSA)
239-246: Strep-tag II (WSHPQFEK)
```

2.4 Characterization of Receptor-Selective TRAIL ('Mutein') Fusion Proteins

HEK293 cells were transiently transfected with expression plasmids encoding for different TRAIL receptor-selective SPD constructs:

| No. | Transfected Expression Vector |
|---|---|
| 1 | TRAILR1mut-A-SPD |
| 2 | TRAILR1mut-A-CCSPD |
| 3 | TRAILR1mut-D-SPD |
| 4 | TRAILR1mut-D-CCSPD |
| 5 | TRAILR2mut-A-SPD |
| 6 | TRAILR2mut-A-CCSPD |
| 7 | TRAILR2mut-D-SPD |
| 8 | TRAILR2mut-D-CCSPD |
| 9 | TRAIL-A-SPD |
| 10 | TRAIL-A-CCSPD |
| 11 | TRAIL-D-SPD |
| 12 | TRAIL-D-CCSPD |

Supernatants were collected three days post-transfection and an aliquot was used for SDS-PAGE and Western Blotting employing an antibody specific for Strep-tag II. Specific bands were detected at around 38 kDa (SPD-fusion proteins) and 28 kDa (coiled-coil-SPD fusion proteins). The amount of expressed protein depended on the ligand itself (TRAILR1 mutein>TRAILR2mutein>TRAIL), secondly the linker length used (A>D) and third the trimerization motif used (SPD>CCSPD). Apparent molecular weights were as expected from the calculated sizes (40 kDa and 27 kDa for SPD and CCSPD fusion proteins, respectively). The results are shown in FIG. 13.

The selectivity of TRAIL-Receptor 1 or TRAIL-Receptor 2 towards fusion proteins of SPD/ccSPD and TRAIL, TRAILR1 mut and TRAILR2mut was shown by Streptactin-ELISA. Therefore, TRAIL-SPD-fusion proteins in supernatants from transiently transfected HEK293 cells were immobilized on Streptactin coated microplates. Cell supernatant from untransfected cells served as negative control. The results are shown in FIG. 14. Specifically bound proteins were detected with constant (A, B) or varying (C, D) concentrations of either TRAIL-Receptor 1-Fc or TRAIL-Receptor 2-Fc. As shown in (A), the ligand TRAILR1 mut fused to SPD variants is detected by TRAIL-Receptor 1, whereas the ligand TRAILR2mut is not. As shown in (B), the ligand TRAILR2mut is preferentially detected by TRAIL-Receptor 2, whereas TRAILR1 mut- and TRAIL wild-type constructs are equally well detected. As shown in C, TRAIL-Receptor 1-Fc bound to TRAIL-R1mut-ASPD and TRAIL-ASPD equally well over the whole receptor titration range, whereas TRAIL-R2mut-ASPD is not detected. As shown in D, TRAIL-Receptor 2-Fc bound to TRAIL-R2mut-ASPD and TRAIL-ASPD equally well over the receptor titration range analyzed, whereas the signal for TRAIL-R1mut-ASPD decreased rapidly with decreasing concentrations of receptor.

One microgram/ml of affinity purified, trimeric TRAIL-ASPD, TRAILR1 mut-ASPD or TRAILR2mut-ASPD in 100 microliter of PBS were used for immobilization via the Strep-tag II on Streptactin-coated microplates. Bound ligands were detected in a ELISA set-up using Fc-fusion proteins of TRAIL-Receptor 1 (A) or TRAIL-Receptor 2 (B). As shown in (A), TRAIL-Receptor 1 bound preferentially to the receptor-selective TRAILR1 mut-ASPD as compared to TRAILR2mut-ASPD. As shown in (B), TRAIL-Receptor 2 preferentially bound to TRAILR2mut-ASPD as compared to TRAILR1 mut-ASPD. In conclusion, the constructed TRAIL variants fused to SPD are receptor selective. The results are shown in FIG. 15.

Affinity purified TRAILR1 mut-ASPD was subjected to SEC by loading 0.5 ml (0.95 mg protein) on a Superdex200 column. The results are shown in FIG. 16. Proteins were resolved at 0.5 ml/minute with PBS as running buffer and 0.5 ml fractions were collected (fractions A1 to A14 are indicated). The retention volume of 12.46 ml corresponded to 140-145 kDa as determined by size exclusion standard. A minor peak at 10.83 ml indicated some aggregated species, importantly however, no peak was detected at the running front (8 ml) indicating that this molecule is much more soluble as compared to proteins containing parts of the wild-type TRAIL amino acid sequence.

An aliquot from size exclusion chromatography of affinity purified TRAILR1 mut-ASPD was used for non-reducing (A) or reducing (B) SDS-PAGE followed by silver staining as shown in FIG. 17. Under non-reducing conditions, two bands were detected at 35 and 70 kDa, whereas a single band of 40 kDa (indicated by an arrow) was detected under reducing conditions. This indicated the formation of disulphide bridged molecules. The trimeric species was present in fractions A8 to A11 and was used for later analyses.

Jurkat cells were incubated in the absence (open bars) or presence (filled bars) of 2.5 microgram/ml of cross-linking antibody with aliquots at a final 80-fold dilution from fractions A1 to A14 from SEC of affinity purified TRAILR1mut-ASPD. The results are shown in FIG. 18. As negative control, Jurkat cells were incubated with medium only. Jurkat cells were lysed after 3 h incubation and the caspase activity was determined with a fluorogenic assay. As Jurkat cells have been shown to mainly express TRAIL- Receptor 2, no fraction induced significant caspase activity, even when TRAILR1 mit-ASPD was cross-linked by Strep-tag II specific antibody. This indicated that TRAILR1 mut-ASPD does not bind to TRAIL-Receptor 2.

Figure 19:
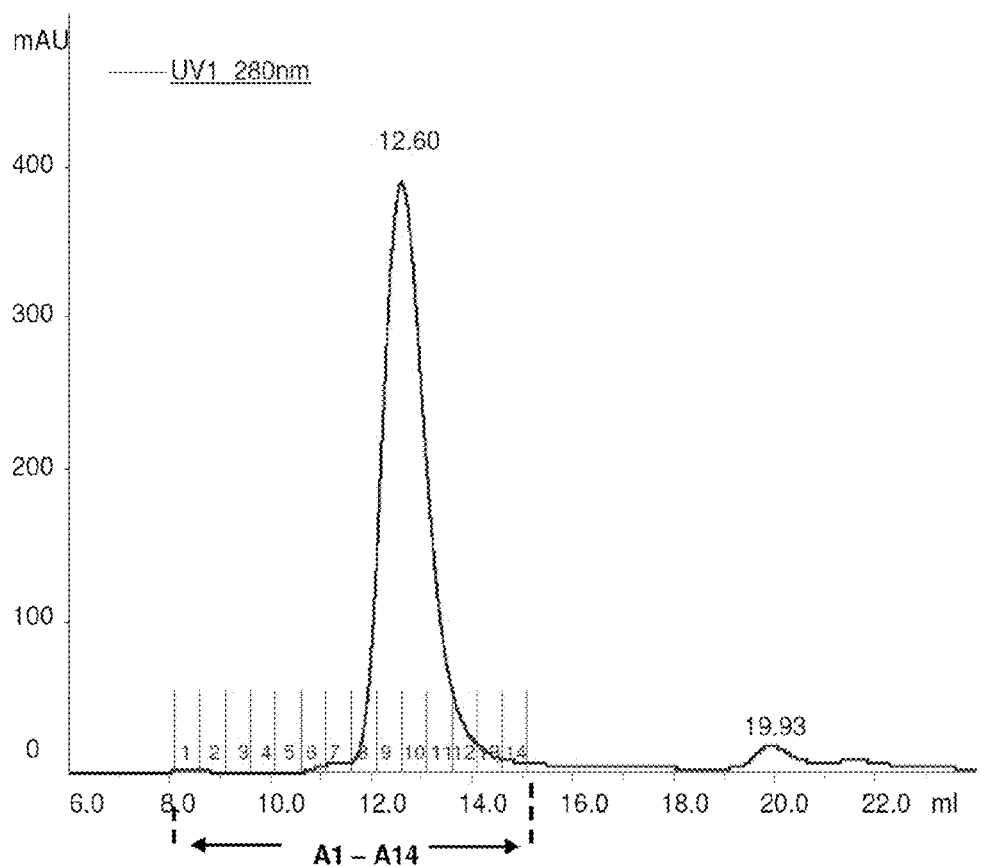
FIG. 19: Size exclusion chromatography of affinity purified TRAILR2mut-ASPD

Affinity purified TRAILR2mut-ASPD was subjected to size exclusion chromatography by loading 0.5 ml (0.5 mg protein) to a Superdex 200 column as shown in FIG. 19. Proteins were resolved at 0.5 ml/minute with PBS as running buffer and 0.5 ml fractions were collected (fractions A1 to A14 are indicated). The retention volume of 12.60 ml corresponds to 130-135 kDa as determined from size exclusion standard. This indicated that TRAILR2mut-ASPD is a homotrimer as calculated from the expected monomeric weight of 40 kDa. Importantly, more than 95% was present in the trimeric peak fraction and no aggregates were detected. The trimeric peak was used for later analyses.

Figure 20:
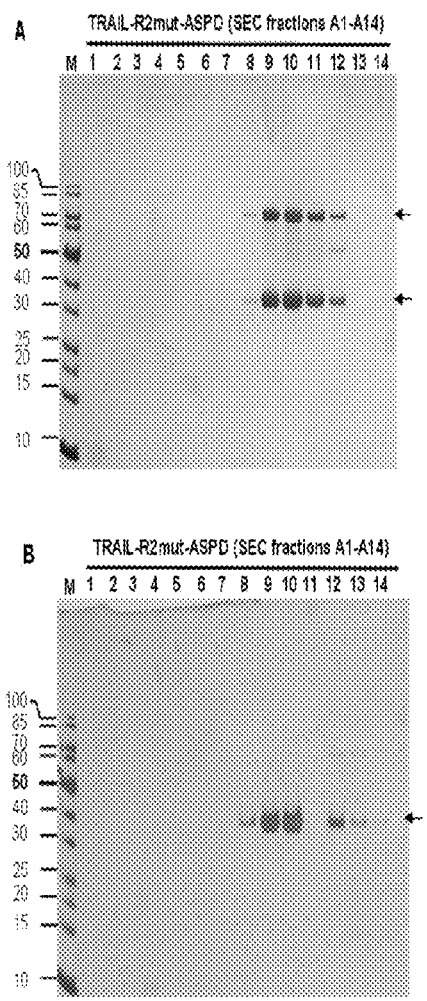
FIG. 20: Silver stained SDS-PAGE of SEC fractions A1-A14 from affinity purified TRAILR2mut-ASPD

An aliquot from size exclusion chromatography of affinity purified TRAILR2mut-ASPD was used for non-reducing (A) or reducing (B) SDS-PAGE followed by silver staining as shown in FIG. 20. Under non-reducing conditions, two bands were detected at 35 and 70 kDa, whereas a single band of approximately 40 kDa (indicated by an arrow) was detected under reducing conditions. This indicated the formation of disulphide bridged molecules. The trimeric species was present in fractions A9 to A11 and was used for later analyses.

Figure 21:
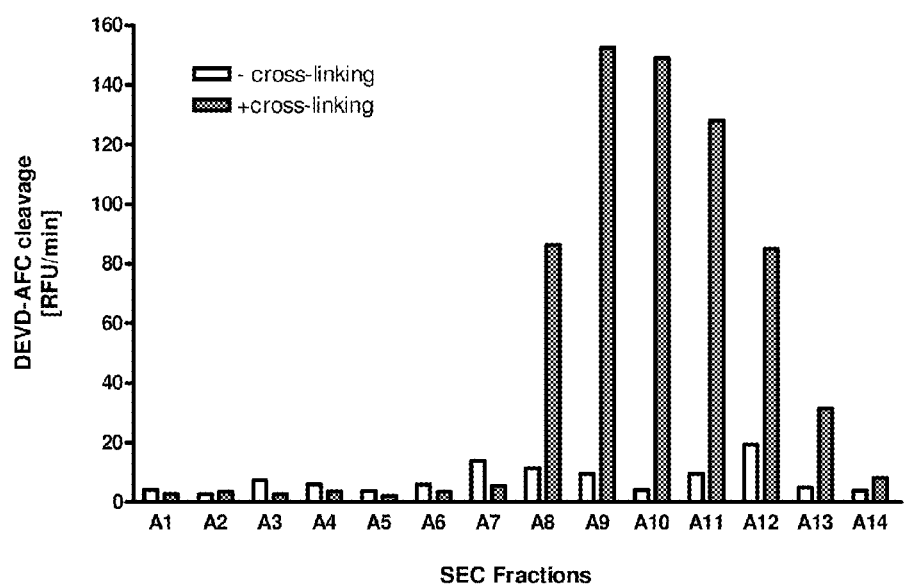
FIG. 21: Jurkat Kill Assay Jurkat of SEC fractions A1-A14 from affinity purified TRAILR2mut-ASPD

The results from a Jurkat cell kill assay with TRAILR2-mut-ASPD are shown in FIG. 21. Jurkat cells were incubated in the absence (clear bars) or presence (filled bars) of cross-linking antibodies (2.5 microgram/ml anti-Strep-tag II) with aliquots from fractions A1 to A14 from SEC of affinity purified TRAILR2mut-ASPD. Samples were used at final 640-fold dilution. Cells were lysed after 3 h of incubation and the caspase activity was determined with a fluorogenic assay. As Jurkat cells have been shown to mainly express TRAIL-Receptor 2 that requires multimerized ligand forms for efficient signalling, TRAILR2mut-ASPD induced caspase activity when cross-linked. This indicated that TRAILR2mut-ASPD is a functional molecule.

Figure 22:
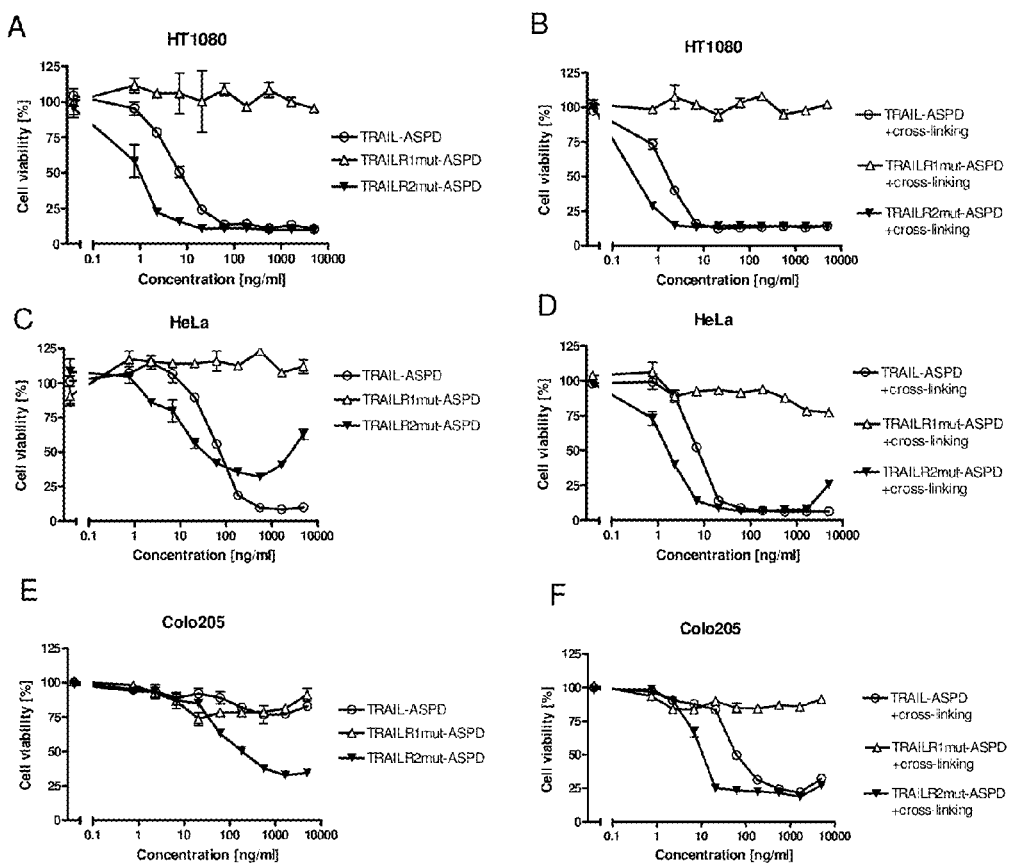
FIG. 22: Cytotoxic activity of TRAIL-ASPD, TRAILR1 mut-ASPD and TRAILR2mut-ASPD on human cancer cells.

The cytotoxic activity of TRAIL-ASPD, TRAILR1 mut-ASPD and TRAILR2mut-ASPD on different human cancer cells is shown in FIG. 22. The indicated cell lines HT1080 (A and B), Hela (C and D) or Colo205 (E and F) were treated with varying concentrations of purified and trimeric TRAIL-ASPD, TRAILR1mut-ASPD or TRAILR2mut-ASPD in the absence (A, C and E) or presence (B, D and F) of cross-linking antibody (anti-Strep-tag II). Cells were incubated for 18 hours with indicated concentrations of ligands and cell death was quantified by crystal violet staining (HT1080 and HeLa) or MTS assay (Colo205). As a result, the ligand TRAIL-ASPD induced cell death on the three cell lines tested and TRAILR2mut-ASPD showed superior cell killing activity. In contrast, TRAIL-Receptor 1 selective TRAILR1 mut-ASPD was not active on any cell line tested.

Figure 23:
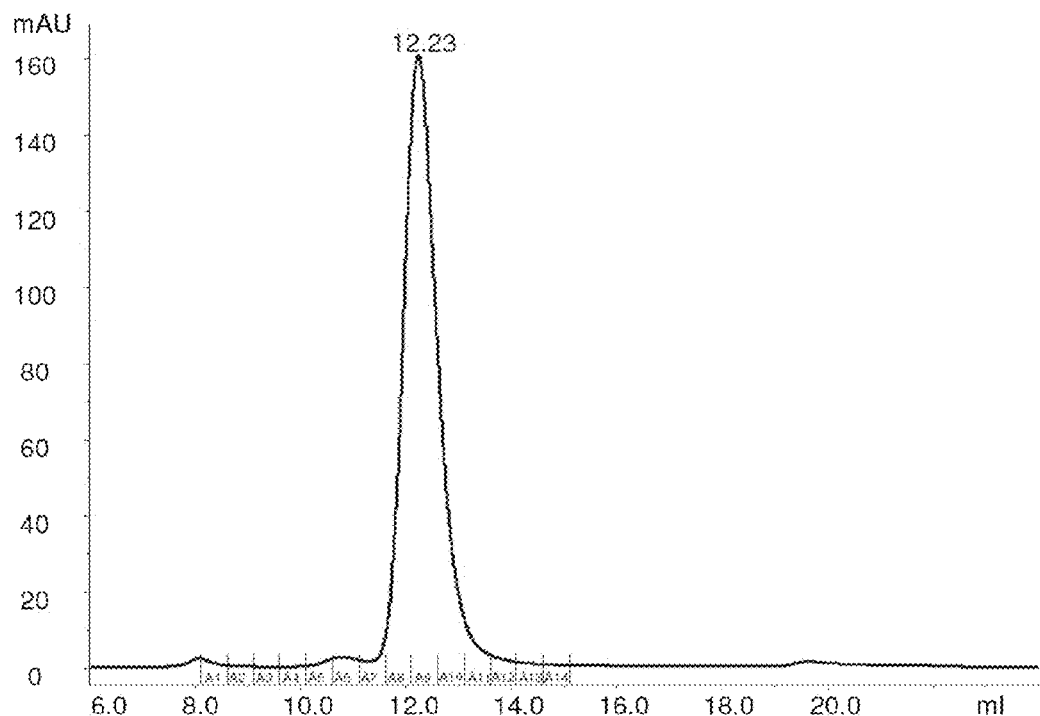
FIG. 23: Receptor selective TRAIL-SPD proteins are highly soluble
Figure 24:
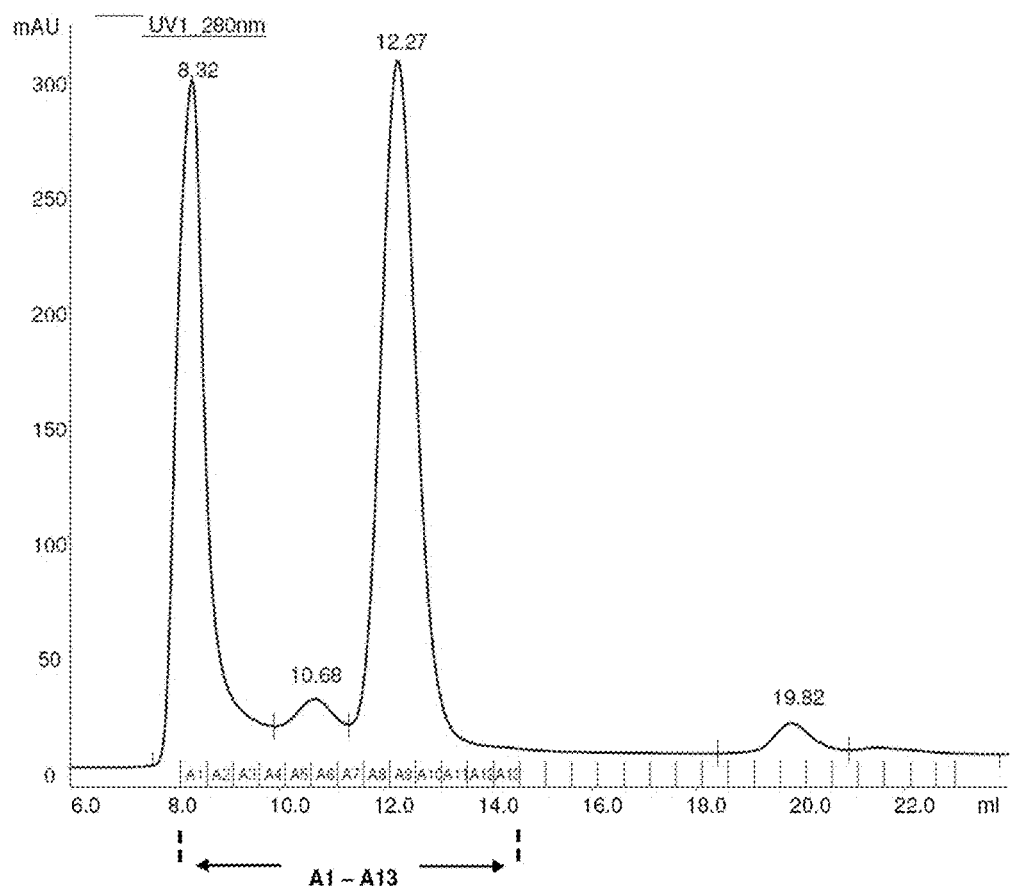
FIG. 24: SEC of affinity purified TRAIL-ASPD_F335A
Figure 25:
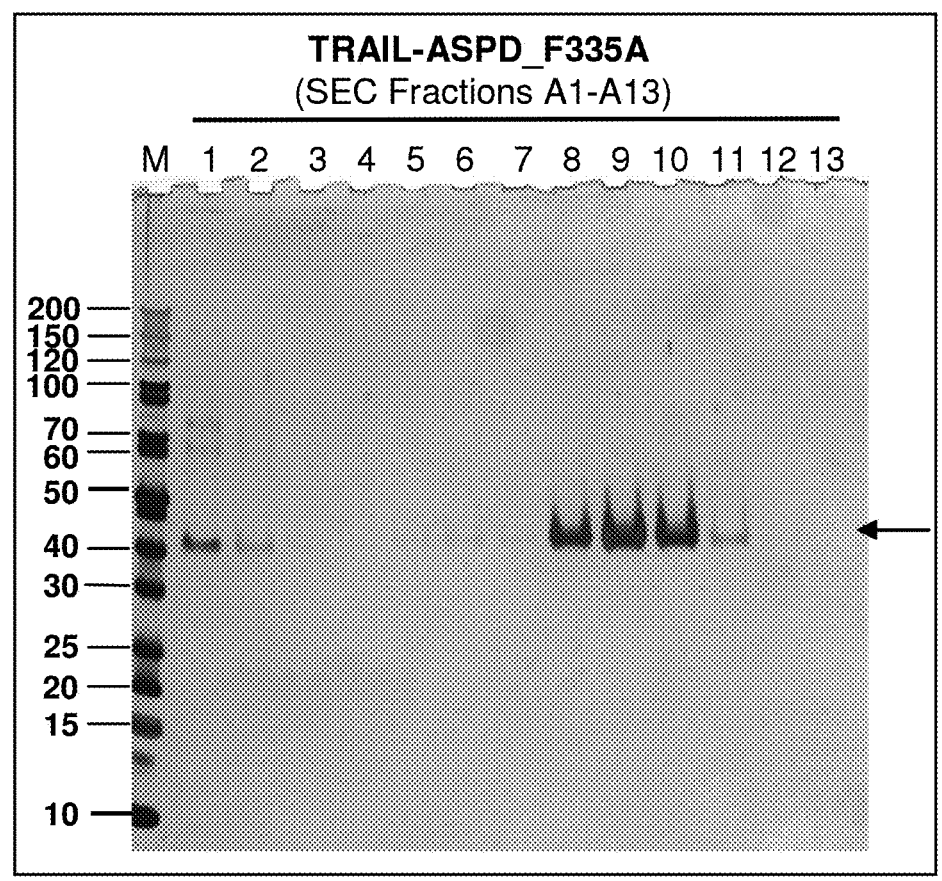
FIG. 25: Silver stained SDS-PAGE of SEC fractions A1-A13

Affinity purified TRAILR2mut-ASPD was concentrated 20-fold in PBS by centrifugation through a 10 kDa membrane to give a solution of 2.5 mg/ml. From the concentrate, 0.1 ml were subjected to size exclusion chromatography. As a result, only the trimeric peak and no aggregates were detected, indicating that this composition has improved production capabilities (FIG. 23). Similar results were achieved for TRAILR1 mut-ASPD, where a concentrated solution of even 5.4 mg/ml showed no signs of aggregation (not shown). In contrast, all fusion proteins tested containing the receptor binding domain composed of the wild type TRAIL sequence showed aggregation with 40% aggregates at concentrations as low as 0.4 mg/ml.

The amino acid sequences of receptor-selective TRAIL mutein fusion polypeptides are shown in the following.

```
Sp-TRAILR1mut-ASPD
Total amino acid number: 367, MW = 40335
ORIGIN
                                                              SEQ ID 47
  1 METDTLLLWV LLLWVPAGNG QRVAAHITGT RGRSNTLSSP NSKNEKALGR KINSWESSRS

61 GHSFLSNLHL RNGELVIHEK GFYYIYSQTA FRFSEEIKEV TRNDKQMVQY IYKWTDYPDP

121 ILLMKSARNS CWSKDAEYGL YSIYQGGIFE LKENDRIFVS VTNEHLIDMD HEASFFGAFL

181 VGSSGSSGSS GSGLPDVASL RQQVEALQGQ VQHLQAAFSQ YKKVELFPNG QSVGEKIFKT

241 AGFVKPFTEA QLLCTQAGGQ LASPRSAAEN AALQQLVVAK NEAAFLSMTD SKTEGKFTYP

301 TGESLVYSNW APGEPNDDGG SEDCVEIFTN GKWNDRACGE KRLVVCEFGG SPSSSSSSAW

361 SHPQFEK
1-20:    Secretion signal peptide (Sp; underlined)
21-181:  TRAILR1mut-receptor binding domain
182-192: Flexible linker element (A-linker; italic)
193-230: Coiled coil "neck" region of human SP-D
231-348: C-type lectin domain of human SP-D
349-359: Linker element (GGSPSSSSSA)
360-367: Strep-tag II (WSHPQFEK)

Sp-TRAILR2mut-ASPD
Total amino acid number: 367, MW = 40401
ORIGIN
                                                              SEQ ID 48
  1 METDTLLLWV LLLWVPAGNG QRVAAHITGT RGRSNTLSSP NSKNEKALGR KINSWESSRS

61 GHSFLSNLHL RNGELVIHEK GFYYIYSQTQ FKFREEIKEN TKNDKQMVQY IYKYTSYPDP

121 ILLMKSARNS CWSKDAEYGL YSIYQGGIFE LKENDRIFVS VTNERLLQMD HEASFFGAFL

181 VGSSGSSGSS GSGLPDVASL RQQVEALQGQ VQHLQAAFSQ YKKVELFPNG QSVGEKIFKT
```

```
241 AGFVKPFTEA QLLCTQAGGQ LASPRSAAEN AALQQLVVAK NEAAFLSMTD SKTEGKFTYP

301 TGESLVYSNW APGEPNDDGG SEDCVEIFTN GKWNDRACGE KRLVVCEFGG SPSSSSSSAW

361 SHPQFEK
1-20: Secretion signal peptide (Sp; underlined)
21-181: TRAILR2mut-receptor binding domain
182-192: Flexible linker element (A-linker; italic)
193-230: Coiled coil "neck" region of human SP-D
231-348: C-type lectin domain of human SP-D
349-359: Linker element (GGSPSSSSSSA)
360-367: Strep-tag II (WSHPQFEK)
```

2.5 Characterization of SPD Carbohydrate-Variants

Affinity purified TRAIL-ASPD_F335A was subjected to Size Exclusion Chromatography by loading 0.5 ml PBS solution (0.4 mg protein) to a Superdex 200 column as shown in FIG. 24. Proteins were resolved at 0.5 ml/minute with PBS as running buffer and 0.5 ml fractions were collected (A1 to A13 are indicated). The retention volume of 12.27 ml corresponds to 135-145 kDa as determined from size exclusion standard. This indicated that TRAIL-ASPD_F335A is a homotrimer as calculated from the expected monomeric weight of 40 kDa. Two additional peaks at 8.32 and 10.68 ml indicated the formation of TRAIL-ASPD_F335A aggregates. Only the trimeric peak was used for later analyses.

From Size exclusion chromatography an aliquot from collected fractions A1 to A13 was resolved by reducing SDS-PAGE and the gel was silver stained (FIG. 25). The band detected at approximately 40 kDa corresponded to the calculated molecular weight of 40 kDa for TRAIL-ASPD_F335A. Positive fractions corresponding the trimeric molecule (A8, A9, A10) of the SEC run were pooled and used for further analyses.

The amino acid sequences of TRAIL-SPD carbohydrate variant fusion proteins is shown in the following.

```
SEQ ID 49: Sp-TRAIL-ASPD_F335A
Total amino acid number: 367, MW = 40328
ORIGIN
  1 METDTLLLWV LLLWVPAGNG QRVAAHITGT RGRSNTLSSP NSKNEKALGR KINSWESSRS

61 GHSFLSNLHL RNGELVIHEK GFYYIYSQTY FRFQEEIKEN TKNDKQMVQY IYKYTSYPDP

121 ILLMKSARNS CWSKDAEYGL YSIYQGGIFE LKENDRIFVS VTNEHLIDMD HEASFFGAFL

181 VGSSGSSGSS GSGLPDVASL RQQVEALQGQ VQHLQAAFSQ YKKVELFPNG QSVGEKIFKT

241 AGFVKPFTEA QLLCTQAGGQ LASPRSAAEN AALQQLVVAK NEAAFLSMTD SKTEGKFTYP

301 TGESLVYSNW APGEPNDDGG SEDCVEIATN GKWNDRACGE KRLVVCEFGG SPSSSSSSAW

361 SHPQFEK
1-20: Secretion signal peptide (Sp; underlined)
21-181: TRAIL-receptor binding domain
182-192: Flexible linker element (A-linker; italic)
193-230: Coiled coil "neck" region of human SP-D
231-348: C-type lectin domain of human SP-D (Phe mutation in bold-face)
349-359: Linker element (GGSPSSSSSSA)
360-367: Strep-tag II (WSHPQFEK)

SEQ ID 50: Sp-TRAIL-ASPD_F335D
Total amino acid number: 367, MW = 40372
ORIGIN
  1 METDTLLLWV LLLWVPAGNG QRVAAHITGT RGRSNTLSSP NSKNEKALGR KINSWESSRS

61 GHSFLSNLHL RNGELVIHEK GFYYIYSQTY FRFQEEIKEN TKNDKQMVQY IYKYTSYPDP

121 ILLMKSARNS CWSKDAEYGL YSIYQGGIFE LKENDRIFVS VTNEHLIDMD HEASFFGAFL

181 VGSSGSSGSS GSGLPDVASL RQQVEALQGQ VQHLQAAFSQ YKKVELFPNG QSVGEKIFKT

241 AGFVKPFTEA QLLCTQAGGQ LASPRSAAEN AALQQLVVAK NEAAFLSMTD SKTEGKFTYP

301 TGESLVYSNW APGEPNDDGG SEDCVEIDTN GKWNDRACGE KRLVVCEFGG SPSSSSSSAW

361 SHPQFEK
1-20: Secretion signal peptide (Sp; underlined)
21-181: TRAIL-receptor binding domain
182-192: Flexible linker element (A-linker; italic)
193-230: Coiled coil "neck" region of human SP-D
231-348: C-type lectin domain of human SP-D (Asp mutation in bold-face)
349-359: Linker element (GGSPSSSSSSA)
360-367: Strep-tag II (WSHPQFEK)
```

Figure 26:
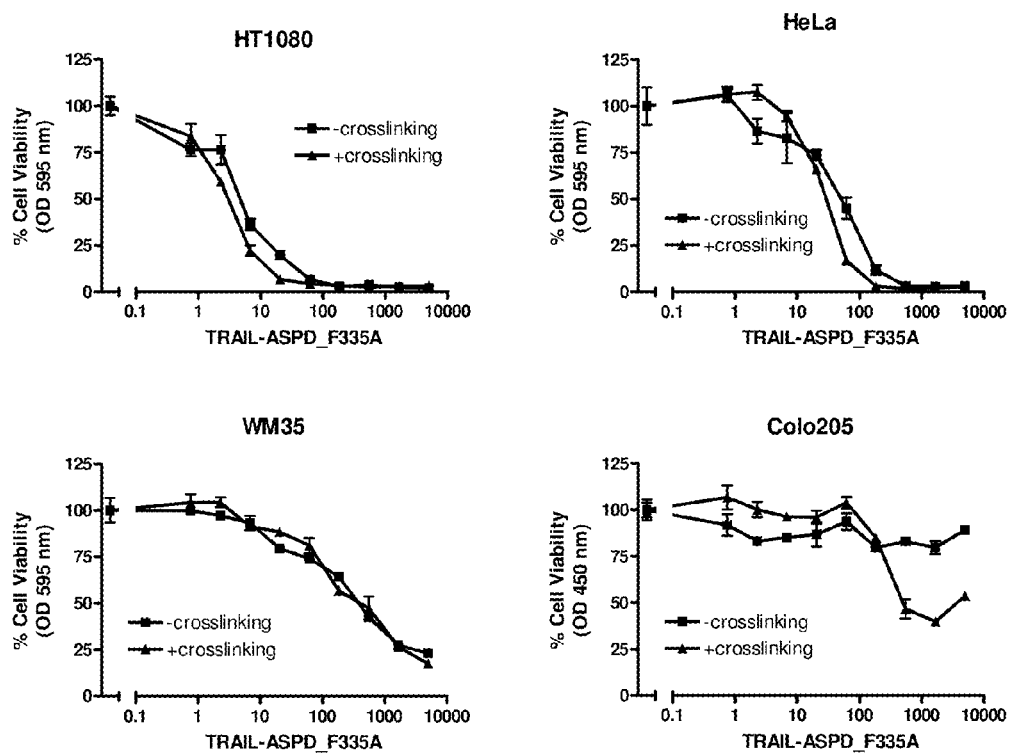
FIG. 26: Cytotoxic effect of TRAIL-ASPD_F335A on human cancer cells

The cytotoxic effect of TRAIL-ASPD_F335A on human cancer cells is shown in FIG. 26. Indicated human cancer cell lines were incubated over night with varying concentrations of affinity and SEC purified, trimeric TRAIL-ASPD_F335A in the presence or absence of cross-linking antibody (2.5 microgram/ml of anti Strep-tag II). Cell viability was quantified by crystal violet staining (HT1080, HeLa and WM35) or MTS (Colo205). The rise of Colo205 cell viability at high ligand concentrations is likely due to limitation of cross-linking antibody.

Figure 27:
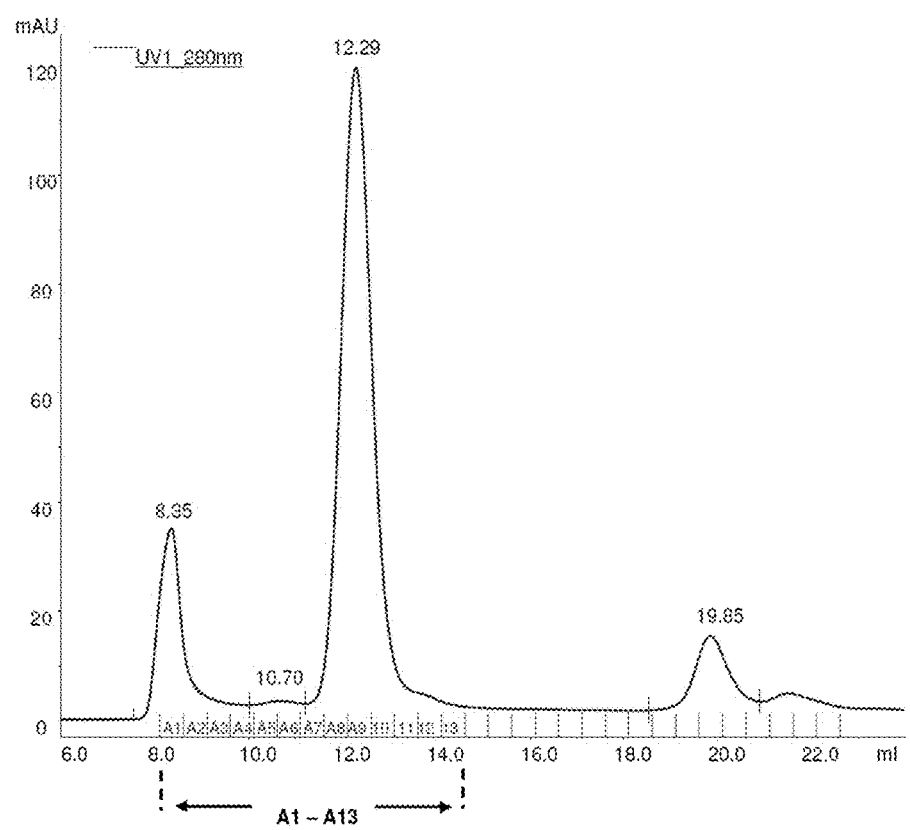
FIG. 27: SEC of affinity purified TRAIL-ASPD_F335D

Affinity purified TRAIL-ASPD_F335D was subjected to Size Exclusion Chromatography by loading 0.5 ml (0.2 mg protein) to a Superdex 200 column as shown in FIG. 27. Proteins were resolved at 0.5 ml/minute with PBS as running buffer and 0.5 ml fractions were collected (A1 to A13 are indicated). The retention volume of 12.29 ml corresponds to 135-145 kDa as determined from size exclusion standard. This indicated that TRAIL-ASPD_F335D is a homotrimer as calculated from the expected monomeric weight of 40 kDa. The peak at 8.35 corresponded to inactive TRAIL-ASPD_F335D aggregates typically found for all fusion proteins containing parts of the wild type TRAIL amino acid sequence.

Figure 28:
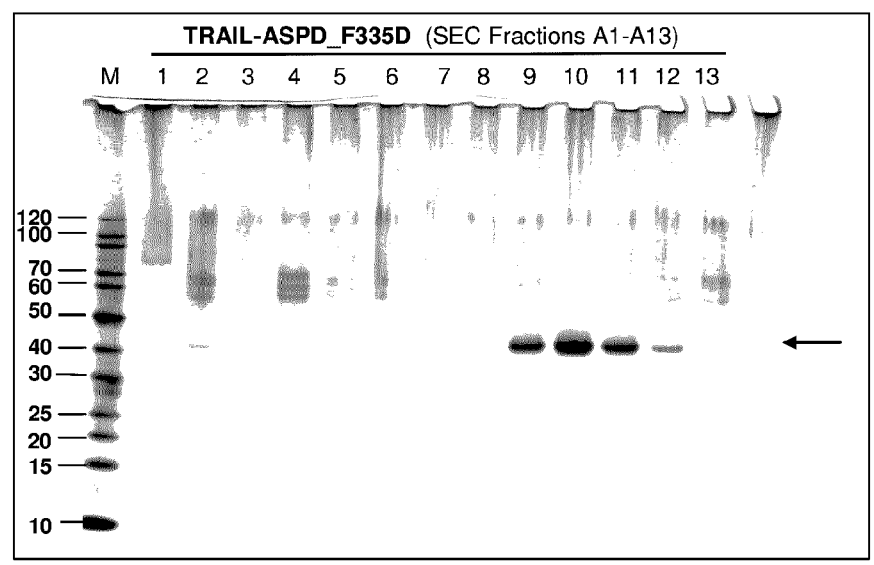
FIG. 28: Silver stained SDS-PAGE of SEC from affinity purified TRAIL-ASPD_F335D

From Size exclusion chromatography aliquots of affinity purified TRAIL-ASPD_F335D from the collected fractions A1 to A13 were resolved by reducing SDS-PAGE and the gel was silver stained (FIG. 28). The bands detected at approximately 40 kDa (indicated by an arrow) corresponded to the calculated molecular weight of 40 kDa for TRAIL-ASPD_F335D. Fractions containing trimeric protein (fractions A8 to A10) were pooled and used for further analyses.

Figure 29:
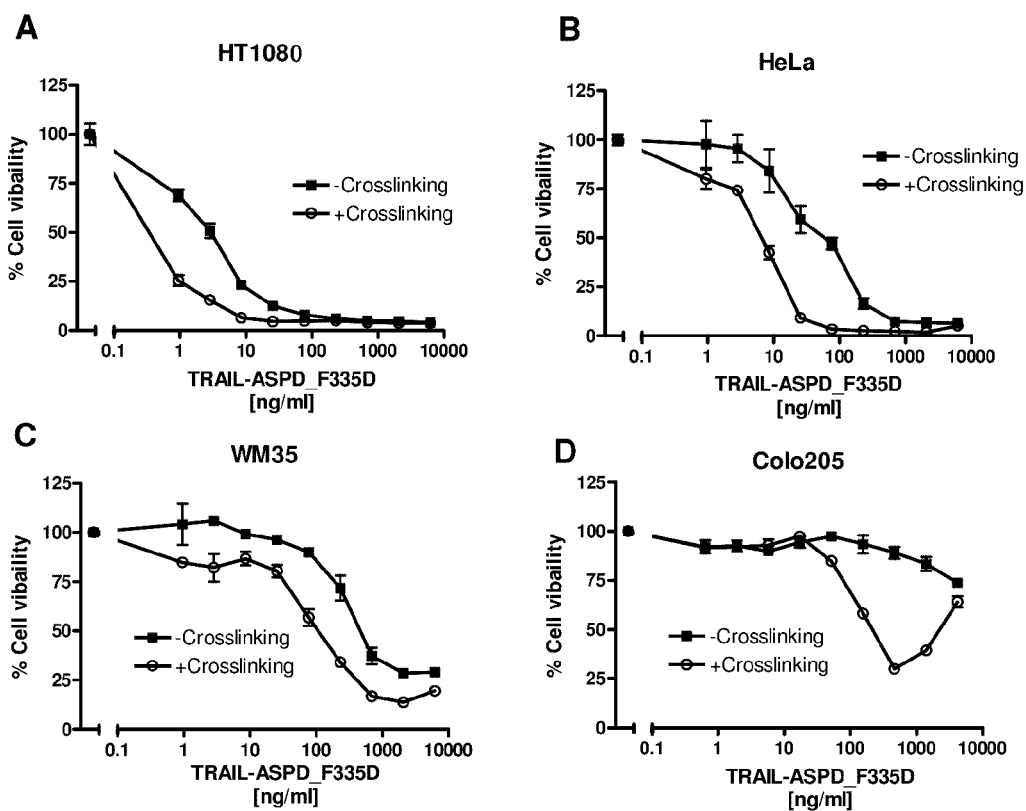
FIG. 29: Cytotoxic effect TRAIL-SPD_F335D on human cancer cells

The human cancer cell lines HT1080 (A), HeLa (B), WM35 (C) or Colo205 (D) were incubated over night with varying concentrations of affinity purified, trimeric TRAIL-ASPD_F335D in the presence or absence of cross-linking antibodies (anti-Strep-tag II). Cell viability was quantified by crystal violet staining (HT1080, HeLa and WM35) or MTS (Colo205). The data show that TRAIL-ASPD_F335D is capable of inducing cell death in exemplified cancer cell lines (FIG. 29). The rise of Colo205 cell viability at high concentrations of ligand is likely due to limitation of cross-linking antibody.

2.6 Analysis of Carbohydrate Binding Characteristics of the SPD Trimerization Motif Variants It has been shown that wild-type, full length and oligomeric SP-D protein from several species, as well as the trimeric neck+CRD of human SP-D bind to several different carbohydrates. In addition, the neck+CRD of human SP-D also has been shown to exert immunomodulatory effects by serving as a chemotactic factor for immuno cells such as neutrophils (Cai et al., 1999, *Am J Physiol Lung Cell Mol Physiol* 276:131-136). Other cells may also be recruited by SP-D. The chemotactic effect of neck+CRD of human SP-D has been shown to depend on the glycobinding function, as the addition of maltose inhibited the chemotactic function. Thus, a ligand of the TNFSF with a SP-D-mediated chemotactic function may be of superior activity as compared to ligands or constructs thereof with natural amino acid sequences. For instance, in a scenario where cellular effects are desirable such as in cancer treatment such a described ligand may be desirable.

In addition, a ligand where SP-D has no carbohydrate function may be desirable in other settings. For human SP-D a mutant has been described in which amino acid phenylalanine 335 (corresponding to amino acid 355 of SEQ ID NO:21) has been mutated to alanine (SPD_F335A, Crouch et al., *JBC* 281: 18008-18014). This mutant showed very weak carbohydrate binding. However, introducing a charged amino acid (e.g. an acidic amino acid) may be even better as compared to F335A if no carbohydrate binding is desired. Therefore the mutant SPD_F335D may be superior towards F335A mutant.

Figure 30:
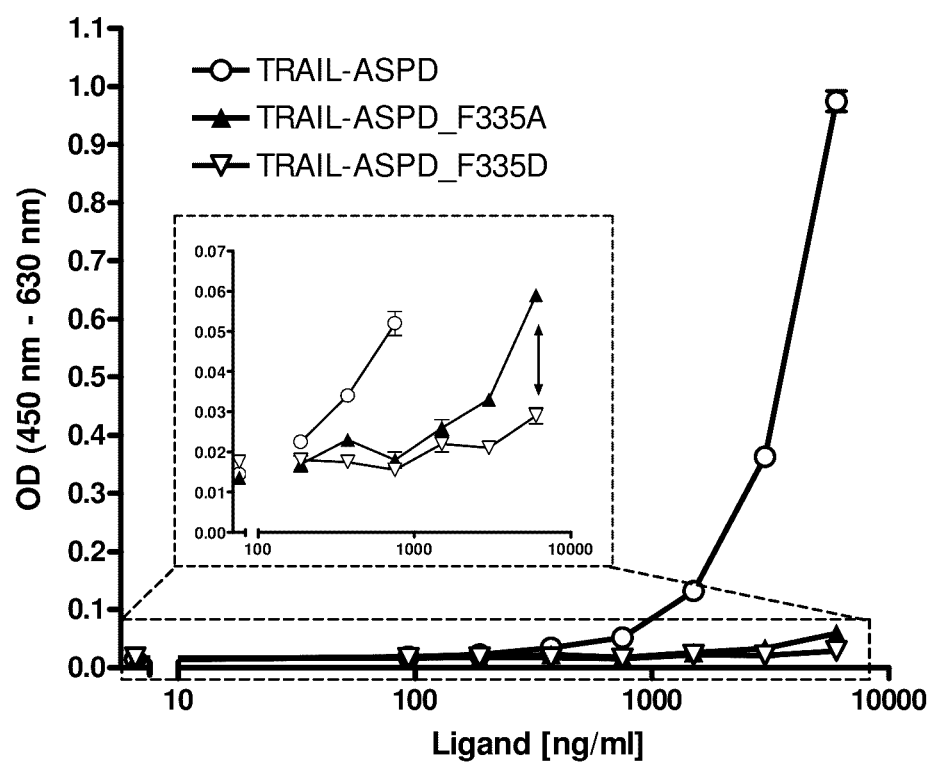
FIG. 30: Binding of TRAIL-ASPD fusion protein to carbohydrates

To analyze the binding of TRAIL-fusion proteins to carbohydrates, mannan from yeast was immobilized on microplates and the binding of TRAIL-SPD, TRAIL-SPD_F335A or TRAIL-SPD_F335D was detected by ELISA. The results are shown in FIG. 30. As expected, the ELISA signal increased with increasing concentrations of TRAIL-ASPD. In contrast, the carbohydrate-mutant form TRAIL-ASPD_F335A showed a very low ELISA signal. In addition, the new constructed variant TRAIL-ASPD_F335D displayed the lowest ELISA signal (see inset and arrow). This indicated that the mutant F335D has a lower mannan-binding affinity as compared to the previously described SP-D mutant form F335A.

2.7 Pharmacokinetics of TRAIL-SPD Fusion Proteins

Figure 31:
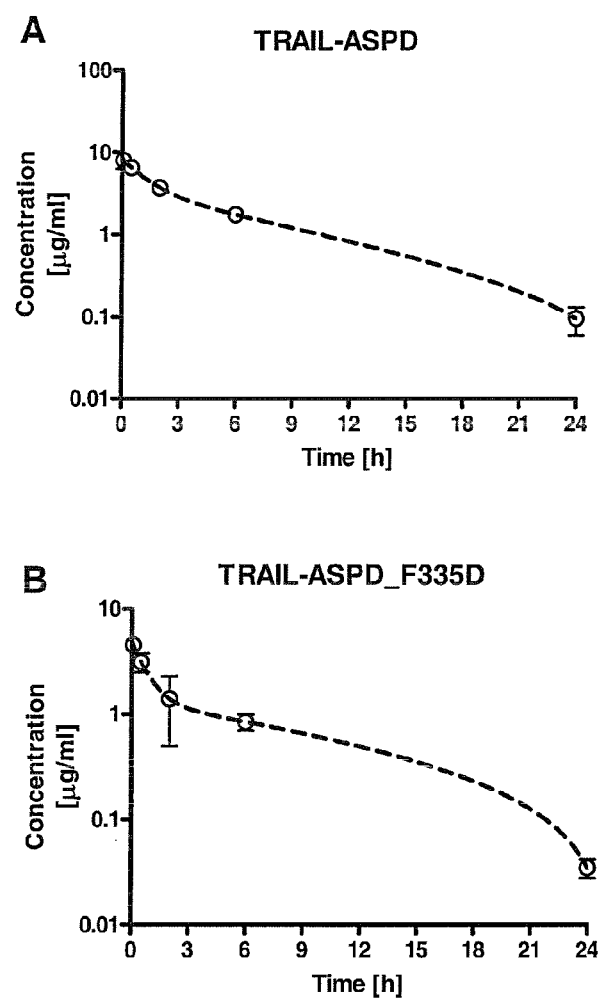
FIG. 31: Pharmacokinetics of TRAIL-ASPD (A) or TRAIL-ASPD_F335 D (B) Fusion Proteins

To determine the half-lifes of TRAIL-SPD fusion protein, ten micrograms of TRAIL-ASPD (A) or TRAIL-ASPD_F335D (B) were injected intravenously into male CD1 mice and serum samples were collected after several time points (predose, 5 min., 30 min., 2 h, 6 h and 24 h). TRAIL proteins in sera of mice were quantified by an ELISA and the data was used to calculate halflifes. The results are shown in FIG. 31. For the two proteins analyzed, a halflife of 7 to 14 hours for TRAIL-ASPD (A) and TRAIL-ASPD_F335D (B) were calculated. No animal died or showed signs of intolerance during the period observed. The data indicate an at least 80-fold improvement of the serum halftime as compared to wild type TRAIL that was reported to have a half time in the range of three to five minutes in rodents (Kelley et. al 2001).

2.8 Cytotoxicity of TRAIL-ASPD Fusion Proteins

Figure 32:
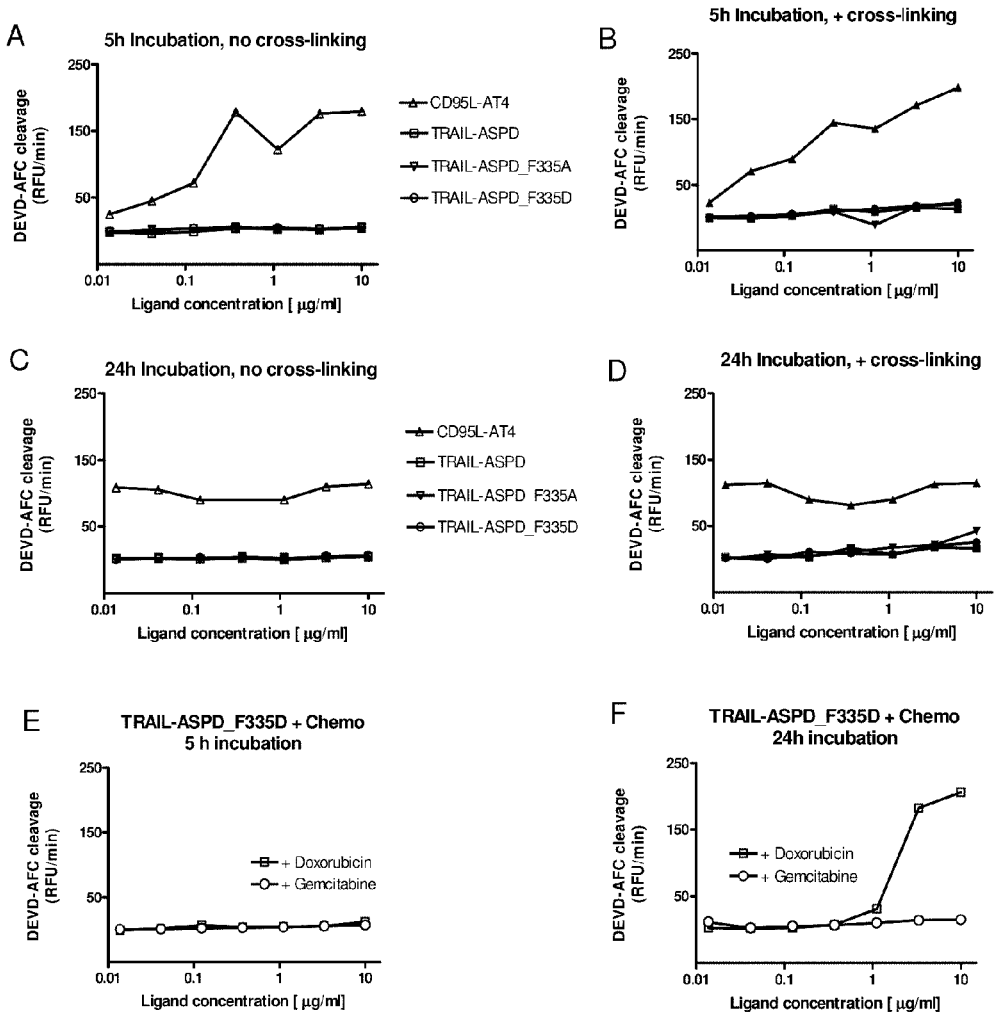
FIG. 32: Caspase activity in primary human hepatocytes

To analyze potential hepatotoxic effects of TRAIL-ASPD, TRAIL-ASPD_F335A or TRAIL-ASPD_F335D, primary human hepatocytes (PHH) were incubated with varying concentrations of indicated TRAIL-SPD-fusion proteins, with or without cross-linking antibodies (anti-Strep-tag II). As a control, a stabilized variant of CD95L, CD95L-T4 (described in WO2008/025516) was used. The results are shown in FIG. 32.

In addition, the effect of a simultaneous incubation of PHH with 5 mM of chemotherapeutic drugs was analyzed for TRAIL-ASPD_F335D. After 5 h (A, B and E) or 24 h (C, D and F) of incubation, cells were lysed and caspase activity was assessed with a fluorogenic assay.

As a result, all analyzed TRAIL-SPD fusion proteins induced no hepatotoxic effects, even if ligands were secondarily cross-linked by antibodies. In contrast, CD95L-T4 is hepatotoxic as indicated by an increase of active caspase (A to D). Five hours of co-incubation of primary human hepatocytes with trimeric TRAIL-ASPD_F335D together with chemotherapeutic drugs induced no caspase activity (E). However, after 24 h of co-incubation with doxorubicin, soluble TRAIL-ASPD_F335D induced a strong caspase activity signal (F).

This indicates that TRAIL fusion proteins of the present invention may not show undesired hepatotoxicity in medical use. Thus, TRAIL fusion proteins are preferably administered in combination with drugs, which are apoptosis sensitizers and/or apoptosis inducers, e.g. a chemotherapeutic drug such as oxaliplatin, cisplatin, 5-fluorouracil, etoposide, gemcitabine, irinotecan and others, or Bcl2 binding molecules, e.g. small molecules or peptidic compounds, which bind to polypeptides of the Bcl2 family, particularly Bcl2 or Bclxl.

2.9 Characterization of APRIL Fusion Proteins

Figure 33:
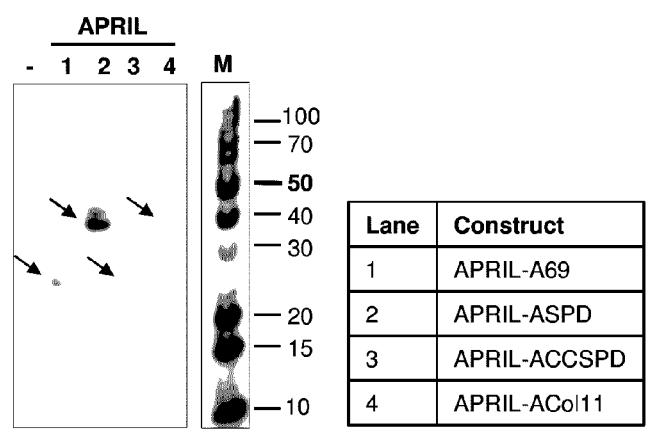
FIG. 33: Western Blot of supernatants from HEK293 cells transiently transfected with trimerized APRIL constructs

HEK293 cells were transiently transfected with expression vectors encoding for APRIL-A69 (WO2008025516), APRIL-ASPD, APRIL-ACCSPD or APRIL-AColl1. After three days supernatants were analyzed for secreted proteins by Western Blotting. The results are shown in FIG. 33. For the detection of APRIL-fusion proteins an antibody specific for Strep-tag II was used. Arrows indicate specific bands that were detected around 40 kDa (APRIL-ASPD and APRIL-AColl1, respectively), as well as at around 25 kDa (APRIL-A69 and APRIL-ACCSPD, respectively). Thus APRIL expression cassettes are functional and the secretion of protein indicated that the proteins are properly folded. As for other TNFSF proteins analyzed, the highest secreted protein levels were found for APRIL fused to the trimerization motif composed of coiled coil "neck"+CRD of human SP-D (APRIL-ASPD, lane No. 2). APRIL-ASPD was used to analyze the binding to the receptor TACI.

Figure 34:
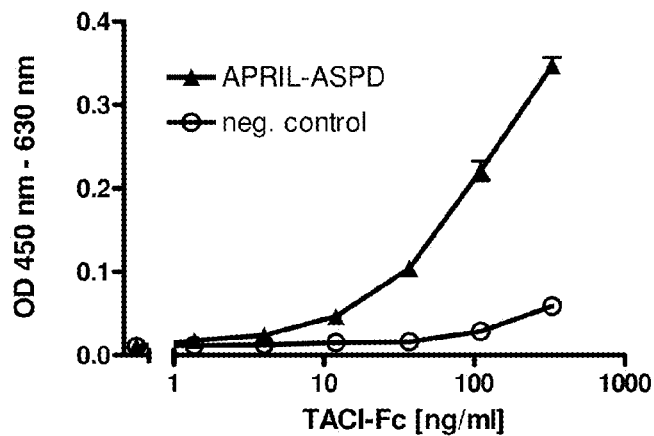
FIG. 34: TACI-Fc binds to APRIL-ASPD
Figure 35:
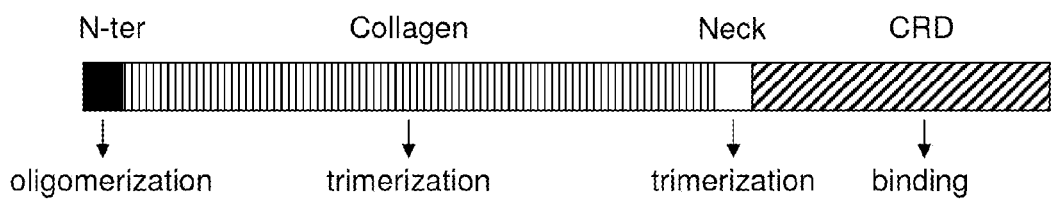
FIG. 35: Schematic drawing of the domain organization of the collectin SP-D. The collagen and neck regions trimerize collectins and the N-terminus further oligomerizes trimers into tetramers or hexamers of trimers. The CRD mediates binding to carbohydrates and is also involved in trimerization.

To show that the constructed APRIL-ASPD fusion protein is functional, the binding to a known receptor of APRIL, namely TACI, was assessed (FIG. 34). Therefore, APRIL-ASPD in supernatant from transiently transfected HEK293 cells was immobilized on Streptactin coated microplates. Cell supernatant from untransfected HEK293 cells served as negative control. Specifically bound proteins were detected with varying concentrations of TACI-Fc followed by incubation with an anti-human, Fc-specific antibody conjugated with peroxidase. As a result, the ELISA signal increased with increasing concentrations of TACI-Fc, indicating that APRIL-ASPD is a functional molecule.

The amino acid sequence of an APRIL fusion protein is shown below.

```
SEQ ID 51: Sp-APRIL-ASPD
Total amino acid number: 344, MW = 37120
ORIGIN
    1 METDTLLLWV LLLWVPAGNG KQHSVLHLVP INATSKDDSD VTEVMWQPAL RRGRGLQAQG

61 YGVRIQDAGV YLLYSQVLFQ DVTFTMGQVV SREGQGRQET LFRCIRSMPS HPDRAYNSCY

121 SAGVFHLHQG DILSVIIPRA RAKLNLSPHG TFLGFVKLGS SGSSGSSGSG LPDVASLRQQ

181 VEALQGQVQH LQAAFSQYKK VELFPNGQSV GEKIFKTAGF VKPFTEAQLL CTQAGGQLAS

241 PRSAAENAAL QQLVVAKNEA AFLSMTDSKT EGKFTYPTGE SLVYSNWAPG EPNDDGGSED

301 CVEIFTNGKW NDRACGEKRL VVCEFGGSPS SSSSSAWSHP QFEK
1-20: Signal secretion peptide (underlined)
21-158: APRIL-RBD
159-169: Flexible linker element (A-linker; GSS GSS GSS GS italic)
170-207: Coiled coil "neck" region of human SP-D
208-325: C-type lectin domain of human SP-D
326-336: Linker element (GGSPSSSSSSA)
337-344: Strep-tag II (WSHPQFEK)
```

Example 3

Generation of a Fusion Protein with a Single Chain Antibody as Effector Polypeptide The amino acid sequences of examples for single chain (sc) Fv-SPD fusion proteins are shown below (SEQ ID 52, 53)

Sp-sc006-ASPD
Total amino acid number: 450

SEQ ID 52
```
  1 METDTLLLWV LLLWVPAGNG EVQLVESGGG LVKPGGSLRL SCAASGFTFN TNAMNWVRQA

61 PGKGLEWVAR IRSKSNNYAT YYADSVKDRF TLSRDDSKNT LYLQMNSLKT EDTAVYYCTR

121 DRGWGAMDYW GQGTTVTVSS GGGGSGGGGS GGGTGDIQMT QSPSSLSASV GDRVTITCSA

181 SQDINNYLNW YQQKPGKAPK LLIYYTSSLH SGVPSRFSGS GSGTDFTLTI SSLQPEDFAT

241 YYCQQFSNLP WTFGGGTKLE IKRTGSSGSS GSSGSGLPDV ASLRQQVEAL QGQVQHLQAA

301 FSQYKKVELF PNGQSVGEKI FKTAGFVKPF TEAQLLCTQA GGQLASPRSA AENAALQQLV

361 VAKNEAAFLS MTDSKTEGKF TYPTGESLVY SNWAPGEPND DGGSEDCVEI FTNGKWNDRA

421 CGEKRLVVCE FGGSPSSSSS SAWSHPQFEK
```
1-20: Signal secretion peptide (underlined)
21-140: Variable domain heavy chain
141-155: Linker element
156-264: Variable domain light chain
265-275: A-Linker
276-431: SPD-motiv (neck + CRD)
432-441: Linker element
442-450: Strep-tag II (WSHPQFEK)

SEQ ID 53 Sp-sc006-ASPD F335D
Total amino acid number: 450
```
  1 METDTLLLWV LLLWVPAGNG EVQLVESGGG LVKPGGSLRL SCAASGFTFN TNAMNWVRQA

61 PGKGLEWVAR IRSKSNNYAT YYADSVKDRF TLSRDDSKNT LYLQMNSLKT EDTAVYYCTR

121 DRGWGAMDYW GQGTTVTVSS GGGGSGGGGS GGGTGDIQMT QSPSSLSASV GDRVTITCSA

181 SQDINNYLNW YQQKPGKAPK LLIYYTSSLH SGVPSRFSGS GSGTDFTLTI SSLQPEDFAT

241 YYCQQFSNLP WTFGGGTKLE IKRTGSSGSS GSSGSGLPDV ASLRQQVEAL QGQVQHLQAA

301 FSQYKKVELF PNGQSVGEKI FKTAGFVKPF TEAQLLCTQA GGQLASPRSA AENAALQQLV

361 VAKNEAAFLS MTDSKTEGKF TYPTGESLVY SNWAPGEPND DGGSEDCVEI DTNGKWNDRA

421 CGEKRLVVCE FGGSPSSSSS SAWSHPQFEK
```
1-20: Signal secretion peptide (underlined)
21-140: Variable domain heavy chain
141-155: Linker element
156-264: Variable domain light chain
265-275: A-Linker
276-431: SPD-motiv (neck + CRD)
432-441: Linker element
442-450: Strep-tag II (WSHPQFEK)

Figure 39:
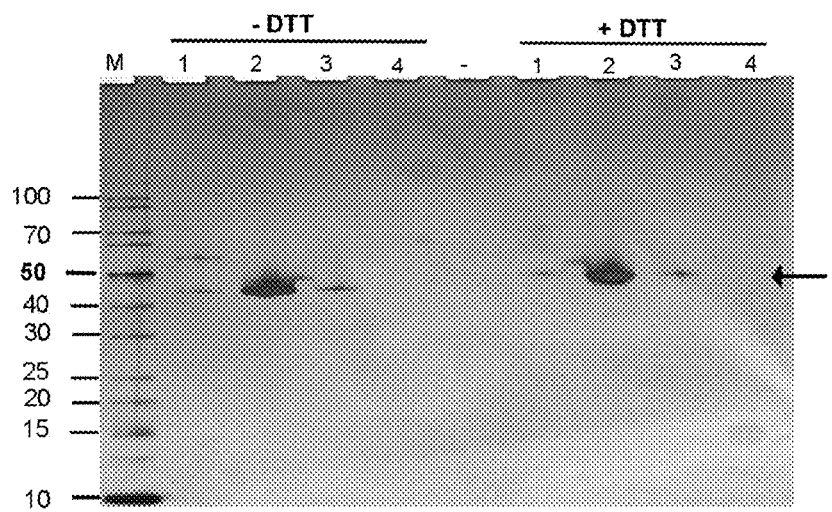
FIG. 39: Silver gel of affinity purified Sp-sc006-ASPD-St.

The protein was expressed and subjected to affinity chromatography as described in section 1.3. An aliquot of the eluate was resolved by SDS-PAGE under reducing or non-reducing conditions. A single band at 40-50 kDa can be detected indicated by an arrow (see FIG. 39) corresponding to sc006-ASPD-St with an expected molecular weight of 45.8 kDa.

Figure 40:
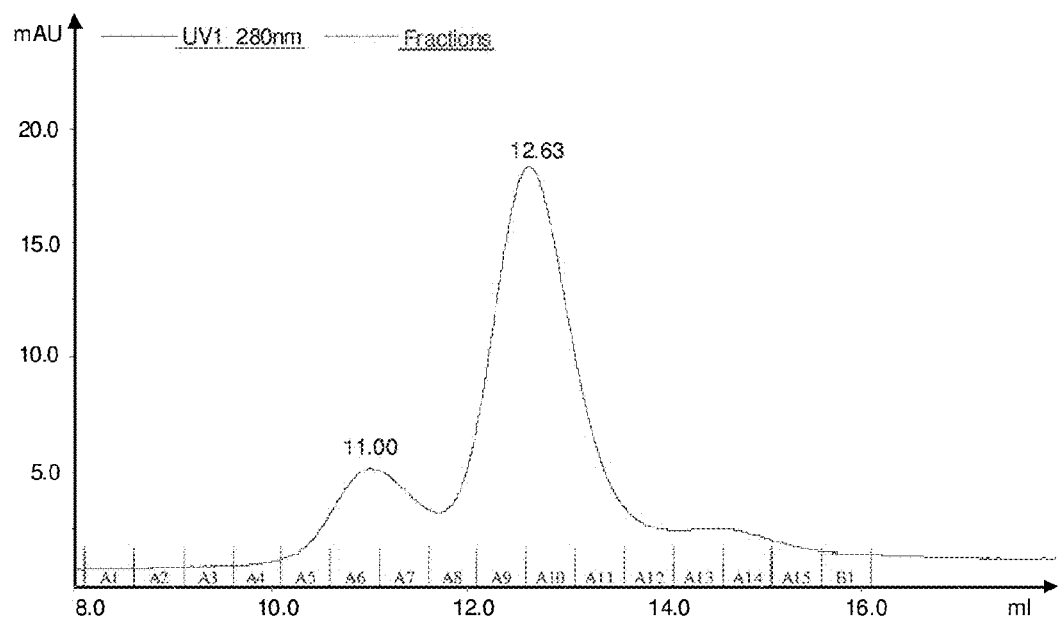
FIG. 40: Size exclusion chromatography of affinity purified Sp-sc006-ASPD-St.

The protein was expressed, affinity purified and subjected to size exclusion chromatography as described in section 1.3. Fifty micrograms of affinity purified protein were loaded onto a Superdex200 column and the chromatogram is shown (see FIG. 40). The main peak at 12.63 ml corresponds to a molecular weight of 160±15 kDa resembling the expected species of three scFv molecules organized into trimers via SPD. The molecules could be tested for functionality in an ELISA setup by immobilizing the antigen and detecting sc006-SPD-St.

The fusion protein generated in this experiment comprises a single chain antibody directed against IL4R-alpha.

---

The invention claimed is:

1. A fusion protein comprising
   (i) a collectin family trimerization domain consisting of the amino acid residues selected from the group consisting of: 217-375, 218-375, 219-375, 220-375, 221-375, 222-375, 223-375, 224-375, and 225-375 of SEQ ID NO: 21, optionally further consisting of an amino acid substitution at residue 355;
   (ii) a linker element; and
   (iii) CD27 ligand (CD27L) or a receptor binding domain thereof;
   wherein said linker element has 25 or less amino acids.

2. The fusion protein claim 1, wherein CD27L is located N-terminally of the collectin family neck region.

3. The fusion protein of claim 2, wherein the linker element consists of amino acids glycine and serine.

4. The fusion protein of claim 3, wherein (iii) comprises 51-193 or 56-193 SEQ ID NO: 7.

5. The fusion protein of claim 2, wherein the linker has the amino acid sequence of SEQ ID NO: 33, which is (GSS)a(SSG)b(GSG)c, wherein a, b, c is each independently 0, 1, 2, 3, 4, 5 or 6 such that the linker has 25 or less amino acid.

6. The fusion protein of claim 2, wherein the linker element has the amino acid sequence of SEQ ID NO: 56, which is GSSGSSGSSGSG.

7. The fusion protein of claim 2, wherein the linker element has the amino acid sequence of SEQ ID NO: 34, which is GSSGSSGSSGS.

8. The fusion protein of claim 2, further comprising an N-terminal signal peptide domain.

9. The fusion protein of claim 2, further comprising a recognition/purification domain selected from the group consisting of a strep-tag domain and a poly-His domain.

10. The fusion protein of claim 2, wherein (iii) is human CD27L having SEQ ID NO: 7.

11. The fusion protein of claim 2, wherein the linker element has the amino acid sequence of SEQ ID NO: 35, which is GSS GSS GS.

12. The fusion protein of claim 1, wherein the amino acid residue 355 in SEQ ID NO: 21 is optionally substituted to a polar amino acid selected from the group consisting of aspartic acid, glutamic acid, asparagine and glutamine.

13. A trimeric complex consisting of three identical fusion proteins of claim 1.

* * * * *